US012054736B2

(12) United States Patent
Wussow et al.

(10) Patent No.: US 12,054,736 B2
(45) Date of Patent: Aug. 6, 2024

(54) GENETICALLY MODIFIED RECOMBINANT VACCINIA ANKARA (RMVA) VACCINES OF IMPROVED STABILITY AND METHODS OF PREPARATION THEREOF

(71) Applicant: CITY OF HOPE, Duarte, CA (US)

(72) Inventors: Felix Wussow, Glendora, CA (US); Don J. Diamond, Glendora, CA (US); Heidi Contreras, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 658 days.

(21) Appl. No.: 17/095,300

(22) Filed: Nov. 11, 2020

(65) Prior Publication Data

US 2021/0062221 A1 Mar. 4, 2021

Related U.S. Application Data

(63) Continuation of application No. PCT/US2019/031866, filed on May 10, 2019.

(60) Provisional application No. 62/670,656, filed on May 11, 2018.

(51) Int. Cl.

| | |
|---|---|
| ***C12N 15/86*** | (2006.01) |
| ***A61K 39/245*** | (2006.01) |
| ***C07K 14/005*** | (2006.01) |
| *A61K 39/00* | (2006.01) |

(52) U.S. Cl.

CPC ............ *C12N 15/86* (2013.01); *A61K 39/245* (2013.01); *C07K 14/005* (2013.01); *A61K 2039/5256* (2013.01); *A61K 2039/70* (2013.01); *C07K 2319/40* (2013.01); *C12N 2710/16122* (2013.01); *C12N 2710/16134* (2013.01); *C12N 2710/24134* (2013.01); *C12N 2710/24143* (2013.01); *C12N 2800/22* (2013.01)

(58) Field of Classification Search

CPC .......... A61K 2039/5256; A61K 39/275; A61K 39/285; A61K 39/245; A61K 2123/00; A61K 2121/00; A61K 49/00; A61K 2039/80; A61K 39/12; A61P 31/20; C12N 15/86; C12N 2710/24143; C12N 2800/22; C12N 2710/24134; C12N 2710/16134; C12N 2710/16122

See application file for complete search history.

(56) References Cited

U.S. PATENT DOCUMENTS 6,835,383 B2 12/2004 Zaia et al.
7,163,685 B2 1/2007 Diamond et al.
7,501,127 B2 3/2009 Howley et al.
7,550,147 B2 6/2009 Howley et al.
8,580,276 B2 * 11/2013 Diamond ............... A61K 39/12 435/235.1
9,931,395 B2 * 4/2018 Diamond ................ A61P 31/12
11,116,834 B2 * 9/2021 Williams ........... C07K 16/2803
2010/0316667 A1 12/2010 Diamond et al.
2011/0081708 A1 4/2011 Liu et al.
2012/0263750 A1 10/2012 Moss et al.
2014/0030292 A1 1/2014 Franti et al.
2015/0216965 A1 * 8/2015 Diamond ............. A61K 39/245 435/320.1
2017/0246292 A1 8/2017 Diamond et al.
2023/0398209 A1 12/2023 Diamond et al.

FOREIGN PATENT DOCUMENTS

CN 104838000 A 8/2015

OTHER PUBLICATIONS

Manual et al. Virology, 2010, vol. 403, pp. 155-162.*
Ricci et al. Virology Journal 2011, vol. 8, pp. 1-11.*
Wusscow et al. PLOS Pathogens, 2014, vol. 10, Issue 11, 21004524, pp. 1-23.*
Asmar, J., et al., "The Putative Zinc Finger of the Human Cytomegalovirus IE2 86-Kilodalton Protein Is Dispensable for DNA Binding and Autorepression, Thereby Demarcating a Concise Core Domain in the C Terminus of the Protein," J. Virol. 78(21):11853-11864 (2004).
Bayliss, C. D., et al., "Vaccinia Virion Protein I8R has Both DNA and RNA Helicase Activities: Implications for Vaccinia Virus Transcription," J. Virol. 70(2):794-800 (1996).
Britt, W. J., et al., "Identification of a 65 000 Dalton Virion Envelope Protein of Human Cytomegalovirus," Virus Res. 4:31-36 (1985).
Chiou, C.J., et al., "Identification and Mapping of Dimerization and DNA-Binding Domains in the C Terminus of the IE2 Regulatory Protein of Human Cytomegalovirus," J. Virol. 67(10):6201-6214 (1993).
Cottingham, M. G., et al., "Recombination-Mediated Genetic Engineering of a Bacterial Artificial Chromosome Clone of Modified Vaccinia Virus Ankara (MVA)," PLoS One 3(2): e1638 (2008).
Cottingham, M. G., et al., "Rapid Generation of Markerless Recombinant MVA Vaccines by En Passant Recombineering of a Self-Excising Bacterial Artificial Chromosome," J. Virol. Methods 168:233-236 (2010).

(Continued)

*Primary Examiner* — Bao Q Li

(74) *Attorney, Agent, or Firm* — Perkins Coie LLP; Lara J. Dueppen; Adeh Vartanian

(57) ABSTRACT

A vaccine composition comprising an immunologically effective amount of recombinant modified vaccinia Ankara (rMVA) virus comprising IE1, IE2 and pp65 or antigenic fragments thereof, which is genetically stable after at least 10 passages. A method of improving the stability of such rMVA upon passage by including one or more of the modifications: (1) inserting one or more nucleic acid sequences encoding the CMV antigens or antigenic fragments thereof into one or more insertion sites including but not limited to 044L/045L, IGR3, G1L/18R, and Del3 but not including Del2; (2) codon optimizing the nucleic acid sequences encoding the CMV antigens by removing consecutive cytosines or guanines; and (3) introducing one or more mutations in the amino acid sequences of the CMV antigens.

19 Claims, 51 Drawing Sheets

Specification includes a Sequence Listing.

(56) References Cited

OTHER PUBLICATIONS

Dimier, J., et al., "Deletion of Major Nonessential Genomic Regions in the Vaccinia Virus Lister Strain Enhances Attenuation without Altering Vaccine Efficacy in Mice," J. Virol. 85(10):5016-5026 (2011).

Hedengren-Olcott, M., et al., "The Vaccinia Virus G1L Putative Metalloproteinase Is Essential for Viral Replication in Vivo," J. Virol. 78(18):9947-9953 (2004).

Hermiston, T. W., et al., "Human Cytomegalovirus Immediate-Early Two Protein Region Involved in Negative Regulation of the Major Immediate-Early Promoter," J. Virol. 64(7):3532-3536 (1990).

La Rosa, C., et al., "MVA Vaccine Encoding CMV Antigens Safely Induces Durable Expansion of CMV-Specific T Cells in Healthy Adults," Blood 129(1):114-125 (2017).

Macias, M. P., et al., "An in Vitro System for Human Cytomegalovirus Immediate Early 2 Protein (IE2)-Mediated Site-Dependent Repression of Transcription and Direct Binding of IE2 to the Major Immediate Early Promoter," Proc. Natl. Acad. Sci. USA 90:707-711 (1993).

Manuel, E. R., et al., "Intergenic Region 3 of Modified Vaccinia Ankara is a Functional Site for Insert Gene Expression and Allows for Potent Antigen-Specific Immune Responses," Virol. 403(2):155-162 (2010).

Meisinger-Henschel, C., et al., "Introduction of the Six Major Genomic Deletions of Modified Vaccinia Virus Ankara (MVA) into the Parental Vaccinia Virus Is Not Sufficient to Reproduce an MVA-Like Phenotype in Cell Culture and in Mice," J. Virol. 84(19):9907-9919 (2010).

Nesvizhskii, A. I., et al., "A Statistical Model for Identifying Proteins by Tandem Mass Spectrometry," Anal. Chem. 75:4646-4658 (2003).

Petrik, D. T., et al., "The Autoregulatory and Transactivating Functions of the Human Cytomegalovirus IE86 Protein Use Independent Mechanisms for Promoter Binding," J. Virol. 81(11):5807-5818 (2007).

Pizzorno, M. C., et al., "The Functionally Active IE2 Immediate-Early Regulatory Protein of Human Cytomegalovirus Is an 80-Kilodalton Polypeptide That Contains Two Distinct Activator Domains and a Duplicated Nuclear Localization Signal," J. Virol. 65(7):3839-3852 (1991).

Plachter, B., et al., "Analysis of Proteins Encoded by IE Regions 1 and 2 of Human Cytomegalovirus Using Monoclonal Antibodies Generated Against Recombinant Antigens," Virology 193:642-652 (1993).

Sanders, R. L., et al., "Human Cytomegalovirus IE2 86 and IE2 40 Proteins Differentially Regulate UL84 Protein Expression Post-transcriptionally in the Absence of Other Viral Gene Products," J. Virol. 84(10):5158-5170 (2010).

Stenberg, R. M., et al., "Promoter-Specific trans Activation and Repression by Human Cytomegalovirus Immediate-Early Proteins Involves Common and Unique Protein Domains," J. Virol. 64(4):1556-1565 (1990).

Sylwester, A. W., et al., "Broadly Targeted Human Cytomegalovirus-Specific CD4+ and CD8+ T Cells Dominate the Memory Compartments of Exposed Subjects," J. Exp. Med. 202(5):673-685 (2005).

Tang, A., et al., "Functionally Inactivated Dominant Viral Antigens of Human Cytomegalovirus Delivered in Replication Incompetent Adenovirus Type 6 Vectors as Vaccine Candidates," Hum. Vaccin. Immunother. 13(12):2763-2771 (2017).

Timm, A., et al., "Genetic Stability of Recombinant MVA-BN," Vaccine 24:4618-4621 (2006).

Tischer, B. K., et al., "A Self-Excisable Infectious Bacterial Artificial Chromosome Clone of Varicella-Zoster Virus Allows Analysis of the Essential Tegument Protein Encoded by ORF9," J. Virol. 81(23):13200-13208 (2007).

Tischer, B. K., et al., "En Passant Mutagenesis: A Two Step Markerless Red Recombination System," Methods Mol. Biol. 634:421-430 (2010).

United States Patent and Trademark Office, International Search Report and Written Opinion dated Oct. 23, 2019 for PCT/US19/31866, 13 pages.

Wang, Z., et al., "Vaccine Properties of a Novel Marker Gene-Free Recombinant Modified Vaccinia Ankara Expressing Immunodominant CMV Antigens pp65 and IE1," Vaccine 25(6):1132-1141 (2007).

Wang, Z., et al., "Modified H5 Promoter Improves Stability of Insert Genes While Maintaining Immunogenicity During Extended Passage of Genetically Engineered MVA Vaccines," Vaccine 28:1547-1557 (2010).

Wang, Z., et al., "A Fusion Protein of HCMV IE1 exon4 and IE2 exon5 Stimulates Potent Cellular Immunity in an MVA Vaccine Vector," Virol. 377(2):379-390 (2008).

White, E. A., et al.,"The IE2 60-Kilodalton and 40-Kilodalton Proteins are Dispensable for Human Cytomegalovirus Replication but are Required for Efficient Delayed Early and Late Gene Expression and Production of Infectious Virus," J. Virol. 81(6):2573-2583 (2007).

Wussow, F., et al., "A Vaccine Based on the Rhesus Cytomegalovirus UL128 Complex Induces Broadly Neutralizing Antibodies in Rhesus Macaques," J. Virol. 87(3):1322-1332 (2013).

Wyatt, L. S., et al., "Elucidating and Minimizing the Loss by Recombinant Vaccinia Virus of Human Immunodeficiency Virus Gene Expression Resulting from Spontaneous Mutations and Positive Selection," J. Virol. 83(14):7176-6184 (2009).

CNIPA, First Office Action for Chinese Application No. 201980046532.X, mailed on Dec. 9, 2023, 14 pages with unofficial English translation.

European Patent Office, extended European Search Report and Opinion dated Mar. 10, 2022 for European Patent Application No. 19800357.6, 11 pages.

Wussow, F., et al., "Human Cytomegalovirus Vaccine Based on the Envelope gH/gL Pentamer Complex," PLoS Pathog. 10(11):e1004524 (2014).

* cited by examiner

Fig. 3A

| | | | 1 | SEQ ID NO: |
|---|---|---|---|---|
| 1 | lEfusion-Vac0 | 100.0% | atggtgaagcaaatcaaggtcagagtggacatggtaagacacagaattaaggaacacatgttgaagaagtatactcaaac | 1 |
| 2 | lEfusion | 74.0% | atggtcaaacagattaaggttcgagtggacatggtgcggcatagaatcaaggagcacatgctgaaaaaatatacccagac | 2 |
| 3 | lEfusion-4nt | 74.9% | atggtcaaacagattaaggttcgagtggacatggtgcggcatagaatcaaggagcacatgctgaagaagtatacccagac | 3 |
| | consensus/100% | | ATGGT.AArCArATyAAGGTy.GAGTGGACATGGTr.GrCAyAGAATyAAGGArCACATGyTGAArAArTATACyCArAC | 25 |
| | consensus/90% | | ATGGT.AArCArATyAAGGTy.GAGTGGACATGGTr.GrCAyAGAATyAAGGArCACATGyTGAArAArTATACyCArAC | 25 |
| | consensus/80% | | ATGGT.AArCArATyAAGGTy.GAGTGGACATGGTr.GrCAyAGAATyAAGGArCACATGyTGAArAArTATACyCArAC | 25 |
| | consensus/70% | | ATGGT.AArCArATyAAGGTy.GAGTGGACATGGTr.GrCAyAGAATyAAGGArCACATGyTGAArAArTATACyCArAC | 25 |

| | | | 81   1 |
|---|---|---|---|
| 1 | lEfusion-Vac0 | 100.0% | agaggagaagttcaccggtgccttcaatatgatgggtggatgtctacagaacgctttggatatcttagataaggtacatg |
| 2 | lEfusion | 74.0% | ggaagagaaattcactggcgcctttaatatgatgggaggatgtttgcagaatgccttagatatcttagataaggttcatg |
| 3 | lEfusion-4nt | 74.9% | ggaagagaaattcactggcgcctttaatatgatgggaggatgtttgcagaatgccttagatatcttagataaggttcatg |
| | consensus/100% | | rGArGAGAArTTCACyGGyGCCTTyAATATGATGGG.GGATGTyTrCAGAAyGCyTTrGATATCTTAGATAAGGT.CATG |
| | consensus/90% | | rGArGAGAArTTCACyGGyGCCTTyAATATGATGGG.GGATGTyTrCAGAAyGCyTTrGATATCTTAGATAAGGT.CATG |
| | consensus/80% | | rGArGAGAArTTCACyGGyGCCTTyAATATGATGGG.GGATGTyTrCAGAAyGCyTTrGATATCTTAGATAAGGT.CATG |
| | consensus/70% | | rGArGAGAArTTCACyGGyGCCTTyAATATGATGGG.GGATGTyTrCAGAAyGCyTTrGATATCTTAGATAAGGT.CATG |

| | | | 161   2   240 |
|---|---|---|---|
| 1 | lEfusion-Vac0 | 100.0% | aaccattcgaagaaatgaagtgcattggattgacaatgcaatcaatgtatgagaactacatagtgccagaggataagcgt |
| 2 | lEfusion | 74.0% | agcctttcgaggagatgaagtgtattgggctaactatgcagagcatgtatgagaactacattgtacctgaggataagcgg |
| 3 | lEfusion-4nt | 74.9% | agcctttcgaggagatgaagtgtattgggctaactatgcagagcatgtatgagaactacattgtacctgaggataagcgg |
| | consensus/100% | | ArCC.TTCGArGArATGAAGTGyATTGGryTrAC.ATGCAr...ATGTATGAGAACTACAT.GTrCC.GAGGATAAGCG. |
| | consensus/90% | | ArCC.TTCGArGArATGAAGTGyATTGGryTrAC.ATGCAr...ATGTATGAGAACTACAT.GTrCC.GAGGATAAGCG. |
| | consensus/80% | | ArCC.TTCGArGArATGAAGTGyATTGGryTrAC.ATGCAr...ATGTATGAGAACTACAT.GTrCC.GAGGATAAGCG. |
| | consensus/70% | | ArCC.TTCGArGArATGAAGTGyATTGGryTrAC.ATGCAr...ATGTATGAGAACTACAT.GTrCC.GAGGATAAGCG. |

Fig. 3A (cont.)

```
                            241   .     .     .     .     .     3     .     .  320
1 IEfusion-Vac0   100.0%   gaaatgtggatggcatgcatcaaggagttacatgatgtatccaaaggagcagccaacaagctaggtggtgctttgcaagc
2 IEfusion         74.0%   gagatgtggatggcttgtattaaggagctgcatgatgtgagcaagggcgccgctaacaagttggggggtgcactgcaggc
3 IEfusion-4nt     74.9%   gagatgtggatggcttgtattaaggagctgcatgatgtgagcaagggcgccgctaacaagttaggaggtgcactgcaggc
  consensus/100%           GArATGTGGATGGC.TGyATyAAGGAGyTrCATGATGTr..CAArGG.GC.GCyAACAAGyTRGG.GGTGC.yTGCArGC
  consensus/90%            GArATGTGGATGGC.TGyATyAAGGAGyTrCATGATGTr..CAArGG.GC.GCyAACAAGyTRGG.GGTGC.yTGCArGC
  consensus/80%            GArATGTGGATGGC.TGyATyAAGGAGyTrCATGATGTr..CAArGG.GC.GCyAACAAGyTRGG.GGTGC.yTGCArGC
  consensus/70%            GArATGTGGATGGC.TGyATyAAGGAGyTrCATGATGTr..CAArGG.GC.GCyAACAAGyTRGG.GGTGC.yTGCArGC

                            321   .     .     .     .     .     .     .     4  400
1 IEfusion-Vac0   100.0%   gaaggcaagagcgaagaaggatgaattgagacgaaagatgatgtacatgtgctatcgaaacatcgaattcttcactaaga
2 IEfusion         74.0%   taaggcccgtgctaaaaaggatgaacttaggagaaagatgatgtatatgtgctacaggaatatagagttctttaccaaga
3 IEfusion-4nt     74.9%   taaggcccgtgctaagaaggatgaacttaggagaaagatgatgtatatgtgctacaggaatatagagttctttaccaaga
  consensus/100%           .AAGGC..G.GC.AArAAGGATGAAyT.AGr.GAAAGATGATGTAyATGTGCTAy.GrAAyAT.GArTTCTTyACyAAGA
  consensus/90%            .AAGGC..G.GC.AArAAGGATGAAyT.AGr.GAAAGATGATGTAyATGTGCTAy.GrAAyAT.GArTTCTTyACyAAGA
  consensus/80%            .AAGGC..G.GC.AArAAGGATGAAyT.AGr.GAAAGATGATGTAyATGTGCTAy.GrAAyAT.GArTTCTTyACyAAGA
  consensus/70%            .AAGGC..G.GC.AArAAGGATGAAyT.AGr.GAAAGATGATGTAyATGTGCTAy.GrAAyAT.GArTTCTTyACyAAGA

                            401   .     .     .     .     .     .     .     .  480
1 IEfusion-Vac0   100.0%   actcagcgtttcctaagactaccaatggatgcagtcaagctatggctgcgcttcagaacttgcctcaatgtagtcctgat
2 IEfusion         74.0%   actcagccttccctaagaccaccaatggctgcagtcaggccatggcggcactgcagaacttgcctcagtgctcccctgat
3 IEfusion-4nt     74.9%   actcagccttccctaagaccaccaatggctgcagtcaggccatggcggcactgcagaacttgcctcagtgctctcctgat
  consensus/100%           ACTCAGC.TTyCCTAAGACyACCAATGG.TGCAGTCArGCyATGGC.GCrCT.CAGAACTTGCCTCArTGy..yCCTGAT
  consensus/90%            ACTCAGC.TTyCCTAAGACyACCAATGG.TGCAGTCArGCyATGGC.GCrCT.CAGAACTTGCCTCArTGy..yCCTGAT
  consensus/80%            ACTCAGC.TTyCCTAAGACyACCAATGG.TGCAGTCArGCyATGGC.GCrCT.CAGAACTTGCCTCArTGy..yCCTGAT
  consensus/70%            ACTCAGC.TTyCCTAAGACyACCAATGG.TGCAGTCArGCyATGGC.GCrCT.CAGAACTTGCCTCArTGy..yCCTGAT
```

Fig. 3A (cont.)

| | | | 481 - 5 - - - - - - 560 |
|---|---|---|---|
| 1 | !Efusion-Vac0 | 100.0% | gaaatcatggcatatgcacagaagatcttcaagatcttagatgaggaaagagacaaggtattgactcatatcgatcacat |
| 2 | !Efusion | 74.0% | gagattatggcttatgcccagaaaatatttaagatttggatgaggagagagacaaggtgctcacgcacattgatcacat |
| 3 | !Efusion-4nt | 74.9% | gagattatggcttatgcccagaagatatttaagatcttggatgaggagagagacaaggtgctcacgcacattgatcacat |
| | consensus/100% | | GArATyATGGC.TATGC.CAGAArAT.TTyAAGATyTTrGATGAGGArAGAGACAAGGTryT.AC.CAyATyGATCACAT |
| | consensus/90% | | GArATyATGGC.TATGC.CAGAArAT.TTyAAGATyTTrGATGAGGArAGAGACAAGGTryT.AC.CAyATyGATCACAT |
| | consensus/80% | | GArATyATGGC.TATGC.CAGAArAT.TTyAAGATyTTrGATGAGGArAGAGACAAGGTryT.AC.CAyATyGATCACAT |
| | consensus/70% | | GArATyATGGC.TATGC.CAGAArAT.TTyAAGATyTTrGATGAGGArAGAGACAAGGTryT.AC.CAyATyGATCACAT |

| | | | 561 - - - 6 - - - - 640 |
|---|---|---|---|
| 1 | !Efusion-Vac0 | 100.0% | attcatggatatactaacaacatgtgtagaaacgatgtgtaacgagtacaaggtaacttcggacgcttgtatgatgacta |
| 2 | !Efusion | 74.0% | atttatggatatcctcactacatgtgtggaaacaatgtgtaatgagtacaaggtcactagtgacgcttgtatgatgacca |
| 3 | !Efusion-4nt | 74.9% | atttatggatatcctcactacatgtgtggaaacaatgtgtaatgagtacaaggtcactagtgacgcttgtatgatgacca |
| | consensus/100% | | ATTyATGGATAT.CT.AC.ACATGTGTrGAAACrATGTGTAAyGAGTACAAGGT.ACT...GACGCTTGTATGATGACyA |
| | consensus/90% | | ATTyATGGATAT.CT.AC.ACATGTGTrGAAACrATGTGTAAyGAGTACAAGGT.ACT...GACGCTTGTATGATGACyA |
| | consensus/80% | | ATTyATGGATAT.CT.AC.ACATGTGTrGAAACrATGTGTAAyGAGTACAAGGT.ACT...GACGCTTGTATGATGACyA |
| | consensus/70% | | ATTyATGGATAT.CT.AC.ACATGTGTrGAAACrATGTGTAAyGAGTACAAGGT.ACT...GACGCTTGTATGATGACyA |

| | | | 641 - - - - - 7 - - 720 |
|---|---|---|---|
| 1 | !Efusion-Vac0 | 100.0% | tgtacggaggaatatctctacttagtgagttctgtcgagttctatgctgttacgtattagaagaaactagtgtaatgtta |
| 2 | !Efusion | 74.0% | tgtacgggggcatctctctcttaagtgagttctgtcgggtgctgtgctgctatgtcttagaggagactagtgtgatgctg |
| 3 | !Efusion-4nt | 74.9% | tgtacggaggcatctctctcttaagtgagttctgtcgggtgctgtgctgctatgtcttagaggagactagtgtgatgctg |
| | consensus/100% | | TGTACGGrGG.AT.TCTCT.yT.AGTGAGTTCTGTCGrGT.CTrTGCTGyTAyGT.TTAGArGArACTAGTGTrATGyTr |
| | consensus/90% | | TGTACGGrGG.AT.TCTCT.yT.AGTGAGTTCTGTCGrGT.CTrTGCTGyTAyGT.TTAGArGArACTAGTGTrATGyTr |
| | consensus/80% | | TGTACGGrGG.AT.TCTCT.yT.AGTGAGTTCTGTCGrGT.CTrTGCTGyTAyGT.TTAGArGArACTAGTGTrATGyTr |
| | consensus/70% | | TGTACGGrGG.AT.TCTCT.yT.AGTGAGTTCTGTCGrGT.CTrTGCTGyTAyGT.TTAGArGArACTAGTGTrATGyTr |

Fig. 3B

| | | | | | SEQ ID NO: |
|---|---|---|---|---|---|
| | | 721 | . . . . . . . 8 | 800 | |
| 1 | lEfusion-Vac0 | 100.0% | gcgaagagaccattgatcactaagcctgaagtgatctcggttatgaagagacgaatagaggagatctgtatgaaggtgtt | | 1 |
| 2 | lEfusion | 74.0% | gccaagcggcctctgataaccaagcctgaggttatcagtgtaatgaagcgccgcattgaggagatctgcatgaaggtctt | | 2 |
| 3 | lEfusion-4nt | 74.9% | gccaagcggcctctgataaccaagcctgaggttatcagtgtaatgaagcgccgcattgaggagatctgcatgaaggtctt | | 3 |
| | consensus/100% | | GC.AAG.GrCC.yTGAT.ACyAAGCCTGArGT.ATC...GT.ATGAAG.G.CG.AT.GAGGAGATCTGyATGAAGGT.TT | | 25 |
| | consensus/90% | | GC.AAG.GrCC.yTGAT.ACyAAGCCTGArGT.ATC...GT.ATGAAG.G.CG.AT.GAGGAGATCTGyATGAAGGT.TT | | 25 |
| | consensus/80% | | GC.AAG.GrCC.yTGAT.ACyAAGCCTGArGT.ATC...GT.ATGAAG.G.CG.AT.GAGGAGATCTGyATGAAGGT.TT | | 25 |
| | consensus/70% | | GC.AAG.GrCC.yTGAT.ACyAAGCCTGArGT.ATC...GT.ATGAAG.G.CG.AT.GAGGAGATCTGyATGAAGGT.TT | | 25 |
| | | 801 | . . . . . . . . | 880 | |
| 1 | lEfusion-Vac0 | 100.0% | cgcacaatacatctttaggagctgatcctctaagagtgtgtagtccatcggtagacgatttgagagctatagcggaggaat | | |
| 2 | lEfusion | 74.0% | tgcccagtacattctgggggccgatcctctgagagtctgctctcctagtgtggatgacctacgggccatcgccgaggagt | | |
| 3 | lEfusion-4nt | 74.9% | tgcccagtacattctaggtgccgatcctctgagagtctgctctcctagtgtggatgacctacgggccatcgccgaggagt | | |
| | consensus/100% | | yGC.CArTACATyyTrGG.GCyGATCCTCTrAGAGT.TGy..TCC....GTrGAyGAyyTr.GrGCyAT.GC.GAGGArT | | |
| | consensus/90% | | yGC.CArTACATyyTrGG.GCyGATCCTCTrAGAGT.TGy..TCC....GTrGAyGAyyTr.GrGCyAT.GC.GAGGArT | | |
| | consensus/80% | | yGC.CArTACATyyTrGG.GCyGATCCTCTrAGAGT.TGy..TCC....GTrGAyGAyyTr.GrGCyAT.GC.GAGGArT | | |
| | consensus/70% | | yGC.CArTACATyyTrGG.GCyGATCCTCTrAGAGT.TGy..TCC....GTrGAyGAyyTr.GrGCyAT.GC.GAGGArT | | |
| | | 881 | . 9 . . . . . . | 960 | |
| 1 | lEfusion-Vac0 | 100.0% | ctgacgaggaagaggcaatagttgcatacacacttgctacagctggagtatccagttctgattctcttgtaagtcctccg | | |
| 2 | lEfusion | 74.0% | cagatgaggaagaggctattgtagcctacactttggccaccgctggtgtcagctcctctgattctctggtgtcacccccca | | |
| 3 | lEfusion-4nt | 74.9% | cagatgaggaagaggctattgtagcctacactttggccaccgctggtgtcagctcctctgattctctggtgtcacctcca | | |
| | consensus/100% | | C.GAyGAGGAAGAGGC.AT.GT.GC.TACAC.yT.GCyAC.GCIGG.GT...C..yTCIGATTCTCT.GTr...CCyCCr | | |
| | consensus/90% | | C.GAyGAGGAAGAGGC.AT.GT.GC.TACAC.yT.GCyAC.GCIGG.GT...C..yTCIGATTCTCT.GTr...CCyCCr | | |
| | consensus/80% | | C.GAyGAGGAAGAGGC.AT.GT.GC.TACAC.yT.GCyAC.GCIGG.GT...C..yTCIGATTCTCT.GTr...CCyCCr | | |
| | consensus/70% | | C.GAyGAGGAAGAGGC.AT.GT.GC.TACAC.yT.GCyAC.GCIGG.GT...C..yTCIGATTCTCT.GTr...CCyCCr | | |

Fig. 3B (cont.)

| | | | 961 . . . 0 . . . . 1040 |
|---|---|---|---|
| 1 | IEfusion-Vac0 | 100.0% | gagtcacctgtgccagcaaccataccgttgagtagtgtgattgtggctgagaactcggatcaggaagagtctgagcaatc |
| 2 | IEfusion | 74.0% | gagtcccctgtacccgcgactatccctctgtcctcagtaattgtggctgagaacagtgatcaggaagaaagtgagcagag |
| 3 | IEfusion-4nt | 74.9% | gagtcacctgtacccgcgactatccctctgtcctcagtaattgtggctgagaacagtgatcaggaagaaagtgagcagag |
| | consensus/100% | | GAGTC.CCTGTrCC.GCrACyAT.CC.yTG..y...GTrATTGIGGCTGAGAAC...GATCAGGAAGAr..TGAGCAr.. |
| | consensus/90% | | GAGTC.CCTGTrCC.GCrACyAT.CC.yTG..y...GTrATTGIGGCTGAGAAC...GATCAGGAAGAr..TGAGCAr.. |
| | consensus/80% | | GAGTC.CCTGTrCC.GCrACyAT.CC.yTG..y...GTrATTGIGGCTGAGAAC...GATCAGGAAGAr..TGAGCAr.. |
| | consensus/70% | | GAGTC.CCTGTrCC.GCrACyAT.CC.yTG..y...GTrATTGIGGCTGAGAAC...GATCAGGAAGAr..TGAGCAr.. |

| | | | 1041 . . . . . 1 . . 1120 |
|---|---|---|---|
| 1 | IEfusion-Vac0 | 100.0% | cgatgaagaagaggaggaaggagcacaagaggagagagaagatactgtctctgtgaagagtgaacctgtatctgaaatcg |
| 2 | IEfusion | 74.0% | tgatgaggaagaggaggagggtgctcaggaggagcgggaggacactgtgtctgtcaagtctgagccagtgtctgagatag |
| 3 | IEfusion-4nt | 74.9% | tgatgaggaagaggaggagggtgctcaggaggagcgggaggacactgtgtctgtcaagtctgagccagtgtctgagatag |
| | consensus/100% | | yGATGArGAAGAGGAGGArGG.GC.CArGAGGAG.GrGArGAyACTGT.TCTGT.AAG..TGArCC.GTrTCIGArAT.G |
| | consensus/90% | | yGATGArGAAGAGGAGGArGG.GC.CArGAGGAG.GrGArGAyACTGT.TCTGT.AAG..TGArCC.GTrTCIGArAT.G |
| | consensus/80% | | yGATGArGAAGAGGAGGArGG.GC.CArGAGGAG.GrGArGAyACTGT.TCTGT.AAG..TGArCC.GTrTCIGArAT.G |
| | consensus/70% | | yGATGArGAAGAGGAGGArGG.GC.CArGAGGAG.GrGArGAyACTGT.TCTGT.AAG..TGArCC.GTrTCIGArAT.G |

| | | | 1121 . . . . . . . 2 1200 |
|---|---|---|---|
| 1 | IEfusion-Vac0 | 100.0% | aggaagtagcacctgaggaagaggaggatggagccgaagaaccaacagcttcgggtggtaagtcaactcatccgatggta |
| 2 | IEfusion | 74.0% | aggaagttgccccagaggaagaggaggatggtgctgaggaacccaccgcctctggaggcaagagcacccaccctatggtg |
| 3 | IEfusion-4nt | 74.9% | aggaagttgctccagaggaagaggaggatggtgctgaggaacccaccgcctctggaggcaagagcacccaccctatggtg |
| | consensus/100% | | AGGAAGT.GC.CC.GAGGAAGAGGAGGATGG.GCyGArGAACC.AC.GCyTC.GG.GGyAAG...ACyCAyCC.ATGGTr |
| | consensus/90% | | AGGAAGT.GC.CC.GAGGAAGAGGAGGATGG.GCyGArGAACC.AC.GCyTC.GG.GGyAAG...ACyCAyCC.ATGGTr |
| | consensus/80% | | AGGAAGT.GC.CC.GAGGAAGAGGAGGATGG.GCyGArGAACC.AC.GCyTC.GG.GGyAAG...ACyCAyCC.ATGGTr |
| | consensus/70% | | AGGAAGT.GC.CC.GAGGAAGAGGAGGATGG.GCyGArGAACC.AC.GCyTC.GG.GGyAAG...ACyCAyCC.ATGGTr |

Fig. 3B (cont.)

| | | | |
|---|---|---|---|
| | | 1201 | . . . . . . . . 1280 |
| 1 | IEfusion-Vac0 | 100.0% | accagatctaaggcagaccagggagacatcctagcacaagcagtgaaccatgctggaattgactcatcttcgaccggacc |
| 2 | IEfusion | 74.0% | actagaagcaaggctgaccagggtgacatcctcgcccaggctgtcaatcatgccggtatcgattccagtagcaccggccc |
| 3 | IEfusion-4nt | 74.9% | actagaagcaaggctgaccagggtgacatcctcgcccaggctgtcaatcatgccggtatcgattccagtagcaccggacc |
| | consensus/100% | | ACyAGA..yAAGGC.GACCAGGG.GACATCCT.GC.CArGC.GT.AAyCATGCyGG.ATyGAyTC...T...ACCGG.CC |
| | consensus/90% | | ACyAGA..yAAGGC.GACCAGGG.GACATCCT.GC.CArGC.GT.AAyCATGCyGG.ATyGAyTC...T...ACCGG.CC |
| | consensus/80% | | ACyAGA..yAAGGC.GACCAGGG.GACATCCT.GC.CArGC.GT.AAyCATGCyGG.ATyGAyTC...T...ACCGG.CC |
| | consensus/70% | | ACyAGA..yAAGGC.GACCAGGG.GACATCCT.GC.CArGC.GT.AAyCATGCyGG.ATyGAyTC...T...ACCGG.CC |

| | | | |
|---|---|---|---|
| | | 1281 | . 3 . . . . . . 1360 |
| 1 | IEfusion-Vac0 | 100.0% | aactctaacgactcattcatgttcggttagttctgctcctcttaacaagcctacacctacctcggtagctgttaccaaca |
| 2 | IEfusion | 74.0% | cacgctgacaacccactcttgcagcgttagcagcgcccctcttaacaagccgacccccaccagcgtcgcggttactaaca |
| 3 | IEfusion-4nt | 74.9% | tacgctgacaacccactcttgcagcgttagcagcgctcctcttaacaagccgactccaaccagcgtcgcggttactaaca |
| | consensus/100% | | .AC.CTrACrACyCAyTC.TGy...GTTAGy..yGCyCCTCTTAACAAGCC.AC.CC.ACC...GT.GC.GTTACyAACA |
| | consensus/90% | | .AC.CTrACrACyCAyTC.TGy...GTTAGy..yGCyCCTCTTAACAAGCC.AC.CC.ACC...GT.GC.GTTACyAACA |
| | consensus/80% | | .AC.CTrACrACyCAyTC.TGy...GTTAGy..yGCyCCTCTTAACAAGCC.AC.CC.ACC...GT.GC.GTTACyAACA |
| | consensus/70% | | .AC.CTrACrACyCAyTC.TGy...GTTAGy..yGCyCCTCTTAACAAGCC.AC.CC.ACC...GT.GC.GTTACyAACA |

| | | | |
|---|---|---|---|
| | | 1361 | . . . 4 . . . . 1440 |
| 1 | IEfusion-Vac0 | 100.0% | cacctttaccaggagcatcagcaacacctgagttgtctccaagaaagaagcctcgtaagaccacgagaccgttcaaggtg |
| 2 | IEfusion | 74.0% | ctcctctccccggggcatccgctactcccgagctcagcccgcgtaagaaaccgcgcaaaaccacgcgtcctttcaaggtg |
| 3 | IEfusion-4nt | 74.9% | ctcctctaccaggagcatccgctactcccgagctcagcccgcgtaagaaaccgcgcaagaccacgcgtcctttcaaggtg |
| | consensus/100% | | C.CCTyT.CC.GGrGCATC.GC.AC.CCyGAGyT...yCCr.G.AAGAArCC.CGyAArACCACG.G.CC.TTCAAGGTG |
| | consensus/90% | | C.CCTyT.CC.GGrGCATC.GC.AC.CCyGAGyT...yCCr.G.AAGAArCC.CGyAArACCACG.G.CC.TTCAAGGTG |
| | consensus/80% | | C.CCTyT.CC.GGrGCATC.GC.AC.CCyGAGyT...yCCr.G.AAGAArCC.CGyAArACCACG.G.CC.TTCAAGGTG |
| | consensus/70% | | C.CCTyT.CC.GGrGCATC.GC.AC.CCyGAGyT...yCCr.G.AAGAArCC.CGyAArACCACG.G.CC.TTCAAGGTG |

Fig. 3C

| | | | | SEQ ID NO: |
|---|---|---|---|---|
| | | | 1441 . . . . . 5 . . 1520 | |
| 1 | IEfusion-Vac0 | 100.0% | atcatcaagccaccagtaccacctgctccgatcatgttgccattgatcaagcaggaggacattaagccagaacctgactt | 1 |
| 2 | IEfusion | 74.0% | attattaaaccgcccgtgcctcccgcgcctatcatgctgcccctcatcaaacaggaagacatcaagcccgagcccgactt | 2 |
| 3 | IEfusion-4nt | 74.9% | attattaaaccgcccgtgcctcccgcgcctatcatgctgccactcatcaaacaggaagacatcaagcccgagcccgactt | 3 |
| | consensus/100% | | ATyATyAArCCrCC.GTrCC.CCyGC.CC.ATCATGyTGCC.yT.ATCAArCAGGArGACATyAAGCC.GArCCyGACTT | 25 |
| | consensus/90% | | ATyATyAArCCrCC.GTrCC.CCyGC.CC.ATCATGyTGCC.yT.ATCAArCAGGArGACATyAAGCC.GArCCyGACTT | 25 |
| | consensus/80% | | ATyATyAArCCrCC.GTrCC.CCyGC.CC.ATCATGyTGCC.yT.ATCAArCAGGArGACATyAAGCC.GArCCyGACTT | 25 |
| | consensus/70% | | ATyATyAArCCrCC.GTrCC.CCyGC.CC.ATCATGyTGCC.yT.ATCAArCAGGArGACATyAAGCC.GArCCyGACTT | 25 |
| | | | 1521 . . . . . . . . 1600 | |
| 1 | IEfusion-Vac0 | 100.0% | cacgatacagtcaccgtaacaagatcatagatacagcaggatgcatagtgatctcagatagtgaagaggagcaaggtgagg | |
| 2 | IEfusion | 74.0% | taccatccagtaccgcaacaagattatcgataccgccggctgtatcgtgatctctgatagcgaggaagaacagggtgaag | |
| 3 | IEfusion-4nt | 74.9% | taccatccagtaccgcaacaagattatcgataccgccggctgtatcgtgatctctgatagcgaggaagaacagggtgaag | |
| | consensus/100% | | yAC.AT.CAGTACCGyAACAAGATyAT.GATAC.GC.GG.TGyAT.GTGATCTC.GATAGyGArGArGArCArGGTGArG | |
| | consensus/90% | | yAC.AT.CAGTACCGyAACAAGATyAT.GATAC.GC.GG.TGyAT.GTGATCTC.GATAGyGArGArGArCArGGTGArG | |
| | consensus/80% | | yAC.AT.CAGTACCGyAACAAGATyAT.GATAC.GC.GG.TGyAT.GTGATCTC.GATAGyGArGArGArCArGGTGArG | |
| | consensus/70% | | yAC.AT.CAGTACCGyAACAAGATyAT.GATAC.GC.GG.TGyAT.GTGATCTC.GATAGyGArGArGArCArGGTGArG | |
| | | | 1601 . . . . . . . . 1680 | |
| 1 | IEfusion-Vac0 | 100.0% | aagtggagactagaggagccacagccagttcgccttccacaggatccggaactcctagagtaactagtccgacacatcca | |
| 2 | IEfusion | 74.0% | aagtcgaaacccgcggtgctaccgcgtcttcccccttccaccggcagcggcacgccgcgagtgacctctcccacgcacccg | |
| 3 | IEfusion-4nt | 74.9% | aagtcgaaacccgcggtgctaccgcgtcttcaccttccaccggcagcggcacgccgcgagtgacctctcccacgcacccg | |
| | consensus/100% | | AAGT.GArACy.G.GG.GCyAC.GC...TTC.CCTTCCAC.GG...CGG.AC.CC..GAGTrACy..TCC.ACrCAyCCr | |
| | consensus/90% | | AAGT.GArACy.G.GG.GCyAC.GC...TTC.CCTTCCAC.GG...CGG.AC.CC..GAGTrACy..TCC.ACrCAyCCr | |
| | consensus/80% | | AAGT.GArACy.G.GG.GCyAC.GC...TTC.CCTTCCAC.GG...CGG.AC.CC..GAGTrACy..TCC.ACrCAyCCr | |
| | consensus/70% | | AAGT.GArACy.G.GG.GCyAC.GC...TTC.CCTTCCAC.GG...CGG.AC.CC..GAGTrACy..TCC.ACrCAyCCr | |

Fig. 3C (cont.)

```
                          1681   .    7    .    .    .    .    .    .  1760
1 IEfusion-Vac0   100.0%  ctttcccagatgaatcatccacctctaccggatcctctaggacgaccagatgaagattcttcttcatctagttcaagttc
2 IEfusion         74.0%  ctctcccagatgaaccaccctcctcttcccgatcccttgggccggcccgatgaagatagttcctcttcgtcttcctcctc
3 IEfusion-4nt     74.9%  ctctcccagatgaaccaccctcctcttcccgatcccttgggccggcccgatgaagatagttcctcttcgtcttcctcctc
  consensus/100%          CTyTCCCAGATGAAyCAyCC.CCTCT.CC.GATCyyTrGG.CGrCC.GATGAAGAT..TTCyTC.TC...TTC...yTC
  consensus/90%           CTyTCCCAGATGAAyCAyCC.CCTCT.CC.GATCyyTrGG.CGrCC.GATGAAGAT..TTCyTC.TC...TTC...yTC
  consensus/80%           CTyTCCCAGATGAAyCAyCC.CCTCT.CC.GATCyyTrGG.CGrCC.GATGAAGAT..TTCyTC.TC...TTC...yTC
  consensus/70%           CTyTCCCAGATGAAyCAyCC.CCTCT.CC.GATCyyTrGG.CGrCC.GATGAAGAT..TTCyTC.TC...TTC...yTC

                          1761   .    .    .    8  .  .    .    .  1840
1 IEfusion-Vac0   100.0%  ttgctcatccgcgagtgatagtgagtcagaaagtgaagagatgaagtgctcttctggtggtggagctagtgtcacttcat
2 IEfusion         74.0%  ctgcagttcggcttcggactcggagagtgagtccgaggagatgaaatgcagcagtggcggaggagcatccgtgacctcga
3 IEfusion-4nt     74.9%  ctgcagttcggcttcggactcggagagtgagtccgaggagatgaaatgcagcagtggcggaggagcatccgtgacctcga
  consensus/100%          yTGC...TC.GC....GAy...GAG...GAr..yGArGAGATGAArTGC..y..TGGyGG.GGAGC...yGT.ACyTCr.
  consensus/90%           yTGC...TC.GC....GAy...GAG...GAr..yGArGAGATGAArTGC..y..TGGyGG.GGAGC...yGT.ACyTCr.
  consensus/80%           yTGC...TC.GC....GAy...GAG...GAr..yGArGAGATGAArTGC..y..TGGyGG.GGAGC...yGT.ACyTCr.
  consensus/70%           yTGC...TC.GC....GAy...GAG...GAr..yGArGAGATGAArTGC..y..TGGyGG.GGAGC...yGT.ACyTCr.

                          1841   .    .    .    .    .    9    .  1920
1 IEfusion-Vac0   100.0%  ctcatcatggacgaggaggatttggaggtgctgcgagtagttccttactaagttgtggacatcagtcatctggtggtgca
2 IEfusion         74.0%  gccaccatgggcgcggcggttttggtggcgcggcctcctcctctctgctgagctgcggccatcagagcagcggcggggcg
3 IEfusion-4nt     74.9%  gccaccatgggcgcggcggatttggtggcgcggcctcctcctctctgctgagctgcggccatcagagcagcggcggtgcg
  consensus/100%          .yCAyCATGGrCG.GG.GG.TTTGG.GGyGC.GC...y..yTCyyTrCTrAGyTGyGG.CATCAG.....yGGyGG.GCr
  consensus/90%           .yCAyCATGGrCG.GG.GG.TTTGG.GGyGC.GC...y..yTCyyTrCTrAGyTGyGG.CATCAG.....yGGyGG.GCr
  consensus/80%           .yCAyCATGGrCG.GG.GG.TTTGG.GGyGC.GC...y..yTCyyTrCTrAGyTGyGG.CATCAG.....yGGyGG.GCr
  consensus/70%           .yCAyCATGGrCG.GG.GG.TTTGG.GGyGC.GC...y..yTCyyTrCTrAGyTGyGG.CATCAG.....yGGyGG.GCr
```

Fig. 3C (cont.)

| | | | 1921 ... 2000 |
|---|---|---|---|
| 1 | IEfusion-Vac0 | 100.0% | tctactggacctagaaagaagaagtcaaagagaatctccgaattggataatgagaaagtgagaaacatcatgaaggacaa |
| 2 | IEfusion | 74.0% | agcaccggaccccgcaagaagaagagcaaacgcatctccgagttggacaacgagaaggtgcgcaatatcatgaaagataa |
| 3 | IEfusion-4nt | 74.9% | agcaccggacctcgcaagaagaagagcaaacgcatctccgagttggacaacgagaaggtgcgcaatatcatgaaagataa |
| | consensus/100% | | ..yACyGGACCy.G.AAGAAGAAG...AAr.G.ATCTCCGArTIGGAyAAyGAGAArGIG.G.AAyATCATGAArGAyAA |
| | consensus/90% | | ..yACyGGACCy.G.AAGAAGAAG...AAr.G.ATCTCCGArTIGGAyAAyGAGAArGIG.G.AAyATCATGAArGAyAA |
| | consensus/80% | | ..yACyGGACCy.G.AAGAAGAAG...AAr.G.ATCTCCGArTIGGAyAAyGAGAArGIG.G.AAyATCATGAArGAyAA |
| | consensus/70% | | ..yACyGGACCy.G.AAGAAGAAG...AAr.G.ATCTCCGArTIGGAyAAyGAGAArGIG.G.AAyATCATGAArGAyAA |

| | | | 2001 ... 2080 |
|---|---|---|---|
| 1 | IEfusion-Vac0 | 100.0% | gaacacgccgttctgcactccgaatgttcagacgagaagaggacgagtgaagatagatgaagtatcacgaatgttcagaa |
| 2 | IEfusion | 74.0% | gaacaccccccttctgcacacccaacgtgcagactcggcggggtcgcgtcaagattgacgaggtgagccgcatgttccgca |
| 3 | IEfusion-4nt | 74.9% | gaacactcccttctgcacacccaacgtgcagactcggcgtggtcgcgtcaagattgacgaggtgagccgcatgttccgca |
| | consensus/100% | | GAACAC.CC.TTCTGCAC.CC.AAyGT.CAGAC..Gr.G.GG.CG.GT.AAGAT.GAyGArGTr...CG.ATGTTC.G.A |
| | consensus/90% | | GAACAC.CC.TTCTGCAC.CC.AAyGT.CAGAC..Gr.G.GG.CG.GT.AAGAT.GAyGArGTr...CG.ATGTTC.G.A |
| | consensus/80% | | GAACAC.CC.TTCTGCAC.CC.AAyGT.CAGAC..Gr.G.GG.CG.GT.AAGAT.GAyGArGTr...CG.ATGTTC.G.A |
| | consensus/70% | | GAACAC.CC.TTCTGCAC.CC.AAyGT.CAGAC..Gr.G.GG.CG.GT.AAGAT.GAyGArGTr...CG.ATGTTC.G.A |

| | | | 2081 ... 2160 |
|---|---|---|---|
| 1 | IEfusion-Vac0 | 100.0% | acacaaatcgttctctagagtacaagaatcttccgttcaccataccttcgatgcaccaagtattagatgaggctatcaag |
| 2 | IEfusion | 74.0% | acaccaatcgctctcttgagtacaagaacctgcccttcacgattcccagtatgcaccaggtgttagatgaggccatcaaa |
| 3 | IEfusion-4nt | 74.9% | acaccaatcgctctcttgagtacaagaacctgcccttcacgattcccagtatgcaccaggtgttagatgaggccatcaaa |
| | consensus/100% | | ACAC.AATCGyTCTCT.GAGTACAAGAAyCT.CC.TTCAC.AT.CCy...ATGCACCArGTrTIAGATGAGGCyATCAAr |
| | consensus/90% | | ACAC.AATCGyTCTCT.GAGTACAAGAAyCT.CC.TTCAC.AT.CCy...ATGCACCArGTrTIAGATGAGGCyATCAAr |
| | consensus/80% | | ACAC.AATCGyTCTCT.GAGTACAAGAAyCT.CC.TTCAC.AT.CCy...ATGCACCArGTrTIAGATGAGGCyATCAAr |
| | consensus/70% | | ACAC.AATCGyTCTCT.GAGTACAAGAAyCT.CC.TTCAC.AT.CCy...ATGCACCArGTrTIAGATGAGGCyATCAAr |

Fig. 3D

| | | | |
|---|---|---|---|
| | | 2161 | 2240 |
| 1 | IEfusion-Vac0 | 100.0% | gcatgtaagaccatgcaagttaacaacaaaggaatacagatcatctacactagaaaccatgaggttaagagtgaggtgga |
| 2 | IEfusion | 74.0% | gcctgcaaaaccatgcaggtgaacaacaagggcatccagattatctacacccgcaatcatgaggtgaagagtgaggtgga |
| 3 | IEfusion-4nt | 74.9% | gcctgcaagaccatgcaggtgaacaacaagggcatccagattatctacacccgcaatcatgaggtgaagagtgaggtgga |
| | consensus/100% | | GC.TGyAArACCATGCArGT.AACAACAArGG.AT.CAGATyATCTACACy.G.AAyCATGAGGT.AAGAGTGAGGTGGA |
| | consensus/90% | | GC.TGyAArACCATGCArGT.AACAACAArGG.AT.CAGATyATCTACACy.G.AAyCATGAGGT.AAGAGTGAGGTGGA |
| | consensus/80% | | GC.TGyAArACCATGCArGT.AACAACAArGG.AT.CAGATyATCTACACy.G.AAyCATGAGGT.AAGAGTGAGGTGGA |
| | consensus/70% | | GC.TGyAArACCATGCArGT.AACAACAArGG.AT.CAGATyATCTACACy.G.AAyCATGAGGT.AAGAGTGAGGTGGA |
| | | 2241 | 2320 |
| 1 | IEfusion-Vac0 | 100.0% | tgccgtacgttgtagattgggaacgatgtgtaaccttgcgctatctactcctttcctaatggagcatactatgcctgtga |
| 2 | IEfusion | 74.0% | tgcggtgcggtgtcgcctgggcaccatgtgcaacctggccctctccactcccttcctcatggagcacaccatgcccgtga |
| 3 | IEfusion-4nt | 74.9% | tgcggtgcggtgtcgcctgggcaccatgtgcaacctggccctctccactcccttcctcatggagcacaccatgcccgtga |
| | consensus/100% | | TGC.GTrCG.TGT.GyTGGG.AC.ATGTGyAACCT.GC.CT.TCyACTCCyTTCCT.ATGGAGCAyACyATGCCyGTGA |
| | consensus/90% | | TGC.GTrCG.TGT.GyTGGG.AC.ATGTGyAACCT.GC.CT.TCyACTCCyTTCCT.ATGGAGCAyACyATGCCyGTGA |
| | consensus/80% | | TGC.GTrCG.TGT.GyTGGG.AC.ATGTGyAACCT.GC.CT.TCyACTCCyTTCCT.ATGGAGCAyACyATGCCyGTGA |
| | consensus/70% | | TGC.GTrCG.TGT.GyTGGG.AC.ATGTGyAACCT.GC.CT.TCyACTCCyTTCCT.ATGGAGCAyACyATGCCyGTGA |
| | | 2321 | 2400 |
| 1 | IEfusion-Vac0 | 100.0% | ctcatcctcctgaagtggctcaaagaacagctgatgcttgtaacgaaggtgtgaaagctgcttggtccctaaaggagtta |
| 2 | IEfusion | 74.0% | cacatccacccgaagtggcgcagcgcacagccgatgcttgtaacgaaggcgtcaaggccgcgtggagcctcaaagaattg |
| 3 | IEfusion-4nt | 74.9% | cacatccacccgaagtggcgcagcgcacagccgatgcttgtaacgaaggcgtcaaggccgcgtggagcctcaaagaattg |
| | consensus/100% | | C.CATCC.CCyGAAGTGGC.CAr.G.ACAGCyGATGCTTGTAACGAAGGyGT.AArGCyGC.TGG..CCT.AArGArTTr |
| | consensus/90% | | C.CATCC.CCyGAAGTGGC.CAr.G.ACAGCyGATGCTTGTAACGAAGGyGT.AArGCyGC.TGG..CCT.AArGArTTr |
| | consensus/80% | | C.CATCC.CCyGAAGTGGC.CAr.G.ACAGCyGATGCTTGTAACGAAGGyGT.AArGCyGC.TGG..CCT.AArGArTTr |
| | consensus/70% | | C.CATCC.CCyGAAGTGGC.CAr.G.ACAGCyGATGCTTGTAACGAAGGyGT.AArGCyGC.TGG..CCT.AArGArTTr |

Fig. 3D (cont.)

```
                           2401    -    -    -    -    -    -    -    - 2480
1 IEfusion-Vac0   100.0%  catacacaccaactttgtccacgatccagtgactacagaaacatgatcattcatgcagctacgcctgtagatctacttgg
2 IEfusion         74.0%  cacacccaccaattatgcccccgttcctccgattaccgcaacatgatcatccacgctgccacccccgtggacctgttggg
3 IEfusion-4nt     74.9%  cacacccaccaattatgtcctcgttcctccgattaccgcaacatgatcatccacgctgccacaccagtggacctgttggg
  consensus/100%          CAyAC.CACCAAyT.TGyCC.CG.TCC..yGAyTAC.G.AACATGATCATyCAyGC.GCyAC.CC.GTrGAyCTryT.GG
  consensus/90%           CAyAC.CACCAAyT.TGyCC.CG.TCC..yGAyTAC.G.AACATGATCATyCAyGC.GCyAC.CC.GTrGAyCTryT.GG
  consensus/80%           CAyAC.CACCAAyT.TGyCC.CG.TCC..yGAyTAC.G.AACATGATCATyCAyGC.GCyAC.CC.GTrGAyCTryT.GG
  consensus/70%           CAyAC.CACCAAyT.TGyCC.CG.TCC..yGAyTAC.G.AACATGATCATyCAyGC.GCyAC.CC.GTrGAyCTryT.GG 2481    -    5    -    -    -    -    -    - 2560
1 IEfusion-Vac0   100.0%  agctcttaacctatgtcttccttgatgcagaagttccctaagcaagtgatggtgagaatcttctcgacgaatcaaggag
2 IEfusion         74.0%  cgctctcaacctgtgcctgcccctgatgcaaaagtttcccaaacaggtcatggtgcgcatcttctccaccaaccagggtg
3 IEfusion-4nt     74.9%  cgctctcaacctgtgcctgccactgatgcagaagtttcccaaacaggtcatggtgcgcatcttctccaccaaccagggtg
  consensus/100%          .GCTCTyAACCTrTGyCT.CC.yTGATGCArAAGTTyCCyAArCArGT.ATGGTG.G.ATCTTCTC.AC.AAyCArGG.G
  consensus/90%           .GCTCTyAACCTrTGyCT.CC.yTGATGCArAAGTTyCCyAArCArGT.ATGGTG.G.ATCTTCTC.AC.AAyCArGG.G
  consensus/80%           .GCTCTyAACCTrTGyCT.CC.yTGATGCArAAGTTyCCyAArCArGT.ATGGTG.G.ATCTTCTC.AC.AAyCArGG.G
  consensus/70%           .GCTCTyAACCTrTGyCT.CC.yTGATGCArAAGTTyCCyAArCArGT.ATGGTG.G.ATCTTCTC.AC.AAyCArGG.G 2561    -    -    -    6    -    -    -    - 2640
1 IEfusion-Vac0   100.0%  gattcatgttaccgatatacgagacagctgcaaaggcttacgctgtcggtcagttcgagcaaccgactgaaacgcctcct
2 IEfusion         74.0%  ggttcatgctgcctatctacgagacggccgcgaaggcctacgccgtggggcagtttgagcagcccaccgagacccctccc
3 IEfusion-4nt     74.9%  ggttcatgctgcctatctacgagacggccgcgaaggcctacgccgttggtcagtttgagcagcccaccgagacacctccc
  consensus/100%          GrTTCATGyTrCC.AT.TACGAGACrGCyGCrAAGGCyTACGCyGT.GG.CAGTTyGAGCArCC.ACyGArAC.CCTCCy
  consensus/90%           GrTTCATGyTrCC.AT.TACGAGACrGCyGCrAAGGCyTACGCyGT.GG.CAGTTyGAGCArCC.ACyGArAC.CCTCCy
  consensus/80%           GrTTCATGyTrCC.AT.TACGAGACrGCyGCrAAGGCyTACGCyGT.GG.CAGTTyGAGCArCC.ACyGArAC.CCTCCy
  consensus/70%           GrTTCATGyTrCC.AT.TACGAGACrGCyGCrAAGGCyTACGCyGT.GG.CAGTTyGAGCArCC.ACyGArAC.CCTCCy
```

Fig. 3D (cont.)

| | | | |
|---|---|---|---|
| | | 2641 | . . . . . 7 ] 2709 |
| 1 | lEfusion-Vac0 | 100.0% | gaggacttagatacattgtctttggcgatagaagcagcgattcaggatcttagaaacaagagtcagtaa |
| 2 | lEfusion | 74.0% | gaagacctggacaccctgagcctggccatcgaggcagccatccaggacctgaggaacaagtctcagtaa |
| 3 | lEfusion-4nt | 74.9% | gaagacctggacaccctgagcctggccatcgaggcagccatccaggacctgaggaacaagtctcagtaa |
| | consensus/100% | | GArGACyTrGAyAC.yTG..yyTGGC.AT.GArGCAGC.ATyCAGGAyCT.AGrAACAAG..TCAGTAA |
| | consensus/90% | | GArGACyTrGAyAC.yTG..yyTGGC.AT.GArGCAGC.ATyCAGGAyCT.AGrAACAAG..TCAGTAA |
| | consensus/80% | | GArGACyTrGAyAC.yTG..yyTGGC.AT.GArGCAGC.ATyCAGGAyCT.AGrAACAAG..TCAGTAA |
| | consensus/70% | | GArGACyTrGAyAC.yTG..yyTGGC.AT.GArGCAGC.ATyCAGGAyCT.AGrAACAAG..TCAGTAA |

Fig. 6A

| | | | | SEQ ID NO: |
|---|---|---|---|---|
| | | 1 | . . . . . . . . 80 | |
| 1 IE2-Vac0 | | 100.0% | atgggagacatcctagcacaagcagtgaaccatgctggaattgactcatcttcgaccggaccaactctaacgactcattc | 7 |
| 2 IE2 | | 71.1% | atgggtgacatcctcgcccaggctgtcaatcatgccggtatcgattccagtagcaccggccccacgctgacaacccactc | 8 |
| 3 IE2-4nt | | 72.6% | atgggtgacatcctcgcccaggctgtcaatcatgccggtatcgattccagtagcaccggacctacgctgacaacccactc | 9 |
| | consensus/100% | | ATGGG.GACATCCT.GC.CArGC.GT.AAyCATGCyGG.ATyGAyTC...T...ACCGG.CC.AC.CTrACrACyCAyTC | 26 |
| | consensus/90% | | ATGGG.GACATCCT.GC.CArGC.GT.AAyCATGCyGG.ATyGAyTC...T...ACCGG.CC.AC.CTrACrACyCAyTC | 26 |
| | consensus/80% | | ATGGG.GACATCCT.GC.CArGC.GT.AAyCATGCyGG.ATyGAyTC...T...ACCGG.CC.AC.CTrACrACyCAyTC | 26 |
| | consensus/70% | | ATGGG.GACATCCT.GC.CArGC.GT.AAyCATGCyGG.ATyGAyTC...T...ACCGG.CC.AC.CTrACrACyCAyTC | 26 |
| | | 81 | . 1 . . . . . . 160 | |
| 1 IE2-Vac0 | | 100.0% | atgttcggttagttctgctcctcttaacaagcctacacctacctcggtagctgttaccaacacacctttaccaggagacat | |
| 2 IE2 | | 71.1% | ttgcagcgttagcagcgcccctcttaacaagccgacccccaccagcgtcgcggttactaacactcctctccccggggcat | |
| 3 IE2-4nt | | 72.6% | ttgcagcgttagcagcgctcctcttaacaagccgactccaaccagcgtcgcggttactaacactcctctaccaggagcat | |
| | consensus/100% | | .TGy...GTTAGy..yGCyCCTCTTAACAAGCC.AC.CC.ACC...GT.GC.GTTACyAACAC.CCTyT.CC.GGrGCAT | |
| | consensus/90% | | .TGy...GTTAGy..yGCyCCTCTTAACAAGCC.AC.CC.ACC...GT.GC.GTTACyAACAC.CCTyT.CC.GGrGCAT | |
| | consensus/80% | | .TGy...GTTAGy..yGCyCCTCTTAACAAGCC.AC.CC.ACC...GT.GC.GTTACyAACAC.CCTyT.CC.GGrGCAT | |
| | consensus/70% | | .TGy...GTTAGy..yGCyCCTCTTAACAAGCC.AC.CC.ACC...GT.GC.GTTACyAACAC.CCTyT.CC.GGrGCAT | |
| | | 161 | . . . 2 . . . . 240 | |
| 1 IE2-Vac0 | | 100.0% | cagcaacacctgagttgtctccaagaaagaagcctcgtaagaccacgagaccgttcaaggtgatcatcaagccaccagta | |
| 2 IE2 | | 71.1% | ccgctactcccgagctcagcccgcgtaagaaaccgcgcaaaaccacgcgtcctttcaaggtgattattaaaccgcccgtg | |
| 3 IE2-4nt | | 72.6% | ccgctactcccgagctcagcccgcgtaagaaaccgcgcaagaccacgcgtcctttcaaggtgattattaaaccgcccgtg | |
| | consensus/100% | | C.GC.AC.CCyGAGyT...yCCr.G.AAGAArCC.CGyAArACCACG.G.CC.TTCAAGGTGATyATyAArCCrCC.GTr | |
| | consensus/90% | | C.GC.AC.CCyGAGyT...yCCr.G.AAGAArCC.CGyAArACCACG.G.CC.TTCAAGGTGATyATyAArCCrCC.GTr | |
| | consensus/80% | | C.GC.AC.CCyGAGyT...yCCr.G.AAGAArCC.CGyAArACCACG.G.CC.TTCAAGGTGATyATyAArCCrCC.GTr | |
| | consensus/70% | | C.GC.AC.CCyGAGyT...yCCr.G.AAGAArCC.CGyAArACCACG.G.CC.TTCAAGGTGATyATyAArCCrCC.GTr | |

Fig. 6A (cont.)

```
                                 241       -    -    -    -    -    3    -    -  320
1 IE2-Vac0          100.0%  ccacctgctccgatcatgttgccattgatcaagcaggaggacattaagccagaacctgacttcacgatacagtaccgtaa
2 IE2                71.1%  cctcccgcgcctatcatgctgcccctcatcaaacaggaagacatcaagcccgagcccgactttaccatccagtaccgcaa
3 IE2-4nt            72.6%  cctcccgcgcctatcatgctgccactcatcaaacaggaagacatcaagcccgagcccgactttaccatccagtaccgcaa
  consensus/100%            CC.CCyGC.CC.ATCATGyTGCC.yT.ATCAArCAGGArGACATyAAGCC.GArCCyGACTTyAC.AT.CAGTACCGyAA
  consensus/90%             CC.CCyGC.CC.ATCATGyTGCC.yT.ATCAArCAGGArGACATyAAGCC.GArCCyGACTTyAC.AT.CAGTACCGyAA
  consensus/80%             CC.CCyGC.CC.ATCATGyTGCC.yT.ATCAArCAGGArGACATyAAGCC.GArCCyGACTTyAC.AT.CAGTACCGyAA
  consensus/70%             CC.CCyGC.CC.ATCATGyTGCC.yT.ATCAArCAGGArGACATyAAGCC.GArCCyGACTTyAC.AT.CAGTACCGyAA

                                 231       -    -    -    -    -    -    -    4  400
1 IE2-Vac0          100.0%  caagatcatagatacagcaggatgcatagtgatctcagatagtgaagaggagcaaggtgaggaagtggagactagaggag
2 IE2                71.1%  caagattatcgataccgccggctgtatcgtgatctctgatagcgaggaagaacagggtgaagaagtcgaaacccgcggtg
3 IE2-4nt            72.6%  caagattatcgataccgccggctgtatcgtgatctctgatagcgaggaagaacagggtgaagaagtcgaaacccgcggtg
  consensus/100%            CAAGATyAT.GATAC.GC.GG.TGyAT.GTGATCTC.GATAGyGArGArGArCArGGTGArGAAGT.GArACy.G.GG.G
  consensus/90%             CAAGATyAT.GATAC.GC.GG.TGyAT.GTGATCTC.GATAGyGArGArGArCArGGTGArGAAGT.GArACy.G.GG.G
  consensus/80%             CAAGATyAT.GATAC.GC.GG.TGyAT.GTGATCTC.GATAGyGArGArGArCArGGTGArGAAGT.GArACy.G.GG.G
  consensus/70%             CAAGATyAT.GATAC.GC.GG.TGyAT.GTGATCTC.GATAGyGArGArGArCArGGTGArGAAGT.GArACy.G.GG.G

                                 401       -    -    -    -    -    -    -    -  480
1 IE2-Vac0          100.0%  ccacagccagttcgccttccacaggatccggaactcctagagtaactagtccgacacatccactttcccagatgaatcat
2 IE2                71.1%  ctaccgcgtcttccccttccaccggcagcggcacgccgcgagtgacctctcccacgcacccgctctcccagatgaaccac
3 IE2-4nt            72.6%  ctaccgcgtcttcaccttccaccggcagcggcacgccgcgagtgacctctcccacgcacccgctctcccagatgaaccac
  consensus/100%            CyAC.GC...TTC.CCTTCCAC.GG...CGG.AC.CC..GAGTrACy..TCC.ACrCAyCCrCTyTCCCAGATGAAyCAy
  consensus/90%             CyAC.GC...TTC.CCTTCCAC.GG...CGG.AC.CC..GAGTrACy..TCC.ACrCAyCCrCTyTCCCAGATGAAyCAy
  consensus/80%             CyAC.GC...TTC.CCTTCCAC.GG...CGG.AC.CC..GAGTrACy..TCC.ACrCAyCCrCTyTCCCAGATGAAyCAy
  consensus/70%             CyAC.GC...TTC.CCTTCCAC.GG...CGG.AC.CC..GAGTrACy..TCC.ACrCAyCCrCTyTCCCAGATGAAyCAy
```

Fig. 6A (cont.)

| | | | |
|---|---|---|---|
| | | 481 | . 5 . . . . . . 560 |
| 1 | IE2-Vac0 | 100.0% | ccacctctaccggatcctctaggacgaccagatgaagattcttcttcatctagttcaagttcttgctcatccgcgagtga |
| 2 | IE2 | 71.1% | cctcctcttcccgatcccttgggccggcccgatgaagatagttcctcttcgtcttcctcctcctgcagttcggcttcgga |
| 3 | IE2-4nt | 72.6% | cctcctcttcccgatcccttgggccggcccgatgaagatagttcctcttcgtcttcctcctcctgcagttcggcttcgga |
| | consensus/100% | | CC.CCTCT.CC.GATCCyyTrGG.CGrCC.GATGAAGAT..TTCyTC.TC...TTC...yTCyTGC...TC.GC....GA |
| | consensus/90% | | CC.CCTCT.CC.GATCCyyTrGG.CGrCC.GATGAAGAT..TTCyTC.TC...TTC...yTCyTGC...TC.GC....GA |
| | consensus/80% | | CC.CCTCT.CC.GATCCyyTrGG.CGrCC.GATGAAGAT..TTCyTC.TC...TTC...yTCyTGC...TC.GC....GA |
| | consensus/70% | | CC.CCTCT.CC.GATCCyyTrGG.CGrCC.GATGAAGAT..TTCyTC.TC...TTC...yTCyTGC...TC.GC....GA |

| | | | |
|---|---|---|---|
| | | 561 | . . . 6 . . . . 640 |
| 1 | IE2-Vac0 | 100.0% | tagtgagtcagaaagtgaagagatgaagtgctcttctggtggtggagctagtgtcacttcatctcatcatggacgaggag |
| 2 | IE2 | 71.1% | ctcggagagtgagtccgaggagatgaaatgcagcagtggcggaggagcatccgtgacctcgagccaccatgggcgcggcg |
| 3 | IE2-4nt | 72.6% | ctcggagagtgagtccgaggagatgaaatgcagcagtggcggaggagcatccgtgacctcgagccaccatgggcgcggcg |
| | consensus/100% | | y...GAG...GAr..yGArGAGATGAArTGC..y..TGGyGG.GGAGC...yGT.ACyTCr..yCAyCATGGrCG.GG.G |
| | consensus/90% | | y...GAG...GAr..yGArGAGATGAArTGC..y..TGGyGG.GGAGC...yGT.ACyTCr..yCAyCATGGrCG.GG.G |
| | consensus/80% | | y...GAG...GAr..yGArGAGATGAArTGC..y..TGGyGG.GGAGC...yGT.ACyTCr..yCAyCATGGrCG.GG.G |
| | consensus/70% | | y...GAG...GAr..yGArGAGATGAArTGC..y..TGGyGG.GGAGC...yGT.ACyTCr..yCAyCATGGrCG.GG.G |

| | | | |
|---|---|---|---|
| | | 641 | . . . . . 7 . . 720 |
| 1 | IE2-Vac0 | 100.0% | gatttggaggtgctgcgagtagttccttactaagttgtggacatcagtcatctggtggtgcatctactggacctagaaag |
| 2 | IE2 | 71.1% | gtttggtggcgcggcctcctcctctctgctgagctgcggccatcagagcagcggcggggcgagcaccggaccccgcaag |
| 3 | IE2-4nt | 72.6% | gatttggtggcgcggcctcctcctctctgctgagctgcggccatcagagcagcggcggtgcgagcaccggacctcgcaag |
| | consensus/100% | | G.TTTGG.GGyGC.GC...y..yTCyyTrCTrAGyTGyGG.CATCAG.....yGGyGG.GCr..yACyGGACCy.G.AAG |
| | consensus/90% | | G.TTTGG.GGyGC.GC...y..yTCyyTrCTrAGyTGyGG.CATCAG.....yGGyGG.GCr..yACyGGACCy.G.AAG |

Fig. 6B

| | | | | |
|---|---|---|---|---|
| consensus/80% | | | G.TTTGG.GGyGC.GC...y..yTCyyTrCTrAGyTGyGG.CATCAG.....yGGyGG.GCr..yACyGGACCy.G.AAG | |
| consensus/70% | | | G.TTTGG.GGyGC.GC...y..yTCyyTrCTrAGyTGyGG.CATCAG.....yGGyGG.GCr..yACyGGACCy.G.AAG | |
| | | 721 | . . . . . . . 8 800 | SEQ ID NO: |
| 1 | IE2-Vac0 | 100.0% | aagaagtcaaagagaatctccgaattggataatgagaaagtgagaaacatcatgaaggacaagaacacgccgttctgcac | 7 |
| 2 | IE2 | 71.1% | aagaagagcaaacgcatctccgagttggacaacgagaaggtgcgcaatatcatgaaagataagaacaccccccttctgcac | 8 |
| 3 | IE2-4nt | 72.6% | aagaagagcaaacgcatctccgagttggacaacgagaaggtgcgcaatatcatgaaagataagaacactccccttctgcac | 9 |
| | consensus/100% | | AAGAAG...AAr.G.ATCTCCGArTIGGAyAAyGAGAArGTG.G.AAyATCATGAArGAyAAGAACAC.CC.TTCTGCAC | 26 |
| | consensus/90% | | AAGAAG...AAr.G.ATCTCCGArTIGGAyAAyGAGAArGTG.G.AAyATCATGAArGAyAAGAACAC.CC.TTCTGCAC | 26 |
| | consensus/80% | | AAGAAG...AAr.G.ATCTCCGArTIGGAyAAyGAGAArGTG.G.AAyATCATGAArGAyAAGAACAC.CC.TTCTGCAC | 26 |
| | consensus/70% | | AAGAAG...AAr.G.ATCTCCGArTIGGAyAAyGAGAArGTG.G.AAyATCATGAArGAyAAGAACAC.CC.TTCTGCAC | 26 |
| | | 801 | . . . . . . . . 880 | |
| 1 | IE2-Vac0 | 100.0% | tccgaatgttcagacgagaagaggacgagtgaagatagatgaagtatcacgaatgttcagaaacacaaatcgttctctag | |
| 2 | IE2 | 71.1% | acccaacgtgcagactcggcggggtcgcgtcaagattgacgaggtgagccgcatgttccgcaacaccaatcgctctcttg | |
| 3 | IE2-4nt | 72.6% | acccaacgtgcagactcggcgtggtcgcgtcaagattgacgaggtgagccgcatgttccgcaacaccaatcgctctcttg | |
| | consensus/100% | | .CC.AAyGT.CAGAC..Gr.G.GG.CG.GT.AAGAT.GAyGArGTr...CG.AIGTTC.G.AACAC.AATCGyTCTCT.G | |
| | consensus/90% | | .CC.AAyGT.CAGAC..Gr.G.GG.CG.GT.AAGAT.GAyGArGTr...CG.AIGTTC.G.AACAC.AATCGyTCTCT.G | |
| | consensus/80% | | .CC.AAyGT.CAGAC..Gr.G.GG.CG.GT.AAGAT.GAyGArGTr...CG.AIGTTC.G.AACAC.AATCGyTCTCT.G | |
| | consensus/70% | | .CC.AAyGT.CAGAC..Gr.G.GG.CG.GT.AAGAT.GAyGArGTr...CG.AIGTTC.G.AACAC.AATCGyTCTCT.G | |
| | | 881 | . 9 . . . . . . 960 | |
| 1 | IE2-Vac0 | 100.0% | agtacaagaatcttccgttcaccatacttcgatgcaccaagtattagatgaggctatcaaggcatgtaagaccatgcaa | |
| 2 | IE2 | 71.1% | agtacaagaacctgcccttcacgattcccagtatgcaccaggtgttagatgaggccatcaaagcctgcaaaaccatgcag | |
| 3 | IE2-4nt | 72.6% | agtacaagaacctgcccttcacgattcccagtatgcaccaggtgttagatgaggccatcaaagcctgcaagaccatgcag | |
| | consensus/100% | | AGTACAAGAAyCT.CC.TTCAC.AT.CCy...ATGCACCArGTrTTAGAIGAGGCyATCAArGC.TGyAArACCATGCAr | |
| | consensus/90% | | AGTACAAGAAyCT.CC.TTCAC.AT.CCy...ATGCACCArGTrTTAGAIGAGGCyATCAArGC.TGyAArACCATGCAr | |
| | consensus/80% | | AGTACAAGAAyCT.CC.TTCAC.AT.CCy...ATGCACCArGTrTTAGAIGAGGCyATCAArGC.TGyAArACCATGCAr | |
| | consensus/70% | | AGTACAAGAAyCT.CC.TTCAC.AT.CCy...ATGCACCArGTrTTAGAIGAGGCyATCAArGC.TGyAArACCATGCAr | |

Fig. 6B (cont.)

```
                             961       .         .         .         0         .         .         .         . 1040
1 IE2-Vac0         100.0%   gttaacaacaaaggaatacagatcatctacactagaaaccatgaggttaagagtgaggtggatgccgtacgttgtagatt
2 IE2               71.1%   gtgaacaacaagggcatccagattatctacacccgcaatcatgaggtgaagagtgaggtggatgcggtgcggtgtcgcct
3 IE2-4nt           72.6%   gtgaacaacaagggcatccagattatctacacccgcaatcatgaggtgaagagtgaggtggatgcggtgcggtgtcgcct
  consensus/100%            GT.AACAACAArGG.AT.CAGATyATCTACACy.G.AAyCATGAGGT.AAGAGlGAGGlGGAlGC.GTrCG.lGT.G.yT
  consensus/90%             GT.AACAACAArGG.AT.CAGATyATCTACACy.G.AAyCATGAGGT.AAGAGlGAGGlGGAlGC.GTrCG.lGT.G.yT
  consensus/80%             GT.AACAACAArGG.AT.CAGATyATCTACACy.G.AAyCATGAGGT.AAGAGlGAGGlGGAlGC.GTrCG.lGT.G.yT
  consensus/70%             GT.AACAACAArGG.AT.CAGATyATCTACACy.G.AAyCATGAGGT.AAGAGlGAGGlGGAlGC.GTrCG.lGT.G.yT

                            1041       .         .         .         .         .         1         .         . 1120
1 IE2-Vac0         100.0%   gggaacgatgtgtaaccttgcgctatctactcctttcctaatggagcatactatgcctgtgactcatcctcctgaagtgg
2 IE2               71.1%   gggcaccatgtgcaacctggccctctccactcccttcctcatggagcacaccatgcccgtgacacatccacccgaagtgg
3 IE2-4nt           72.6%   gggcaccatgtgcaacctggccctctccactcccttcctcatggagcacaccatgcccgtgacacatccacccgaagtgg
  consensus/100%            GGG.AC.ATGlGyAACCT.GC.CT.TCyACTCCyTTCCT.ATGGAGCAyACyATGCCyGTGAC.CATCC.CCyGAAGlGG
  consensus/90%             GGG.AC.ATGlGyAACCT.GC.CT.TCyACTCCyTTCCT.ATGGAGCAyACyATGCCyGTGAC.CATCC.CCyGAAGlGG
  consensus/80%             GGG.AC.ATGlGyAACCT.GC.CT.TCyACTCCyTTCCT.ATGGAGCAyACyATGCCyGTGAC.CATCC.CCyGAAGlGG
  consensus/70%             GGG.AC.ATGlGyAACCT.GC.CT.TCyACTCCyTTCCT.ATGGAGCAyACyATGCCyGTGAC.CATCC.CCyGAAGlGG

                            1121       .         .         .         .         .         .         .         2 1200
1 IE2-Vac0         100.0%   ctcaaagaacagctgatgcttgtaacgaaggtgtgaaagctgcttggtccctaaaggagttacatacacaccaactttgt
2 IE2               71.1%   cgcagcgcacagccgatgcttgtaacgaaggcgtcaaggccgcgtggagcctcaaagaattgcacacccaccaattatgc
3 IE2-4nt           72.6%   cgcagcgcacagccgatgcttgtaacgaaggcgtcaaggccgcgtggagcctcaaagaattgcacacccaccaattatgt
  consensus/100%            C.CAr.G.ACAGCyGATGCTlGTAACGAAGGyGT.AArGCyGC.lGG..CCT.AArGArTTrCAyAC.CACCAAyT.lGy
  consensus/90%             C.CAr.G.ACAGCyGATGCTlGTAACGAAGGyGT.AArGCyGC.lGG..CCT.AArGArTTrCAyAC.CACCAAyT.lGy
  consensus/80%             C.CAr.G.ACAGCyGATGCTlGTAACGAAGGyGT.AArGCyGC.lGG..CCT.AArGArTTrCAyAC.CACCAAyT.lGy
  consensus/70%             C.CAr.G.ACAGCyGATGCTlGTAACGAAGGyGT.AArGCyGC.lGG..CCT.AArGArTTrCAyAC.CACCAAyT.lGy
```

Fig. 6B (cont.)

```
                         1201      .        .        .        .        .        .        .        .  1280
1 IE2-Vac0        100.0%  ccacgatccagtgactacagaaacatgatcattcatgcagctacgcctgtagatctacttggagctcttaacctatgtct
2 IE2              71.1%  ccccgttcctccgattaccgcaacatgatcatccacgctgccaccccgtggacctgttgggcgctctcaacctgtgcct
3 IE2-4nt          72.6%  cctcgttcctccgattaccgcaacatgatcatccacgctgccacaccagtggacctgttgggcgctctcaacctgtgcct
  consensus/100%          CC.CG.TCC..yGAyTAC.G.AACAlGATCATyCAyGC.GCyAC.CC.GTrGAyCTryT.GG.GCTCTyAACCTrTGyCT
  consensus/90%           CC.CG.TCC..yGAyTAC.G.AACAlGATCATyCAyGC.GCyAC.CC.GTrGAyCTryT.GG.GCTCTyAACCTrTGyCT
  consensus/80%           CC.CG.TCC..yGAyTAC.G.AACAlGATCATyCAyGC.GCyAC.CC.GTrGAyCTryT.GG.GCTCTyAACCTrTGyCT
  consensus/70%           CC.CG.TCC..yGAyTAC.G.AACAlGATCATyCAyGC.GCyAC.CC.GTrGAyCTryT.GG.GCTCTyAACCTrTGyCT

                         1281      .        3        .        .        .        .        .        .  1360
1 IE2-Vac0        100.0%  tcctttgatgcagaagttccctaagcaagtgatggtgagaatcttctcgacgaatcaaggaggattcatgttaccgatat
2 IE2              71.1%  gcccctgatgcaaaagtttcccaaacaggtcatggtgcgcatcttctccaccaaccagggtgggttcatgctgcctatct
3 IE2-4nt          72.6%  gccactgatgcagaagtttcccaaacaggtcatggtgcgcatcttctccaccaaccagggtgggttcatgctgcctatct
  consensus/100%          .CC.ylGATGCArAAGTTyCCyAArCArGT.ATGGTG.G.ATCTTCTC.AC.AAyCArGG.GGrTTCAlGyTrCC.AT.T
  consensus/90%           .CC.ylGATGCArAAGTTyCCyAArCArGT.ATGGTG.G.ATCTTCTC.AC.AAyCArGG.GGrTTCAlGyTrCC.AT.T
  consensus/80%           .CC.ylGATGCArAAGTTyCCyAArCArGT.ATGGTG.G.ATCTTCTC.AC.AAyCArGG.GGrTTCAlGyTrCC.AT.T
  consensus/70%           .CC.ylGATGCArAAGTTyCCyAArCArGT.ATGGTG.G.ATCTTCTC.AC.AAyCArGG.GGrTTCAlGyTrCC.AT.T

                         1361      .        .        .        4        .        .        .        .  1440
1 IE2-Vac0        100.0%  acgagacagctgcaaaggcttacgctgtcggtcagttcgagcaaccgactgaaacgcctcctgaggacttagatacattg
2 IE2              71.1%  acgagacggccgcgaaggcctacgccgtggggcagtttgagcagcccaccgagacccctcccgaagacctggacaccctg
3 IE2-4nt          72.6%  acgagacggccgcgaaggcctacgccgttggtcagtttgagcagcccaccgagacacctcccgaagacctggacaccctg
  consensus/100%          ACGAGACrGCyGCrAAGGCylACGCyGT.GG.CAGTTyGAGCArCC.ACyGArAC.CCTCCyGArGACyTrGAyAC.yTG
  consensus/90%           ACGAGACrGCyGCrAAGGCylACGCyGT.GG.CAGTTyGAGCArCC.ACyGArAC.CCTCCyGArGACyTrGAyAC.yTG
  consensus/80%           ACGAGACrGCyGCrAAGGCylACGCyGT.GG.CAGTTyGAGCArCC.ACyGArAC.CCTCCyGArGACyTrGAyAC.yTG
  consensus/70%           ACGAGACrGCyGCrAAGGCylACGCyGT.GG.CAGTTyGAGCArCC.ACyGArAC.CCTCCyGArGACyTrGAyAC.yTG
```

Fig. 6C

| | | | 1441 . . . . . 5 ] 1504 | SEQ ID NO: |
|---|---|---|---|---|
| 1 | IE2-Vac0 | 100.0% | tctttggcgatagaagcagcgattcaggatcttagaaacaagagtcagtaa-------------- | 7 |
| 2 | IE2 | 71.1% | agcctggccatcgaggcagccatccaggacctgaggaacaagtctcagtaacaagtctcagtaa | 8 |
| 3 | IE2-4nt | 72.6% | agcctggccatcgaggcagccatccaggacctgaggaacaagtctcagtaa-------------- | 9 |
| | consensus/100% | | ..yyTGGC.AT.GArGCAGC.ATyCAGGAyCT.AGrAACAAG..TCAGtAA.............. | 26 |
| | consensus/90% | | ..yyTGGC.AT.GArGCAGC.ATyCAGGAyCT.AGrAACAAG..TCAGtAA.............. | 26 |
| | consensus/80% | | ..yyTGGC.AT.GArGCAGC.ATyCAGGAyCT.AGrAACAAG..TCAGtAA.............. | 26 |
| | consensus/70% | | ..yyTGGC.AT.GArGCAGC.ATyCAGGAyCT.AGrAACAAG..TCAGtAA.............. | 26 |

Fig. 6D

| | | cov | pid | 1 [ - - - - - - - - 80 | SEQ ID NO: |
|---|---|---|---|---|---|
| 1 | IE1Vac0 | 100.0% | 100.0% | atggtgaagcaaatcaaggtcagagtggacatggtaagacacagaattaaggaacacatgttgaagaagtatactcaaac | 27 |
| 2 | IE1 | 97.5% | 76.8% | ------------------------------atggtgcggcatagaatcaaggagcacatgctgaaaaaatatacccagac | 28 |
| 3 | IE14nt | 100.0% | 77.8% | atggtcaaacagattaaggttcgagtggacatggtgctgcatagaatcaaggagcacatgctgaagaagtatacccagac | 29 |
| | consensus/100% | | | ..............................ATGGTusGuCAsAGAATsAAGGAuCACATGsTGAAuAAuTATACsCAuAC | 30 |
| | consensus/90% | | | ..............................ATGGTusGuCAsAGAATsAAGGAuCACATGsTGAAuAAuTATACsCAuAC | 30 |
| | consensus/80% | | | ..............................ATGGTusGuCAsAGAATsAAGGAuCACATGsTGAAuAAuTATACsCAuAC | 30 |
| | consensus/70% | | | ..............................ATGGTusGuCAsAGAATsAAGGAuCACATGsTGAAuAAuTATACsCAuAC | 30 |

| | | cov | pid | 81 - 1 - - - - - - 160 |
|---|---|---|---|---|
| 1 | IE1Vac0 | 100.0% | 100.0% | agaggagaagttcaccggtgccttcaatatgatgggtggatgtctacagaacgctttggatatcttagataaggtacatg |
| 2 | IE1 | 97.5% | 76.8% | ggaagagaaattcactggcgcctttaatatgatgggaggatgtttgcagaatgccttagatatcttagataaggttcatg |
| 3 | IE14nt | 100.0% | 77.8% | ggaagagaaattcactggcgcctttaatatgatgggaggatgtttgcagaatgccttagatatcttagataaggttcatg |
| | consensus/100% | | | uGAuGAGAAuTTCACsGGsGCCTTsAATATGATGGGsGGATGTsTuCAGAAsGCsTTuGATATCTTAGATAAGGTsCATG |
| | consensus/90% | | | uGAuGAGAAuTTCACsGGsGCCTTsAATATGATGGGsGGATGTsTuCAGAAsGCsTTuGATATCTTAGATAAGGTsCATG |
| | consensus/80% | | | uGAuGAGAAuTTCACsGGsGCCTTsAATATGATGGGsGGATGTsTuCAGAAsGCsTTuGATATCTTAGATAAGGTsCATG |
| | consensus/70% | | | uGAuGAGAAuTTCACsGGsGCCTTsAATATGATGGGsGGATGTsTuCAGAAsGCsTTuGATATCTTAGATAAGGTsCATG |

| | | cov | pid | 161 - - - 2 - - - - 240 |
|---|---|---|---|---|
| 1 | IE1Vac0 | 100.0% | 100.0% | aaccattcgaagaaatgaagtgcattggattgacaatgcaatcaatgtatgagaactacatagtgccagaggataagcgt |
| 2 | IE1 | 97.5% | 76.8% | agcctttcgaggagatgaagtgtattgggctaactatgcagagcatgtatgagaactacattgtacctgaggataagcgg |
| 3 | IE14nt | 100.0% | 77.8% | agcctttcgaggagatgaagtgtattgggctaactatgcagagcatgtatgagaactacattgtacctgaggataagcgg |
| | consensus/100% | | | AuCCsTTCGAuGAuATGAAGTGsATTGGusTuACsATGCAusssATGTATGAGAACTACATsGTuCCsGAGGATAAGCGs |
| | consensus/90% | | | AuCCsTTCGAuGAuATGAAGTGsATTGGusTuACsATGCAusssATGTATGAGAACTACATsGTuCCsGAGGATAAGCGs |
| | consensus/80% | | | AuCCsTTCGAuGAuATGAAGTGsATTGGusTuACsATGCAusssATGTATGAGAACTACATsGTuCCsGAGGATAAGCGs |
| | consensus/70% | | | AuCCsTTCGAuGAuATGAAGTGsATTGGusTuACsATGCAusssATGTATGAGAACTACATsGTuCCsGAGGATAAGCGs |

Fig. 6D (cont.)

| | | cov | pid | 241 . . . . . 3 . . 320 |
|---|---|---|---|---|
| 1 | IE1Vac0 | 100.0% | 100.0% | gaaatgtggatggcatgcatcaaggagttacatgatgtatccaaaggagcagccaacaagctaggtggtgctttgcaagc |
| 2 | IE1 | 97.5% | 76.8% | gagatgtggatggcttgtattaaggagctgcatgatgtgagcaagggcgccgctaacaagttgggggtgcactgcaggc |
| 3 | IE14nt | 100.0% | 77.8% | gagatgtggatggcttgtattaaggagctgcatgatgtgagcaagggcgccgctaacaagttaggaggtgcactgcaggc |
| | consensus/100% | | | GAuATGTGGATGGCsTGsATsAAGGAGsTuCATGATGTussCAAuGGsGCsGCsAACAAGsTuGGsGGTGCssTGCAuGC |
| | consensus/90% | | | GAuATGTGGATGGCsTGsATsAAGGAGsTuCATGATGTussCAAuGGsGCsGCsAACAAGsTuGGsGGTGCssTGCAuGC |
| | consensus/80% | | | GAuATGTGGATGGCsTGsATsAAGGAGsTuCATGATGTussCAAuGGsGCsGCsAACAAGsTuGGsGGTGCssTGCAuGC |
| | consensus/70% | | | GAuATGTGGATGGCsTGsATsAAGGAGsTuCATGATGTussCAAuGGsGCsGCsAACAAGsTuGGsGGTGCssTGCAuGC |

| | | cov | pid | 331 . . . . . . . 4 400 |
|---|---|---|---|---|
| 1 | IE1Vac0 | 100.0% | 100.0% | gaaggcaagagcgaagaaggatgaattgagacgaaagatgatgtacatgtgctatcgaaacatcgaattcttcactaaga |
| 2 | IE1 | 97.5% | 76.8% | taaggcccgtgctaaaaaggatgaacttaggagaaagatgatgtatatgtgctacaggaatatagagttctttaccaaga |
| 3 | IE14nt | 100.0% | 77.8% | taaggcccgtgctaagaaggatgaacttaggagaaagatgatgtatatgtgctacaggaatatagagttctttaccaaga |
| | consensus/100% | | | sAAGGCssGsGCsAAuAAGGATGAAsTsAGusGAAAGATGATGTAsATGTGCTAssGuAAsATsGAuTTCTTsACsAAGA |
| | consensus/90% | | | sAAGGCssGsGCsAAuAAGGATGAAsTsAGusGAAAGATGATGTAsATGTGCTAssGuAAsATsGAuTTCTTsACsAAGA |
| | consensus/80% | | | sAAGGCssGsGCsAAuAAGGATGAAsTsAGusGAAAGATGATGTAsATGTGCTAssGuAAsATsGAuTTCTTsACsAAGA |
| | consensus/70% | | | sAAGGCssGsGCsAAuAAGGATGAAsTsAGusGAAAGATGATGTAsATGTGCTAssGuAAsATsGAuTTCTTsACsAAGA |

| | | cov | pid | 401 . . . . . . . . 480 |
|---|---|---|---|---|
| 1 | IE1Vac0 | 100.0% | 100.0% | actcagcgtttcctaagactaccaatggatgcagtcaagctatggctgcgcttcagaacttgcctcaatgtagtcctgat |
| 2 | IE1 | 97.5% | 76.8% | actcagccttccctaagaccaccaatggctgcagtcaggccatggcggcactgcagaacttgcctcagtgctcccctgat |
| 3 | IE14nt | 100.0% | 77.8% | actcagccttccctaagaccaccaatggctgcagtcaggccatggcggcactgcagaacttgcctcagtgctctcctgat |
| | consensus/100% | | | ACTCAGCsTTsCCTAAGACsACCAATGGsTGCAGTCAuGCsATGGCsGCuCTsCAGAACTTGCCTCAuTGssssCCTGAT |
| | consensus/90% | | | ACTCAGCsTTsCCTAAGACsACCAATGGsTGCAGTCAuGCsATGGCsGCuCTsCAGAACTTGCCTCAuTGssssCCTGAT |
| | consensus/80% | | | ACTCAGCsTTsCCTAAGACsACCAATGGsTGCAGTCAuGCsATGGCsGCuCTsCAGAACTTGCCTCAuTGssssCCTGAT |
| | consensus/70% | | | ACTCAGCsTTsCCTAAGACsACCAATGGsTGCAGTCAuGCsATGGCsGCuCTsCAGAACTTGCCTCAuTGssssCCTGAT |

Fig. 6D (cont.)

| | | cov | pid | 481 . 5 . . . . . . 560 |
|---|---|---|---|---|
| 1 | IE1Vac0 | 100.0% | 100.0% | gaaatcatggcatatgcacagaagatcttcaagatcttagatgaggaaagagacaaggtattgactcatatcgatcacat |
| 2 | IE1 | 97.5% | 76.8% | gagattatggcttatgcccagaaaatatttaagattttggatgaggagagagacaaggtgctcacgcacattgatcacat |
| 3 | IE14nt | 100.0% | 77.8% | gagattatggcttatgcccagaagatatttaagatcttggatgaggagagagacaaggtgctcacgcacattgatcacat |
| | consensus/100% | | | GAuATsATGGCsTATGCsCAGAAuATsTTsAAGATsTTuGATGAGGAuAGAGACAAGGTusTsACsCAsATsGATCACAT |
| | consensus/90% | | | GAuATsATGGCsTATGCsCAGAAuATsTTsAAGATsTTuGATGAGGAuAGAGACAAGGTusTsACsCAsATsGATCACAT |
| | consensus/80% | | | GAuATsATGGCsTATGCsCAGAAuATsTTsAAGATsTTuGATGAGGAuAGAGACAAGGTusTsACsCAsATsGATCACAT |
| | consensus/70% | | | GAuATsATGGCsTATGCsCAGAAuATsTTsAAGATsTTuGATGAGGAuAGAGACAAGGTusTsACsCAsATsGATCACAT |

| | | cov | pid | 561 . . . 6 . . . . 640 |
|---|---|---|---|---|
| 1 | IE1Vac0 | 100.0% | 100.0% | attcatggatatactaacaacatgtgtagaaacgatgtgtaacgagtacaaggtaacttcggacgcttgtatgatgacta |
| 2 | IE1 | 97.5% | 76.8% | atttatggatatcctcactacatgtgtggaaacaatgtgtaatgagtacaaggtcactagtgacgcttgtatgatgacca |
| 3 | IE14nt | 100.0% | 77.8% | atttatggatatcctcactacatgtgtggaaacaatgtgtaatgagtacaaggtcactagtgacgcttgtatgatgacca |
| | consensus/100% | | | ATTsATGGATATsCTsACsACATGTGTuGAAACuATGTGTAAsGAGTACAAGGTsACTsssGACGCTTGTATGATGACsA |
| | consensus/90% | | | ATTsATGGATATsCTsACsACATGTGTuGAAACuATGTGTAAsGAGTACAAGGTsACTsssGACGCTTGTATGATGACsA |
| | consensus/80% | | | ATTsATGGATATsCTsACsACATGTGTuGAAACuATGTGTAAsGAGTACAAGGTsACTsssGACGCTTGTATGATGACsA |
| | consensus/70% | | | ATTsATGGATATsCTsACsACATGTGTuGAAACuATGTGTAAsGAGTACAAGGTsACTsssGACGCTTGTATGATGACsA |

| | | cov | pid | 641 . . . . . 7 . . 720 |
|---|---|---|---|---|
| 1 | IE1Vac0 | 100.0% | 100.0% | tgtacggaggaatatctctacttagtgagttctgtcgagttctatgctgttacgtattagaagaaactagtgtaatgtta |
| 2 | IE1 | 97.5% | 76.8% | tgtacgggggcatctctctcttaagtgagttctgtcgggtgctgtgctgctatgtcttagaggagactagtgtgatgctg |
| 3 | IE14nt | 100.0% | 77.8% | tgtacggaggcatctctctcttaagtgagttctgtcgggtgctgtgctgctatgtcttagaggagactagtgtgatgctg |
| | consensus/100% | | | TGTACGGuGGsATsTCTCTssTsAGTGAGTTCTGTCGuGTsCTuTGCTGsTAsGTsTTAGAuGAuACTAGTGTuATGsTu |
| | consensus/90% | | | TGTACGGuGGsATsTCTCTssTsAGTGAGTTCTGTCGuGTsCTuTGCTGsTAsGTsTTAGAuGAuACTAGTGTuATGsTu |
| | consensus/80% | | | TGTACGGuGGsATsTCTCTssTsAGTGAGTTCTGTCGuGTsCTuTGCTGsTAsGTsTTAGAuGAuACTAGTGTuATGsTu |
| | consensus/70% | | | TGTACGGuGGsATsTCTCTssTsAGTGAGTTCTGTCGuGTsCTuTGCTGsTAsGTsTTAGAuGAuACTAGTGTuATGsTu |

Fig. 6E

| | | cov | pid | 721 . . . . . . . 8 800 | SEQ ID NO: |
|---|---|---|---|---|---|
| 1 | IE1Vac0 | 100.0% | 100.0% | gcgaagagaccattgatcactaagcctgaagtgatctcggttatgaagagacgaatagaggagatctgtatgaaggtgtt | 27 |
| 2 | IE1 | 97.5% | 76.8% | gccaagcggcctctgataaccaagcctgaggttatcagtgtaatgaagcgccgcattgaggagatctgcatgaaggtctt | 28 |
| 3 | IE14nt | 100.0% | 77.8% | gccaagcggcctctgataaccaagcctgaggttatcagtgtaatgaagcgccgcattgaggagatctgcatgaaggtctt | 29 |
| | consensus/100% | | | GCsAAGsGuCCssTGATsACsAAGCCTGAuGTsATCsssGTsATGAAGsGsCGsATsGAGGAGATCTGsATGAAGGTsTT | 30 |
| | consensus/90% | | | GCsAAGsGuCCssTGATsACsAAGCCTGAuGTsATCsssGTsATGAAGsGsCGsATsGAGGAGATCTGsATGAAGGTsTT | 30 |
| | consensus/80% | | | GCsAAGsGuCCssTGATsACsAAGCCTGAuGTsATCsssGTsATGAAGsGsCGsATsGAGGAGATCTGsATGAAGGTsTT | 30 |
| | consensus/70% | | | GCsAAGsGuCCssTGATsACsAAGCCTGAuGTsATCsssGTsATGAAGsGsCGsATsGAGGAGATCTGsATGAAGGTsTT | 30 |

| | | cov | pid | 801 . . . . . . . . 880 |
|---|---|---|---|---|
| 1 | IE1Vac0 | 100.0% | 100.0% | cgcacaatacatcttaggagctgatcctctaagagtgtgtagtccatcggtagacgatttgagagctatagcggaggaat |
| 2 | IE1 | 97.5% | 76.8% | tgcccagtacattctgggggccgatcctctgagagtctgctctcctagtgtggatgacctacgggccatcgccgaggagt |
| 3 | IE14nt | 100.0% | 77.8% | tgcccagtacattctaggtgccgatcctctgagagtctgctctcctagtgtggatgacctacgggccatcgccgaggagt |
| | consensus/100% | | | sGCsCAuTACATssTuGGsGCsGATCCTCTuAGAGTsTGsssTCCssssGTuGAsGAssTusGuGCsATsGCsGAGGAuT |
| | consensus/90% | | | sGCsCAuTACATssTuGGsGCsGATCCTCTuAGAGTsTGsssTCCssssGTuGAsGAssTusGuGCsATsGCsGAGGAuT |
| | consensus/80% | | | sGCsCAuTACATssTuGGsGCsGATCCTCTuAGAGTsTGsssTCCssssGTuGAsGAssTusGuGCsATsGCsGAGGAuT |
| | consensus/70% | | | sGCsCAuTACATssTuGGsGCsGATCCTCTuAGAGTsTGsssTCCssssGTuGAsGAssTusGuGCsATsGCsGAGGAuT |

| | | cov | pid | 881 . 9 . . . . . . 960 |
|---|---|---|---|---|
| 1 | IE1Vac0 | 100.0% | 100.0% | ctgacgaggaagaggcaatagttgcatacacacttgctacagctggagtatccagttctgattctcttgtaagtcctccg |
| 2 | IE1 | 97.5% | 76.8% | cagatgaggaagaggctattgtagcctacactttggccaccgctggtgtcagctcctctgattctctggtgtcacccca |
| 3 | IE14nt | 100.0% | 77.8% | cagatgaggaagaggctattgtagcctacactttggccaccgctggtgtcagctcctctgattctctggtgtcacctcca |
| | consensus/100% | | | CsGAsGAGGAAGAGGCsATsGTsGCsTACACssTsGCsACsGCTGGsGTsssCsssTCTGATTCTCTsGTusssCCsCCu |
| | consensus/90% | | | CsGAsGAGGAAGAGGCsATsGTsGCsTACACssTsGCsACsGCTGGsGTsssCsssTCTGATTCTCTsGTusssCCsCCu |
| | consensus/80% | | | CsGAsGAGGAAGAGGCsATsGTsGCsTACACssTsGCsACsGCTGGsGTsssCsssTCTGATTCTCTsGTusssCCsCCu |
| | consensus/70% | | | CsGAsGAGGAAGAGGCsATsGTsGCsTACACssTsGCsACsGCTGGsGTsssCsssTCTGATTCTCTsGTusssCCsCCu |

Fig. 6E (cont.)

| | | cov | pid | 961 . . . 0 . . . . 1040 |
|---|---|---|---|---|
| 1 | IE1Vac0 | 100.0% | 100.0% | gagtcacctgtgccagcaaccataccgttgagtagtgtgattgtggctgagaactcggatcaggaagagtctgagcaatc |
| 2 | IE1 | 97.5% | 76.8% | gagtcccctgtacccgcgactatccctctgtcctcagtaattgtggctgagaacagtgatcaggaagaaagtgagcagag |
| 3 | IE14nt | 100.0% | 77.8% | gagtcacctgtacccgcgactatccctctgtcctcagtaattgtggctgagaacagtgatcaggaagaaagtgagcagag |
| | consensus/100% | | | GAGTCsCCTGTuCCsGCuACsATsCCssTGssssssGTuATTGTGGCTGAGAACsssGATCAGGAAGAussTGAGCAuss |
| | consensus/90% | | | GAGTCsCCTGTuCCsGCuACsATsCCssTGssssssGTuATTGTGGCTGAGAACsssGATCAGGAAGAussTGAGCAuss |
| | consensus/80% | | | GAGTCsCCTGTuCCsGCuACsATsCCssTGssssssGTuATTGTGGCTGAGAACsssGATCAGGAAGAussTGAGCAuss |
| | consensus/70% | | | GAGTCsCCTGTuCCsGCuACsATsCCssTGssssssGTuATTGTGGCTGAGAACsssGATCAGGAAGAussTGAGCAuss |

| | | cov | pid | 1041 . . . . . 1 . . 1120 |
|---|---|---|---|---|
| 1 | IE1Vac0 | 100.0% | 100.0% | cgatgaagaagaggaggaaggagcacaagaggagagagaagatactgtctctgtgaagagtgaacctgtatctgaaatcg |
| 2 | IE1 | 97.5% | 76.8% | tgatgaggaagaggaggagggtgctcaggaggagcgggaggacactgtgtctgtcaagtctgagccagtgtctgagatag |
| 3 | IE14nt | 100.0% | 77.8% | tgatgaggaagaggaggagggtgctcaggaggagcgggaggacactgtgtctgtcaagtctgagccagtgtctgagatag |
| | consensus/100% | | | sGATGAuGAAGAGGAGGAuGGsGCsCAuGAGGAGsGuGAuGAsACTGTsTCTGTsAAGssTGAuCCsGTuTCTGAuATsG |
| | consensus/90% | | | sGATGAuGAAGAGGAGGAuGGsGCsCAuGAGGAGsGuGAuGAsACTGTsTCTGTsAAGssTGAuCCsGTuTCTGAuATsG |
| | consensus/80% | | | sGATGAuGAAGAGGAGGAuGGsGCsCAuGAGGAGsGuGAuGAsACTGTsTCTGTsAAGssTGAuCCsGTuTCTGAuATsG |
| | consensus/70% | | | sGATGAuGAAGAGGAGGAuGGsGCsCAuGAGGAGsGuGAuGAsACTGTsTCTGTsAAGssTGAuCCsGTuTCTGAuATsG |

| | | cov | pid | 1121 . . . . . . . 2 1200 |
|---|---|---|---|---|
| 1 | IE1Vac0 | 100.0% | 100.0% | aggaagtagcacctgaggaagaggaggatggagccgaagaaccaacagcttcgggtggtaagtcaactcatccgatggta |
| 2 | IE1 | 97.5% | 76.8% | aggaagttgccccagaggaagaggaggatggtgctgaggaacccaccgcctctggaggcaagagcacccaccctatggtg |
| 3 | IE14nt | 100.0% | 77.8% | aggaagttgctccagaggaagaggaggatggtgctgaggaacccaccgcctctggaggcaagagcacccaccctatggtg |
| | consensus/100% | | | AGGAAGTsGCsCCsGAGGAAGAGGAGGATGGsGCsGAuGAACCsACsGCsTCsGGsGGsAAGsssACsCAsCCsATGGTu |
| | consensus/90% | | | AGGAAGTsGCsCCsGAGGAAGAGGAGGATGGsGCsGAuGAACCsACsGCsTCsGGsGGsAAGsssACsCAsCCsATGGTu |
| | consensus/80% | | | AGGAAGTsGCsCCsGAGGAAGAGGAGGATGGsGCsGAuGAACCsACsGCsTCsGGsGGsAAGsssACsCAsCCsATGGTu |
| | consensus/70% | | | AGGAAGTsGCsCCsGAGGAAGAGGAGGATGGsGCsGAuGAACCsACsGCsTCsGGsGGsAAGsssACsCAsCCsATGGTu |

Fig. 6E (cont.)

| | | cov | pid | 1201 - - ] 1224 |
|---|---|---|---|---|
| 1 | IE1Vac0 | 100.0% | 100.0% | accagatctaaggcagaccagtaa |
| 2 | IE1 | 97.5% | 76.8% | actagaagcaaggctgaccagtaa |
| 3 | IE14nt | 100.0% | 77.8% | actagaagcaaggctgaccagtaa |
| | consensus/100% | | | ACsAGAsssAAGGCsGACCAGTAA |
| | consensus/90% | | | ACsAGAsssAAGGCsGACCAGTAA |
| | consensus/80% | | | ACsAGAsssAAGGCsGACCAGTAA |
| | consensus/70% | | | ACsAGAsssAAGGCsGACCAGTAA |

SEQUENCE LISTING

<160> NUMBER OF SEQ ID NOS: 29

<210> SEQ ID NO 1
<211> LENGTH: 2709
<212> TYPE: DNA
<213> ORGANISM: Artificial Sequence
<220> FEATURE:
<223> OTHER INFORMATION: Description of Artificial Sequence: Synthetic
polynucleotide IEfusion-VacO DNA sequence -continued

<400> SEQUENCE: 1

```
atggtgaagc aaatcaaggt cagagtggac atggtaagac acagaattaa ggaacacatg     60
ttgaagaagt atactcaaac agaggagaag ttcaccggtg ccttcaatat gatgggtgga    120
tgtctacaga acgctttgga tatcttagat aaggtacatg aaccattcga agaaatgaag    180
tgcattggat tgacaatgca atcaatgtat gagaactaca tagtgccaga ggataagcgt    240
gaaatgtgga tggcatgcat caaggagtta catgatgtat ccaaaggagc agccaacaag    300
ctaggtggtg ctttgcaagc gaaggcaaga gcgaagaagg atgaattgag acgaaagatg    360
atgtacatgt gctatcgaaa catcgaattc ttcactaaga actcagcgtt tcctaagact    420
accaatggat gcagtcaagc tatggctgcg cttcagaact tgcctcaatg tagtcctgat    480
gaaatcatgg catatgcaca gaagatcttc aagatcttag atgaggaaag agacaaggta    540
ttgactcata tcgatcacat attcatggat atactaacaa catgtgtaga aacgatgtgt    600
aacgagtaca aggtaacttc ggacgcttgt atgatgacta tgtacggagg aatatctcta    660
cttagtgagt tctgtcgagt tctatgctgt tacgtattag aagaaactag tgtaatgtta    720
gcgaagagac cattgatcac taagcctgaa gtgatctcgg ttatgaagag acgaatagag    780
gagatctgta tgaaggtgtt cgcacaatac atcttaggag ctgatcctct aagagtgtgt    840
agtccatcgg tagacgattt gagagctata gcggaggaat ctgacgagga agaggcaata    900
gttgcataca cacttgctac agctggagta tccagttctg attctcttgt aagtcctccg    960
gagtcacctg tgccagcaac cataccgttg agtagtgtga ttgtggctga gaactcggat   1020
caggaagagt ctgagcaatc cgatgaagaa gaggaggaag gagcacaaga ggagagagaa   1080
gatactgtct ctgtgaagag tgaacctgta tctgaaatcg aggaagtagc acctgaggaa   1140
gaggaggatg gagccgaaga accaacagct tcgggtggta agtcaactca tccgatggta   1200
accagatcta aggcagacca gggagacatc ctagcacaag cagtgaacca tgctggaatt   1260
gactcatctt cgaccggacc aactctaacg actcattcat gttcggttag ttctgctcct   1320
cttaacaagc ctacacctac ctcggtagct gttaccaaca cacctttacc aggagcatca   1380
gcaacacctg agttgtctcc aagaaagaag cctcgtaaga ccacgagacc gttcaaggtg   1440
atcatcaagc caccagtacc acctgctccg atcatgttgc cattgatcaa gcaggaggac   1500
attaagccag aacctgactt cacgatacag taccgtaaca agatcataga tacagcagga   1560
tgcatagtga tctcagatag tgaagaggag caaggtgagg aagtggagac tagaggagcc   1620
acagccagtt cgccttccac aggatccgga actcctagag taactagtcc gacacatcca   1680
ctttcccaga tgaatcatcc acctctaccg gatcctctag gacgaccaga tgaagattct   1740
tcttcatcta gttcaagttc ttgctcatcc gcgagtgata gtgagtcaga aagtgaagag   1800
atgaagtgct cttctggtgg tggagctagt gtcacttcat ctcatcatgg acgaggagga   1860
tttggaggtg ctgcgagtag ttccttacta agttgtggac atcagtcatc tggtggtgca   1920
tctactggac ctagaaagaa gaagtcaaag agaatctccg aattggataa tgagaaagtg   1980
agaaacatca tgaaggacaa gaacacgccg ttctgcactc cgaatgttca gacgagaaga   2040
ggacgagtga agatagatga agtatcacga atgttcagaa acacaaatcg ttctctagag   2100
tacaagaatc ttccgttcac cataccttcg atgcaccaag tattagatga ggctatcaag   2160
gcatgtaaga ccatgcaagt taacaacaaa ggaatacaga tcatctacac tagaaaccat   2220
gaggttaaga gtgaggtgga tgccgtacgt tgtagattgg gaacgatgtg taaccttgcg   2280
ctatctactc ctttcctaat ggagcatact atgcctgtga ctcatcctcc tgaagtggct   2340
```

```
caaagaacag ctgatgcttg taacgaaggt gtgaaagctg cttggtccct aaaggagtta   2400

catacacacc aactttgtcc acgatccagt gactacagaa acatgatcat tcatgcagct   2460

acgcctgtag atctacttgg agctcttaac ctatgtcttc ctttgatgca gaagttccct   2520

aagcaagtga tggtgagaat cttctcgacg aatcaaggag gattcatgtt accgatatac   2580

gagacagctg caaaggctta cgctgtcggt cagttcgagc aaccgactga aacgcctcct   2640

gaggacttag atacattgtc tttggcgata gaagcagcga ttcaggatct tagaaacaag   2700

agtcagtaa                                                          2709


<210> SEQ ID NO 2
<211> LENGTH: 2709
<212> TYPE: DNA
<213> ORGANISM: Artificial Sequence
<220> FEATURE:
<223> OTHER INFORMATION: Description of Artificial Sequence: Synthetic
      polynucleotide IEfusion DNA sequence

<400> SEQUENCE: 2

atggtcaaac agattaaggt tcgagtggac atggtgcggc atagaatcaa ggagcacatg     60

ctgaaaaaat atacccagac ggaagagaaa ttcactggcg cctttaatat gatgggagga    120

tgtttgcaga atgccttaga tatcttagat aaggttcatg agcctttcga ggagatgaag    180

tgtattgggc taactatgca gagcatgtat gagaactaca ttgtacctga ggataagcgg    240

gagatgtgga tggcttgtat taaggagctg catgatgtga gcaagggcgc cgctaacaag    300

ttggggggtg cactgcaggc taaggcccgt gctaaaaagg atgaacttag gagaaagatg    360

atgtatatgt gctacaggaa tatagagttc tttaccaaga actcagcctt ccctaagacc    420

accaatggct gcagtcaggc catggcggca ctgcagaact tgcctcagtg ctcccctgat    480

gagattatgg cttatgccca gaaaatattt aagattttgg atgaggagag agacaaggtg    540

ctcacgcaca ttgatcacat atttatggat atcctcacta catgtgtgga aacaatgtgt    600

aatgagtaca aggtcactag tgacgcttgt atgatgacca tgtacggggg catctctctc    660

ttaagtgagt tctgtcgggt gctgtgctgc tatgtcttag aggagactag tgtgatgctg    720

gccaagcggc ctctgataac caagcctgag gttatcagtg taatgaagcg ccgcattgag    780

gagatctgca tgaaggtctt tgcccagtac attctggggg ccgatcctct gagagtctgc    840

tctcctagtg tggatgacct acgggccatc gccgaggagt cagatgagga agaggctatt    900

gtagcctaca ctttggccac cgctggtgtc agctcctctg attctctggt gtcaccccca    960

gagtcccctg tacccgcgac tatccctctg tcctcagtaa ttgtggctga gaacagtgat   1020

caggaagaaa gtgagcagag tgatgaggaa gaggaggagg gtgctcagga ggagcgggag   1080

gacactgtgt ctgtcaagtc tgagccagtg tctgagatag aggaagttgc cccagaggaa   1140

gaggaggatg gtgctgagga acccaccgcc tctggaggca agagcaccca ccctatggtg   1200

actagaagca aggctgacca gggtgacatc ctcgcccagg ctgtcaatca tgccggtatc   1260

gattccagta gcaccggccc cacgctgaca acccactctt gcagcgttag cagcgcccct   1320

cttaacaagc cgacccccac cagcgtcgcg gttactaaca ctcctctccc cggggcatcc   1380

gctactcccg agctcagccc gcgtaagaaa ccgcgcaaaa ccacgcgtcc tttcaaggtg   1440

attattaaac cgcccgtgcc tcccgcgcct atcatgctgc ccctcatcaa acaggaagac   1500

atcaagcccg agcccgactt taccatccag taccgcaaca agattatcga taccgccggc   1560

tgtatcgtga tctctgatag cgaggaagaa cagggtgaag aagtcgaaac ccgcggtgct   1620
```

-continued accgcgtctt ccccttccac cggcagcggc acgccgcgag tgacctctcc cacgcacccg 1680
ctctcccaga tgaaccaccc tcctcttccc gatcccttgg gccggcccga tgaagatagt 1740
tcctcttcgt cttcctcctc ctgcagttcg gcttcggact cggagagtga gtccgaggag 1800
atgaaatgca gcagtggcgg aggagcatcc gtgacctcga gccaccatgg gcgcggcggt 1860
tttggtggcg cggcctcctc ctctctgctg agctgcggcc atcagagcag cggcggggcg 1920
agcaccggac cccgcaagaa gaagagcaaa cgcatctccg agttggacaa cgagaaggtg 1980
cgcaatatca tgaaagataa gaacaccccc ttctgcacac ccaacgtgca gactcggcgg 2040
ggtcgcgtca agattgacga ggtgagccgc atgttccgca acaccaatcg ctctcttgag 2100
tacaagaacc tgcccttcac gattcccagt atgcaccagg tgttagatga ggccatcaaa 2160
gcctgcaaaa ccatgcaggt gaacaacaag ggcatccaga ttatctacac ccgcaatcat 2220
gaggtgaaga gtgaggtgga tgcggtgcgg tgtcgcctgg gcaccatgtg caacctggcc 2280
ctctccactc ccttcctcat ggagcacacc atgcccgtga cacatccacc cgaagtggcg 2340
cagcgcacag ccgatgcttg taacgaaggc gtcaaggccg cgtggagcct caaagaattg 2400
cacacccacc aattatgccc ccgttcctcc gattaccgca acatgatcat ccacgctgcc 2460
acccccgtgg acctgttggg cgctctcaac ctgtgcctgc ccctgatgca aaagtttccc 2520
aaacaggtca tggtgcgcat cttctccacc aaccagggtg ggttcatgct gcctatctac 2580
gagacggccg cgaaggccta cgccgtgggg cagtttgagc agcccaccga gacccctccc 2640
gaagacctgg acaccctgag cctggccatc gaggcagcca tccaggacct gaggaacaag 2700
tctcagtaa 2709

<210> SEQ ID NO 3
<211> LENGTH: 2709
<212> TYPE: DNA
<213> ORGANISM: Artificial Sequence
<220> FEATURE:
<223> OTHER INFORMATION: Description of Artificial Sequence: Synthetic
polynucleotide IEfusion-4nt DNA sequence

<400> SEQUENCE: 3
atggtcaaac agattaaggt tcgagtggac atggtgcggc atagaatcaa ggagcacatg 60
ctgaagaagt atacccagac ggaagagaaa ttcactggcg cctttaatat gatgggagga 120
tgtttgcaga atgccttaga tatcttagat aaggttcatg agcctttcga ggagatgaag 180
tgtattgggc taactatgca gagcatgtat gagaactaca ttgtacctga ggataagcgg 240
gagatgtgga tggcttgtat taaggagctg catgatgtga gcaagggcgc cgctaacaag 300
ttaggaggtg cactgcaggc taaggcccgt gctaagaagg atgaacttag gagaaagatg 360
atgtatatgt gctacaggaa tatagagttc tttaccaaga actcagcctt ccctaagacc 420
accaatggct gcagtcaggc catggcggca ctgcagaact tgcctcagtg ctctcctgat 480
gagattatgg cttatgccca gaagatattt aagatcttgg atgaggagag agacaaggtg 540
ctcacgcaca ttgatcacat atttatggat atcctcacta catgtgtgga aacaatgtgt 600
aatgagtaca aggtcactag tgacgcttgt atgatgacca tgtacggagg catctctctc 660
ttaagtgagt tctgtcgggt gctgtgctgc tatgtcttag aggagactag tgtgatgctg 720
gccaagcggc ctctgataac caagcctgag gttatcagtg taatgaagcg ccgcattgag 780
gagatctgca tgaaggtctt tgcccagtac attctaggtg ccgatcctct gagagtctgc 840
tctcctagtg tggatgacct acgggccatc gccgaggagt cagatgagga agaggctatt 900

-continued

```
gtagcctaca ctttggccac cgctggtgtc agctcctctg attctctggt gtcacctcca    960
gagtcacctg tacccgcgac tatccctctg tcctcagtaa ttgtggctga gaacagtgat   1020
caggaagaaa gtgagcagag tgatgaggaa gaggaggagg gtgctcagga ggagcgggag   1080
gacactgtgt ctgtcaagtc tgagccagtg tctgagatag aggaagttgc tccagaggaa   1140
gaggaggatg gtgctgagga acccaccgcc tctggaggca agagcaccca ccctatggtg   1200
actagaagca aggctgacca gggtgacatc ctcgcccagg ctgtcaatca tgccggtatc   1260
gattccagta gcaccggacc tacgctgaca acccactctt gcagcgttag cagcgctcct   1320
cttaacaagc cgactccaac cagcgtcgcg gttactaaca ctcctctacc aggagcatcc   1380
gctactcccg agctcagccc gcgtaagaaa ccgcgcaaga ccacgcgtcc tttcaaggtg   1440
attattaaac cgcccgtgcc tcccgcgcct atcatgctgc cactcatcaa acaggaagac   1500
atcaagcccg agcccgactt taccatccag taccgcaaca agattatcga taccgccggc   1560
tgtatcgtga tctctgatag cgaggaagaa cagggtgaag aagtcgaaac ccgcggtgct   1620
accgcgtctt caccttccac cggcagcggc acgccgcgag tgacctctcc cacgcacccg   1680
ctctcccaga tgaaccaccc tcctcttccc gatcccttgg gccggcccga tgaagatagt   1740
tcctcttcgt cttcctcctc ctgcagttcg gcttcggact cggagagtga gtccgaggag   1800
atgaaatgca gcagtggcgg aggagcatcc gtgacctcga gccaccatgg gcgcggcgga   1860
tttggtggcg cggcctcctc ctctctgctg agctgcggcc atcagagcag cggcggtgcg   1920
agcaccggac ctcgcaagaa gaagagcaaa cgcatctccg agttggacaa cgagaaggtg   1980
cgcaatatca tgaaagataa gaacactccc ttctgcacac ccaacgtgca gactcggcgt   2040
ggtcgcgtca agattgacga ggtgagccgc atgttccgca acaccaatcg ctctcttgag   2100
tacaagaacc tgcccttcac gattcccagt atgcaccagg tgttagatga ggccatcaaa   2160
gcctgcaaga ccatgcaggt gaacaacaag ggcatccaga ttatctacac ccgcaatcat   2220
gaggtgaaga gtgaggtgga tgcggtgcgg tgtcgcctgg gcaccatgtg caacctggcc   2280
ctctccactc ccttcctcat ggagcacacc atgcccgtga cacatccacc cgaagtggcg   2340
cagcgcacag ccgatgcttg taacgaaggc gtcaaggccg cgtggagcct caaagaattg   2400
cacacccacc aattatgtcc tcgttcctcc gattaccgca acatgatcat ccacgctgcc   2460
acaccagtgg acctgttggg cgctctcaac ctgtgcctgc cactgatgca gaagtttccc   2520
aaacaggtca tggtgcgcat cttctccacc aaccagggtg ggttcatgct gcctatctac   2580
gagacggccg cgaaggccta cgccgttggt cagtttgagc agcccaccga gacacctccc   2640
gaagacctgg acaccctgag cctggccatc gaggcagcca tccaggacct gaggaacaag   2700
tctcagtaa                                                           2709
```

<210> SEQ ID NO 4
<211> LENGTH: 902
<212> TYPE: PRT
<213> ORGANISM: Artificial Sequence
<220> FEATURE:
<223> OTHER INFORMATION: Description of Artificial Sequence: Synthetic
polypeptide IEfusion-VacO amino acid sequence

<400> SEQUENCE: 4

```
Met Val Lys Gln Ile Lys Val Arg Val Asp Met Val Arg His Arg Ile
1               5                   10                  15

Lys Glu His Met Leu Lys Lys Tyr Thr Gln Thr Glu Glu Lys Phe Thr
            20                  25                  30
```

-continued

```
Gly Ala Phe Asn Met Met Gly Gly Cys Leu Gln Asn Ala Leu Asp Ile
        35                  40                  45

Leu Asp Lys Val His Glu Pro Phe Glu Glu Met Lys Cys Ile Gly Leu
    50                  55                  60

Thr Met Gln Ser Met Tyr Glu Asn Tyr Ile Val Pro Glu Asp Lys Arg
65                  70                  75                  80

Glu Met Trp Met Ala Cys Ile Lys Glu Leu His Asp Val Ser Lys Gly
                85                  90                  95

Ala Ala Asn Lys Leu Gly Gly Ala Leu Gln Ala Lys Ala Arg Ala Lys
            100                 105                 110

Lys Asp Glu Leu Arg Arg Lys Met Met Tyr Met Cys Tyr Arg Asn Ile
        115                 120                 125

Glu Phe Phe Thr Lys Asn Ser Ala Phe Pro Lys Thr Thr Asn Gly Cys
    130                 135                 140

Ser Gln Ala Met Ala Ala Leu Gln Asn Leu Pro Gln Cys Ser Pro Asp
145                 150                 155                 160

Glu Ile Met Ala Tyr Ala Gln Lys Ile Phe Lys Ile Leu Asp Glu Glu
                165                 170                 175

Arg Asp Lys Val Leu Thr His Ile Asp His Ile Phe Met Asp Ile Leu
            180                 185                 190

Thr Thr Cys Val Glu Thr Met Cys Asn Glu Tyr Lys Val Thr Ser Asp
        195                 200                 205

Ala Cys Met Met Thr Met Tyr Gly Gly Ile Ser Leu Leu Ser Glu Phe
    210                 215                 220

Cys Arg Val Leu Cys Cys Tyr Val Leu Glu Glu Thr Ser Val Met Leu
225                 230                 235                 240

Ala Lys Arg Pro Leu Ile Thr Lys Pro Glu Val Ile Ser Val Met Lys
                245                 250                 255

Arg Arg Ile Glu Glu Ile Cys Met Lys Val Phe Ala Gln Tyr Ile Leu
            260                 265                 270

Gly Ala Asp Pro Leu Arg Val Cys Ser Pro Ser Val Asp Asp Leu Arg
        275                 280                 285

Ala Ile Ala Glu Glu Ser Asp Glu Glu Glu Ala Ile Val Ala Tyr Thr
    290                 295                 300

Leu Ala Thr Ala Gly Val Ser Ser Ser Asp Ser Leu Val Ser Pro Pro
305                 310                 315                 320

Glu Ser Pro Val Pro Ala Thr Ile Pro Leu Ser Ser Val Ile Val Ala
                325                 330                 335

Glu Asn Ser Asp Gln Glu Glu Ser Glu Gln Ser Asp Glu Glu Glu Glu
            340                 345                 350

Glu Gly Ala Gln Glu Glu Arg Glu Asp Thr Val Ser Val Lys Ser Glu
        355                 360                 365

Pro Val Ser Glu Ile Glu Glu Val Ala Pro Glu Glu Glu Glu Asp Gly
    370                 375                 380

Ala Glu Glu Pro Thr Ala Ser Gly Gly Lys Ser Thr His Pro Met Val
385                 390                 395                 400

Thr Arg Ser Lys Ala Asp Gln Gly Asp Ile Leu Ala Gln Ala Val Asn
                405                 410                 415

His Ala Gly Ile Asp Ser Ser Ser Thr Gly Pro Thr Leu Thr Thr His
            420                 425                 430

Ser Cys Ser Val Ser Ser Ala Pro Leu Asn Lys Pro Thr Pro Thr Ser
        435                 440                 445
```

-continued

```
Val Ala Val Thr Asn Thr Pro Leu Pro Gly Ala Ser Ala Thr Pro Glu
    450                 455                 460

Leu Ser Pro Arg Lys Lys Pro Arg Lys Thr Thr Arg Pro Phe Lys Val
465                 470                 475                 480

Ile Ile Lys Pro Pro Val Pro Pro Ala Pro Ile Met Leu Pro Leu Ile
                485                 490                 495

Lys Gln Glu Asp Ile Lys Pro Glu Pro Asp Phe Thr Ile Gln Tyr Arg
            500                 505                 510

Asn Lys Ile Ile Asp Thr Ala Gly Cys Ile Val Ile Ser Asp Ser Glu
        515                 520                 525

Glu Glu Gln Gly Glu Glu Val Glu Thr Arg Gly Ala Thr Ala Ser Ser
    530                 535                 540

Pro Ser Thr Gly Ser Gly Thr Pro Arg Val Thr Ser Pro Thr His Pro
545                 550                 555                 560

Leu Ser Gln Met Asn His Pro Pro Leu Pro Asp Pro Leu Gly Arg Pro
                565                 570                 575

Asp Glu Asp Ser Ser Ser Ser Ser Ser Ser Ser Cys Ser Ser Ala Ser
            580                 585                 590

Asp Ser Glu Ser Glu Ser Glu Glu Met Lys Cys Ser Ser Gly Gly Gly
        595                 600                 605

Ala Ser Val Thr Ser Ser His His Gly Arg Gly Gly Phe Gly Gly Ala
    610                 615                 620

Ala Ser Ser Ser Leu Leu Ser Cys Gly His Gln Ser Ser Gly Gly Ala
625                 630                 635                 640

Ser Thr Gly Pro Arg Lys Lys Lys Ser Lys Arg Ile Ser Glu Leu Asp
                645                 650                 655

Asn Glu Lys Val Arg Asn Ile Met Lys Asp Lys Asn Thr Pro Phe Cys
            660                 665                 670

Thr Pro Asn Val Gln Thr Arg Arg Gly Arg Val Lys Ile Asp Glu Val
        675                 680                 685

Ser Arg Met Phe Arg Asn Thr Asn Arg Ser Leu Glu Tyr Lys Asn Leu
    690                 695                 700

Pro Phe Thr Ile Pro Ser Met His Gln Val Leu Asp Glu Ala Ile Lys
705                 710                 715                 720

Ala Cys Lys Thr Met Gln Val Asn Asn Lys Gly Ile Gln Ile Ile Tyr
                725                 730                 735

Thr Arg Asn His Glu Val Lys Ser Glu Val Asp Ala Val Arg Cys Arg
            740                 745                 750

Leu Gly Thr Met Cys Asn Leu Ala Leu Ser Thr Pro Phe Leu Met Glu
        755                 760                 765

His Thr Met Pro Val Thr His Pro Pro Glu Val Ala Gln Arg Thr Ala
    770                 775                 780

Asp Ala Cys Asn Glu Gly Val Lys Ala Ala Trp Ser Leu Lys Glu Leu
785                 790                 795                 800

His Thr His Gln Leu Cys Pro Arg Ser Ser Asp Tyr Arg Asn Met Ile
                805                 810                 815

Ile His Ala Ala Thr Pro Val Asp Leu Leu Gly Ala Leu Asn Leu Cys
            820                 825                 830

Leu Pro Leu Met Gln Lys Phe Pro Lys Gln Val Met Val Arg Ile Phe
        835                 840                 845

Ser Thr Asn Gln Gly Gly Phe Met Leu Pro Ile Tyr Glu Thr Ala Ala
    850                 855                 860

Lys Ala Tyr Ala Val Gly Gln Phe Glu Gln Pro Thr Glu Thr Pro Pro
```

865 870 875 880

Glu Asp Leu Asp Thr Leu Ser Leu Ala Ile Glu Ala Ala Ile Gln Asp
885 890 895

Leu Arg Asn Lys Ser Gln
900

<210> SEQ ID NO 5
<211> LENGTH: 902
<212> TYPE: PRT
<213> ORGANISM: Artificial Sequence
<220> FEATURE:
<223> OTHER INFORMATION: Description of Artificial Sequence: Synthetic polypeptide IEfusion amino acid sequence

<400> SEQUENCE: 5

Met Val Lys Gln Ile Lys Val Arg Val Asp Met Val Arg His Arg Ile
1 5 10 15

Lys Glu His Met Leu Lys Lys Tyr Thr Gln Thr Glu Glu Lys Phe Thr
20 25 30

Gly Ala Phe Asn Met Met Gly Gly Cys Leu Gln Asn Ala Leu Asp Ile
35 40 45

Leu Asp Lys Val His Glu Pro Phe Glu Glu Met Lys Cys Ile Gly Leu
50 55 60

Thr Met Gln Ser Met Tyr Glu Asn Tyr Ile Val Pro Glu Asp Lys Arg
65 70 75 80

Glu Met Trp Met Ala Cys Ile Lys Glu Leu His Asp Val Ser Lys Gly
85 90 95

Ala Ala Asn Lys Leu Gly Gly Ala Leu Gln Ala Lys Ala Arg Ala Lys
100 105 110

Lys Asp Glu Leu Arg Arg Lys Met Met Tyr Met Cys Tyr Arg Asn Ile
115 120 125

Glu Phe Phe Thr Lys Asn Ser Ala Phe Pro Lys Thr Thr Asn Gly Cys
130 135 140

Ser Gln Ala Met Ala Ala Leu Gln Asn Leu Pro Gln Cys Ser Pro Asp
145 150 155 160

Glu Ile Met Ala Tyr Ala Gln Lys Ile Phe Lys Ile Leu Asp Glu Glu
165 170 175

Arg Asp Lys Val Leu Thr His Ile Asp His Ile Phe Met Asp Ile Leu
180 185 190

Thr Thr Cys Val Glu Thr Met Cys Asn Glu Tyr Lys Val Thr Ser Asp
195 200 205

Ala Cys Met Met Thr Met Tyr Gly Gly Ile Ser Leu Leu Ser Glu Phe
210 215 220

Cys Arg Val Leu Cys Cys Tyr Val Leu Glu Glu Thr Ser Val Met Leu
225 230 235 240

Ala Lys Arg Pro Leu Ile Thr Lys Pro Glu Val Ile Ser Val Met Lys
245 250 255

Arg Arg Ile Glu Glu Ile Cys Met Lys Val Phe Ala Gln Tyr Ile Leu
260 265 270

Gly Ala Asp Pro Leu Arg Val Cys Ser Pro Ser Val Asp Asp Leu Arg
275 280 285

Ala Ile Ala Glu Glu Ser Asp Glu Glu Glu Ala Ile Val Ala Tyr Thr
290 295 300

Leu Ala Thr Ala Gly Val Ser Ser Ser Asp Ser Leu Val Ser Pro Pro
305 310 315 320

```
Glu Ser Pro Val Pro Ala Thr Ile Pro Leu Ser Ser Val Ile Val Ala
                325                 330                 335

Glu Asn Ser Asp Gln Glu Glu Ser Glu Gln Ser Asp Glu Glu Glu Glu
            340                 345                 350

Glu Gly Ala Gln Glu Glu Arg Glu Asp Thr Val Ser Val Lys Ser Glu
        355                 360                 365

Pro Val Ser Glu Ile Glu Glu Val Ala Pro Glu Glu Glu Glu Asp Gly
    370                 375                 380

Ala Glu Glu Pro Thr Ala Ser Gly Gly Lys Ser Thr His Pro Met Val
385                 390                 395                 400

Thr Arg Ser Lys Ala Asp Gln Gly Asp Ile Leu Ala Gln Ala Val Asn
                405                 410                 415

His Ala Gly Ile Asp Ser Ser Ser Thr Gly Pro Thr Leu Thr Thr His
            420                 425                 430

Ser Cys Ser Val Ser Ser Ala Pro Leu Asn Lys Pro Thr Pro Thr Ser
        435                 440                 445

Val Ala Val Thr Asn Thr Pro Leu Pro Gly Ala Ser Ala Thr Pro Glu
    450                 455                 460

Leu Ser Pro Arg Lys Lys Pro Arg Lys Thr Thr Arg Pro Phe Lys Val
465                 470                 475                 480

Ile Ile Lys Pro Pro Val Pro Pro Ala Pro Ile Met Leu Pro Leu Ile
                485                 490                 495

Lys Gln Glu Asp Ile Lys Pro Glu Pro Asp Phe Thr Ile Gln Tyr Arg
            500                 505                 510

Asn Lys Ile Ile Asp Thr Ala Gly Cys Ile Val Ile Ser Asp Ser Glu
        515                 520                 525

Glu Glu Gln Gly Glu Glu Val Glu Thr Arg Gly Ala Thr Ala Ser Ser
    530                 535                 540

Pro Ser Thr Gly Ser Gly Thr Pro Arg Val Thr Ser Pro Thr His Pro
545                 550                 555                 560

Leu Ser Gln Met Asn His Pro Pro Leu Pro Asp Pro Leu Gly Arg Pro
                565                 570                 575

Asp Glu Asp Ser Ser Ser Ser Ser Ser Ser Ser Cys Ser Ser Ala Ser
            580                 585                 590

Asp Ser Glu Ser Glu Ser Glu Glu Met Lys Cys Ser Ser Gly Gly Gly
        595                 600                 605

Ala Ser Val Thr Ser Ser His His Gly Arg Gly Gly Phe Gly Gly Ala
    610                 615                 620

Ala Ser Ser Ser Leu Leu Ser Cys Gly His Gln Ser Ser Gly Gly Ala
625                 630                 635                 640

Ser Thr Gly Pro Arg Lys Lys Lys Ser Lys Arg Ile Ser Glu Leu Asp
                645                 650                 655

Asn Glu Lys Val Arg Asn Ile Met Lys Asp Lys Asn Thr Pro Phe Cys
            660                 665                 670

Thr Pro Asn Val Gln Thr Arg Arg Gly Arg Val Lys Ile Asp Glu Val
        675                 680                 685

Ser Arg Met Phe Arg Asn Thr Asn Arg Ser Leu Glu Tyr Lys Asn Leu
    690                 695                 700

Pro Phe Thr Ile Pro Ser Met His Gln Val Leu Asp Glu Ala Ile Lys
705                 710                 715                 720

Ala Cys Lys Thr Met Gln Val Asn Asn Lys Gly Ile Gln Ile Ile Tyr
                725                 730                 735

Thr Arg Asn His Glu Val Lys Ser Glu Val Asp Ala Val Arg Cys Arg
```

```
            740                 745                 750

Leu Gly Thr Met Cys Asn Leu Ala Leu Ser Thr Pro Phe Leu Met Glu
        755                 760                 765

His Thr Met Pro Val Thr His Pro Pro Glu Val Ala Gln Arg Thr Ala
    770                 775                 780

Asp Ala Cys Asn Glu Gly Val Lys Ala Ala Trp Ser Leu Lys Glu Leu
785                 790                 795                 800

His Thr His Gln Leu Cys Pro Arg Ser Ser Asp Tyr Arg Asn Met Ile
                805                 810                 815

Ile His Ala Ala Thr Pro Val Asp Leu Leu Gly Ala Leu Asn Leu Cys
            820                 825                 830

Leu Pro Leu Met Gln Lys Phe Pro Lys Gln Val Met Val Arg Ile Phe
        835                 840                 845

Ser Thr Asn Gln Gly Gly Phe Met Leu Pro Ile Tyr Glu Thr Ala Ala
    850                 855                 860

Lys Ala Tyr Ala Val Gly Gln Phe Glu Gln Pro Thr Glu Thr Pro Pro
865                 870                 875                 880

Glu Asp Leu Asp Thr Leu Ser Leu Ala Ile Glu Ala Ala Ile Gln Asp
                885                 890                 895

Leu Arg Asn Lys Ser Gln
            900


<210> SEQ ID NO 6
<211> LENGTH: 902
<212> TYPE: PRT
<213> ORGANISM: Artificial Sequence
<220> FEATURE:
<223> OTHER INFORMATION: Description of Artificial Sequence: Synthetic
      polypeptide IEfusion-4NT amino acid sequence

<400> SEQUENCE: 6

Met Val Lys Gln Ile Lys Val Arg Val Asp Met Val Arg His Arg Ile
1               5                   10                  15

Lys Glu His Met Leu Lys Lys Tyr Thr Gln Thr Glu Glu Lys Phe Thr
            20                  25                  30

Gly Ala Phe Asn Met Met Gly Gly Cys Leu Gln Asn Ala Leu Asp Ile
        35                  40                  45

Leu Asp Lys Val His Glu Pro Phe Glu Glu Met Lys Cys Ile Gly Leu
    50                  55                  60

Thr Met Gln Ser Met Tyr Glu Asn Tyr Ile Val Pro Glu Asp Lys Arg
65                  70                  75                  80

Glu Met Trp Met Ala Cys Ile Lys Glu Leu His Asp Val Ser Lys Gly
                85                  90                  95

Ala Ala Asn Lys Leu Gly Gly Ala Leu Gln Ala Lys Ala Arg Ala Lys
            100                 105                 110

Lys Asp Glu Leu Arg Arg Lys Met Met Tyr Met Cys Tyr Arg Asn Ile
        115                 120                 125

Glu Phe Phe Thr Lys Asn Ser Ala Phe Pro Lys Thr Thr Asn Gly Cys
    130                 135                 140

Ser Gln Ala Met Ala Ala Leu Gln Asn Leu Pro Gln Cys Ser Pro Asp
145                 150                 155                 160

Glu Ile Met Ala Tyr Ala Gln Lys Ile Phe Lys Ile Leu Asp Glu Glu
                165                 170                 175

Arg Asp Lys Val Leu Thr His Ile Asp His Ile Phe Met Asp Ile Leu
            180                 185                 190
```

-continued

```
Thr Thr Cys Val Glu Thr Met Cys Asn Glu Tyr Lys Val Thr Ser Asp
        195                 200                 205

Ala Cys Met Met Thr Met Tyr Gly Gly Ile Ser Leu Leu Ser Glu Phe
    210                 215                 220

Cys Arg Val Leu Cys Cys Tyr Val Leu Glu Glu Thr Ser Val Met Leu
225                 230                 235                 240

Ala Lys Arg Pro Leu Ile Thr Lys Pro Glu Val Ile Ser Val Met Lys
                245                 250                 255

Arg Arg Ile Glu Glu Ile Cys Met Lys Val Phe Ala Gln Tyr Ile Leu
            260                 265                 270

Gly Ala Asp Pro Leu Arg Val Cys Ser Pro Ser Val Asp Asp Leu Arg
        275                 280                 285

Ala Ile Ala Glu Glu Ser Asp Glu Glu Glu Ala Ile Val Ala Tyr Thr
    290                 295                 300

Leu Ala Thr Ala Gly Val Ser Ser Ser Asp Ser Leu Val Ser Pro Pro
305                 310                 315                 320

Glu Ser Pro Val Pro Ala Thr Ile Pro Leu Ser Ser Val Ile Val Ala
                325                 330                 335

Glu Asn Ser Asp Gln Glu Glu Ser Glu Gln Ser Asp Glu Glu Glu Glu
            340                 345                 350

Glu Gly Ala Gln Glu Glu Arg Glu Asp Thr Val Ser Val Lys Ser Glu
        355                 360                 365

Pro Val Ser Glu Ile Glu Glu Val Ala Pro Glu Glu Glu Glu Asp Gly
    370                 375                 380

Ala Glu Glu Pro Thr Ala Ser Gly Gly Lys Ser Thr His Pro Met Val
385                 390                 395                 400

Thr Arg Ser Lys Ala Asp Gln Gly Asp Ile Leu Ala Gln Ala Val Asn
                405                 410                 415

His Ala Gly Ile Asp Ser Ser Ser Thr Gly Pro Thr Leu Thr Thr His
            420                 425                 430

Ser Cys Ser Val Ser Ser Ala Pro Leu Asn Lys Pro Thr Pro Thr Ser
        435                 440                 445

Val Ala Val Thr Asn Thr Pro Leu Pro Gly Ala Ser Ala Thr Pro Glu
    450                 455                 460

Leu Ser Pro Arg Lys Lys Pro Arg Lys Thr Thr Arg Pro Phe Lys Val
465                 470                 475                 480

Ile Ile Lys Pro Pro Val Pro Pro Ala Pro Ile Met Leu Pro Leu Ile
                485                 490                 495

Lys Gln Glu Asp Ile Lys Pro Glu Pro Asp Phe Thr Ile Gln Tyr Arg
            500                 505                 510

Asn Lys Ile Ile Asp Thr Ala Gly Cys Ile Val Ile Ser Asp Ser Glu
        515                 520                 525

Glu Glu Gln Gly Glu Glu Val Glu Thr Arg Gly Ala Thr Ala Ser Ser
    530                 535                 540

Pro Ser Thr Gly Ser Gly Thr Pro Arg Val Thr Ser Pro Thr His Pro
545                 550                 555                 560

Leu Ser Gln Met Asn His Pro Pro Leu Pro Asp Pro Leu Gly Arg Pro
                565                 570                 575

Asp Glu Asp Ser Ser Ser Ser Ser Ser Ser Ser Cys Ser Ser Ala Ser
            580                 585                 590

Asp Ser Glu Ser Glu Ser Glu Glu Met Lys Cys Ser Ser Gly Gly Gly
        595                 600                 605

Ala Ser Val Thr Ser Ser His His Gly Arg Gly Gly Phe Gly Gly Ala
```

```
    610                 615                 620

Ala Ser Ser Ser Leu Leu Ser Cys Gly His Gln Ser Ser Gly Gly Ala
625                 630                 635                 640

Ser Thr Gly Pro Arg Lys Lys Lys Ser Lys Arg Ile Ser Glu Leu Asp
                645                 650                 655

Asn Glu Lys Val Arg Asn Ile Met Lys Asp Lys Asn Thr Pro Phe Cys
            660                 665                 670

Thr Pro Asn Val Gln Thr Arg Arg Gly Arg Val Lys Ile Asp Glu Val
        675                 680                 685

Ser Arg Met Phe Arg Asn Thr Asn Arg Ser Leu Glu Tyr Lys Asn Leu
    690                 695                 700

Pro Phe Thr Ile Pro Ser Met His Gln Val Leu Asp Glu Ala Ile Lys
705                 710                 715                 720

Ala Cys Lys Thr Met Gln Val Asn Asn Lys Gly Ile Gln Ile Ile Tyr
                725                 730                 735

Thr Arg Asn His Glu Val Lys Ser Glu Val Asp Ala Val Arg Cys Arg
            740                 745                 750

Leu Gly Thr Met Cys Asn Leu Ala Leu Ser Thr Pro Phe Leu Met Glu
        755                 760                 765

His Thr Met Pro Val Thr His Pro Pro Glu Val Ala Gln Arg Thr Ala
    770                 775                 780

Asp Ala Cys Asn Glu Gly Val Lys Ala Ala Trp Ser Leu Lys Glu Leu
785                 790                 795                 800

His Thr His Gln Leu Cys Pro Arg Ser Ser Asp Tyr Arg Asn Met Ile
                805                 810                 815

Ile His Ala Ala Thr Pro Val Asp Leu Leu Gly Ala Leu Asn Leu Cys
            820                 825                 830

Leu Pro Leu Met Gln Lys Phe Pro Lys Gln Val Met Val Arg Ile Phe
        835                 840                 845

Ser Thr Asn Gln Gly Gly Phe Met Leu Pro Ile Tyr Glu Thr Ala Ala
    850                 855                 860

Lys Ala Tyr Ala Val Gly Gln Phe Glu Gln Pro Thr Glu Thr Pro Pro
865                 870                 875                 880

Glu Asp Leu Asp Thr Leu Ser Leu Ala Ile Glu Ala Ala Ile Gln Asp
                885                 890                 895

Leu Arg Asn Lys Ser Gln
            900


<210> SEQ ID NO 7
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide IE2-VacO DNA sequence

<400> SEQUENCE: 7

atgggagaca tcctagcaca agcagtgaac catgctggaa ttgactcatc ttcgaccgga     60

ccaactctaa cgactcattc atgttcggtt agttctgctc ctcttaacaa gcctacacct    120

acctcggtag ctgttaccaa cacacccttta ccaggagcat cagcaacacc tgagttgtct    180

ccaagaaaga agcctcgtaa gaccacgaga ccgttcaagg tgatcatcaa gccaccagta    240

ccacctgctc cgatcatgtt gccattgatc aagcaggagg acattaagcc agaacctgac    300

ttcacgatac agtaccgtaa caagatcata gatacagcag gatgcatagt gatctcagat    360
```

```
agtgaagagg agcaaggtga ggaagtggag actagaggag ccacagccag ttcgccttcc    420

acaggatccg gaactcctag agtaactagt ccgacacatc cactttccca gatgaatcat    480

ccacctctac cggatcctct aggacgacca gatgaagatt cttcttcatc tagttcaagt    540

tcttgctcat ccgcgagtga tagtgagtca gaaagtgaag agatgaagtg ctcttctggt    600

ggtggagcta gtgtcacttc atctcatcat ggacgaggag gatttggagg tgctgcgagt    660

agttccttac taagttgtgg acatcagtca tctggtggtg catctactgg acctagaaag    720

aagaagtcaa agagaatctc cgaattggat aatgagaaag tgagaaacat catgaaggac    780

aagaacacgc cgttctgcac tccgaatgtt cagacgagaa gaggacgagt gaagatagat    840

gaagtatcac gaatgttcag aaacacaaat cgttctctag agtacaagaa tcttccgttc    900

accatacctt cgatgcacca agtattagat gaggctatca aggcatgtaa gaccatgcaa    960

gttaacaaca aaggaataca gatcatctac actagaaacc atgaggttaa gagtgaggtg   1020

gatgccgtac gttgtagatt gggaacgatg tgtaaccttg cgctatctac tcctttccta   1080

atggagcata ctatgcctgt gactcatcct cctgaagtgg ctcaaagaac agctgatgct   1140

tgtaacgaag gtgtgaaagc tgcttggtcc ctaaaggagt tacatacaca ccaactttgt   1200

ccacgatcca gtgactacag aaacatgatc attcatgcag ctacgcctgt agatctactt   1260

ggagctctta acctatgtct tcctttgatg cagaagttcc ctaagcaagt gatggtgaga   1320

atcttctcga cgaatcaagg aggattcatg ttaccgatat acgagacagc tgcaaaggct   1380

tacgctgtcg gtcagttcga gcaaccgact gaaacgcctc ctgaggactt agatacattg   1440

tctttggcga tagaagcagc gattcaggat cttagaaaca agagtcagta a            1491
```

```
<210> SEQ ID NO 8
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide IE2 DNA sequence

<400> SEQUENCE: 8
```

```
atgggtgaca tcctcgccca ggctgtcaat catgccggta tcgattccag tagcaccggc     60

cccacgctga caacccactc ttgcagcgtt agcagcgccc ctcttaacaa gccgaccccc    120

accagcgtcg cggttactaa cactcctctc cccggggcat ccgctactcc cgagctcagc    180

ccgcgtaaga aaccgcgcaa aaccacgcgt cctttcaagg tgattattaa accgcccgtg    240

cctcccgcgc ctatcatgct gcccctcatc aaacaggaag acatcaagcc cgagcccgac    300

tttaccatcc agtaccgcaa caagattatc gataccgccg gctgtatcgt gatctctgat    360

agcgaggaag aacagggtga agaagtcgaa acccgcggtg ctaccgcgtc ttccccttcc    420

accggcagcg gcacgccgcg agtgacctct cccacgcacc cgctctccca gatgaaccac    480

cctcctcttc ccgatccctt gggccggccc gatgaagata gttcctcttc gtcttcctcc    540

tcctgcagtt cggcttcgga ctcggagagt gagtccgagg agatgaaatg cagcagtggc    600

ggaggagcat ccgtgacctc gagccaccat gggcgcggcg gttttggtgg cgcggcctcc    660

tcctctctgc tgagctgcgg ccatcagagc agcggcgggg cgagcaccgg accccgcaag    720

aagaagagca aacgcatctc cgagttggac aacgagaagg tgcgcaatat catgaaagat    780

aagaacaccc ccttctgcac acccaacgtg cagactcggc ggggtcgcgt caagattgac    840

gaggtgagcc gcatgttccg caacaccaat cgctctcttg agtacaagaa cctgcccttc    900
```

-continued

```
acgattccca gtatgcacca ggtgttagat gaggccatca aagcctgcaa aaccatgcag    960

gtgaacaaca agggcatcca gattatctac acccgcaatc atgaggtgaa gagtgaggtg   1020

gatgcggtgc ggtgtcgcct gggcaccatg tgcaacctgg ccctctccac tcccttcctc   1080

atggagcaca ccatgcccgt gacacatcca cccgaagtgg cgcagcgcac agccgatgct   1140

tgtaacgaag gcgtcaaggc cgcgtggagc ctcaaagaat tgcacaccca ccaattatgc   1200

ccccgttcct ccgattaccg caacatgatc atccacgctg ccacccccgt ggacctgttg   1260

ggcgctctca acctgtgcct gcccctgatg caaaagtttc ccaaacaggt catggtgcgc   1320

atcttctcca ccaaccaggg tgggttcatg ctgcctatct acgagacggc cgcgaaggcc   1380

tacgccgtgg ggcagtttga gcagcccacc gagacccctc ccgaagacct ggacaccctg   1440

agcctggcca tcgaggcagc catccaggac ctgaggaaca agtctcagta a            1491
```

<210> SEQ ID NO 9
<211> LENGTH: 1491
<212> TYPE: DNA
<213> ORGANISM: Artificial Sequence
<220> FEATURE:
<223> OTHER INFORMATION: Description of Artificial Sequence: Synthetic
polynucleotide IE2-4nt DNA sequence

<400> SEQUENCE: 9

```
atgggtgaca tcctcgccca ggctgtcaat catgccggta tcgattccag tagcaccgga     60

cctacgctga caacccactc ttgcagcgtt agcagcgctc ctcttaacaa gccgactcca    120

accagcgtcg cggttactaa cactcctcta ccaggagcat ccgctactcc cgagctcagc    180

ccgcgtaaga aaccgcgcaa gaccacgcgt cctttcaagg tgattattaa accgcccgtg    240

cctcccgcgc ctatcatgct gccactcatc aaacaggaag acatcaagcc cgagcccgac    300

tttaccatcc agtaccgcaa caagattatc gataccgccg gctgtatcgt gatctctgat    360

agcgaggaag aacagggtga agaagtcgaa acccgcggtg ctaccgcgtc ttcaccttcc    420

accggcagcg gcacgccgcg agtgacctct cccacgcacc cgctctccca gatgaaccac    480

cctcctcttc ccgatccctt gggccggccc gatgaagata gttcctcttc gtcttcctcc    540

tcctgcagtt cggcttcgga ctcggagagt gagtccgagg agatgaaatg cagcagtggc    600

ggaggagcat ccgtgacctc gagccaccat gggcgcggcg gatttggtgg cgcggcctcc    660

tcctctctgc tgagctgcgg ccatcagagc agcggcggtg cgagcaccgg acctcgcaag    720

aagaagagca aacgcatctc cgagttggac aacgagaagg tgcgcaatat catgaaagat    780

aagaacactc ccttctgcac acccaacgtg cagactcggc gtggtcgcgt caagattgac    840

gaggtgagcc gcatgttccg caacaccaat cgctctcttg agtacaagaa cctgcccttc    900

acgattccca gtatgcacca ggtgttagat gaggccatca aagcctgcaa gaccatgcag    960

gtgaacaaca agggcatcca gattatctac acccgcaatc atgaggtgaa gagtgaggtg   1020

gatgcggtgc ggtgtcgcct gggcaccatg tgcaacctgg ccctctccac tcccttcctc   1080

atggagcaca ccatgcccgt gacacatcca cccgaagtgg cgcagcgcac agccgatgct   1140

tgtaacgaag gcgtcaaggc cgcgtggagc ctcaaagaat tgcacaccca ccaattatgt   1200

cctcgttcct ccgattaccg caacatgatc atccacgctg ccacaccagt ggacctgttg   1260

ggcgctctca acctgtgcct gccactgatg cagaagtttc ccaaacaggt catggtgcgc   1320

atcttctcca ccaaccaggg tgggttcatg ctgcctatct acgagacggc cgcgaaggcc   1380

tacgccgttg gtcagtttga gcagcccacc gagacacctc ccgaagacct ggacaccctg   1440
```

```
agcctggcca tcgaggcagc catccaggac ctgaggaaca agtctcagta a           1491


<210> SEQ ID NO 10
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide IE2 4nt H363A DNA sequence

<400> SEQUENCE: 10

atgggtgaca tcctcgccca ggctgtcaat catgccggta tcgattccag tagcaccgga     60

cctacgctga caacccactc ttgcagcgtt agcagcgctc ctcttaacaa gccgactcca    120

accagcgtcg cggttactaa cactcctcta ccaggagcat ccgctactcc cgagctcagc    180

ccgcgtaaga aaccgcgcaa gaccacgcgt cctttcaagg tgattattaa accgcccgtg    240

cctcccgcgc ctatcatgct gccactcatc aaacaggaag acatcaagcc cgagcccgac    300

tttaccatcc agtaccgcaa caagattatc gataccgccg gctgtatcgt gatctctgat    360

agcgaggaag aacagggtga agaagtcgaa acccgcggtg ctaccgcgtc ttcaccttcc    420

accggcagcg gcacgccgcg agtgacctct cccacgcacc cgctctccca gatgaaccac    480

cctcctcttc ccgatccctt gggccggccc gatgaagata gttcctcttc gtcttcctcc    540

tcctgcagtt cggcttcgga ctcggagagt gagtccgagg agatgaaatg cagcagtggc    600

ggaggagcat ccgtgacctc gagccaccat gggcgcggcg gatttggtgg cgcggcctcc    660

tcctctctgc tgagctgcgg ccatcagagc agcggcggtg cgagcaccgg acctcgcaag    720

aagaagagca aacgcatctc cgagttggac aacgagaagg tgcgcaatat catgaaagat    780

aagaacactc ccttctgcac acccaacgtg cagactcggc gtggtcgcgt caagattgac    840

gaggtgagcc gcatgttccg caacaccaat cgctctcttg agtacaagaa cctgcccttc    900

acgattccca gtatgcacca ggtgttagat gaggccatca aagcctgcaa gaccatgcag    960

gtgaacaaca agggcatcca gattatctac acccgcaatc atgaggtgaa gagtgaggtg   1020

gatgcggtgc ggtgtcgcct gggcaccatg tgcaacctgg ccctctccac tcccttcctc   1080

atggaggcaa ccatgcccgt gacacatcca cccgaagtgg cgcagcgcac agccgatgct   1140

tgtaacgaag gcgtcaaggc cgcgtggagc ctcaaagaat tgcacaccca ccaattatgt   1200

cctcgttcct ccgattaccg caacatgatc atccacgctg ccacaccagt ggacctgttg   1260

ggcgctctca acctgtgcct gccactgatg cagaagtttc ccaaacaggt catggtgcgc   1320

atcttctcca ccaaccaggg tgggttcatg ctgcctatct acgagacggc cgcgaaggcc   1380

tacgccgttg gtcagtttga gcagcccacc gagacacctc ccgaagacct ggacaccctg   1440

agcctggcca tcgaggcagc catccaggac ctgaggaaca agtctcagta a           1491


<210> SEQ ID NO 11
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide IE2 4nt H369A DNA sequence

<400> SEQUENCE: 11

atgggtgaca tcctcgccca ggctgtcaat catgccggta tcgattccag tagcaccgga     60

cctacgctga caacccactc ttgcagcgtt agcagcgctc ctcttaacaa gccgactcca    120

accagcgtcg cggttactaa cactcctcta ccaggagcat ccgctactcc cgagctcagc    180
```

```
ccgcgtaaga aaccgcgcaa gaccacgcgt cctttcaagg tgattattaa accgcccgtg    240

cctcccgcgc ctatcatgct gccactcatc aaacaggaag acatcaagcc cgagcccgac    300

tttaccatcc agtaccgcaa caagattatc gataccgccg gctgtatcgt gatctctgat    360

agcgaggaag aacagggtga agaagtcgaa acccgcggtg ctaccgcgtc ttcaccttcc    420

accggcagcg gcacgccgcg agtgacctct cccacgcacc cgctctccca gatgaaccac    480

cctcctcttc ccgatccctt gggccggccc gatgaagata gttcctcttc gtcttcctcc    540

tcctgcagtt cggcttcgga ctcggagagt gagtccgagg agatgaaatg cagcagtggc    600

ggaggagcat ccgtgacctc gagccaccat gggcgcggcg gatttggtgg cgcggcctcc    660

tcctctctgc tgagctgcgg ccatcagagc agcggcggtg cgagcaccgg acctcgcaag    720

aagaagagca aacgcatctc cgagttggac aacgagaagg tgcgcaatat catgaaagat    780

aagaacactc ccttctgcac acccaacgtg cagactcggc gtggtcgcgt caagattgac    840

gaggtgagcc gcatgttccg caacaccaat cgctctcttg agtacaagaa cctgcccttc    900

acgattccca gtatgcacca ggtgttagat gaggccatca aagcctgcaa gaccatgcag    960

gtgaacaaca agggcatcca gattatctac acccgcaatc atgaggtgaa gagtgaggtg   1020

gatgcggtgc ggtgtcgcct gggcaccatg tgcaacctgg ccctctccac tcccttcctc   1080

atggagcaca ccatgcccgt gacagcacca cccgaagtgg cgcagcgcac agccgatgct   1140

tgtaacgaag gcgtcaaggc cgcgtggagc ctcaaagaat tgcacaccca ccaattatgt   1200

cctcgttcct ccgattaccg caacatgatc atccacgctg ccacaccagt ggacctgttg   1260

ggcgctctca acctgtgcct gccactgatg cagaagtttc ccaaacaggt catggtgcgc   1320

atcttctcca ccaaccaggg tgggttcatg ctgcctatct acgagacggc cgcgaaggcc   1380

tacgccgttg gtcagtttga gcagcccacc gagacacctc ccgaagacct ggacaccctg   1440

agcctggcca tcgaggcagc catccaggac ctgaggaaca agtctcagta a            1491
```

<210> SEQ ID NO 12
<211> LENGTH: 1491
<212> TYPE: DNA
<213> ORGANISM: Artificial Sequence
<220> FEATURE:
<223> OTHER INFORMATION: Description of Artificial Sequence: Synthetic polynucleotide IE2 4nt H363A/H369A DNA sequence

<400> SEQUENCE: 12

```
atgggtgaca tcctcgccca ggctgtcaat catgccggta tcgattccag tagcaccgga     60

cctacgctga caacccactc ttgcagcgtt agcagcgctc ctcttaacaa gccgactcca    120

accagcgtcg cggttactaa cactcctcta ccaggagcat ccgctactcc cgagctcagc    180

ccgcgtaaga aaccgcgcaa gaccacgcgt cctttcaagg tgattattaa accgcccgtg    240

cctcccgcgc ctatcatgct gccactcatc aaacaggaag acatcaagcc cgagcccgac    300

tttaccatcc agtaccgcaa caagattatc gataccgccg gctgtatcgt gatctctgat    360

agcgaggaag aacagggtga agaagtcgaa acccgcggtg ctaccgcgtc ttcaccttcc    420

accggcagcg gcacgccgcg agtgacctct cccacgcacc cgctctccca gatgaaccac    480

cctcctcttc ccgatccctt gggccggccc gatgaagata gttcctcttc gtcttcctcc    540

tcctgcagtt cggcttcgga ctcggagagt gagtccgagg agatgaaatg cagcagtggc    600

ggaggagcat ccgtgacctc gagccaccat gggcgcggcg gatttggtgg cgcggcctcc    660

tcctctctgc tgagctgcgg ccatcagagc agcggcggtg cgagcaccgg acctcgcaag    720
```

```
aagaagagca aacgcatctc cgagttggac aacgagaagg tgcgcaatat catgaaagat    780

aagaacactc ccttctgcac acccaacgtg cagactcggc gtggtcgcgt caagattgac    840

gaggtgagcc gcatgttccg caacaccaat cgctctcttg agtacaagaa cctgcccttc    900

acgattccca gtatgcacca ggtgttagat gaggccatca aagcctgcaa gaccatgcag    960

gtgaacaaca agggcatcca gattatctac acccgcaatc atgaggtgaa gagtgaggtg   1020

gatgcggtgc ggtgtcgcct gggcaccatg tgcaacctgg ccctctccac tcccttcctc   1080

atggaggcaa ccatgcccgt gacagcacca cccgaagtgg cgcagcgcac agccgatgct   1140

tgtaacgaag gcgtcaaggc cgcgtggagc ctcaaagaat tgcacaccca ccaattatgt   1200

cctcgttcct ccgattaccg caacatgatc atccacgctg ccacaccagt ggacctgttg   1260

ggcgctctca acctgtgcct gccactgatg cagaagtttc ccaaacaggt catggtgcgc   1320

atcttctcca ccaaccaggg tgggttcatg ctgcctatct acgagacggc cgcgaaggcc   1380

tacgccgttg gtcagtttga gcagcccacc gagacacctc ccgaagacct ggacaccctg   1440

agcctggcca tcgaggcagc catccaggac ctgaggaaca agtctcagta a            1491
```

```
<210> SEQ ID NO 13
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide IE2 H363A DNA sequence

<400> SEQUENCE: 13

atgggtgaca tcctcgccca ggctgtcaat catgccggta tcgattccag tagcaccggc     60

cccacgctga caacccactc ttgcagcgtt agcagcgccc ctcttaacaa gccgaccccc    120

accagcgtcg cggttactaa cactcctctc cccggggcat ccgctactcc cgagctcagc    180

ccgcgtaaga aaccgcgcaa aaccacgcgt cctttcaagg tgattattaa accgcccgtg    240

cctcccgcgc ctatcatgct gcccctcatc aaacaggaag acatcaagcc cgagcccgac    300

tttaccatcc agtaccgcaa caagattatc gataccgccg gctgtatcgt gatctctgat    360

agcgaggaag aacagggtga agaagtcgaa acccgcggtg ctaccgcgtc ttccccttcc    420

accggcagcg gcacgccgcg agtgacctct cccacgcacc cgctctccca gatgaaccac    480

cctcctcttc ccgatccctt gggccggccc gatgaagata gttcctcttc gtcttcctcc    540

tcctgcagtt cggcttcgga ctcggagagt gagtccgagg agatgaaatg cagcagtggc    600

ggaggagcat ccgtgacctc gagccaccat gggcgcggcg gttttggtgg cgcggcctcc    660

tcctctctgc tgagctgcgg ccatcagagc agcggcgggg cgagcaccgg accccgcaag    720

aagaagagca aacgcatctc cgagttggac aacgagaagg tgcgcaatat catgaaagat    780

aagaacaccc ccttctgcac acccaacgtg cagactcggc ggggtcgcgt caagattgac    840

gaggtgagcc gcatgttccg caacaccaat cgctctcttg agtacaagaa cctgcccttc    900

acgattccca gtatgcacca ggtgttagat gaggccatca aagcctgcaa aaccatgcag    960

gtgaacaaca agggcatcca gattatctac acccgcaatc atgaggtgaa gagtgaggtg   1020

gatgcggtgc ggtgtcgcct gggcaccatg tgcaacctgg ccctctccac tcccttcctc   1080

atggaggcaa ccatgcccgt gacacatcca cccgaagtgg cgcagcgcac agccgatgct   1140

tgtaacgaag gcgtcaaggc cgcgtggagc ctcaaagaat tgcacaccca ccaattatgc   1200

ccccgttcct ccgattaccg caacatgatc atccacgctg ccaccccgt ggacctgttg    1260
```

-continued

```
ggcgctctca acctgtgcct gcccctgatg caaaagtttc ccaaacaggt catggtgcgc   1320

atcttctcca ccaaccaggg tgggttcatg ctgcctatct acgagacggc cgcgaaggcc   1380

tacgccgtgg ggcagtttga gcagcccacc gagacccctc ccgaagacct ggacaccctg   1440

agcctggcca tcgaggcagc catccaggac ctgaggaaca agtctcag                1488
```

<210> SEQ ID NO 14
<211> LENGTH: 1488
<212> TYPE: DNA
<213> ORGANISM: Artificial Sequence
<220> FEATURE:
<223> OTHER INFORMATION: Description of Artificial Sequence: Synthetic
polynucleotide IE2 H369A DNA sequence

<400> SEQUENCE: 14

```
atgggtgaca tcctcgccca ggctgtcaat catgccggta tcgattccag tagcaccggc     60

cccacgctga caacccactc ttgcagcgtt agcagcgccc ctcttaacaa gccgaccccc    120

accagcgtcg cggttactaa cactcctctc cccggggcat ccgctactcc cgagctcagc    180

ccgcgtaaga aaccgcgcaa aaccacgcgt cctttcaagg tgattattaa accgcccgtg    240

cctcccgcgc ctatcatgct gcccctcatc aaacaggaag acatcaagcc cgagcccgac    300

tttaccatcc agtaccgcaa caagattatc gataccgccg gctgtatcgt gatctctgat    360

agcgaggaag aacagggtga agaagtcgaa acccgcggtg ctaccgcgtc ttccccttcc    420

accggcagcg gcacgccgcg agtgacctct cccacgcacc cgctctccca gatgaaccac    480

cctcctcttc ccgatccctt gggccggccc gatgaagata gttcctcttc gtcttcctcc    540

tcctgcagtt cggcttcgga ctcggagagt gagtccgagg agatgaaatg cagcagtggc    600

ggaggagcat ccgtgacctc gagccaccat gggcgcggcg gttttggtgg cgcggcctcc    660

tcctctctgc tgagctgcgg ccatcagagc agcggcgggg cgagcaccgg accccgcaag    720

aagaagagca aacgcatctc cgagttggac aacgagaagg tgcgcaatat catgaaagat    780

aagaacaccc ccttctgcac acccaacgtg cagactcggc ggggtcgcgt caagattgac    840

gaggtgagcc gcatgttccg caacaccaat cgctctcttg agtacaagaa cctgcccttc    900

acgattccca gtatgcacca ggtgttagat gaggccatca aagcctgcaa aaccatgcag    960

gtgaacaaca agggcatcca gattatctac acccgcaatc atgaggtgaa gagtgaggtg   1020

gatgcggtgc ggtgtcgcct gggcaccatg tgcaacctgg ccctctccac tcccttcctc   1080

atggagcaca ccatgcccgt gacagcacca cccgaagtgg cgcagcgcac agccgatgct   1140

tgtaacgaag gcgtcaaggc cgcgtggagc ctcaaagaat tgcacaccca ccaattatgc   1200

ccccgttcct ccgattaccg caacatgatc atccacgctg ccaccccccgt ggacctgttg   1260

ggcgctctca acctgtgcct gcccctgatg caaaagtttc ccaaacaggt catggtgcgc   1320

atcttctcca ccaaccaggg tgggttcatg ctgcctatct acgagacggc cgcgaaggcc   1380

tacgccgtgg ggcagtttga gcagcccacc gagacccctc ccgaagacct ggacaccctg   1440

agcctggcca tcgaggcagc catccaggac ctgaggaaca agtctcag                1488
```

<210> SEQ ID NO 15
<211> LENGTH: 1488
<212> TYPE: DNA
<213> ORGANISM: Artificial Sequence
<220> FEATURE:
<223> OTHER INFORMATION: Description of Artificial Sequence: Synthetic
polynucleotide IE2 H363A/H369A DNA sequence

<400> SEQUENCE: 15

```
atgggtgaca tcctcgccca ggctgtcaat catgccggta tcgattccag tagcaccggc     60

cccacgctga caacccactc ttgcagcgtt agcagcgccc ctcttaacaa gccgaccccc    120

accagcgtcg cggttactaa cactcctctc cccggggcat ccgctactcc cgagctcagc    180

ccgcgtaaga aaccgcgcaa aaccacgcgt cctttcaagg tgattattaa accgcccgtg    240

cctcccgcgc ctatcatgct gcccctcatc aaacaggaag acatcaagcc cgagcccgac    300

tttaccatcc agtaccgcaa caagattatc gataccgccg gctgtatcgt gatctctgat    360

agcgaggaag aacagggtga agaagtcgaa acccgcggtg ctaccgcgtc ttccccttcc    420

accggcagcg gcacgccgcg agtgacctct cccacgcacc cgctctccca gatgaaccac    480

cctcctcttc ccgatccctt gggccggccc gatgaagata gttcctcttc gtcttcctcc    540

tcctgcagtt cggcttcgga ctcggagagt gagtccgagg agatgaaatg cagcagtggc    600

ggaggagcat ccgtgacctc gagccaccat gggcgcggcg gttttggtgg cgcggcctcc    660

tcctctctgc tgagctgcgg ccatcagagc agcggcgggg cgagcaccgg accccgcaag    720

aagaagagca aacgcatctc cgagttggac aacgagaagg tgcgcaatat catgaaagat    780

aagaacaccc ccttctgcac acccaacgtg cagactcggc ggggtcgcgt caagattgac    840

gaggtgagcc gcatgttccg caacaccaat cgctctcttg agtacaagaa cctgcccttc    900

acgattccca gtatgcacca ggtgttagat gaggccatca aagcctgcaa aaccatgcag    960

gtgaacaaca agggcatcca gattatctac acccgcaatc atgaggtgaa gagtgaggtg   1020

gatgcggtgc ggtgtcgcct gggcaccatg tgcaacctgg ccctctccac tcccttcctc   1080

atggaggcaa ccatgcccgt gacagcacca cccgaagtgg cgcagcgcac agccgatgct   1140

tgtaacgaag gcgtcaaggc cgcgtggagc ctcaaagaat tgcacaccca ccaattatgc   1200

ccccgttcct ccgattaccg caacatgatc atccacgctg ccacccccgt ggacctgttg   1260

ggcgctctca acctgtgcct gcccctgatg caaaagtttc ccaaacaggt catggtgcgc   1320

atcttctcca ccaaccaggg tgggttcatg ctgcctatct acgagacggc cgcgaaggcc   1380

tacgccgtgg ggcagtttga gcagcccacc gagacccctc ccgaagacct ggacaccctg   1440

agcctggcca tcgaggcagc catccaggac ctgaggaaca agtctcag                1488
```

<210> SEQ ID NO 16
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide IE2 VacO H363A DNA sequence

<400> SEQUENCE: 16

```
atgggagaca tcctagcaca agcagtgaac catgctggaa ttgactcatc ttcgaccgga     60

ccaactctaa cgactcattc atgttcggtt agttctgctc ctcttaacaa gcctacacct    120

acctcggtag ctgttaccaa cacacccttta ccaggagcat cagcaacacc tgagttgtct    180

ccaagaaaga agcctcgtaa gaccacgaga ccgttcaagg tgatcatcaa gccaccagta    240

ccacctgctc cgatcatgtt gccattgatc aagcaggagg acattaagcc agaacctgac    300

ttcacgatac agtaccgtaa caagatcata gatacagcag gatgcatagt gatctcagat    360

agtgaagagg agcaaggtga ggaagtggag actagaggag ccacagccag ttcgccttcc    420

acaggatccg gaactcctag agtaactagt ccgacacatc cactttccca gatgaatcat    480
```

-continued

```
ccacctctac cggatcctct aggacgacca gatgaagatt cttcttcatc tagttcaagt    540

tcttgctcat ccgcgagtga tagtgagtca gaaagtgaag agatgaagtg ctcttctggt    600

ggtggagcta gtgtcacttc atctcatcat ggacgaggag gatttggagg tgctgcgagt    660

agttccttac taagttgtgg acatcagtca tctggtggtg catctactgg acctagaaag    720

aagaagtcaa agagaatctc cgaattggat aatgagaaag tgagaaacat catgaaggac    780

aagaacacgc cgttctgcac tccgaatgtt cagacgagaa gaggacgagt gaagatagat    840

gaagtatcac gaatgttcag aaacacaaat cgttctctag agtacaagaa tcttccgttc    900

accatacctt cgatgcacca agtattagat gaggctatca aggcatgtaa gaccatgcaa    960

gttaacaaca aaggaataca gatcatctac actagaaacc atgaggttaa gagtgaggtg   1020

gatgccgtac gttgtagatt gggaacgatg tgtaaccttg cgctatctac tcctttccta   1080

atggaggcta ctatgcctgt gactcatcct cctgaagtgg ctcaaagaac agctgatgct   1140

tgtaacgaag gtgtgaaagc tgcttggtcc ctaaaggagt tacatacaca ccaactttgt   1200

ccacgatcca gtgactacag aaacatgatc attcatgcag ctacgcctgt agatctactt   1260

ggagctctta acctatgtct tcctttgatg cagaagttcc ctaagcaagt gatggtgaga   1320

atcttctcga cgaatcaagg aggattcatg ttaccgatat acgagacagc tgcaaaggct   1380

tacgctgtcg gtcagttcga gcaaccgact gaaacgcctc ctgaggactt agatacattg   1440

tctttggcga tagaagcagc gattcaggat cttagaaaca agagtcag                1488


<210> SEQ ID NO 17
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide IE2 VacO H369A DNA sequence

<400> SEQUENCE: 17

atgggagaca tcctagcaca agcagtgaac catgctggaa ttgactcatc ttcgaccgga     60

ccaactctaa cgactcattc atgttcggtt agttctgctc ctcttaacaa gcctacacct    120

acctcggtag ctgttaccaa cacacccttta ccaggagcat cagcaacacc tgagttgtct   180

ccaagaaaga agcctcgtaa gaccacgaga ccgttcaagg tgatcatcaa gccaccagta    240

ccacctgctc cgatcatgtt gccattgatc aagcaggagg acattaagcc agaacctgac    300

ttcacgatac agtaccgtaa caagatcata gatacagcag gatgcatagt gatctcagat    360

agtgaagagg agcaaggtga ggaagtggag actagaggag ccacagccag ttcgccttcc    420

acaggatccg gaactcctag agtaactagt ccgacacatc cactttccca gatgaatcat    480

ccacctctac cggatcctct aggacgacca gatgaagatt cttcttcatc tagttcaagt    540

tcttgctcat ccgcgagtga tagtgagtca gaaagtgaag agatgaagtg ctcttctggt    600

ggtggagcta gtgtcacttc atctcatcat ggacgaggag gatttggagg tgctgcgagt    660

agttccttac taagttgtgg acatcagtca tctggtggtg catctactgg acctagaaag    720

aagaagtcaa agagaatctc cgaattggat aatgagaaag tgagaaacat catgaaggac    780

aagaacacgc cgttctgcac tccgaatgtt cagacgagaa gaggacgagt gaagatagat    840

gaagtatcac gaatgttcag aaacacaaat cgttctctag agtacaagaa tcttccgttc    900

accatacctt cgatgcacca agtattagat gaggctatca aggcatgtaa gaccatgcaa    960

gttaacaaca aaggaataca gatcatctac actagaaacc atgaggttaa gagtgaggtg   1020
```

-continued gatgccgtac gttgtagatt gggaacgatg tgtaaccttg cgctatctac tcctttccta 1080
atggagcata ctatgcctgt gactgctcct cctgaagtgg ctcaaagaac agctgatgct 1140
tgtaacgaag gtgtgaaagc tgcttggtcc ctaaaggagt tacatacaca ccaactttgt 1200
ccacgatcca gtgactacag aaacatgatc attcatgcag ctacgcctgt agatctactt 1260
ggagctctta acctatgtct tcctttgatg cagaagttcc ctaagcaagt gatggtgaga 1320
atcttctcga cgaatcaagg aggattcatg ttaccgatat acgagacagc tgcaaaggct 1380
tacgctgtcg gtcagttcga gcaaccgact gaaacgcctc ctgaggactt agatacattg 1440
tctttggcga tagaagcagc gattcaggat cttagaaaca agagtcag 1488

<210> SEQ ID NO 18
<211> LENGTH: 1488
<212> TYPE: DNA
<213> ORGANISM: Artificial Sequence
<220> FEATURE:
<223> OTHER INFORMATION: Description of Artificial Sequence: Synthetic polynucleotide IE2 VacO H363A/H369A DNA sequence

<400> SEQUENCE: 18
atgggagaca tcctagcaca agcagtgaac catgctggaa ttgactcatc ttcgaccgga 60
ccaactctaa cgactcattc atgttcggtt agttctgctc ctcttaacaa gcctacacct 120
acctcggtag ctgttaccaa cacaccttta ccaggagcat cagcaacacc tgagttgtct 180
ccaagaaaga agcctcgtaa gaccacgaga ccgttcaagg tgatcatcaa gccaccagta 240
ccacctgctc cgatcatgtt gccattgatc aagcaggagg acattaagcc agaacctgac 300
ttcacgatac agtaccgtaa caagatcata gatacagcag gatgcatagt gatctcagat 360
agtgaagagg agcaaggtga ggaagtggag actagaggag ccacagccag ttcgccttcc 420
acaggatccg gaactcctag agtaactagt ccgacacatc cactttccca gatgaatcat 480
ccacctctac cggatcctct aggacgacca gatgaagatt cttcttcatc tagttcaagt 540
tcttgctcat ccgcgagtga tagtgagtca gaaagtgaag agatgaagtg ctcttctggt 600
ggtggagcta gtgtcacttc atctcatcat ggacgaggag gatttggagg tgctgcgagt 660
agttccttac taagttgtgg acatcagtca tctggtggtg catctactgg acctagaaag 720
aagaagtcaa agagaatctc cgaattggat aatgagaaag tgagaaacat catgaaggac 780
aagaacacgc cgttctgcac tccgaatgtt cagacgagaa gaggacgagt gaagatagat 840
gaagtatcac gaatgttcag aaacacaaat cgttctctag agtacaagaa tcttccgttc 900
accatacctt cgatgcacca agtattagat gaggctatca aggcatgtaa gaccatgcaa 960
gttaacaaca aaggaataca gatcatctac actagaaacc atgaggttaa gagtgaggtg 1020
gatgccgtac gttgtagatt gggaacgatg tgtaaccttg cgctatctac tcctttccta 1080
atggaggcta ctatgcctgt gactgctcct cctgaagtgg ctcaaagaac agctgatgct 1140
tgtaacgaag gtgtgaaagc tgcttggtcc ctaaaggagt tacatacaca ccaactttgt 1200
ccacgatcca gtgactacag aaacatgatc attcatgcag ctacgcctgt agatctactt 1260
ggagctctta acctatgtct tcctttgatg cagaagttcc ctaagcaagt gatggtgaga 1320
atcttctcga cgaatcaagg aggattcatg ttaccgatat acgagacagc tgcaaaggct 1380
tacgctgtcg gtcagttcga gcaaccgact gaaacgcctc ctgaggactt agatacattg 1440
tctttggcga tagaagcagc gattcaggat cttagaaaca agagtcag 1488

<210> SEQ ID NO 19

-continued

```
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide IE2-VacO amino acid sequence

<400> SEQUENCE: 19

Met Gly Asp Ile Leu Ala Gln Ala Val Asn His Ala Gly Ile Asp Ser
1               5                   10                  15

Ser Ser Thr Gly Pro Thr Leu Thr Thr His Ser Cys Ser Val Ser Ser
            20                  25                  30

Ala Pro Leu Asn Lys Pro Thr Pro Thr Ser Val Ala Val Thr Asn Thr
        35                  40                  45

Pro Leu Pro Gly Ala Ser Ala Thr Pro Glu Leu Ser Pro Arg Lys Lys
    50                  55                  60

Pro Arg Lys Thr Thr Arg Pro Phe Lys Val Ile Ile Lys Pro Pro Val
65                  70                  75                  80

Pro Pro Ala Pro Ile Met Leu Pro Leu Ile Lys Gln Glu Asp Ile Lys
                85                  90                  95

Pro Glu Pro Asp Phe Thr Ile Gln Tyr Arg Asn Lys Ile Ile Asp Thr
            100                 105                 110

Ala Gly Cys Ile Val Ile Ser Asp Ser Glu Glu Glu Gln Gly Glu Glu
        115                 120                 125

Val Glu Thr Arg Gly Ala Thr Ala Ser Ser Pro Ser Thr Gly Ser Gly
    130                 135                 140

Thr Pro Arg Val Thr Ser Pro Thr His Pro Leu Ser Gln Met Asn His
145                 150                 155                 160

Pro Pro Leu Pro Asp Pro Leu Gly Arg Pro Asp Glu Asp Ser Ser Ser
                165                 170                 175

Ser Ser Ser Ser Ser Cys Ser Ser Ala Ser Asp Ser Glu Ser Glu Ser
            180                 185                 190

Glu Glu Met Lys Cys Ser Ser Gly Gly Gly Ala Ser Val Thr Ser Ser
        195                 200                 205

His His Gly Arg Gly Gly Phe Gly Gly Ala Ala Ser Ser Ser Leu Leu
    210                 215                 220

Ser Cys Gly His Gln Ser Ser Gly Gly Ala Ser Thr Gly Pro Arg Lys
225                 230                 235                 240

Lys Lys Ser Lys Arg Ile Ser Glu Leu Asp Asn Glu Lys Val Arg Asn
                245                 250                 255

Ile Met Lys Asp Lys Asn Thr Pro Phe Cys Thr Pro Asn Val Gln Thr
            260                 265                 270

Arg Arg Gly Arg Val Lys Ile Asp Glu Val Ser Arg Met Phe Arg Asn
        275                 280                 285

Thr Asn Arg Ser Leu Glu Tyr Lys Asn Leu Pro Phe Thr Ile Pro Ser
    290                 295                 300

Met His Gln Val Leu Asp Glu Ala Ile Lys Ala Cys Lys Thr Met Gln
305                 310                 315                 320

Val Asn Asn Lys Gly Ile Gln Ile Ile Tyr Thr Arg Asn His Glu Val
                325                 330                 335

Lys Ser Glu Val Asp Ala Val Arg Cys Arg Leu Gly Thr Met Cys Asn
            340                 345                 350

Leu Ala Leu Ser Thr Pro Phe Leu Met Glu His Thr Met Pro Val Thr
        355                 360                 365

His Pro Pro Glu Val Ala Gln Arg Thr Ala Asp Ala Cys Asn Glu Gly
```

```
    370                 375                 380

Val Lys Ala Ala Trp Ser Leu Lys Glu Leu His Thr His Gln Leu Cys
385                 390                 395                 400

Pro Arg Ser Ser Asp Tyr Arg Asn Met Ile Ile His Ala Ala Thr Pro
                405                 410                 415

Val Asp Leu Leu Gly Ala Leu Asn Leu Cys Leu Pro Leu Met Gln Lys
            420                 425                 430

Phe Pro Lys Gln Val Met Val Arg Ile Phe Ser Thr Asn Gln Gly Gly
        435                 440                 445

Phe Met Leu Pro Ile Tyr Glu Thr Ala Ala Lys Ala Tyr Ala Val Gly
    450                 455                 460

Gln Phe Glu Gln Pro Thr Glu Thr Pro Pro Glu Asp Leu Asp Thr Leu
465                 470                 475                 480

Ser Leu Ala Ile Glu Ala Ala Ile Gln Asp Leu Arg Asn Lys Ser Gln
                485                 490                 495


<210> SEQ ID NO 20
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide IE2 amino acid sequence

<400> SEQUENCE: 20

Met Gly Asp Ile Leu Ala Gln Ala Val Asn His Ala Gly Ile Asp Ser
1               5                   10                  15

Ser Ser Thr Gly Pro Thr Leu Thr Thr His Ser Cys Ser Val Ser Ser
            20                  25                  30

Ala Pro Leu Asn Lys Pro Thr Pro Thr Ser Val Ala Val Thr Asn Thr
        35                  40                  45

Pro Leu Pro Gly Ala Ser Ala Thr Pro Glu Leu Ser Pro Arg Lys Lys
    50                  55                  60

Pro Arg Lys Thr Thr Arg Pro Phe Lys Val Ile Ile Lys Pro Pro Val
65                  70                  75                  80

Pro Pro Ala Pro Ile Met Leu Pro Leu Ile Lys Gln Glu Asp Ile Lys
                85                  90                  95

Pro Glu Pro Asp Phe Thr Ile Gln Tyr Arg Asn Lys Ile Ile Asp Thr
            100                 105                 110

Ala Gly Cys Ile Val Ile Ser Asp Ser Glu Glu Glu Gln Gly Glu Glu
        115                 120                 125

Val Glu Thr Arg Gly Ala Thr Ala Ser Ser Pro Ser Thr Gly Ser Gly
    130                 135                 140

Thr Pro Arg Val Thr Ser Pro Thr His Pro Leu Ser Gln Met Asn His
145                 150                 155                 160

Pro Pro Leu Pro Asp Pro Leu Gly Arg Pro Asp Glu Asp Ser Ser Ser
                165                 170                 175

Ser Ser Ser Ser Ser Cys Ser Ser Ala Ser Asp Ser Glu Ser Glu Ser
            180                 185                 190

Glu Glu Met Lys Cys Ser Ser Gly Gly Gly Ala Ser Val Thr Ser Ser
        195                 200                 205

His His Gly Arg Gly Gly Phe Gly Gly Ala Ala Ser Ser Ser Leu Leu
    210                 215                 220

Ser Cys Gly His Gln Ser Ser Gly Gly Ala Ser Thr Gly Pro Arg Lys
225                 230                 235                 240
```

-continued

```
Lys Lys Ser Lys Arg Ile Ser Glu Leu Asp Asn Glu Lys Val Arg Asn
                245                 250                 255

Ile Met Lys Asp Lys Asn Thr Pro Phe Cys Thr Pro Asn Val Gln Thr
            260                 265                 270

Arg Arg Gly Arg Val Lys Ile Asp Glu Val Ser Arg Met Phe Arg Asn
        275                 280                 285

Thr Asn Arg Ser Leu Glu Tyr Lys Asn Leu Pro Phe Thr Ile Pro Ser
    290                 295                 300

Met His Gln Val Leu Asp Glu Ala Ile Lys Ala Cys Lys Thr Met Gln
305                 310                 315                 320

Val Asn Asn Lys Gly Ile Gln Ile Ile Tyr Thr Arg Asn His Glu Val
                325                 330                 335

Lys Ser Glu Val Asp Ala Val Arg Cys Arg Leu Gly Thr Met Cys Asn
            340                 345                 350

Leu Ala Leu Ser Thr Pro Phe Leu Met Glu His Thr Met Pro Val Thr
        355                 360                 365

His Pro Pro Glu Val Ala Gln Arg Thr Ala Asp Ala Cys Asn Glu Gly
    370                 375                 380

Val Lys Ala Ala Trp Ser Leu Lys Glu Leu His Thr His Gln Leu Cys
385                 390                 395                 400

Pro Arg Ser Ser Asp Tyr Arg Asn Met Ile Ile His Ala Ala Thr Pro
                405                 410                 415

Val Asp Leu Leu Gly Ala Leu Asn Leu Cys Leu Pro Leu Met Gln Lys
            420                 425                 430

Phe Pro Lys Gln Val Met Val Arg Ile Phe Ser Thr Asn Gln Gly Gly
        435                 440                 445

Phe Met Leu Pro Ile Tyr Glu Thr Ala Ala Lys Ala Tyr Ala Val Gly
    450                 455                 460

Gln Phe Glu Gln Pro Thr Glu Thr Pro Pro Glu Asp Leu Asp Thr Leu
465                 470                 475                 480

Ser Leu Ala Ile Glu Ala Ala Ile Gln Asp Leu Arg Asn Lys Ser Gln
                485                 490                 495


<210> SEQ ID NO 21
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide IE2-4nt amino acid sequence

<400> SEQUENCE: 21

Met Gly Asp Ile Leu Ala Gln Ala Val Asn His Ala Gly Ile Asp Ser
1               5                   10                  15

Ser Ser Thr Gly Pro Thr Leu Thr Thr His Ser Cys Ser Val Ser Ser
            20                  25                  30

Ala Pro Leu Asn Lys Pro Thr Pro Thr Ser Val Ala Val Thr Asn Thr
        35                  40                  45

Pro Leu Pro Gly Ala Ser Ala Thr Pro Glu Leu Ser Pro Arg Lys Lys
    50                  55                  60

Pro Arg Lys Thr Thr Arg Pro Phe Lys Val Ile Ile Lys Pro Pro Val
65                  70                  75                  80

Pro Pro Ala Pro Ile Met Leu Pro Leu Ile Lys Gln Glu Asp Ile Lys
                85                  90                  95

Pro Glu Pro Asp Phe Thr Ile Gln Tyr Arg Asn Lys Ile Ile Asp Thr
            100                 105                 110
```

-continued

```
Ala Gly Cys Ile Val Ile Ser Asp Ser Glu Glu Glu Gln Gly Glu Glu
        115                 120                 125

Val Glu Thr Arg Gly Ala Thr Ala Ser Ser Pro Ser Thr Gly Ser Gly
    130                 135                 140

Thr Pro Arg Val Thr Ser Pro Thr His Pro Leu Ser Gln Met Asn His
145                 150                 155                 160

Pro Pro Leu Pro Asp Pro Leu Gly Arg Pro Asp Glu Asp Ser Ser Ser
                165                 170                 175

Ser Ser Ser Ser Ser Cys Ser Ser Ala Ser Asp Ser Glu Ser Glu Ser
            180                 185                 190

Glu Glu Met Lys Cys Ser Ser Gly Gly Gly Ala Ser Val Thr Ser Ser
        195                 200                 205

His His Gly Arg Gly Gly Phe Gly Gly Ala Ala Ser Ser Ser Leu Leu
    210                 215                 220

Ser Cys Gly His Gln Ser Ser Gly Gly Ala Ser Thr Gly Pro Arg Lys
225                 230                 235                 240

Lys Lys Ser Lys Arg Ile Ser Glu Leu Asp Asn Glu Lys Val Arg Asn
                245                 250                 255

Ile Met Lys Asp Lys Asn Thr Pro Phe Cys Thr Pro Asn Val Gln Thr
            260                 265                 270

Arg Arg Gly Arg Val Lys Ile Asp Glu Val Ser Arg Met Phe Arg Asn
        275                 280                 285

Thr Asn Arg Ser Leu Glu Tyr Lys Asn Leu Pro Phe Thr Ile Pro Ser
    290                 295                 300

Met His Gln Val Leu Asp Glu Ala Ile Lys Ala Cys Lys Thr Met Gln
305                 310                 315                 320

Val Asn Asn Lys Gly Ile Gln Ile Ile Tyr Thr Arg Asn His Glu Val
                325                 330                 335

Lys Ser Glu Val Asp Ala Val Arg Cys Arg Leu Gly Thr Met Cys Asn
            340                 345                 350

Leu Ala Leu Ser Thr Pro Phe Leu Met Glu His Thr Met Pro Val Thr
        355                 360                 365

His Pro Pro Glu Val Ala Gln Arg Thr Ala Asp Ala Cys Asn Glu Gly
    370                 375                 380

Val Lys Ala Ala Trp Ser Leu Lys Glu Leu His Thr His Gln Leu Cys
385                 390                 395                 400

Pro Arg Ser Ser Asp Tyr Arg Asn Met Ile Ile His Ala Ala Thr Pro
                405                 410                 415

Val Asp Leu Leu Gly Ala Leu Asn Leu Cys Leu Pro Leu Met Gln Lys
            420                 425                 430

Phe Pro Lys Gln Val Met Val Arg Ile Phe Ser Thr Asn Gln Gly Gly
        435                 440                 445

Phe Met Leu Pro Ile Tyr Glu Thr Ala Ala Lys Ala Tyr Ala Val Gly
    450                 455                 460

Gln Phe Glu Gln Pro Thr Glu Thr Pro Pro Glu Asp Leu Asp Thr Leu
465                 470                 475                 480

Ser Leu Ala Ile Glu Ala Ala Ile Gln Asp Leu Arg Asn Lys Ser Gln
                485                 490                 495
```

<210> SEQ ID NO 22
<211> LENGTH: 496
<212> TYPE: PRT
<213> ORGANISM: Artificial Sequence
<220> FEATURE:

<223> OTHER INFORMATION: Description of Artificial Sequence: Synthetic
polypeptide IE2 H363A amino acid sequence

<400> SEQUENCE: 22

```
Met Gly Asp Ile Leu Ala Gln Ala Val Asn His Ala Gly Ile Asp Ser
1               5                   10                  15

Ser Ser Thr Gly Pro Thr Leu Thr Thr His Ser Cys Ser Val Ser Ser
            20                  25                  30

Ala Pro Leu Asn Lys Pro Thr Pro Thr Ser Val Ala Val Thr Asn Thr
        35                  40                  45

Pro Leu Pro Gly Ala Ser Ala Thr Pro Glu Leu Ser Pro Arg Lys Lys
    50                  55                  60

Pro Arg Lys Thr Thr Arg Pro Phe Lys Val Ile Ile Lys Pro Pro Val
65                  70                  75                  80

Pro Pro Ala Pro Ile Met Leu Pro Leu Ile Lys Gln Glu Asp Ile Lys
                85                  90                  95

Pro Glu Pro Asp Phe Thr Ile Gln Tyr Arg Asn Lys Ile Ile Asp Thr
            100                 105                 110

Ala Gly Cys Ile Val Ile Ser Asp Ser Glu Glu Glu Gln Gly Glu Glu
        115                 120                 125

Val Glu Thr Arg Gly Ala Thr Ala Ser Ser Pro Ser Thr Gly Ser Gly
    130                 135                 140

Thr Pro Arg Val Thr Ser Pro Thr His Pro Leu Ser Gln Met Asn His
145                 150                 155                 160

Pro Pro Leu Pro Asp Pro Leu Gly Arg Pro Asp Glu Asp Ser Ser Ser
                165                 170                 175

Ser Ser Ser Ser Ser Cys Ser Ser Ala Ser Asp Ser Glu Ser Glu Ser
            180                 185                 190

Glu Glu Met Lys Cys Ser Ser Gly Gly Gly Ala Ser Val Thr Ser Ser
        195                 200                 205

His His Gly Arg Gly Gly Phe Gly Gly Ala Ala Ser Ser Ser Leu Leu
    210                 215                 220

Ser Cys Gly His Gln Ser Ser Gly Gly Ala Ser Thr Gly Pro Arg Lys
225                 230                 235                 240

Lys Lys Ser Lys Arg Ile Ser Glu Leu Asp Asn Glu Lys Val Arg Asn
                245                 250                 255

Ile Met Lys Asp Lys Asn Thr Pro Phe Cys Thr Pro Asn Val Gln Thr
            260                 265                 270

Arg Arg Gly Arg Val Lys Ile Asp Glu Val Ser Arg Met Phe Arg Asn
        275                 280                 285

Thr Asn Arg Ser Leu Glu Tyr Lys Asn Leu Pro Phe Thr Ile Pro Ser
    290                 295                 300

Met His Gln Val Leu Asp Glu Ala Ile Lys Ala Cys Lys Thr Met Gln
305                 310                 315                 320

Val Asn Asn Lys Gly Ile Gln Ile Ile Tyr Thr Arg Asn His Glu Val
                325                 330                 335

Lys Ser Glu Val Asp Ala Val Arg Cys Arg Leu Gly Thr Met Cys Asn
            340                 345                 350

Leu Ala Leu Ser Thr Pro Phe Leu Met Glu Ala Thr Met Pro Val Thr
        355                 360                 365

His Pro Pro Glu Val Ala Gln Arg Thr Ala Asp Ala Cys Asn Glu Gly
    370                 375                 380

Val Lys Ala Ala Trp Ser Leu Lys Glu Leu His Thr His Gln Leu Cys
385                 390                 395                 400
```

```
Pro Arg Ser Ser Asp Tyr Arg Asn Met Ile Ile His Ala Ala Thr Pro
                405                 410                 415

Val Asp Leu Leu Gly Ala Leu Asn Leu Cys Leu Pro Leu Met Gln Lys
            420                 425                 430

Phe Pro Lys Gln Val Met Val Arg Ile Phe Ser Thr Asn Gln Gly Gly
        435                 440                 445

Phe Met Leu Pro Ile Tyr Glu Thr Ala Ala Lys Ala Tyr Ala Val Gly
    450                 455                 460

Gln Phe Glu Gln Pro Thr Glu Thr Pro Pro Glu Asp Leu Asp Thr Leu
465                 470                 475                 480

Ser Leu Ala Ile Glu Ala Ala Ile Gln Asp Leu Arg Asn Lys Ser Gln
                485                 490                 495


<210> SEQ ID NO 23
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide IE2 H369A amino acid sequence

<400> SEQUENCE: 23

Met Gly Asp Ile Leu Ala Gln Ala Val Asn His Ala Gly Ile Asp Ser
1               5                   10                  15

Ser Ser Thr Gly Pro Thr Leu Thr Thr His Ser Cys Ser Val Ser Ser
            20                  25                  30

Ala Pro Leu Asn Lys Pro Thr Pro Thr Ser Val Ala Val Thr Asn Thr
        35                  40                  45

Pro Leu Pro Gly Ala Ser Ala Thr Pro Glu Leu Ser Pro Arg Lys Lys
    50                  55                  60

Pro Arg Lys Thr Thr Arg Pro Phe Lys Val Ile Ile Lys Pro Pro Val
65                  70                  75                  80

Pro Pro Ala Pro Ile Met Leu Pro Leu Ile Lys Gln Glu Asp Ile Lys
                85                  90                  95

Pro Glu Pro Asp Phe Thr Ile Gln Tyr Arg Asn Lys Ile Ile Asp Thr
            100                 105                 110

Ala Gly Cys Ile Val Ile Ser Asp Ser Glu Glu Glu Gln Gly Glu Glu
        115                 120                 125

Val Glu Thr Arg Gly Ala Thr Ala Ser Ser Pro Ser Thr Gly Ser Gly
    130                 135                 140

Thr Pro Arg Val Thr Ser Pro Thr His Pro Leu Ser Gln Met Asn His
145                 150                 155                 160

Pro Pro Leu Pro Asp Pro Leu Gly Arg Pro Asp Glu Asp Ser Ser Ser
                165                 170                 175

Ser Ser Ser Ser Ser Cys Ser Ser Ala Ser Asp Ser Glu Ser Glu Ser
            180                 185                 190

Glu Glu Met Lys Cys Ser Ser Gly Gly Gly Ala Ser Val Thr Ser Ser
        195                 200                 205

His His Gly Arg Gly Gly Phe Gly Gly Ala Ala Ser Ser Ser Leu Leu
    210                 215                 220

Ser Cys Gly His Gln Ser Ser Gly Gly Ala Ser Thr Gly Pro Arg Lys
225                 230                 235                 240

Lys Lys Ser Lys Arg Ile Ser Glu Leu Asp Asn Glu Lys Val Arg Asn
                245                 250                 255

Ile Met Lys Asp Lys Asn Thr Pro Phe Cys Thr Pro Asn Val Gln Thr
```

260 265 270

Arg Arg Gly Arg Val Lys Ile Asp Glu Val Ser Arg Met Phe Arg Asn
275 280 285

Thr Asn Arg Ser Leu Glu Tyr Lys Asn Leu Pro Phe Thr Ile Pro Ser
290 295 300

Met His Gln Val Leu Asp Glu Ala Ile Lys Ala Cys Lys Thr Met Gln
305 310 315 320

Val Asn Asn Lys Gly Ile Gln Ile Ile Tyr Thr Arg Asn His Glu Val
325 330 335

Lys Ser Glu Val Asp Ala Val Arg Cys Arg Leu Gly Thr Met Cys Asn
340 345 350

Leu Ala Leu Ser Thr Pro Phe Leu Met Glu His Thr Met Pro Val Thr
355 360 365

Ala Pro Pro Glu Val Ala Gln Arg Thr Ala Asp Ala Cys Asn Glu Gly
370 375 380

Val Lys Ala Ala Trp Ser Leu Lys Glu Leu His Thr His Gln Leu Cys
385 390 395 400

Pro Arg Ser Ser Asp Tyr Arg Asn Met Ile Ile His Ala Ala Thr Pro
405 410 415

Val Asp Leu Leu Gly Ala Leu Asn Leu Cys Leu Pro Leu Met Gln Lys
420 425 430

Phe Pro Lys Gln Val Met Val Arg Ile Phe Ser Thr Asn Gln Gly Gly
435 440 445

Phe Met Leu Pro Ile Tyr Glu Thr Ala Ala Lys Ala Tyr Ala Val Gly
450 455 460

Gln Phe Glu Gln Pro Thr Glu Thr Pro Pro Glu Asp Leu Asp Thr Leu
465 470 475 480

Ser Leu Ala Ile Glu Ala Ala Ile Gln Asp Leu Arg Asn Lys Ser Gln
485 490 495

<210> SEQ ID NO 24
<211> LENGTH: 496
<212> TYPE: PRT
<213> ORGANISM: Artificial Sequence
<220> FEATURE:
<223> OTHER INFORMATION: Description of Artificial Sequence: Synthetic polypeptide IE2 H363A/H369A amino acid sequence

<400> SEQUENCE: 24

Met Gly Asp Ile Leu Ala Gln Ala Val Asn His Ala Gly Ile Asp Ser
1 5 10 15

Ser Ser Thr Gly Pro Thr Leu Thr Thr His Ser Cys Ser Val Ser Ser
20 25 30

Ala Pro Leu Asn Lys Pro Thr Pro Thr Ser Val Ala Val Thr Asn Thr
35 40 45

Pro Leu Pro Gly Ala Ser Ala Thr Pro Glu Leu Ser Pro Arg Lys Lys
50 55 60

Pro Arg Lys Thr Thr Arg Pro Phe Lys Val Ile Ile Lys Pro Pro Val
65 70 75 80

Pro Pro Ala Pro Ile Met Leu Pro Leu Ile Lys Gln Glu Asp Ile Lys
85 90 95

Pro Glu Pro Asp Phe Thr Ile Gln Tyr Arg Asn Lys Ile Ile Asp Thr
100 105 110

Ala Gly Cys Ile Val Ile Ser Asp Ser Glu Glu Glu Gln Gly Glu Glu
115 120 125

-continued

```
Val Glu Thr Arg Gly Ala Thr Ala Ser Ser Pro Ser Thr Gly Ser Gly
    130                 135                 140

Thr Pro Arg Val Thr Ser Pro Thr His Pro Leu Ser Gln Met Asn His
145                 150                 155                 160

Pro Pro Leu Pro Asp Pro Leu Gly Arg Pro Asp Glu Asp Ser Ser Ser
                165                 170                 175

Ser Ser Ser Ser Ser Cys Ser Ser Ala Ser Asp Ser Glu Ser Glu Ser
            180                 185                 190

Glu Glu Met Lys Cys Ser Ser Gly Gly Gly Ala Ser Val Thr Ser Ser
        195                 200                 205

His His Gly Arg Gly Gly Phe Gly Gly Ala Ala Ser Ser Ser Leu Leu
    210                 215                 220

Ser Cys Gly His Gln Ser Ser Gly Gly Ala Ser Thr Gly Pro Arg Lys
225                 230                 235                 240

Lys Lys Ser Lys Arg Ile Ser Glu Leu Asp Asn Glu Lys Val Arg Asn
                245                 250                 255

Ile Met Lys Asp Lys Asn Thr Pro Phe Cys Thr Pro Asn Val Gln Thr
            260                 265                 270

Arg Arg Gly Arg Val Lys Ile Asp Glu Val Ser Arg Met Phe Arg Asn
        275                 280                 285

Thr Asn Arg Ser Leu Glu Tyr Lys Asn Leu Pro Phe Thr Ile Pro Ser
    290                 295                 300

Met His Gln Val Leu Asp Glu Ala Ile Lys Ala Cys Lys Thr Met Gln
305                 310                 315                 320

Val Asn Asn Lys Gly Ile Gln Ile Ile Tyr Thr Arg Asn His Glu Val
                325                 330                 335

Lys Ser Glu Val Asp Ala Val Arg Cys Arg Leu Gly Thr Met Cys Asn
            340                 345                 350

Leu Ala Leu Ser Thr Pro Phe Leu Met Glu Ala Thr Met Pro Val Thr
        355                 360                 365

Ala Pro Pro Glu Val Ala Gln Arg Thr Ala Asp Ala Cys Asn Glu Gly
    370                 375                 380

Val Lys Ala Ala Trp Ser Leu Lys Glu Leu His Thr His Gln Leu Cys
385                 390                 395                 400

Pro Arg Ser Ser Asp Tyr Arg Asn Met Ile Ile His Ala Ala Thr Pro
                405                 410                 415

Val Asp Leu Leu Gly Ala Leu Asn Leu Cys Leu Pro Leu Met Gln Lys
            420                 425                 430

Phe Pro Lys Gln Val Met Val Arg Ile Phe Ser Thr Asn Gln Gly Gly
        435                 440                 445

Phe Met Leu Pro Ile Tyr Glu Thr Ala Ala Lys Ala Tyr Ala Val Gly
    450                 455                 460

Gln Phe Glu Gln Pro Thr Glu Thr Pro Pro Glu Asp Leu Asp Thr Leu
465                 470                 475                 480

Ser Leu Ala Ile Glu Ala Ala Ile Gln Asp Leu Arg Asn Lys Ser Gln
                485                 490                 495
```

<210> SEQ ID NO 25

<400> SEQUENCE: 25

000

<210> SEQ ID NO 26

<400> SEQUENCE: 26

000

<210> SEQ ID NO 27
<211> LENGTH: 1224
<212> TYPE: DNA
<213> ORGANISM: Artificial Sequence
<220> FEATURE:
<223> OTHER INFORMATION: Description of Artificial Sequence: Synthetic
polynucleotide IE1 VacO

<400> SEQUENCE: 27
atggtgaagc aaatcaaggt cagagtggac atggtaagac acagaattaa ggaacacatg 60
ttgaagaagt atactcaaac agaggagaag ttcaccggtg ccttcaatat gatgggtgga 120
tgtctacaga acgctttgga tatcttagat aaggtacatg aaccattcga agaaatgaag 180
tgcattggat tgacaatgca atcaatgtat gagaactaca tagtgccaga ggataagcgt 240
gaaatgtgga tggcatgcat caaggagtta catgatgtat ccaaaggagc agccaacaag 300
ctaggtggtg ctttgcaagc gaaggcaaga gcgaagaagg atgaattgag acgaaagatg 360
atgtacatgt gctatcgaaa catcgaattc ttcactaaga actcagcgtt tcctaagact 420
accaatggat gcagtcaagc tatggctgcg cttcagaact tgcctcaatg tagtcctgat 480
gaaatcatgg catatgcaca gaagatcttc aagatcttag atgaggaaag agacaaggta 540
ttgactcata tcgatcacat attcatggat atactaacaa catgtgtaga aacgatgtgt 600
aacgagtaca aggtaacttc ggacgcttgt atgatgacta tgtacggagg aatatctcta 660
cttagtgagt tctgtcgagt tctatgctgt tacgtattag aagaaactag tgtaatgtta 720
gcgaagagac cattgatcac taagcctgaa gtgatctcgg ttatgaagag acgaatagag 780
gagatctgta tgaaggtgtt cgcacaatac atcttaggag ctgatcctct aagagtgtgt 840
agtccatcgg tagacgattt gagagctata gcggaggaat ctgacgagga agaggcaata 900
gttgcataca cacttgctac agctggagta tccagttctg attctcttgt aagtcctccg 960
gagtcacctg tgccagcaac cataccgttg agtagtgtga ttgtggctga gaactcggat 1020
caggaagagt ctgagcaatc cgatgaagaa gaggaggaag gagcacaaga ggagagagaa 1080
gatactgtct ctgtgaagag tgaacctgta tctgaaatcg aggaagtagc acctgaggaa 1140
gaggaggatg gagccgaaga accaacagct tcgggtggta agtcaactca tccgatggta 1200
accagatcta aggcagacca gtaa 1224

<210> SEQ ID NO 28
<211> LENGTH: 1194
<212> TYPE: DNA
<213> ORGANISM: Artificial Sequence
<220> FEATURE:
<223> OTHER INFORMATION: Description of Artificial Sequence: Synthetic
polynucleotide IE1

<400> SEQUENCE: 28
atggtgcggc atagaatcaa ggagcacatg ctgaaaaaat atacccagac ggaagagaaa 60
ttcactggcg cctttaatat gatgggagga tgtttgcaga atgccttaga tatcttagat 120
aaggttcatg agcctttcga ggagatgaag tgtattgggc taactatgca gagcatgtat 180
gagaactaca ttgtacctga ggataagcgg gagatgtgga tggcttgtat taaggagctg 240
catgatgtga gcaagggcgc cgctaacaag ttgggggggtg cactgcaggc taaggcccgt 300
gctaaaaagg atgaacttag gagaaagatg atgtatatgt gctacaggaa tatagagttc 360

```
tttaccaaga actcagcctt ccctaagacc accaatggct gcagtcaggc catggcggca    420

ctgcagaact tgcctcagtg ctccccctgat gagattatgg cttatgccca gaaaatattt    480

aagattttgg atgaggagag agacaaggtg ctcacgcaca ttgatcacat atttatggat    540

atcctcacta catgtgtgga aacaatgtgt aatgagtaca aggtcactag tgacgcttgt    600

atgatgacca tgtacggggg catctctctc ttaagtgagt tctgtcgggt gctgtgctgc    660

tatgtcttag aggagactag tgtgatgctg gccaagcggc ctctgataac caagcctgag    720

gttatcagtg taatgaagcg ccgcattgag gagatctgca tgaaggtctt tgcccagtac    780

attctggggg ccgatcctct gagagtctgc tctcctagtg tggatgacct acgggccatc    840

gccgaggagt cagatgagga agaggctatt gtagcctaca ctttggccac cgctggtgtc    900

agctcctctg attctctggt gtcacccccca gagtcccctg tacccgcgac tatccctctg    960

tcctcagtaa ttgtggctga gaacagtgat caggaagaaa gtgagcagag tgatgaggaa   1020

gaggaggagg gtgctcagga ggagcgggag gacactgtgt ctgtcaagtc tgagccagtg   1080

tctgagatag aggaagttgc cccagaggaa gaggaggatg gtgctgagga acccaccgcc   1140

tctggaggca agagcaccca ccctatggtg actagaagca aggctgacca gtaa         1194
```

<210> SEQ ID NO 29
<211> LENGTH: 1224
<212> TYPE: DNA
<213> ORGANISM: Artificial Sequence
<220> FEATURE:
<223> OTHER INFORMATION: Description of Artificial Sequence: Synthetic
      polynucleotide IE1-4nt

<400> SEQUENCE: 29

```
atggtcaaac agattaaggt tcgagtggac atggtgcggc atagaatcaa ggagcacatg     60

ctgaagaagt atacccagac ggaagagaaa ttcactggcg cctttaatat gatgggagga    120

tgtttgcaga atgccttaga tatcttagat aaggttcatg agcctttcga ggagatgaag    180

tgtattgggc taactatgca gagcatgtat gagaactaca ttgtacctga ggataagcgg    240

gagatgtgga tggcttgtat taaggagctg catgatgtga gcaagggcgc cgctaacaag    300

ttaggaggtg cactgcaggc taaggcccgt gctaagaagg atgaacttag gagaaagatg    360

atgtatatgt gctacaggaa tatagagttc tttaccaaga actcagcctt ccctaagacc    420

accaatggct gcagtcaggc catggcggca ctgcagaact tgcctcagtg ctctcctgat    480

gagattatgg cttatgccca gaagatattt aagatcttgg atgaggagag agacaaggtg    540

ctcacgcaca ttgatcacat atttatggat atcctcacta catgtgtgga aacaatgtgt    600

aatgagtaca aggtcactag tgacgcttgt atgatgacca tgtacggagg catctctctc    660

ttaagtgagt tctgtcgggt gctgtgctgc tatgtcttag aggagactag tgtgatgctg    720

gccaagcggc ctctgataac caagcctgag gttatcagtg taatgaagcg ccgcattgag    780

gagatctgca tgaaggtctt tgcccagtac attctaggtg ccgatcctct gagagtctgc    840

tctcctagtg tggatgacct acgggccatc gccgaggagt cagatgagga agaggctatt    900

gtagcctaca ctttggccac cgctggtgtc agctcctctg attctctggt gtcacctcca    960

gagtcacctg tacccgcgac tatccctctg tcctcagtaa ttgtggctga gaacagtgat   1020
```

-continued

```
caggaagaaa gtgagcagag tgatgaggaa gaggaggagg gtgctcagga ggagcgggag   1080

gacactgtgt ctgtcaagtc tgagccagtg tctgagatag aggaagttgc tccagaggaa   1140

gaggaggatg gtgctgagga acccaccgcc tctggaggca agagcaccca ccctatggtg   1200

actagaagca aggctgacca gtaa                                          1224
```

GENETICALLY MODIFIED RECOMBINANT VACCINIA ANKARA (RMVA) VACCINES OF IMPROVED STABILITY AND METHODS OF PREPARATION THEREOF

PRIORITY CLAIM

This application is a continuation of International Application No. PCT/US2019/031866, filed May 10, 2019, which claims priority to U.S. Provisional Application No. 62/670, 656, filed on May 11, 2018, both of which are incorporated by reference herein in their entirety, including drawings.

STATEMENT OF GOVERNMENT INTEREST

This invention was made with government support under Grant Number CA077544, awarded by the National Institutes of Health. The government has certain rights in the invention.

SEQUENCE LISTING

This application contains a Sequence Listing, which was submitted n ASCII format via EFS-Web, and is hereby incorporated by reference in its entirety. The ASCII copy, created on Nov. 11, 2020, is named SequenceListing.txt and is 91 KB in size.

BACKGROUND

Modified Vaccinia Ankara (MVA) is a genetically engineered, highly attenuated strain of vaccinia virus that does not propagate in most mammalian cells. This property minimally impacts viral or foreign gene expression because the ability of MVA to propagate in mammalian cells is blocked at late stage viral assembly. However, the DNA continues to replicate and therefore acts as an efficient template for RNA biosynthesis leading to high levels of protein synthesis. MVA also has a large foreign gene capacity and multiple integration sites, two features that make it a desirable vector for expressing vaccine antigens. MVA has a well-established safety record and versatility for the production of heterologous proteins. In fact, MVA-based vaccines for treatment of infectious disease and cancer have been developed and reached Phase I/II clinical trials.

MVA has an extensive history of successful delivery into rodents, Rhesus macaques, and other non-human primates, and more recently as a clinical vaccine in cancer patients. The original MVA virus was administered to 120,000 young and elderly in Europe in the 1970s. MVA is avirulent because of the loss of two important host-range genes among 25 mutations and deletions that occurred during its repeated serial passage in chicken cells.

MVA is appealing as a vaccine vector for CMV antigens in individuals who are both severely immunosuppressed and experiencing additional complications such as malignancy or organ failure, thereby requiring a transplant. CMV infection is an important complication of transplantation procedures and affects a wide variety of individuals including newborns and HIV patients with advanced disease. Human cytomegalovirus (HCMV) is a major risk factor for recipients of solid organ and hematopoietic stem cell transplants. Individuals who are previously CMV-infected or receiving a CMV-infected solid organ or stem cell allograft are candidates for a vaccine strategy that targets the cellular reservoir of the virus.

It has been reported that in vitro expression levels of foreign antigens by an rMVA vaccine are correlated with the rMVA vaccine's immunogenicity. However, after serial passage, the foreign antigen expression may be reduced, which can result in diminished immunogenicity. Thus, while MVA is an attractive viral vector for recombinant vaccine development, genetic instability and diminished immunogenicity are significant concerns after serial passage. The beneficial effect of high antigen expression levels and improved immunogenicity can be limited by the propensity of rMVA to delete genes unnecessary for its lifecycle.

A first generation "Triplex" vaccine was constructed to attenuate or suppress ongoing CMV viremia and its propagation. The first-generation Triplex includes three immunodominant proteins: pp65 (major tegument protein) and a fusion between immediate early proteins IE1 and IE2 (IEfusion). These antigens have previously been combined and expressed in a single MVA vector; however, the current assembly of these antigens within MVA is not optimal for mass production of a vaccine. Upon extended viral passage, a decrease in expression of IEfusion was observed. This vaccine was successfully evaluated in a Phase I safety and dose escalation trial in 24 healthy volunteers [31].

It will be advantageous to develop an rMVA vaccine with improved stable expression of foreign protein antigens and potent immunogenicity after extended serial passage, which will enable large scale manufacturing of MVA expressing certain HCMV antigens as a clinical vector for a broader portfolio of infectious pathogens and cancer antigens.

SUMMARY

In one aspect, this disclosure is directed to an expression system for co-expressing two or more cytomegalovirus (CMV) antigens, e.g. human CMV antigens. The expression system includes a genetically recombinant modified Vaccinia Ankara (rMVA) vector inserted with two or more nucleic acid sequences encoding two or more CMV antigens or antigenic portions thereof. In some embodiments, the CMV antigens or antigenic fragments thereof include IE1 exon 4 (IE1/e4), IE2 exon 5 (IE2/e5), IEfusion (e.g. fusion of IE1/e4 and IE2/e5), and pp65. In various embodiments, pp65 can be co-expressed with IE1/e4, IE2/e5, or IEfusion. The expression system can co-express the CMV antigens simultaneously from a single vector. In some embodiments, the nucleic acid sequences encoding the two or more CMV antigens are inserted in one or more insertion sites including 044L/045L, IGR3, G1L/18R, and Del3. Additional insertion sites include those listed in Table 1.

In some embodiments, two or more nucleic acid sequences are operably linked to and under the control of a single promoter, such as the mH5 promoter. In other embodiments, each nucleic acid sequence is operably linked to and under the control of a separate mH5 promoter. Additionally, other poxvirus promoters can be used and the use of an mH5 promoter is not required. In some embodiments, one or more nucleic acid sequences are codon optimized to remove consecutive cytosines or guanines while expressing without alteration of the same amino acids. In some embodiments, the amino acid sequences of the CMV antigens comprise one or more mutations to improve the genetic stability of the rMVA upon viral passaging. In some embodiments, IE1 and IE2 or antigenic fragments thereof are expressed as an IE fusion protein such as a fusion of IE1/exon 4 and IE2/exon 5. In some embodiments, the MVA expressing the CMV antigens is genetically stable for at least 10 passages.

Another aspect of this disclosure is directed to a vaccine comprising an immunologically effective amount of the recombinant modified vaccinia Ankara (rMVA) disclosed herein which is genetically stable after at least 10 passages.

Another aspect of this disclosure is directed to a method of eliciting or modifying an immune response and clinical protection against viremia and diseases caused by uncontrolled propagation of CMV in a subject by administering a vaccine composition as described above to the subject. In some embodiments, the subject is a mammal, such as a human.

Yet another aspect of this disclosure is directed to a method of improving the stability upon passage of an rMVA expressing two or more CMV antigens or antigenic fragments thereof by incorporating one or more of the following modifications: (1) inserting one or more nucleic acid sequences encoding the CMV antigens or antigenic fragments thereof into one or more insertion sites including 044L/045L, IGR3, G1L/18R, and Del3, as well as additional insertion sites listed in Table 1, not including Del2; (2) codon optimizing the nucleic acid sequences encoding the CMV antigens by removing consecutive cytosines or guanines; and (3) introducing one or more mutations in the amino acid sequences of the CMV antigens. In some embodiments, the CMV antigens or antigenic fragments thereof include IE1 exon 4 (IE1/e4), IE2 exon 5 (IE2/e5), IEfusion (e.g. fusion of IE1 and IE2 or IE1/e4 and IE2/e5), and pp65.

BRIEF DESCRIPTION OF THE DRAWINGS

FIG. 2A shows an abbreviated schematic of the original construction of IEfusion in Triplex. HCMV AD169 exons 4 and 5 for IE1 and IE2, respectively, were engineered with an ApaI site for a seamless junction, resulting in IEfusion. IEfusion was inserted into the Del2 site of MVA, controlled by the mH5 promoter. In the MVA Del3 site is pp65, also controlled by the mH5 promoter. FIG. 2B shows Western blot analysis of clinical Triplex passaged up to seven additional times (P6-P12) in CEF. Lane labeled "CEF" is uninfected, negative control; lane labeled "MVA" is wild-type MVA not expressing CMV antigens; lane labeled "Triplex" is virus used to generate clinical lots of Triplex at P5. IEfusion was probed using a purified anti-IE1 mouse monoclonal antibody (mAB) p63-27 [11]; pp65 was probed using purified mouse mAB 28-103 [4]. As an infection/loading control, BR5 antibody was used to probe against an envelope MVA glycoprotein. FIG. 2C shows 1% agarose gel visualizing PCR-amplification of IEfusion in Del2 from P6-P12, with primers flanking the gene within the Del2 site.

FIGS. 3A-3D show the nucleic acid sequence alignment of IEfusion constructs with mutations to the consecutive cytosines and guanines thereby reducing instability and/or vaccinia codon optimization for protein expression. SEQ ID NOs: 1-3.

FIG. 4A shows a schematic representing the insertion of IEfusion (4nt) into the IGR3 site (shown with an arrow). All evaluated MVA BAC insertion sites, G1L/18R, 044L/045L, and IGR3, are noted with arrows. FIG. 4B shows 1% agarose gel of PCR product analyzing stability of IEfusion (4nt) in IGR3, passaged up to ten times (P1-P10) in chicken embryonic fibroblasts (CEFs). FIG. 4C shows Western blot analysis of IEfusion (4nt) passaged up to P10 in CEF cells. IEfusion was probed using a purified anti-IE1 mouse monoclonal antibody (mAB) p63-27 [11]; pp65 was probed using purified mouse mAB 28-103 [4]. As an infection/loading control, BR5 antibody was used to probe against an envelope MVA glycoprotein. For FIGS. 4B and 4C, lane labeled "CEF" is uninfected, negative control; lane labeled "MVA" is wildtype MVA not expressing any antigen; lane labeled "Triplex" is virus (at P6) used to generate clinical lots of Triplex.

FIGS. 6A-6E show the nucleic acid sequence alignment of constructs expressing IE2 protein variants (6A-6C) (SEQ ID NOs: 7-9 and 26) and the nucleic acid sequence alignment of constructs expressing IE1 protein variants (6D-6E). SEQ ID NOS: 27-29.

FIG. 7A shows a schematic representing the insertion of IE2 into the 044L/045L site (shown with an arrow). FIG. 7B shows 1% agarose gel of PCR product analyzing stability of IE2 in 044L/045L, passaged up to ten times (P1-P10) in chicken embryonic fibroblasts (CEFs). FIG. 7C shows Western blot analysis of IE2 passaged up to P10 in CEF cells. IE2 was probed using an anti-IE2 mouse monoclonal antibody (mAB) 2.9.5 [11]; pp65 was probed using purified mouse mAB 28-103 [4]. As an infection/loading control, BR5 antibody was used to probe against an envelope MVA glycoprotein. For FIGS. 7B and 7C, lane labeled "CEF" is uninfected, negative control; lane labeled "MVA" is wildtype MVA not expressing any antigen; lane labeled "Triplex" is virus used to generate clinical lots of Triplex at P6.

FIG. 8A shows a schematic representation of IE2, showing the location of two histidine residues at positions 363 and 369 (H363 and H369) within the specific and essential modulator (SEM, heavily shaded gray with corresponding arrow) and core (lightly shaded with corresponding arrow). Within the IE2 amino acid sequence, an internal TATA box for the transcription of a putative ~40 kDa product is labeled [18]. This amino acid annotation is consistent with the amino acid numbers corresponding to IE2 lacking a nuclear localization signal or a signal peptide. FIG. 8B shows 1% agarose gel of PCR product analyzing stability of IE2 H363A in 044L/045L, passaged up to ten times (P1-P10) in chicken embryonic fibroblasts (CEFs). FIG. 8C shows Western blot analysis of IE2 H363A passaged up to P10 in CEF cells. IE2 H363A was probed using an anti-IE2 mouse monoclonal antibody (mAB) 2.9.5 [11]. As an infection/loading control, BR5 antibody was used to probe against an envelope MVA glycoprotein. For FIGS. 8B and 8C, lane labeled "CEF" is uninfected, negative control; lane labeled "MVA" is wild-type MVA not expressing any antigen; lane labeled "IE2 (044L/045L)" is virus previously shown to express non-codon optimized IE2 (FIG. 7C).

and pp65 was probed using purified mouse mAB 28-103. As an infection/loading control (bottom), BR5 antibody was used to probe against an envelope MVA glycoprotein. “CEF” is uninfected, negative control; lane labeled “MVA” is wild-type MVA not expressing any antigen; lane labeled (+) is virus used to generate clinical lots of Triplex.

Figure 19:
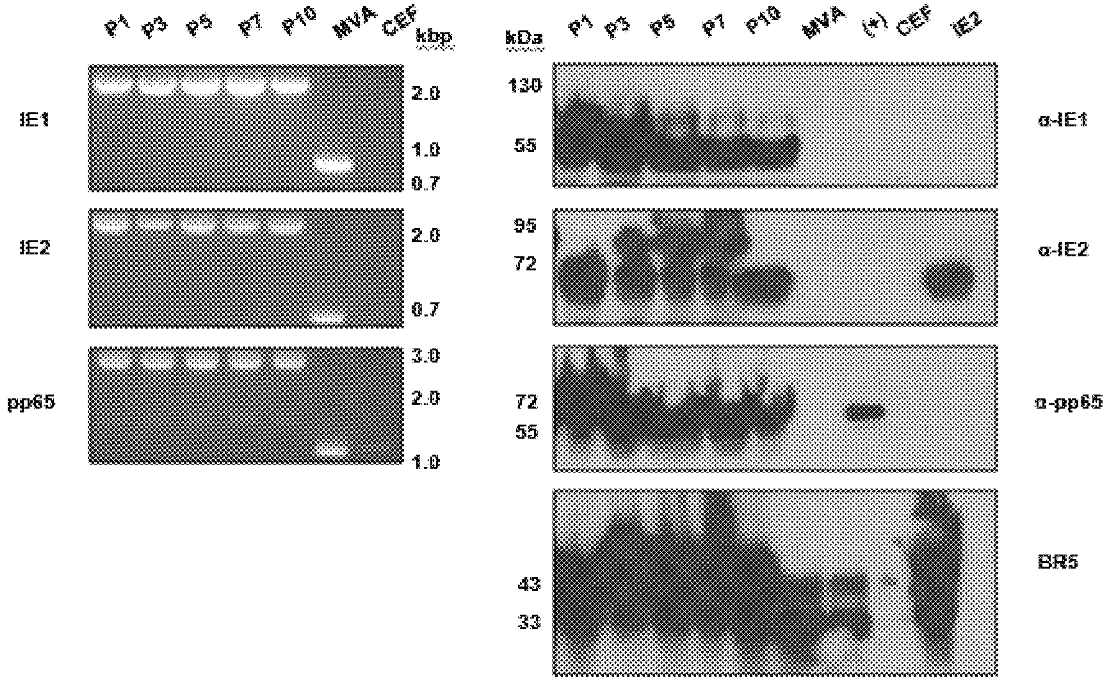

FIG. 19 shows stability analysis of construct A(vi). PCR (left) and Western blot analyses (right) of IE1, IE2, and pp65. Left: 1.0% agarose gel of PCR product analyzing stability of IE1 in IGR3, IE2 in 044/045L, and pp65 in Del3, passaged up to P10 in CEF. Right: Western blot analysis of IEfusion and pp65 passaged up to P10 in CEF cells. IE1 was probed using a purified anti-IE1 mouse monoclonal antibody (mAB) p63-27; IE2 was probed using an anti-IE2 mAB 2.9.5; and pp65 was probed using purified mouse mAB 28-103. As an infection/loading control (bottom), BR5 antibody was used to probe against an envelope MVA glycoprotein. “CEF” is uninfected, negative control; lane labeled “MVA” is wild-type MVA not expressing any antigen; lane labeled (+) is virus used to generate clinical lots of Triplex.

Figure 20:
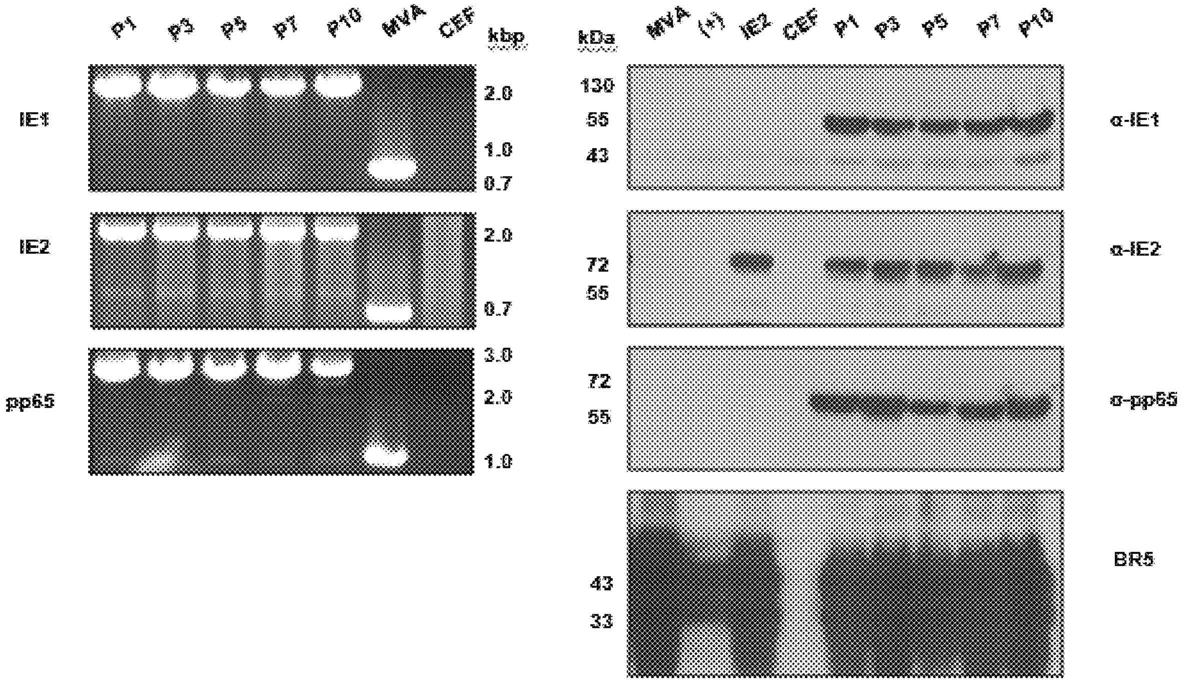

FIG. 20 shows stability analysis of construct B(i). PCR (left) and Western blot analyses (right) of IE1, IE2, and pp65. Left: 1.0% agarose gel of PCR product analyzing stability of IE1 in IGR3, IE2 in 044/045L, and pp65 in Del3, passaged up to P10 in CEF. Right: Western blot analysis of IEfusion and pp65 passaged up to P10 in CEF cells. IE1 was probed using a purified anti-IE1 mouse monoclonal antibody (mAB) p63-27; IE2 was probed using an anti-IE2 mAB 2.9.5; and pp65 was probed using purified mouse mAB 28-103. In this figure (+) did not work, hence no bands observed for α-pp65 or α-IE1 Western blot. As an infection/loading control (bottom), BR5 antibody was used to probe against an envelope MVA glycoprotein. “CEF” is uninfected, negative control; lane labeled “MVA” is wild-type MVA not expressing any antigen; lane labeled (+) is virus used to generate clinical lots of Triplex.

Figure 21:
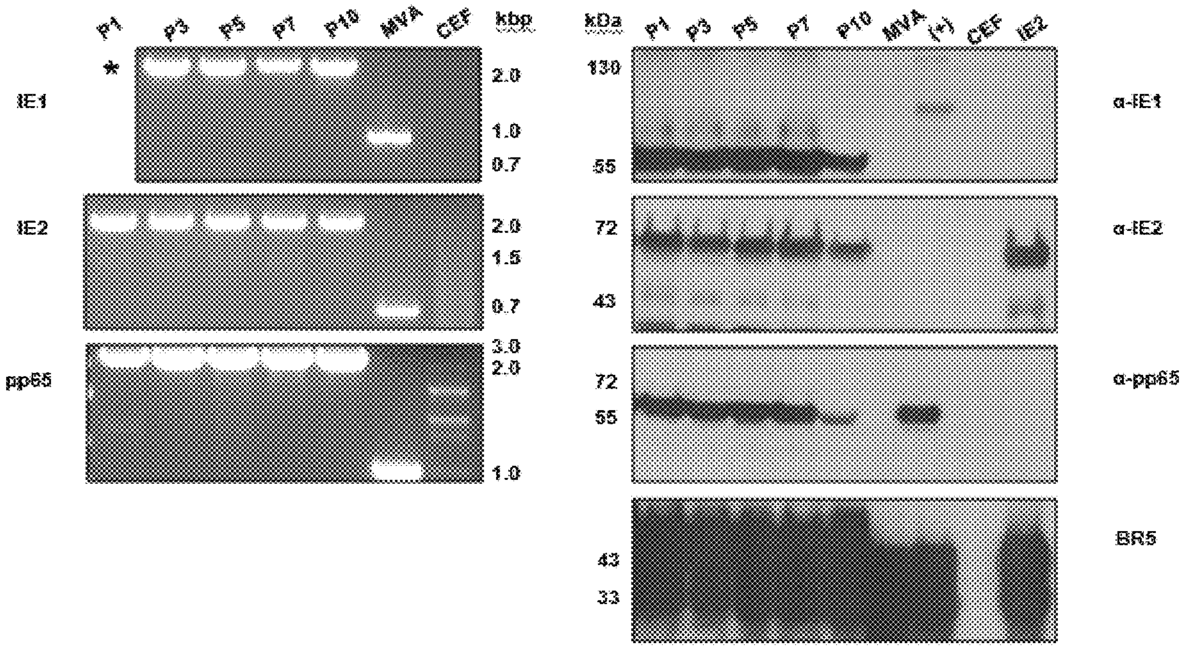

FIG. 21 shows stability analysis of construct B(ii). PCR (left) and Western blot analyses (right) of IE1, IE2, and pp65. Left: 1.0% agarose gel of PCR product analyzing stability of IE1 in IGR3, IE2 in 044/045L, and pp65 in Del3, passaged up to P10 in CEF. Right: Western blot analysis of IEfusion and pp65 passaged up to P10 in CEF cells. IE1 was probed using a purified anti-IE1 mouse monoclonal antibody (mAB) p63-27; IE2 was probed using an anti-IE2 mAB 2.9.5; and pp65 was probed using purified mouse mAB 28-103. As an infection/loading control (bottom), BR5 antibody was used to probe against an envelope MVA glycoprotein. “CEF” is uninfected, negative control; lane labeled “MVA” is wild-type MVA not expressing any antigen; lane labeled (+) is virus used to generate clinical lots of Triplex. (*) for P1 PCR indicates missing lane.

Figure 22:
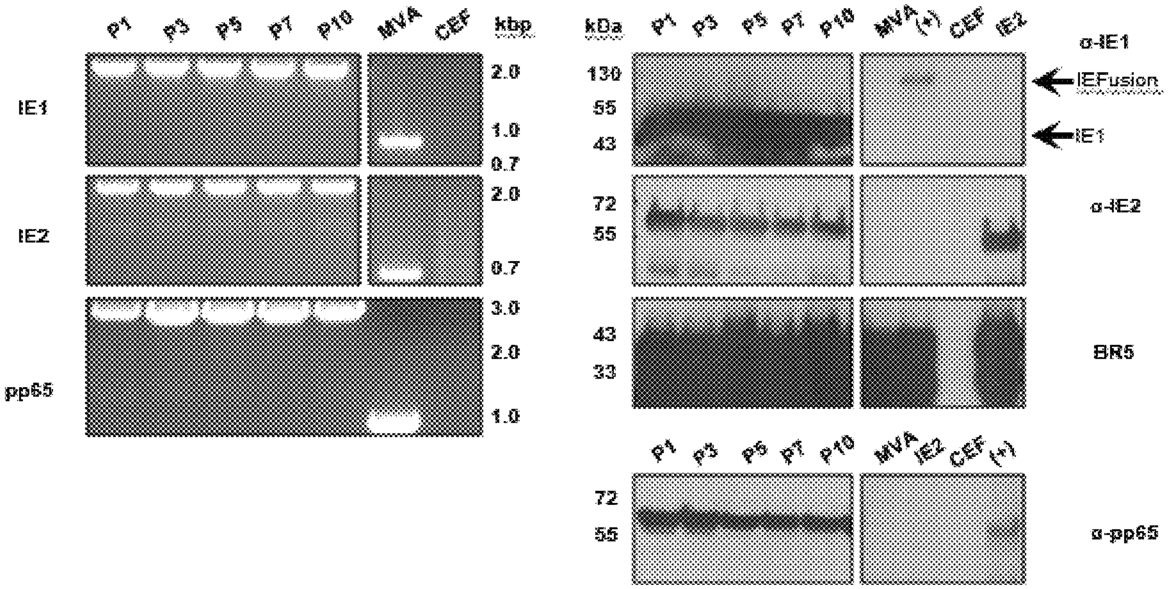

FIG. 22 shows stability analysis of construct B(iii). PCR (left) and Western blot analyses (right) of IE1, IE2, and pp65. Left: 1.0% agarose gel of PCR product analyzing stability of IE1 in IGR3, IE2 in 044/045L, and pp65 in Del3, passaged up to P10 in CEF. Right: Western blot analysis of IEfusion and pp65 passaged up to P10 in CEF cells. IE1 was probed using a purified anti-IE1 mouse monoclonal antibody (mAB) p63-27; IE2 was probed using an anti-IE2 mAB 2.9.5; and pp65 was probed using purified mouse mAB 28-103. As an infection/loading control (bottom), BR5 antibody was used to probe against an envelope MVA glycoprotein. “CEF” is uninfected, negative control; lane labeled “MVA” is wild-type MVA not expressing any antigen; lane labeled (+) is virus used to generate clinical lots of Triplex. For clarity of protein identification based on molecular weight, IEfusion and IE1 are indicated by arrows.

Figure 23:
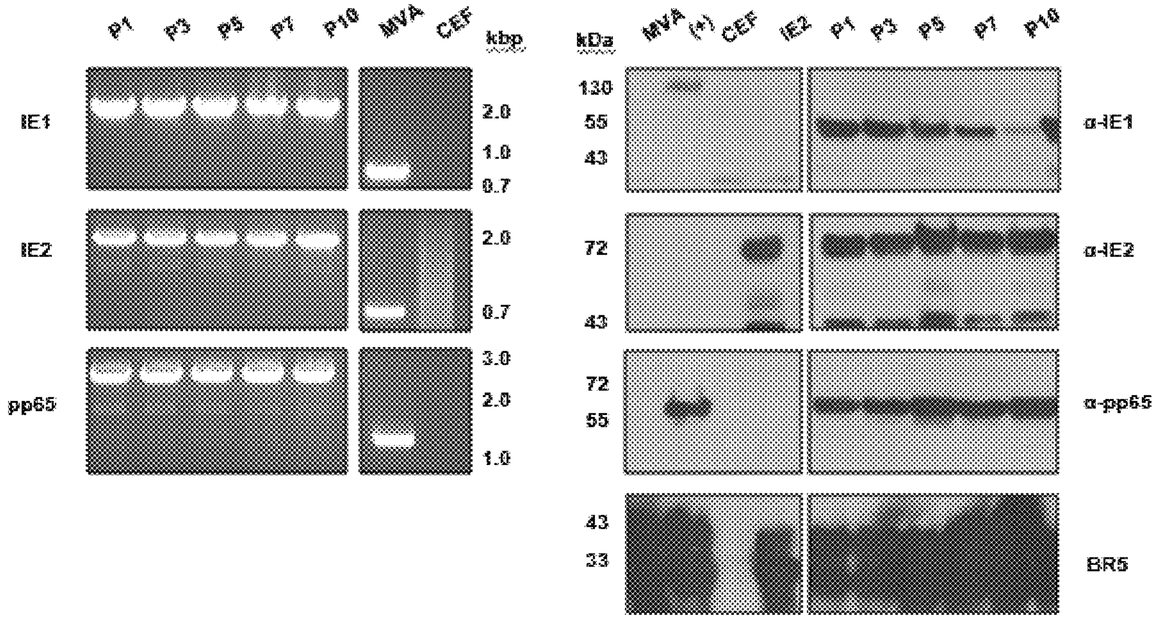

FIG. 23 shows stability analysis of construct B(v). PCR (left) and Western blot analyses (right) of IE1, IE2, and pp65. Left: 1.0% agarose gel of PCR product analyzing stability of IE1 in IGR3, IE2 in 044/045L, and pp65 in Del3, passaged up to P10 in CEF. Right: Western blot analysis of IEfusion and pp65 passaged up to P10 in CEF cells. IE1 was probed using a purified anti-IE1 mouse monoclonal antibody (mAB) p63-27; IE2 was probed using an anti-IE2 mAB 2.9.5; and pp65 was probed using purified mouse mAB 28-103. As an infection/loading control (bottom), BR5 antibody was used to probe against an envelope MVA glycoprotein. “CEF” is uninfected, negative control; lane labeled “MVA” is wild-type MVA not expressing any antigen; lane labeled (+) is virus used to generate clinical lots of Triplex.

Figure 24:
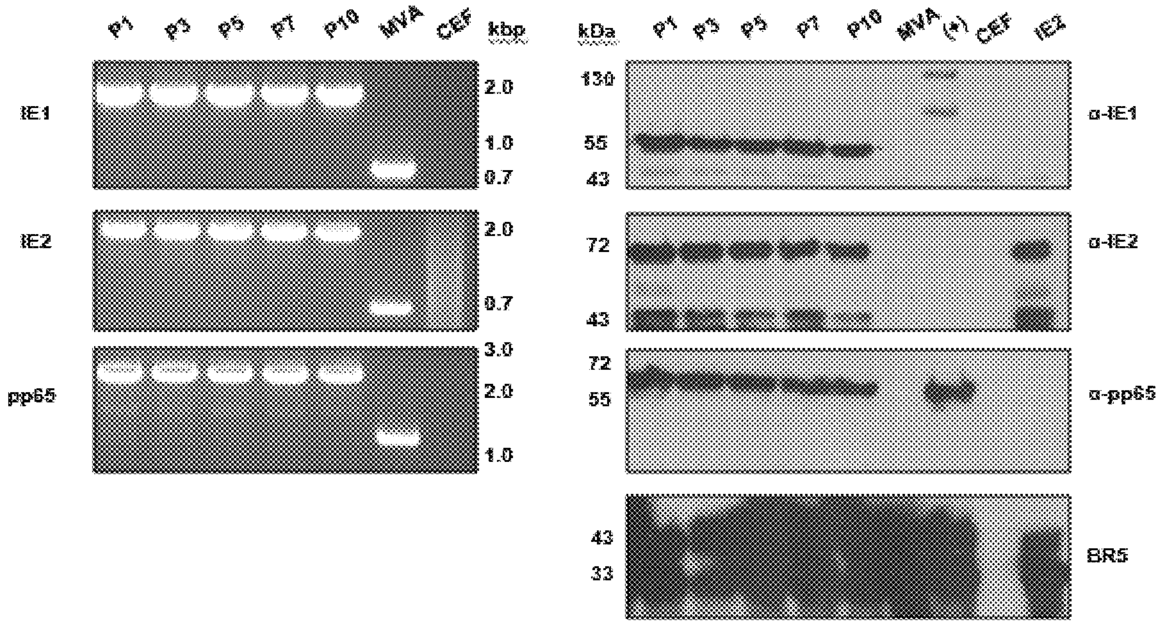

FIG. 24 shows stability analysis of construct B(vii). PCR (left) and Western blot analyses (right) of IE1, IE2, and pp65. Left: 1.0% agarose gel of PCR product analyzing stability of IE1 in IGR3, IE2 in 044/045L, and pp65 in Del3, passaged up to P10 in CEF. Right: Western blot analysis of IEfusion and pp65 passaged up to P10 in CEF cells. IE1 was probed using a purified anti-IE1 mouse monoclonal antibody (mAB) p63-27; IE2 was probed using an anti-IE2 mAB 2.9.5; and pp65 was probed using purified mouse mAB 28-103. As an infection/loading control (bottom), BR5 antibody was used to probe against an envelope MVA glycoprotein. “CEF” is uninfected, negative control; lane labeled “MVA” is wild-type MVA not expressing any antigen; lane labeled (+) is virus used to generate clinical lots of Triplex.

Figure 25:
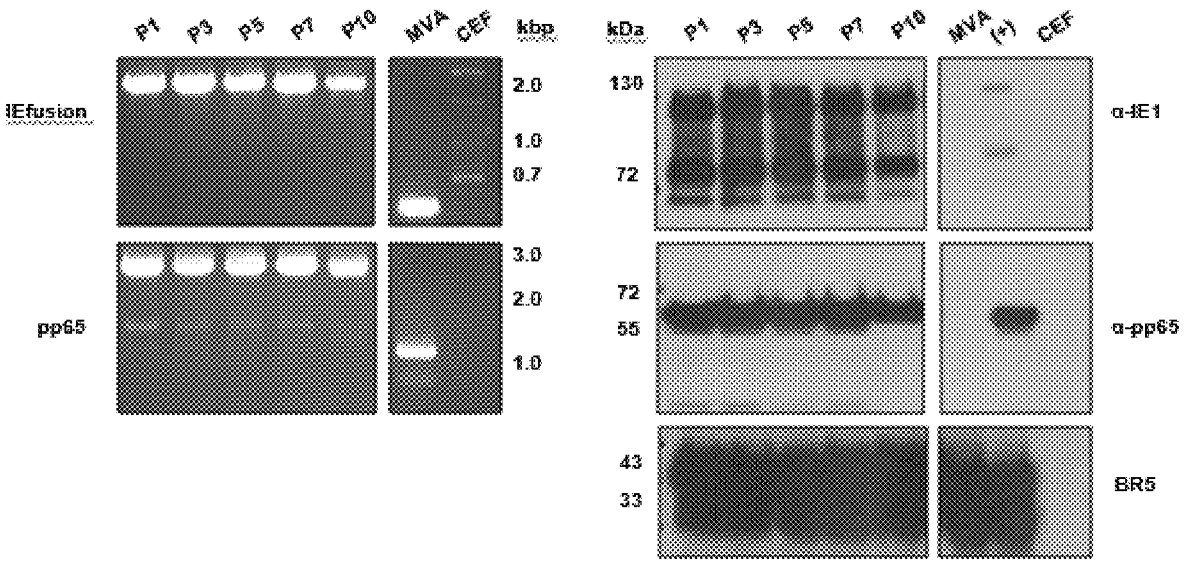

FIG. 25 shows stability analysis of IEfusion 4nt H363A (IGR3):pp65(Del3). PCR (left) and Western blot analyses (right) of IEfusion 4nt H363A and pp65. Left: 1.0% agarose gel of PCR product analyzing stability of IEfusion in IGR3 and pp65 in Del3, passaged up to P10 in CEF. Right: Western blot analysis of IEfusion and pp65 passaged up to P10 in CEF cells. IEfusion was probed using a purified anti-IE1 mouse monoclonal antibody (mAB) p63-27; pp65 was probed using purified mouse mAB 28-103. As an infection/loading control (bottom), BR5 antibody was used to probe against an envelope MVA glycoprotein. “CEF” is uninfected, negative control; lane labeled “MVA” is wild-type MVA not expressing any antigen; lane labeled (+) is virus used to generate clinical lots of Triplex.

Figure 26:
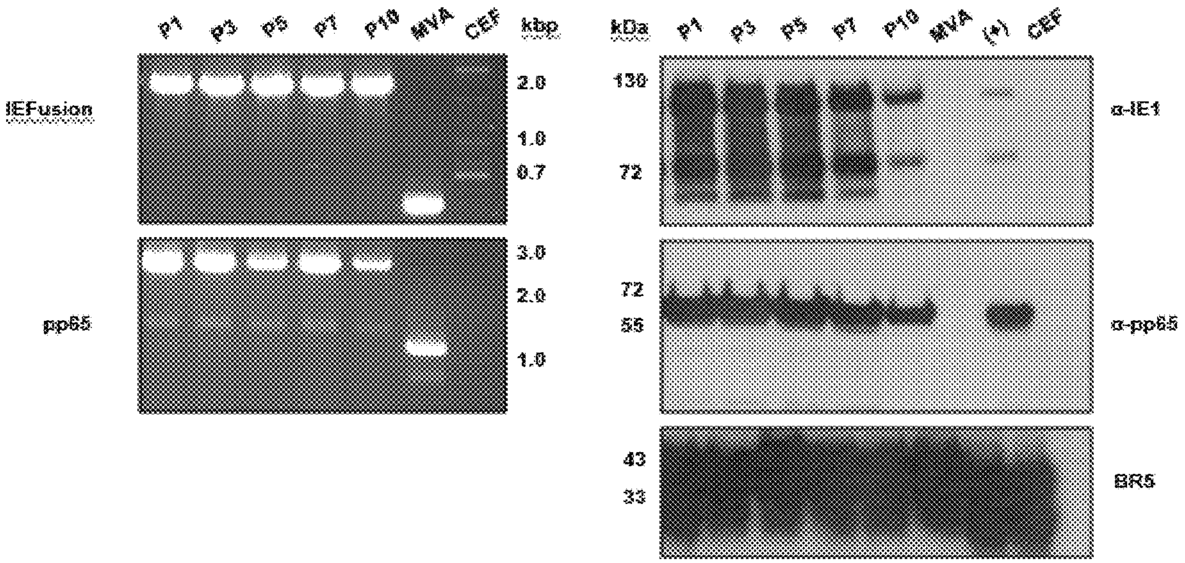

FIG. 26 shows stability analysis of IEfusion 4nt H369A (IGR3):pp65(Del3). PCR (left) and Western blot analyses (right) of IEfusion 4nt H369A and pp65. Left: 1.0% agarose gel of PCR product analyzing stability of IEfusion in IGR3 and pp65 in Del3, passaged up to P10 in CEF. Right: Western blot analysis of IEfusion and pp65 passaged up to P10 in CEF cells. IEfusion was probed using a purified anti-IE1 mouse monoclonal antibody (mAB) p63-27; pp65 was probed using purified mouse mAB 28-103. As an infection/loading control (bottom), BR5 antibody was used to probe against an envelope MVA glycoprotein. “CEF” is uninfected, negative control; lane labeled “MVA” is wild-type MVA not expressing any antigen; lane labeled (+) is virus used to generate clinical lots of Triplex.

Figures 27A, 27B:
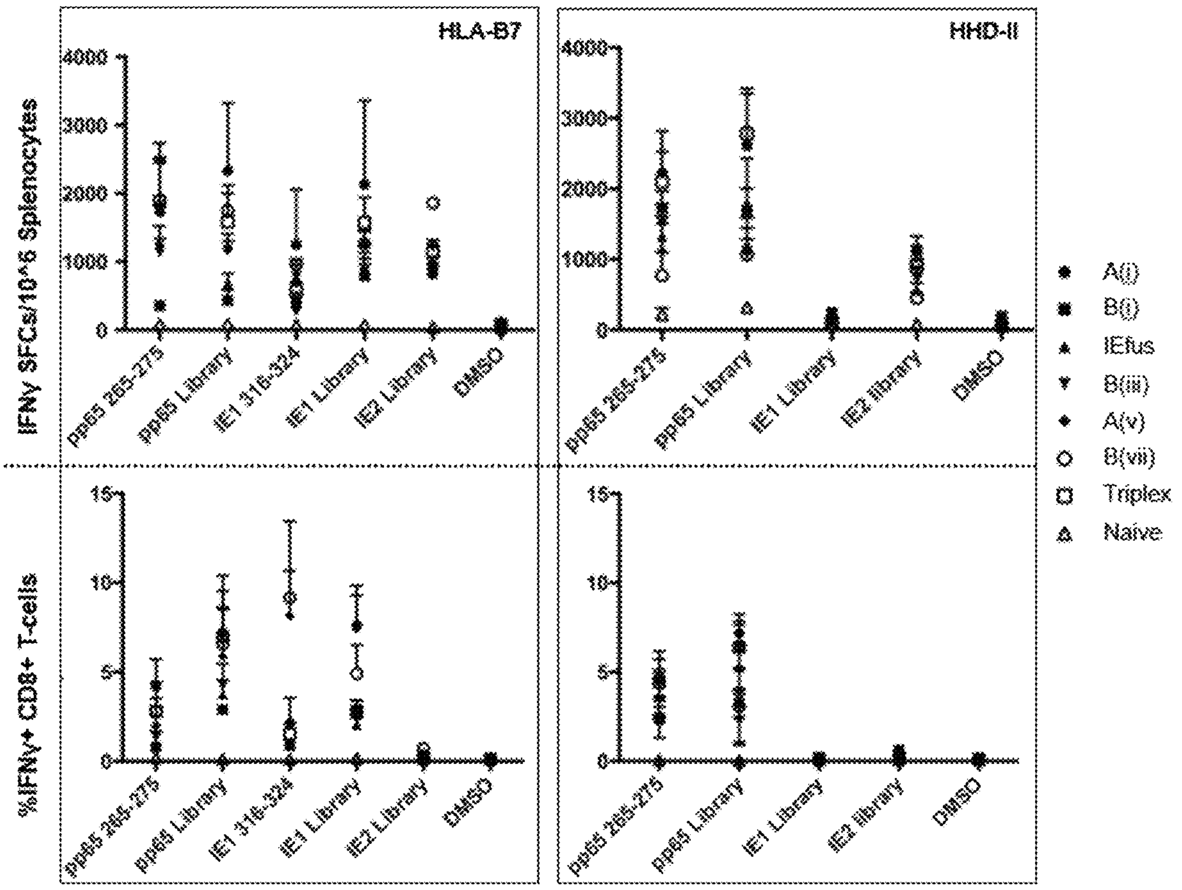

FIGS. 27A-27B show T-cell responses and stimulation post second-generation Triplex immunization. FIG. 27A: Human MHC-restricted T-cell responses elicited by second-generation Triplex. Graphical representation of data from Table 6. FIG. 27B: HLA-B*0702—or HLA-A*0201-restricted CD8+ T-cell stimulation by second-generation Triplex. Graphical representation of data from Table 7. Error bars are SEM calculated and reported in Tables 6 and 7.

Figure 28A:
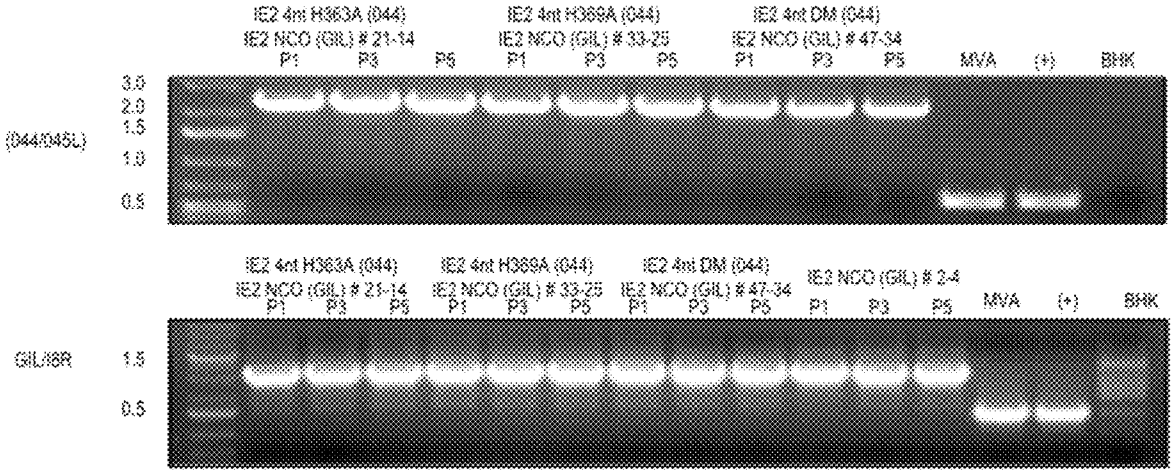
Figure 28B:
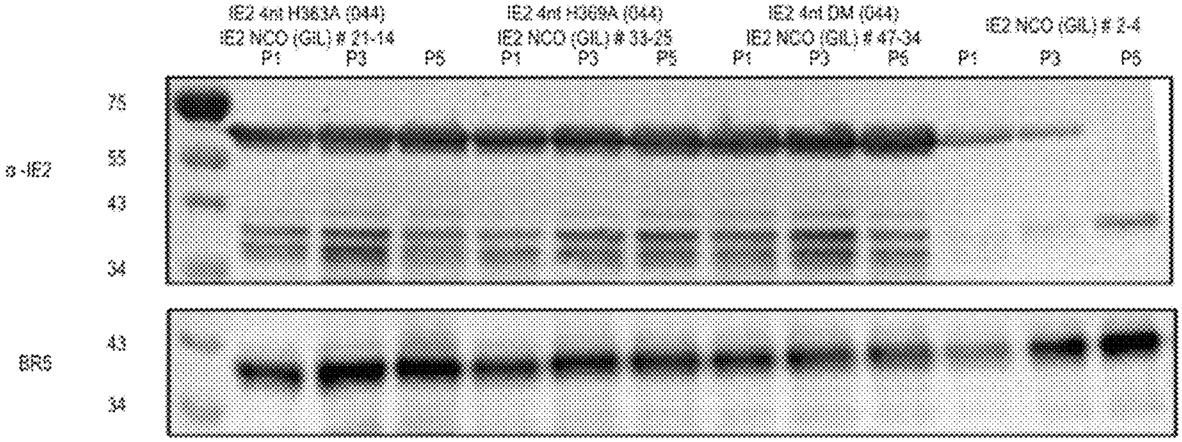

FIGS. 28A-28B show stability analysis of constructs expressing duplicate IE2 genes. PCR (top) and Western blot analyses (bottom) of IE2 and IE2 mutants. FIG. 28A: 1.0% agarose gel of PCR product analyzing stability of IE2 in G1L and three versions of IE2 mutants in 044/045L, passaged up to P5 in CEF. FIG. 28B: Western blot analysis of IE2 and three mutants were passaged up P5 in CEF cells. IE2 was probed using an anti-IE2 mAB 2.9.5. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.

DETAILED DESCRIPTION OF THE INVENTION

The current Triplex vaccine formulation includes three immunodominant proteins: pp65 and a fusion of immediate early proteins IE1 and IE2, but has restrictive manufacturing properties: 1) it must undergo limited passaging to maintain the stability of the IEfusion insertion; 2) restricted growth conditions to allow virus propagation without IEfusion instability; and 3) for mass production of large scale clinical lots, the current Triplex formulation is not the most efficient, long-term production strategy.

Utilizing the modified vaccinia Ankara (MVA) vaccine platform in combination with the bacterial artificial chromosome (BAC) technology, a new form of Triplex that stably expresses both IE1 and IE2 proteins in separate insertion sites over ten passages is generated. MVA is a well-characterized and clinically well-tolerated vaccine vector that is widely used for developing therapeutic vaccine strategies to treat or prevent infectious diseases or cancer. Induction of cellular immune responses by HCMV antigens IE1, IE2, and pp65 is thought to be imperative for the construction of a vaccine candidate to prevent infection or re-infection of individuals that have or will undergo hematopoietic stem cell or solid organ transplants. Disclosed herein are the construction of MVA vectors simultaneously expressing multiple HCMV antigens with insertion sites within MVA, modifications to the IE1 and IE2 components of IEfusion, and splitting IEfusion into its individual components of IE1 (exon 4) and IE2 (exon 5). The inserted HCMV antigen sequences are based on their natural HCMV DNA sequences or have been codon-optimized for efficient vaccinia virus expression. The individual HCMV antigens are separately inserted into three unique MVA insertion sites. There are four candidate insertion sites that include MVA deletion site III (Del3), a site between MVA essential genes 18R and G1L, intergenic region IGR3, and MVA 044/045L site. An ectopically inserted modified promoter H5 induces expression of the HCMV antigens from the MVA vector. Furthermore, a His to Ala amino acid substitution on the C-terminal DNA-binding domain of IE2 has aided in the stable expression of IE2 over a minimum of ten passages. Therefore, His to Ala substitutions were inserted via site-directed mutagenesis to further stabilize IE2. These mutations have helped stabilize expression of IE2 through ten passages.

In one aspect, this disclosure relates to improving the stability upon extended passage of Triplex and to retaining immunogenicity while maintaining all three antigens needed for an effective vaccine formulation. For example, one or more modifications can be made to yield an MVA that stably expresses IE1, IE2, and pp65 for efficient viral vaccine production, including but not limited to: 1) use of multiple, unique gene insertion sites in MVA that could be the preferred environment for gene stability; 2) removal of DNA mutation "hot spots" within the gene sequence that have been previously identified to include mutations at the codon "wobble" position thereby disrupting consecutive C or G nucleotides; and 3) pox virus codon-optimization for increased protein expression. In some embodiments, IEfusion is inserted into other sites within MVA. Candidate sites include Del3 [5, 6], G1L/18R [7, 8], IGR3 [9], and 044L/045L [10]. Additional insertion sites are listed in Table 1. In some embodiments, the insertion sites do not include Del2. In some embodiments, 3 or more, 4 or more, 5 or more, 6 or more consecutive C or G nucleotides in the gene sequence are disrupted by wobble base substitution that maintain identical amino acid identity.

Disclosed herein are the most stable combinations of insertion sites and gene modifications to generate an MVA that stably expresses all three CMV antigens at a minimum of 10 passages for large-scale propagation of the vaccine. Various combinations are contemplated to find the most stable combination of insertion sites that allows stable expression of IE1, IE2, and pp65: 1) splitting IEfusion into its IE1 and IE2 gene components; 2) inserting all three genes into separate insertion sites in MVA and using variant gene sequences of the inserts; and 3) explore new insertion sites in MVA. Some examples of the insertion sites are provided in Table 1:

TABLE 1

MVA Insertion Sites

| MVA Insertion Sites | Descriptive Name |
|---|---|
| IGR007/008 | |
| IGR021/023 | Del2 |
| IGR044/045 | 44L/45L |
| IGR047/048 | |
| IGR055/056 | |
| IGR064/065 | IGR3 |
| IGR069/070 | G1L/I8R |
| IGR081/082 | |
| IGR090/091 | |
| IGR092/093 | |
| IGR107/108 | |
| IGR116/117 | |
| IGR122/123 | |
| IGR136/137 | Del6 |
| IGR148/149 | |
| IGR164/165 | Del3 |

Figure 1:
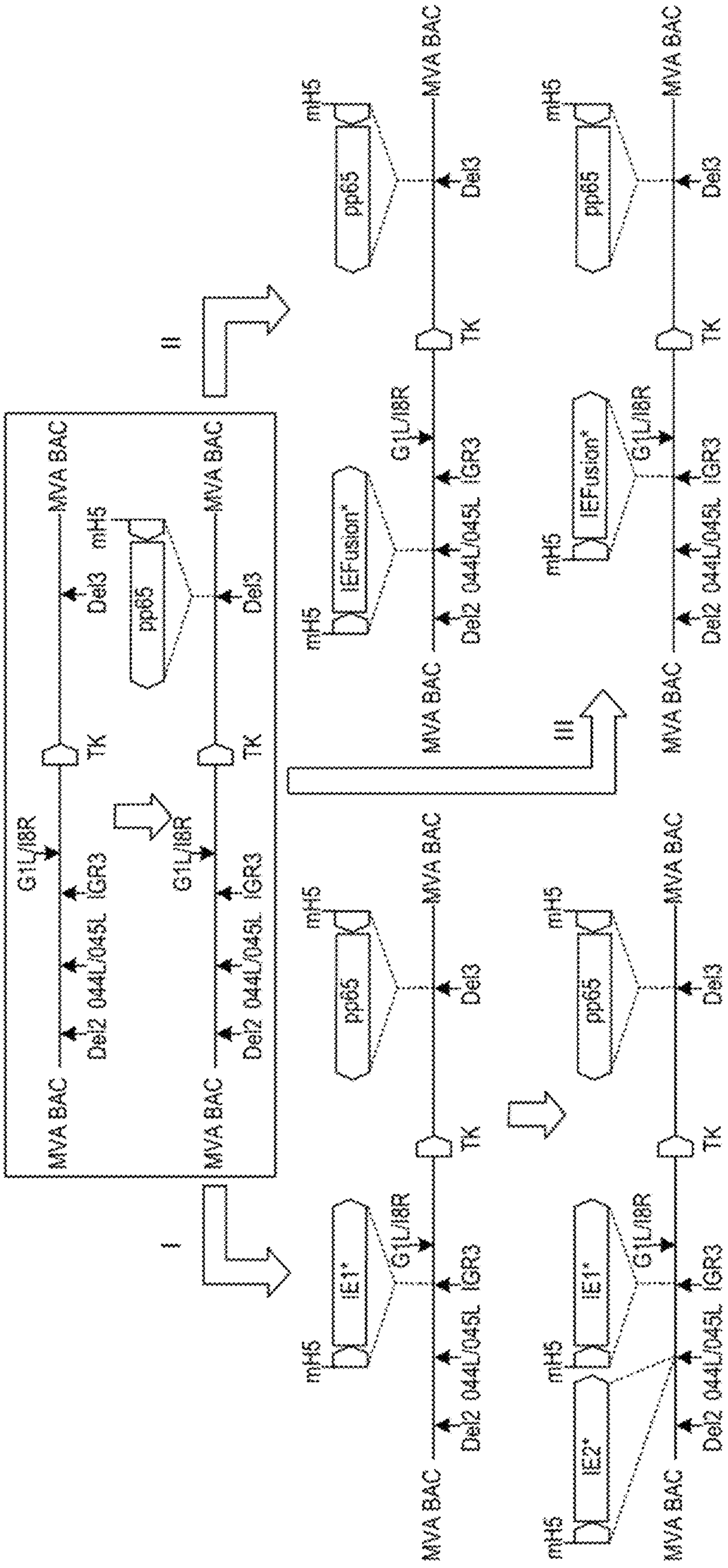
FIG. 1 shows a schematic diagram portraying the development of the rederived Triplex. MVA BAC expressing pp65 is used as the basis for the addition of other HCMV antigens for Triplex. Utilizing BAC technology and en passant mutagenesis, genes expressing desired Triplex antigens are sequentially incorporated into MVA. After all desired antigens are present and the final constructs have been analyzed for stability, BAC is removed from MVA. Solid black arrows signify final rederived Triplex construct; gray arrows signify intermediate steps. There are three examples of the final potential Triplex candidates: I) IE2, IE1, and pp65 in different sites on MVA; II) IEfusion in 044L/045L; and III) IEfusion in IGR3. All three example constructs have pp65 in Del3; (*) signifies variants of genes that are inserted into the sites.

Various modifications and/or insertion sites selection are made with the purpose of increasing the stability of Triplex simultaneously expressing IE1, IE2 and pp65 in a single MVA vector, as illustrated in FIG. 1. Some MVA insertion sites provide for an environment that creates greater stability for either IE1 or IE2, possibly based on their nucleotide sequence. For example, one or more of the IE1, IE2 and pp65 genes are inserted in one or more insertion sites, including 044L/045L, IGR3, G1L/18R, and Del3. In some embodiments, the insertion site does not include Del2. In addition or in the alternative, the DNA sequence of the IE1 gene and/or IE2 gene, and/or the amino acid sequence of the IE1 protein and/or IE2 protein is modified to be more compatible with the MVA life cycle or the absence of cell toxicity. In some embodiments, the DNA sequence of the IE1 gene and/or IE2 gene is codon optimized. For example, consecutive DNA sequences of cytosines or guanines are codon optimized and replaced by DNA sequences encoding the same amino acid residues without the consecutive cytosines or guanines. In some embodiments, the amino acid sequence of the IE1 protein or the IE2 protein contains one or more mutations such that the stability of the mutant IE1 protein or mutant IE2 protein is improved compared to that of the wildtype IE1 protein or wildtype IE2 protein. In some embodiments, one or more amino acid mutations disrupt the Zn-finger domain of the IE2 protein. For example, the amino acid sequence of the IE2 protein contains one or more His→Ala mutations in the C-terminus. In some embodiments, the amino acid sequence of the IE2 protein contains an H363A mutation, an H369A mutation, or both.

An "immunologically effective amount" as used herein means an amount that is both safe to a subject (animal or human) to be immunized and sufficient to improve the immunity of the subject. The immunologically effective amount can vary and can be determined by means of known art through routine trials.

In another embodiment, a CMV vaccine containing an immunologically effective amount of rMVA virus, which is genetically stable after serial passage can be produced by the methods disclosed herein, incorporating one or more modifications described above.

A CMV antigen can be a CMV protein antigen, a fragment of a CMV protein antigen, a modified CMV protein antigen, a fragment of a modified CMV protein antigen, a mutated CMV protein antigen or a fusion CMV protein antigen. Examples of CMV protein antigens and CMV fragments may include pp65, IE1 exon 4 (IE1/e4), IE2 exon 5 (IE2/e5), and antigenic fragments thereof. Examples of modified CMV protein antigens and fragments thereof may be found in U.S. Pat. No. 7,163,685 to Diamond et al. and is incorporated herein by reference in its entirety. Examples of mutated CMV protein antigens may be found in U.S. Pat. No. 6,835,383 to Zaia et al. and is incorporated herein by reference in its entirety. Moreover, all ranked antigens established by assessing immune response in healthy adults can be added up until reaching the maximal capacity of the MVA vector for gene insertions (see FIGS. 1C and 4D) [32].

Fusion CMV protein antigens may comprise two or more CMV proteins, modified CMV proteins, mutated CMV proteins or any antigenic fragments thereof. In one aspect, an exemplar fusion protein is a fusion of IE1 exon 4 (IE1/e4) and IE2 exon 5 (IE2/e5), IE1/e4-IE2/e5 ("IEfusion"). In one embodiment, the use of fusion proteins involves creating an IEfusion protein that comprises exon4 from IE1 and exon5 from the IE2 gene into a single gene without additional genetic material. The IEfusion protein comprises a unique representation of the immediate-early antigens than either protein alone. In another embodiment, the nucleic acid sequence encoding the IEfusion is codon optimized. In yet another embodiment, the amino acid sequence of the IEfusion protein comprises one or more His to Ala mutations in the C-terminus of IE2.

The term "genetic stability" as used herein refers to a measure of the resistance to change, with serial passage of virus, of the DNA sequence of a gene, the expression level of the gene, or both. The genetic stability of the target gene in an rMVA vector is a concern in the development of a vaccine. A reduction of the genetic stability of the target gene may have the effect of reducing the immunogenicity of the rMVA vector due to changes in gene sequence or expression level. Genetic instability of the insert gene sequence can lead to alterations of the sequence flanking the gene insertion. Suppressing the instability of the insert gene seems to curtail instability of the flanking virus DNA sequence.

Genetic stability of recombinant virus can be measured or assessed by numerous methods known in the art, e.g., testing foreign protein expression levels at each passage by Western blot (WB) or immunostaining virus plaques and calculating the percentage of foreign protein producing foci before and after serial passage. An alternative means to assess genetic stability is by real-time quantitative PCR (RT-qPCR) method, which amplifies isolated MVA genomic DNA and calculates the copy numbers of the inserted gene of interest and MVA vector after each passage. The ratio of the gene of interest copy number versus the MVA backbone vector copy number is used to determine the genetic stability of the gene or the MVA vaccine carrying the gene. A higher ratio of the gene of interest copy number to the MVA backbone vector copy number reflects a higher genetic stability, with the highest ratio=1 means approximately 100% gene expression remains after serial passage. RT-qPCR is more sensitive, high-throughput and provides highly reproducible results relative to other methods, such as Western blot or immunostaining. The method of RT-qPCR can be performed following well-known procedures in the art or the manuals of commercially available RT-qPCR kit. However, this method may not detect single nucleotide changes without accompanying sequence information. Disruptions of the coding sequence of the IE1 or IE2 inserts can prevent recognition by monoclonal antibodies that recognize intact forms.

An rMVA vaccine carrying a gene of interest is genetically stable when the DNA sequence of the gene and the expression of the gene is substantially unchanged during serial passage of the vaccine, particularly, after 10 or more passages.

Another aspect is a method for the prevention or treatment of infections or cancer in a mammal subject by administering to the subject a genetically stable rMVA vaccine disclosed herein, wherein the rMVA vaccine contains two or more CMV antigens under control of a mH5 or other poxvirus promoters, including IE1, IE2, and pp65 or antigenic fragments thereof. In some embodiments, the mammal subject is a human subject.

The nucleic acid sequences and amino acid sequences of certain IEfusions, IE proteins, and variants thereof are disclosed below.

```
IEfusion-VacO DNA sequence (SEQ ID NO: 1):
atggtgaagcaaatcaaggtcagagtggacatggtaagacacagaattaa

ggaacacatgttgaagaagtatactcaaacagaggagaagttcaccggtg

ccttcaatatgatgggtggatgtctacagaacgctttggatatcttagat

aaggtacatgaaccattcgaagaaatgaagtgcattggattgacaatgca

atcaatgtatgagaactacatagtgccagaggataagcgtgaaatgtgga

tggcatgcatcaaggagttacatgatgtatccaaaggagcagccaacaag

ctaggtggtgctttgcaagcgaaggcaagagcgaagaaggatgaattgag

acgaaagatgatgtacatgtgctatcgaaacatcgaattcttcactaaga

actcagcgtttcctaagactaccaatggatgcagtcaagctatggctgcg

cttcagaacttgcctcaatgtagtcctgatgaaatcatggcatatgcaca

gaagatcttcaagatcttagatgaggaaagagacaaggtattgactcata

tcgatcacatattcatggatatactaacaacatgtgtagaaacgatgtgt

aacgagtacaaggtaacttcggacgcttgtatgatgactatgtacggagg

aatatctctacttagtgagttctgtcgagttctatgctgttacgtattag

aagaaactagtgtaatgttagcgaagagaccattgatcactaagcctgaa
```

-continued gtgatctcggttatgaagagacgaatagaggagatctgtatgaaggtgtt cgcacaatacatcttaggagctgatcctctaagagtgtgtagtccatcgg tagacgatttgagagctatagcggaggaatctgacgaggaagaggcaata gttgcatacacacttgctacagctggagtatccagttctgattctcttgt aagtcctccggagtcacctgtgccagcaaccataccgttgagtagtgtga ttgtggctgagaactcggatcaggaagagtctgagcaatccgatgaagaa gaggaggaaggagcacaagaggagagagaagatactgtctctgtgaagag tgaacctgtatctgaaatcgaggaagtagcacctgaggaagaggaggatg gagccgaagaaccaacagcttcgggtggtaagtcaactcatccgatggta accagatctaaggcagaccagggagacatcctagcacaagcagtgaacca tgctggaattgactcatcttcgaccggaccaactctaacgactcattcat gttcggttagttctgctcctcttaacaagcctacacctacctcggtagct gttaccaacacacctttaccaggagcatcagcaacacctgagttgtctcc aagaaagaagcctcgtaagaccacgagaccgttcaaggtgatcatcaagc caccagtaccacctgctccgatcatgttgccattgatcaagcaggaggac attaagccagaacctgacttcacgatacagtaccgtaacaagatcataga tacagcaggatgcatagtgatctcagatagtgaagaggagcaaggtgagg aagtggagactagaggagccacagccagttcgccttccacaggatccgga actcctagagtaactagtccgacacatccactttcccagatgaatcatcc acctctaccggatcctctaggacgaccagatgaagattcttcttcatcta gttcaagttcttgctcatccgcgagtgatagtgagtcagaaagtgaagag atgaagtgctcttctggtggtggagctagtgtcacttcatctcatcatgg acgaggaggatttggaggtgctgcgagtagttccttactaagttgtggac atcagtcatctggtggtgcatctactggacctagaaagaagaagtcaaag agaatctccgaattggataatgagaaagtgagaaacatcatgaaggacaa gaacacgccgttctgcactccgaatgttcagacgagaagaggacgagtga agatagatgaagtatcacgaatgttcagaaacacaaatcgttctctagag tacaagaatcttccgttcaccataccttcgatgcaccaagtattagatga ggctatcaaggcatgtaagaccatgcaagttaacaacaaaggaatacaga tcatctacactagaaaccatgaggttaagagtgaggtggatgccgtacgt tgtagattgggaacgatgtgtaaccttgcgctatctactcctttcctaat ggagcatactatgcctgtgactcatcctcctgaagtggctcaaagaacag ctgatgcttgtaacgaaggtgtgaaagctgcttggtccctaaaggagtta catacacaccaactttgtccacgatccagtgactacagaaacatgatcat tcatgcagctacgcctgtagatctacttggagctcttaacctatgtcttc ctttgatgcagaagttccctaagcaagtgatggtgagaatcttctcgacg aatcaaggaggattcatgttaccgatatacgagacagctgcaaaggctta cgctgtcggtcagttcgagcaaccgactgaaacgcctcctgaggacttag atacattgtctttggcgatagaagcagcgattcaggatcttagaaacaag agtcagtaa -continued IEfusion DNA sequence (SEQ ID NO: 2):

atggtcaaacagattaaggttcgagtggacatggtgcggcatagaatcaa ggagcacatgctgaaaaaatatacccagacggaagagaaattcactggcg cctttaatatgatgggaggatgtttgcagaatgccttagatatcttagat aaggttcatgagcctttcgaggagatgaagtgtattgggctaactatgca gagcatgtatgagaactacattgtacctgaggataagcgggagatgtgga tggcttgtattaaggagctgcatgatgtgagcaagggcgccgctaacaag ttgggggtgcactgcaggctaaggcccgtgctaaaaaggatgaacttag gagaaagatgatgtatatgtgctacaggaatatagagttctttaccaaga actcagccttccctaagaccaccaatggctgcagtcaggccatggcggca ctgcagaacttgcctcagtgctcccctgatgagattatggcttatgccca gaaaatatttaagattttggatgaggagagagacaaggtgctcacgcaca ttgatcacatatttatggatatcctcactacatgtgtggaaacaatgtgt aatgagtacaaggtcactagtgacgcttgtatgatgaccatgtacggggg catctctctcttaagtgagttctgtcgggtgctgtgctgctatgtcttag aggagactagtgtgatgctggccaagcggcctctgataaccaagcctgag gttatcagtgtaatgaagcgccgcattgaggagatctgcatgaaggtctt tgcccagtacattctgggggccgatcctctgagagtctgctctcctagtg tggatgacctacgggccatcgccgaggagtcagatgaggaagaggctatt gtagcctacactttggccaccgctggtgtcagctcctctgattctctggt gtcacccccagagtcccctgtacccgcgactatccctctgtcctcagtaa ttgtggctgagaacagtgatcaggaagaaagtgagcagagtgatgaggaa gaggaggagggtgctcaggaggagcgggaggacactgtgtctgtcaagtc tgagccagtgtctgagatagaggaagttgccccagaggaagaggaggatg gtgctgaggaacccaccgcctctggaggcaagagcacccaccctatggtg actagaagcaaggctgaccagggtgacatcctcgcccaggctgtcaatca tgccggtatcgattccagtagcaccggccccacgctgacaacccactctt gcagcgttagcagcgcccctcttaacaagccgacccccaccagcgtcgcg gttactaacactcctctccccggggcatccgctactcccgagctcagccc gcgtaagaaaccgcgcaaaaccacgcgtcctttcaaggtgattattaaac cgcccgtgcctcccgcgcctatcatgctgcccctcatcaaacaggaagac atcaagcccgagcccgactttaccatccagtaccgcaacaagattatcga taccgccggctgtatcgtgatctctgatagcgaggaagaacagggtgaag aagtcgaaacccgcggtgctaccgcgtcttccccttccaccggcagcggc acgccgcgagtgacctctcccacgcacccgctctcccagatgaaccaccc tcctcttcccgatcccttgggccggcccgatgaagatagttcctcttcgt cttcctcctcctgcagttcggcttcggactcggagagtgagtccgaggag atgaaatgcagcagtggcggaggagcatccgtgacctcgagccaccatgg gcgcggcggttttggtggcgcggcctcctcctctctgctgagctgcggcc atcagagcagcggcggggcgagcaccggaccccgcaagaagaagagcaaa cgcatctccgagttggacaacgagaaggtgcgcaatatcatgaaagataa -continued gaacacccccttctgcacacccaacgtgcagactcggcggggtcgcgtca agattgacgaggtgagccgcatgttccgcaacaccaatcgctctcttgag tacaagaacctgcccttcacgattcccagtatgcaccaggtgttagatga ggccatcaaagcctgcaaaaccatgcaggtgaacaacaagggcatccaga ttatctacacccgcaatcatgaggtgaagagtgaggtggatgcggtgcgg tgtcgcctgggcaccatgtgcaacctggccctctccactcccttcctcat ggagcacaccatgcccgtgacacatccacccgaagtggcgcagcgcacag ccgatgcttgtaacgaaggcgtcaaggccgcgtggagcctcaaagaattg cacacccaccaattatgcccccgttcctccgattaccgcaacatgatcat ccacgctgccacccccgtggacctgttgggcgctctcaacctgtgcctgc ccctgatgcaaaagtttcccaaacaggtcatggtgcgcatcttctccacc aaccagggtgggttcatgctgcctatctacgagacggccgcgaaggccta cgccgtggggcagtttgagcagcccaccgagacccctcccgaagacctgg acaccctgagcctggccatcgaggcagccatccaggacctgaggaacaag tctcagtaa IEfusion-4 nt DNA sequence (SEQ ID NO: 3):
atggtcaaacagattaaggttcgagtggacatggtgcggcatagaatcaa ggagcacatgctgaagaagtatacccagacggaagagaaattcactggcg cctttaatatgatgggaggatgtttgcagaatgccttagatatcttagat aaggttcatgagcctttcgaggagatgaagtgtattgggctaactatgca gagcatgtatgagaactacattgtacctgaggataagcgggagatgtgga tggcttgtattaaggagctgcatgatgtgagcaagggcgccgctaacaag ttaggaggtgcactgcaggctaaggcccgtgctaagaaggatgaacttag gagaaagatgatgtatatgtgctacaggaatatagagttctttaccaaga actcagccttccctaagaccaccaatggctgcagtcaggccatggcggca ctgcagaacttgcctcagtgctctcctgatgagattatggcttatgccca gaagatatttaagatcttggatgaggagagagacaaggtgctcacgcaca ttgatcacatatttatggatatcctcactacatgtgtggaaacaatgtgt aatgagtacaaggtcactagtgacgcttgtatgatgaccatgtacggagg catctctctcttaagtgagttctgtcgggtgctgtgctgctatgtcttag aggagactagtgtgatgctggccaagcggcctctgataaccaagcctgag gttatcagtgtaatgaagcgccgcattgaggagatctgcatgaaggtctt tgcccagtacattctaggtgccgatcctctgagagtctgctctcctagtg tggatgacctacgggccatcgccgaggagtcagatgaggaagaggctatt gtagcctacactttggccaccgctggtgtcagctcctctgattctctggt gtcacctccagagtcacctgtacccgcgactatccctctgtcctcagtaa ttgtggctgagaacagtgatcaggaagaaagtgagcagagtgatgaggaa gaggaggagggtgctcaggaggagcgggaggacactgtgtctgtcaagtc tgagccagtgtctgagatagaggaagttgctccagaggaagaggaggatg gtgctgaggaacccaccgcctctggaggcaagagcacccaccctatggtg actagaagcaaggctgaccagggtgacatcctcgcccaggctgtcaatca -continued tgccggtatcgattccagtagcaccggacctacgctgacaacccactctt gcagcgttagcagcgctcctcttaacaagccgactccaaccagcgtcgcg gttactaacactcctctaccaggagcatccgctactcccgagctcagccc gcgtaagaaaccgcgcaagaccacgcgtcctttcaaggtgattattaaac cgcccgtgcctcccgcgcctatcatgctgccactcatcaaacaggaagac atcaagcccgagcccgactttaccatccagtaccgcaacaagattatcga taccgccggctgtatcgtgatctctgatagcgaggaagaacagggtgaag aagtcgaaacccgcggtgctaccgcgtcttcaccttccaccggcagcggc acgccgcgagtgacctctcccacgcacccgctctcccagatgaaccaccc tcctcttcccgatcccttgggccggcccgatgaagatagttcctcttcgt cttcctcctcctgcagttcggcttcggactcggagagtgagtccgaggag atgaaatgcagcagtggcggaggagcatccgtgacctcgagccaccatgg gcgcggcggatttggtggcgcggcctcctcctctctgctgagctgcggcc atcagagcagcggcggtgcgagcaccggacctcgcaagaagaagagcaaa cgcatctccgagttggacaacgagaaggtgcgcaatatcatgaaagataa gaacactcccttctgcacacccaacgtgcagactcggcgtggtcgcgtca agattgacgaggtgagccgcatgttccgcaacaccaatcgctctcttgag tacaagaacctgcccttcacgattcccagtatgcaccaggtgttagatga ggccatcaaagcctgcaagaccatgcaggtgaacaacaagggcatccaga ttatctacacccgcaatcatgaggtgaagagtgaggtggatgcggtgcgg tgtcgcctgggcaccatgtgcaacctggccctctccactcccttcctcat ggagcacaccatgcccgtgacacatccacccgaagtggcgcagcgcacag ccgatgcttgtaacgaaggcgtcaaggccgcgtggagcctcaaagaattg cacacccaccaattatgtcctcgttcctccgattaccgcaacatgatcat ccacgctgccacaccagtggacctgttgggcgctctcaacctgtgcctgc cactgatgcagaagtttcccaaacaggtcatggtgcgcatcttctccacc aaccagggtgggttcatgctgcctatctacgagacggccgcgaaggccta cgccgttggtcagtttgagcagcccaccgagacacctcccgaagacctgg acaccctgagcctggccatcgaggcagccatccaggacctgaggaacaag tctcagtaa IEfusion-VacO amino acid sequence (SEQ ID NO: 4):
MVKQIKVRVDMVRHRIKEHMLKKYTQTEEKFTGAFNMMGGCLQNALDILD

KVHEPFEEMKCIGLTMQSMYENYIVPEDKREMWMACIKELHDVSKGAANK

LGGALQAKARAKKDELRRKMMYMCYRNIEFFTKNSAFPKTTNGCSQAMAA

LQNLPQCSPDEIMAYAQKIFKILDEERDKVLTHIDHIFMDILTTCVETMC

NEYKVTSDACMMTMYGGISLLSEFCRVLCCYVLEETSVMLAKRPLITKPE

VISVMKRRIEEICMKVFAQYILGADPLRVCSPSVDDLRAIAEESDEEEAI

VAYTLATAGVSSSDSLVSPPESPVPATIPLSSVIVAENSDQEESEQSDEE

EEEGAQEEREDTVSVKSEPVSEIEEVAPEEEEDGAEEPTASGGKSTHPMV

TRSKADQGDILAQAVNHAGIDSSSTGPTLTTHSCSVSSAPLNKPTPTSVA

VTNTPLPGASATPELSPRKKPRKTTRPFKVIIKPPVPPAPIMLPLIKQED

-continued

IKPEPDFTIQYRNKIIDTAGCIVISDSEEEQGEEVETRGATASSPSTGSG

TPRVTSPTHPLSQMNHPPLPDPLGRPDEDSSSSSSSSCSSASDSESESEE

MKCSSGGGASVTSSHHGRGGFGGAASSSLLSCGHQSSGGASTGPRKKKSK

RISELDNEKVRNIMKDKNTPFCTPNVQTRRGRVKIDEVSRMFRNTNRSLE

YKNLPFTIPSMHQVLDEAIKACKTMQVNNKGIQIIYTRNHEVKSEVDAVR

CRLGTMCNLALSTPFLMEHTMPVTHPPEVAQRTADACNEGVKAAWSLKEL

HTHQLCPRSSDYRNMIIHAATPVDLLGALNLCLPLMQKFPKQVMVRIFST

NQGGFMLPIYETAAKAYAVGQFEQPTETPPEDLDTLSLAIEAAIQDLRNK

SQ

IEfusion amino acid sequence (SEQ ID NO: 5):
MVKQIKVRVDMVRHRIKEHMLKKYTQTEEKFTGAFNMMGGCLQNALDILD

KVHEPFEEMKCIGLTMQSMYENYIVPEDKREMWMACIKELHDVSKGAANK

LGGALQAKARAKKDELRRKMMYMCYRNIEFFTKNSAFPKTTNGCSQAMAA

LQNLPQCSPDEIMAYAQKIFKILDEERDKVLTHIDHIFMDILTTCVETMC

NEYKVTSDACMMTMYGGISLLSEFCRVLCCYVLEETSVMLAKRPLITKPE

VISVMKRRIEEICMKVFAQYILGADPLRVCSPSVDDLRAIAEESDEEEAI

VAYTLATAGVSSSDSLVSPPESPVPATIPLSSVIVAENSDQEESEQSDEE

EEEGAQEEREDTVSVKSEPVSEIEEVAPEEEEDGAEEPTASGGKSTHPMV

TRSKADQGDILAQAVNHAGIDSSSTGPTLTTHSCSVSSAPLNKPTPTSVA

VTNTPLPGASATPELSPRKKPRKTTRPFKVIIKPPVPPAPIMLPLIKQED

IKPEPDFTIQYRNKIIDTAGCIVISDSEEEQGEEVETRGATASSPSTGSG

TPRVTSPTHPLSQMNHPPLPDPLGRPDEDSSSSSSSSCSSASDSESESEE

MKCSSGGGASVTSSHHGRGGFGGAASSSLLSCGHQSSGGASTGPRKKKSK

RISELDNEKVRNIMKDKNTPFCTPNVQTRRGRVKIDEVSRMFRNTNRSLE

YKNLPFTIPSMHQVLDEAIKACKTMQVNNKGIQIIYTRNHEVKSEVDAVR

CRLGTMCNLALSTPFLMEHTMPVTHPPEVAQRTADACNEGVKAAWSLKEL

HTHQLCPRSSDYRNMIIHAATPVDLLGALNLCLPLMQKFPKQVMVRIFST

NQGGFMLPIYETAAKAYAVGQFEQPTETPPEDLDTLSLAIEAAIQDLRNK

SQ

IEfusion-4 NT amino acid sequence (SEQ ID NO: 6):
MVKQIKVRVDMVRHRIKEHMLKKYTQTEEKFTGAFNMMGGCLQNALDILD

KVHEPFEEMKCIGLTMQSMYENYIVPEDKREMWMACIKELHDVSKGAANK

LGGALQAKARAKKDELRRKMMYMCYRNIEFFTKNSAFPKTTNGCSQAMAA

LQNLPQCSPDEIMAYAQKIFKILDEERDKVLTHIDHIFMDILTTCVETMC

NEYKVTSDACMMTMYGGISLLSEFCRVLCCYVLEETSVMLAKRPLITKPE

VISVMKRRIEEICMKVFAQYILGADPLRVCSPSVDDLRAIAEESDEEEAI

VAYTLATAGVSSSDSLVSPPESPVPATIPLSSVIVAENSDQEESEQSDEE

EEEGAQEEREDTVSVKSEPVSEIEEVAPEEEEDGAEEPTASGGKSTHPMV

TRSKADQGDILAQAVNHAGIDSSSTGPTLTTHSCSVSSAPLNKPTPTSVA

VTNTPLPGASATPELSPRKKPRKTTRPFKVIIKPPVPPAPIMLPLIKQED

IKPEPDFTIQYRNKIIDTAGCIVISDSEEEQGEEVETRGATASSPSTGSG

TPRVTSPTHPLSQMNHPPLPDPLGRPDEDSSSSSSSSCSSASDSESESEE

-continued

MKCSSGGGASVTSSHHGRGGFGGAASSSLLSCGHQSSGGASTGPRKKKSK

RISELDNEKVRNIMKDKNTPFCTPNVQTRRGRVKIDEVSRMFRNTNRSLE

YKNLPFTIPSMHQVLDEAIKACKTMQVNNKGIQIIYTRNHEVKSEVDAVR

CRLGTMCNLALSTPFLMEHTMPVTHPPEVAQRTADACNEGVKAAWSLKEL

HTHQLCPRSSDYRNMIIHAATPVDLLGALNLCLPLMQKFPKQVMVRIFST

NQGGFMLPIYETAAKAYAVGQFEQPTETPPEDLDTLSLAIEAAIQDLRNK

SQ

IE2-VacO DNA sequence (SEQ ID NO: 7):
atgggagacatcctagcacaagcagtgaaccatgctggaattgactcatc ttcgaccggaccaactctaacgactcattcatgttcggttagttctgctc ctcttaacaagcctacacctacctcggtagctgttaccaacacaccttta ccaggagcatcagcaacacctgagttgtctccaagaaagaagcctcgtaa gaccacgagaccgttcaaggtgatcatcaagccaccagtaccacctgctc cgatcatgttgccattgatcaagcaggaggacattaagccagaacctgac ttcacgatacagtaccgtaacaagatcatagatacagcaggatgcatagt gatctcagatagtgaagaggagcaaggtgaggaagtggagactagaggag ccacagccagttcgccttccacaggatccggaactcctagagtaactagt ccgacacatccactttcccagatgaatcatccacctctaccggatcctct aggacgaccagatgaagattcttcttcatctagttcaagttcttgctcat ccgcgagtgatagtgagtcagaaagtgaagagatgaagtgctcttctggt ggtggagctagtgtcacttcatctcatcatggacgaggaggatttggagg tgctgcgagtagttccttactaagttgtggacatcagtcatctggtggtg catctactggacctagaaagaagaagtcaaagagaatctccgaattggat aatgagaaagtgagaaacatcatgaaggacaagaacacgccgttctgcac tccgaatgttcagacgagaagaggacgagtgaagatagatgaagtatcac gaatgttcagaaacacaaatcgttctctagagtacaagaatcttccgttc accataccttcgatgcaccaagtattagatgaggctatcaaggcatgtaa gaccatgcaagttaacaacaaaggaatacagatcatctacactagaaacc atgaggttaagagtgaggtggatgccgtacgttgtagattgggaacgatg tgtaaccttgcgctatctactcctttcctaatggagcatactatgcctgt gactcatcctcctgaagtggctcaaagaacagctgatgcttgtaacgaag gtgtgaaagctgcttggtccctaaaggagttacatacacaccaactttgt ccacgatccagtgactacagaaacatgatcattcatgcagctacgcctgt agatctacttggagctcttaacctatgtcttcctttgatgcagaagttcc ctaagcaagtgatggtgagaatcttctcgacgaatcaaggaggattcatg ttaccgatatacgagacagctgcaaaggcttacgctgtcggtcagttcga gcaaccgactgaaacgcctcctgaggacttagatacattgtctttggcga tagaagcagcgattcaggatcttagaaacaagagtcagtaa IE2 DNA sequence (SEQ ID NO: 8):
atgggtgacatcctcgcccaggctgtcaatcatgccggtatcgattccag tagcaccggccccacgctgacaacccactcttgcagcgttagcagcgccc -continued ctcttaacaagccgacccccaccagcgtcgcggttactaacactcctctc cccggggcatccgctactcccgagctcagcccgcgtaagaaaccgcgcaa aaccacgcgtcctttcaaggtgattattaaaccgcccgtgcctcccgcgc ctatcatgctgcccctcatcaaacaggaagacatcaagcccgagcccgac tttaccatccagtaccgcaacaagattatcgataccgccggctgtatcgt gatctctgatagcgaggaagaacagggtgaagaagtcgaaacccgcggtg ctaccgcgtcttccccttccaccggcagcggcacgccgcgagtgacctct cccacgcacccgctctcccagatgaaccaccctcctcttcccgatccctt gggccggcccgatgaagatagttcctcttcgtcttcctcctcctgcagtt cggcttcggactcggagagtgagtccgaggagatgaaatgcagcagtggc ggaggagcatccgtgacctcgagccaccatgggcgcggcggttttggtgg cgcggcctcctcctctctgctgagctgcggccatcagagcagcggcgggg cgagcaccggaccccgcaagaagaagagcaaacgcatctccgagttggac aacgagaaggtgcgcaatatcatgaaagataagaacacccccttctgcac acccaacgtgcagactcggcggggtcgcgtcaagattgacgaggtgagcc gcatgttccgcaacaccaatcgctctcttgagtacaagaacctgcccttc acgattcccagtatgcaccaggtgttagatgaggccatcaaagcctgcaa aaccatgcaggtgaacaacaagggcatccagattatctacacccgcaatc atgaggtgaagagtgaggtggatgcggtgcggtgtcgcctgggcaccatg tgcaacctggccctctccactcccttcctcatggagcacaccatgcccgt gacacatccacccgaagtggcgcagcgcacagccgatgcttgtaacgaag gcgtcaaggccgcgtggagcctcaaagaattgcacacccaccaattatgc ccccgttcctccgattaccgcaacatgatcatccacgctgccacccccgt ggacctgttgggcgctctcaacctgtgcctgcccctgatgcaaaagtttc ccaaacaggtcatggtgcgcatcttctccaccaaccagggtgggttcatg ctgcctatctacgagacggccgcgaaggcctacgccgtggggcagtttga gcagcccaccgagacccctcccgaagacctggacaccctgagcctggcca tcgaggcagccatccaggacctgaggaacaagtctcagtaa IE2-4 nt DNA sequence (SEQ ID NO: 9):

atgggtgacatcctcgcccaggctgtcaatcatgccggtatcgattccag tagcaccggacctacgctgacaacccactcttgcagcgttagcagcgctc ctcttaacaagccgactccaaccagcgtcgcggttactaacactcctcta ccaggagcatccgctactcccgagctcagcccgcgtaagaaaccgcgcaa gaccacgcgtcctttcaaggtgattattaaaccgcccgtgcctcccgcgc ctatcatgctgccactcatcaaacaggaagacatcaagcccgagcccgac tttaccatccagtaccgcaacaagattatcgataccgccggctgtatcgt gatctctgatagcgaggaagaacagggtgaagaagtcgaaacccgcggtg ctaccgcgtcttcaccttccaccggcagcggcacgccgcgagtgacctct cccacgcacccgctctcccagatgaaccaccctcctcttcccgatccctt gggccggcccgatgaagatagttcctcttcgtcttcctcctcctgcagtt cggcttcggactcggagagtgagtccgaggagatgaaatgcagcagtggc ggaggagcatccgtgacctcgagccaccatgggcgcggcggatttggtgg cgcggcctcctcctctctgctgagctgcggccatcagagcagcggcggtg cgagcaccggacctcgcaagaagaagagcaaacgcatctccgagttggac aacgagaaggtgcgcaatatcatgaaagataagaacactcccttctgcac acccaacgtgcagactcggcgtggtcgcgtcaagattgacgaggtgagcc gcatgttccgcaacaccaatcgctctcttgagtacaagaacctgcccttc acgattcccagtatgcaccaggtgttagatgaggccatcaaagcctgcaa gaccatgcaggtgaacaacaagggcatccagattatctacacccgcaatc atgaggtgaagagtgaggtggatgcggtgcggtgtcgcctgggcaccatg tgcaacctggccctctccactcccttcctcatggagcacaccatgcccgt gacacatccacccgaagtggcgcagcgcacagccgatgcttgtaacgaag gcgtcaaggccgcgtggagcctcaaagaattgcacacccaccaattatgt cctcgttcctccgattaccgcaacatgatcatccacgctgccacaccagt ggacctgttgggcgctctcaacctgtgcctgccactgatgcagaagtttc ccaaacaggtcatggtgcgcatcttctccaccaaccagggtgggttcatg ctgcctatctacgagacggccgcgaaggcctacgccgttggtcagtttga gcagcccaccgagacacctcccgaagacctggacaccctgagcctggcca tcgaggcagccatccaggacctgaggaacaagtctcagtaa IE2 4 nt H363A DNA sequence (mutations are shown in bold and underlined) (SEQ ID NO: 10):

atgggtgacatcctcgcccaggctgtcaatcatgccggtatcgattccag tagcaccggacctacgctgacaacccactcttgcagcgttagcagcgctc ctcttaacaagccgactccaaccagcgtcgcggttactaacactcctcta ccaggagcatccgctactcccgagctcagcccgcgtaagaaaccgcgcaa gaccacgcgtcctttcaaggtgattattaaaccgcccgtgcctcccgcgc ctatcatgctgccactcatcaaacaggaagacatcaagcccgagcccgac tttaccatccagtaccgcaacaagattatcgataccgccggctgtatcgt gatctctgatagcgaggaagaacagggtgaagaagtcgaaacccgcggtg ctaccgcgtcttcaccttccaccggcagcggcacgccgcgagtgacctct cccacgcacccgctctcccagatgaaccaccctcctcttcccgatccctt gggccggcccgatgaagatagttcctcttcgtcttcctcctcctgcagtt cggcttcggactcggagagtgagtccgaggagatgaaatgcagcagtggc ggaggagcatccgtgacctcgagccaccatgggcgcggcggatttggtgg cgcggcctcctcctctctgctgagctgcggccatcagagcagcggcggtg cgagcaccggacctcgcaagaagaagagcaaacgcatctccgagttggac aacgagaaggtgcgcaatatcatgaaagataagaacactcccttctgcac acccaacgtgcagactcggcgtggtcgcgtcaagattgacgaggtgagcc gcatgttccgcaacaccaatcgctctcttgagtacaagaacctgcccttc acgattcccagtatgcaccaggtgttagatgaggccatcaaagcctgcaa gaccatgcaggtgaacaacaagggcatccagattatctacacccgcaatc atgaggtgaagagtgaggtggatgcggtgcggtgtcgcctgggcaccatg tgcaacctggccctctccactcccttcctcatggaggcaaccatgcccgt -continued gacacatccacccgaagtggcgcagcgcacagccgatgcttgtaacgaag gcgtcaaggccgcgtggagcctcaaagaattgcacacccaccaattatgt cctcgttcctccgattaccgcaacatgatcatccacgctgccacaccagt ggacctgttgggcgctctcaacctgtgcctgccactgatgcagaagtttc ccaaacaggtcatggtgcgcatcttctccaccaaccagggtgggttcatg ctgcctatctacgagacggccgcgaaggcctacgccgttggtcagtttga gcagcccaccgagacacctcccgaagacctggacaccctgagcctggcca tcgaggcagccatccaggacctgaggaacaagtctcagtaa IE2 4 nt H369A DNA sequence (mutations are shown in bold and underlined) (SEQ ID NO: 11):

atgggtgacatcctcgcccaggctgtcaatcatgccggtatcgattccag tagcaccggacctacgctgacaacccactcttgcagcgttagcagcgctc ctcttaacaagccgactccaaccagcgtcgcggttactaacactcctcta ccaggagcatccgctactcccgagctcagcccgcgtaagaaaccgcgcaa gaccacgcgtcctttcaaggtgattattaaaccgcccgtgcctcccgcgc ctatcatgctgccactcatcaaacaggaagacatcaagcccgagcccgac tttaccatccagtaccgcaacaagattatcgataccgccggctgtatcgt gatctctgatagcgaggaagaacagggtgaagaagtcgaaacccgcggtg ctaccgcgtcttcaccttccaccggcagcggcacgccgcgagtgacctct cccacgcacccgctctcccagatgaaccaccctcctcttcccgatccctt gggccggcccgatgaagatagttcctcttcgtcttcctcctcctgcagtt cggcttcggactcggagagtgagtccgaggagatgaaatgcagcagtggc ggaggagcatccgtgacctcgagccaccatgggcgcggcggatttggtgg cgcggcctcctcctctctgctgagctgcggccatcagagcagcggcggtg cgagcaccggacctcgcaagaagaagagcaaacgcatctccgagttggac aacgagaaggtgcgcaatatcatgaaagataagaacactcccttctgcac acccaacgtgcagactcggcgtggtcgcgtcaagattgacgaggtgagcc gcatgttccgcaacaccaatcgctctcttgagtacaagaacctgcccttc acgattcccagtatgcaccaggtgttagatgaggccatcaaagcctgcaa gaccatgcaggtgaacaacaagggcatccagattatctacacccgcaatc atgaggtgaagagtgaggtggatgcggtgcggtgtcgcctgggcaccatg tgcaacctggccctctccactcccttcctcatggaggcaccaccatgccc gtgacamccacccgaagtggcgcagcgcacagccgatgcttgtaacgaag gcgtcaaggccgcgtggagcctcaaagaattgcacacccaccaattatgt cctcgttcctccgattaccgcaacatgatcatccacgctgccacaccagt ggacctgttgggcgctctcaacctgtgcctgccactgatgcagaagtttc ccaaacaggtcatggtgcgcatcttctccaccaaccagggtgggttcatg ctgcctatctacgagacggccgcgaaggcctacgccgttggtcagtttga gcagcccaccgagacacctcccgaagacctggacaccctgagcctggcca tcgaggcagccatccaggacctgaggaacaagtctcagtaa -continued IE2 4 nt H363A/H369A DNA sequence (mutations are shown in bold and underlined) (SEQ ID NO: 12):

atgggtgacatcctcgcccaggctgtcaatcatgccggtatcgattccag tagcaccggacctacgctgacaacccactcttgcagcgttagcagcgctc ctcttaacaagccgactccaaccagcgtcgcggttactaacactcctcta ccaggagcatccgctactcccgagctcagcccgcgtaagaaaccgcgcaa gaccacgcgtcctttcaaggtgattattaaaccgcccgtgcctcccgcgc ctatcatgctgccactcatcaaacaggaagacatcaagcccgagcccgac tttaccatccagtaccgcaacaagattatcgataccgccggctgtatcgt gatctctgatagcgaggaagaacagggtgaagaagtcgaaacccgcggtg ctaccgcgtcttcaccttccaccggcagcggcacgccgcgagtgacctct cccacgcacccgctctcccagatgaaccaccctcctcttcccgatccctt gggccggcccgatgaagatagttcctcttcgtcttcctcctcctgcagtt cggcttcggactcggagagtgagtccgaggagatgaaatgcagcagtggc ggaggagcatccgtgacctcgagccaccatgggcgcggcggatttggtgg cgcggcctcctcctctctgctgagctgcggccatcagagcagcggcggtg cgagcaccggacctcgcaagaagaagagcaaacgcatctccgagttggac aacgagaaggtgcgcaatatcatgaaagataagaacactcccttctgcac acccaacgtgcagactcggcgtggtcgcgtcaagattgacgaggtgagcc gcatgttccgcaacaccaatcgctctcttgagtacaagaacctgcccttc acgattcccagtatgcaccaggtgttagatgaggccatcaaagcctgcaa gaccatgcaggtgaacaacaagggcatccagattatctacacccgcaatc atgaggtgaagagtgaggtggatgcggtgcggtgtcgcctgggcaccatg tgcaacctggccctctccactcccttcctcatggaggcaaccatgcccgt gacagcaccacccgaagtggcgcagcgcacagccgatgcttgtaacgaag gcgtcaaggccgcgtggagcctcaaagaattgcacacccaccaattatgt cctcgttcctccgattaccgcaacatgatcatccacgctgccacaccagt ggacctgttgggcgctctcaacctgtgcctgccactgatgcagaagtttc ccaaacaggtcatggtgcgcatcttctccaccaaccagggtgggttcatg ctgcctatctacgagacggccgcgaaggcctacgccgttggtcagtttga gcagcccaccgagacacctcccgaagacctggacaccctgagcctggcca tcgaggcagccatccaggacctgaggaacaagtctcagtaa IE2 H363A DNA sequence (mutations are shown in bold and underlined) (SEQ ID NO: 13):

atgggtgacatcctcgcccaggctgtcaatcatgccggtatcgattccag tagcaccggccccacgctgacaacccactcttgcagcgttagcagcgccc ctcttaacaagccgacccccaccagcgtcgcggttactaacactcctctc cccggggcatccgctactcccgagctcagcccgcgtaagaaaccgcgcaa aaccacgcgtcctttcaaggtgattattaaaccgcccgtgcctcccgcgc ctatcatgctgcccctcatcaaacaggaagacatcaagcccgagcccgac tttaccatccagtaccgcaacaagattatcgataccgccggctgtatcgt gatctctgatagcgaggaagaacagggtgaagaagtcgaaacccgcggtg ctaccgcgtcttccccttccaccggcagcggcacgccgcgagtgacctct -continued cccacgcacccgctctcccagatgaaccaccctcctcttcccgatccctt
gggccggcccgatgaagatagttcctcttcgtcttcctcctcctgcagtt
cggcttcggactcggagagtgagtccgaggagatgaaatgcagcagtggc
ggaggagcatccgtgacctcgagccaccatgggcgcggcggttttggtgg
cgcggcctcctcctctctgctgagctgcggccatcagagcagcggcgggg
cgagcaccggaccccgcaagaagaagagcaaacgcatctccgagttggac
aacgagaaggtgcgcaatatcatgaaagataagaacacccccttctgcac
acccaacgtgcagactcggcggggtcgcgtcaagattgacgaggtgagcc
gcatgttccgcaacaccaatcgctctcttgagtacaagaacctgcccttc
acgattcccagtatgcaccaggtgttagatgaggccatcaaagcctgcaa
aaccatgcaggtgaacaacaagggcatccagattatctacacccgcaatc
atgaggtgaagagtgaggtggatgcggtgcggtgtcgcctgggcaccatg
tgcaacctggccctctccactcccttcctcatggaggcaaccatgcccgt
gacacatccacccgaagtggcgcagcgcacagccgatgcttgtaacgaag
gcgtcaaggccgcgtggagcctcaaagaattgcacacccaccaattatgc
ccccgttcctccgattaccgcaacatgatcatccacgctgccacccccgt
ggacctgttgggcgctctcaacctgtgcctgcccctgatgcaaaagtttc
ccaaacaggtcatggtgcgcatcttctccaccaaccagggtgggttcatg
ctgcctatctacgagacggccgcgaaggcctacgccgtggggcagtttga
gcagcccaccgagacccctcccgaagacctggacaccctgagcctggcca
tcgaggcagccatccaggacctgaggaacaagtctcag IE2 H369A DNA sequence (mutations are shown in bold and underlined) (SEQ ID NO: 14):

atgggtgacatcctcgcccaggctgtcaatcatgccggtatcgattccag
tagcaccggccccacgctgacaacccactcttgcagcgttagcagcgccc
ctcttaacaagccgacccccaccagcgtcgcggttactaacactcctctc
cccggggcatccgctactcccgagctcagcccgcgtaagaaaccgcgcaa
aaccacgcgtcctttcaaggtgattattaaaccgcccgtgcctcccgcgc
ctatcatgctgcccctcatcaaacaggaagacatcaagcccgagcccgac
tttaccatccagtaccgcaacaagattatcgataccgccggctgtatcgt
gatctctgatagcgaggaagaacagggtgaagaagtcgaaacccgcggtg
ctaccgcgtcttccccttccaccggcagcggcacgccgcgagtgacctct
cccacgcacccgctctcccagatgaaccaccctcctcttcccgatccctt
gggccggcccgatgaagatagttcctcttcgtcttcctcctcctgcagtt
cggcttcggactcggagagtgagtccgaggagatgaaatgcagcagtggc
ggaggagcatccgtgacctcgagccaccatgggcgcggcggttttggtgg
cgcggcctcctcctctctgctgagctgcggccatcagagcagcggcgggg
cgagcaccggaccccgcaagaagaagagcaaacgcatctccgagttggac
aacgagaaggtgcgcaatatcatgaaagataagaacacccccttctgcac
acccaacgtgcagactcggcggggtcgcgtcaagattgacgaggtgagcc
gcatgttccgcaacaccaatcgctctcttgagtacaagaacctgcccttc -continued acgattcccagtatgcaccaggtgttagatgaggccatcaaagcctgcaa
aaccatgcaggtgaacaacaagggcatccagattatctacacccgcaatc
atgaggtgaagagtgaggtggatgcggtgcggtgtcgcctgggcaccatg
tgcaacctggccctctccactcccttcctcatggagcacaccatgcccgt
gacagcaccacccgaagtggcgcagcgcacagccgatgcttgtaacgaag
gcgtcaaggccgcgtggagcctcaaagaattgcacacccaccaattatgc
ccccgttcctccgattaccgcaacatgatcatccacgctgccacccccgt
ggacctgttgggcgctctcaacctgtgcctgcccctgatgcaaaagtttc
ccaaacaggtcatggtgcgcatcttctccaccaaccagggtgggttcatg
ctgcctatctacgagacggccgcgaaggcctacgccgtggggcagtttga
gcagcccaccgagacccctcccgaagacctggacaccctgagcctggcca
tcgaggcagccatccaggacctgaggaacaagtctcag IE2 H363A/H369A DNA sequence (mutations are shown in bold and underlined) (SEQ ID NO: 15):

atgggtgacatcctcgcccaggctgtcaatcatgccggtatcgattccag
tagcaccggccccacgctgacaacccactcttgcagcgttagcagcgccc
ctcttaacaagccgacccccaccagcgtcgcggttactaacactcctctc
cccggggcatccgctactcccgagctcagcccgcgtaagaaaccgcgcaa
aaccacgcgtcctttcaaggtgattattaaaccgcccgtgcctcccgcgc
ctatcatgctgcccctcatcaaacaggaagacatcaagcccgagcccgac
tttaccatccagtaccgcaacaagattatcgataccgccggctgtatcgt
gatctctgatagcgaggaagaacagggtgaagaagtcgaaacccgcggtg
ctaccgcgtcttccccttccaccggcagcggcacgccgcgagtgacctct
cccacgcacccgctctcccagatgaaccaccctcctcttcccgatccctt
gggccggcccgatgaagatagttcctcttcgtcttcctcctcctgcagtt
cggcttcggactcggagagtgagtccgaggagatgaaatgcagcagtggc
ggaggagcatccgtgacctcgagccaccatgggcgcggcggttttggtgg
cgcggcctcctcctctctgctgagctgcggccatcagagcagcggcgggg
cgagcaccggaccccgcaagaagaagagcaaacgcatctccgagttggac
aacgagaaggtgcgcaatatcatgaaagataagaacacccccttctgcac
acccaacgtgcagactcggcggggtcgcgtcaagattgacgaggtgagcc
gcatgttccgcaacaccaatcgctctcttgagtacaagaacctgcccttc
acgattcccagtatgcaccaggtgttagatgaggccatcaaagcctgcaa
aaccatgcaggtgaacaacaagggcatccagattatctacacccgcaatc
atgaggtgaagagtgaggtggatgcggtgcggtgtcgcctgggcaccatg
tgcaacctggccctctccactcccttcctcatggaggcaaccatgcccgt
gacagcaccacccgaagtggcgcagcgcacagccgatgcttgtaacgaag
gcgtcaaggccgcgtggagcctcaaagaattgcacacccaccaattatgc
ccccgttcctccgattaccgcaacatgatcatccacgctgccacccccgt
ggacctgttgggcgctctcaacctgtgcctgcccctgatgcaaaagtttc
ccaaacaggtcatggtgcgcatcttctccaccaaccagggtgggttcatg
ctgcctatctacgagacggccgcgaaggcctacgccgtggggcagtttga -continued gcagcccaccgagacccctcccgaagacctggacaccctgagcctggcca tcgaggcagccatccaggacctgaggaacaagtctcag IE2 VacO H363A DNA sequence (mutations are shown in bold and underlined) (SEQ ID NO: 16):

atgggagacatcctagcacaagcagtgaaccatgctggaattgactcatc ttcgaccggaccaactctaacgactcattcatgttcggttagttctgctc ctcttaacaagcctacacctacctcggtagctgttaccaacacaccttta ccaggagcatcagcaacacctgagttgtctccaagaaagaagcctcgtaa gaccacgagaccgttcaaggtgatcatcaagccaccagtaccacctgctc cgatcatgttgccattgatcaagcaggaggacattaagccagaacctgac ttcacgatacagtaccgtaacaagatcatagatacagcaggatgcatagt gatctcagatagtgaagaggagcaaggtgaggaagtggagactagaggag ccacagccagttcgccttccacaggatccggaactcctagagtaactagt ccgacacatccactttcccagatgaatcatccacctctaccggatcctct aggacgaccagatgaagattcttcttcatctagttcaagttcttgctcat ccgcgagtgatagtgagtcagaaagtgaagagatgaagtgctcttctggt ggtggagctagtgtcacttcatctcatcatggacgaggaggatttggagg tgctgcgagtagttccttactaagttgtggacatcagtcatctggtggtg catctactggacctagaaagaagaagtcaaagagaatctccgaattggat aatgagaaagtgagaaacatcatgaaggacaagaacacgccgttctgcac tccgaatgttcagacgagaagaggacgagtgaagatagatgaagtatcac gaatgttcagaaacacaaatcgttctctagagtacaagaatcttccgttc accataccttcgatgcaccaagtattagatgaggctatcaaggcatgtaa gaccatgcaagttaacaacaaaggaatacagatcatctacactagaaacc atgaggttaagagtgaggtggatgccgtacgttgtagattgggaacgatg tgtaaccttgcgctatctactcctttcctaatggaggctactatgcctgt gactcatcctcctgaagtggctcaaagaacagctgatgcttgtaacgaag gtgtgaaagctgcttggtccctaaaggagttacatacacaccaactttgt ccacgatccagtgactacagaaacatgatcattcatgcagctacgcctgt agatctacttggagctcttaacctatgtcttcctttgatgcagaagttcc ctaagcaagtgatggtgagaatcttctcgacgaatcaaggaggattcatg ttaccgatatacgagacagctgcaaaggcttacgctgtcggtcagttcga gcaaccgactgaaacgcctcctgaggacttagatacattgtctttggcga tagaagcagcgattcaggatcttagaaacaagagtcag IE2 VacO H369A DNA sequence (mutations are shown in bold and underlined) (SEQ ID NO: 17):

atgggagacatcctagcacaagcagtgaaccatgctggaattgactcatc ttcgaccggaccaactctaacgactcattcatgttcggttagttctgctc ctcttaacaagcctacacctacctcggtagctgttaccaacacaccttta ccaggagcatcagcaacacctgagttgtctccaagaaagaagcctcgtaa gaccacgagaccgttcaaggtgatcatcaagccaccagtaccacctgctc cgatcatgttgccattgatcaagcaggaggacattaagccagaacctgac -continued ttcacgatacagtaccgtaacaagatcatagatacagcaggatgcatagt gatctcagatagtgaagaggagcaaggtgaggaagtggagactagaggag ccacagccagttcgccttccacaggatccggaactcctagagtaactagt ccgacacatccactttcccagatgaatcatccacctctaccggatcctct aggacgaccagatgaagattcttcttcatctagttcaagttcttgctcat ccgcgagtgatagtgagtcagaaagtgaagagatgaagtgctcttctggt ggtggagctagtgtcacttcatctcatcatggacgaggaggatttggagg tgctgcgagtagttccttactaagttgtggacatcagtcatctggtggtg catctactggacctagaaagaagaagtcaaagagaatctccgaattggat aatgagaaagtgagaaacatcatgaaggacaagaacacgccgttctgcac tccgaatgttcagacgagaagaggacgagtgaagatagatgaagtatcac gaatgttcagaaacacaaatcgttctctagagtacaagaatcttccgttc accataccttcgatgcaccaagtattagatgaggctatcaaggcatgtaa gaccatgcaagttaacaacaaaggaatacagatcatctacactagaaacc atgaggttaagagtgaggtggatgccgtacgttgtagattgggaacgatg tgtaaccttgcgctatctactcctttcctaatggagcatactatgcctgt gactgctcctcctgaagtggctcaaagaacagctgatgcttgtaacgaag gtgtgaaagctgcttggtccctaaaggagttacatacacaccaactttgt ccacgatccagtgactacagaaacatgatcattcatgcagctacgcctgt agatctacttggagctcttaacctatgtcttcctttgatgcagaagttcc ctaagcaagtgatggtgagaatcttctcgacgaatcaaggaggattcatg ttaccgatatacgagacagctgcaaaggcttacgctgtcggtcagttcga gcaaccgactgaaacgcctcctgaggacttagatacattgtctttggcga tagaagcagcgattcaggatcttagaaacaagagtcag IE2 VacO H363A/H369A DNA sequence (mutations are shown in bold and underlined) (SEQ ID NO: 18):

atgggagacatcctagcacaagcagtgaaccatgctggaattgactcatc ttcgaccggaccaactctaacgactcattcatgttcggttagttctgctc ctcttaacaagcctacacctacctcggtagctgttaccaacacaccttta ccaggagcatcagcaacacctgagttgtctccaagaaagaagcctcgtaa gaccacgagaccgttcaaggtgatcatcaagccaccagtaccacctgctc cgatcatgttgccattgatcaagcaggaggacattaagccagaacctgac ttcacgatacagtaccgtaacaagatcatagatacagcaggatgcatagt gatctcagatagtgaagaggagcaaggtgaggaagtggagactagaggag ccacagccagttcgccttccacaggatccggaactcctagagtaactagt ccgacacatccactttcccagatgaatcatccacctctaccggatcctct aggacgaccagatgaagattcttcttcatctagttcaagttcttgctcat ccgcgagtgatagtgagtcagaaagtgaagagatgaagtgctcttctggt ggtggagctagtgtcacttcatctcatcatggacgaggaggatttggagg tgctgcgagtagttccttactaagttgtggacatcagtcatctggtggtg catctactggacctagaaagaagaagtcaaagagaatctccgaattggat aatgagaaagtgagaaacatcatgaaggacaagaacacgccgttctgcac -continued tccgaatgttcagacgagaagaggacgagtgaagatagatgaagtatcac gaatgttcagaaacacaaatcgttctctagagtacaagaatcttccgttc accataccttcgatgcaccaagtattagatgaggctatcaaggcatgtaa gaccatgcaagttaacaacaaaggaatacagatcatctacactagaaacc atgaggttaagagtgaggtggatgccgtacgttgtagattgggaacgatg tgtaaccttgcgctatctactcctttcctaatggaggctactatgcctgt gactgctcctcctgaagtggctcaaagaacagctgatgcttgtaacgaag gtgtgaaagctgcttggtccctaaaggagttacatacacaccaactttgt ccacgatccagtgactacagaaacatgatcattcatgcagctacgcctgt agatctacttggagctcttaacctatgtcttcctttgatgcagaagttcc ctaagcaagtgatggtgagaatcttctcgacgaatcaaggaggattcatg ttaccgatatacgagacagctgcaaaggcttacgctgtcggtcagttcga gcaaccgactgaaacgcctcctgaggacttagatacattgtctttggcga tagaagcagcgattcaggatcttagaaacaagagtcag IE2-Vac0 amino acid sequence (SEQ ID NO: 19):
MGDILAQAVNHAGIDSSSTGPTLTTHSCSVSSAPLNKPTPTSVAVTNTPL

PGASATPELSPRKKPRKTTRPFKVIIKPPVPPAPIMLPLIKQEDIKPEPD

FTIQYRNKIIDTAGCIVISDSEEEQGEEVETRGATASSPSTGSGTPRVTS

PTHPLSQMNHPPLPDPLGRPDEDSSSSSSSSCSSASDSESESEEMKCSSG

GGASVTSSHHGRGGFGGAASSSLLSCGHQSSGGASTGPRKKKSKRISELD

NEKVRNIMKDKNTPFCTPNVQTRRGRVKIDEVSRMFRNTNRSLEYKNLPF

TIPSMHQVLDEAIKACKTMQVNNKGIQIIYTRNHEVKSEVDAVRCRLGTM

CNLALSTPFLMEHTMPVTHPPEVAQRTADACNEGVKAAWSLKELHTHQLC

PRSSDYRNMIIHAATPVDLLGALNLCLPLMQKFPKQVMVRIFSTNQGGFM

LPIYETAAKAYAVGQFEQPTETPPEDLDTLSLAIEAAIQDLRNKSQ

IE2 amino acid sequence (SEQ ID NO: 20):
MGDILAQAVNHAGIDSSSTGPTLTTHSCSVSSAPLNKPTPTSVAVTNTPL

PGASATPELSPRKKPRKTTRPFKVIIKPPVPPAPIMLPLIKQEDIKPEPD

FTIQYRNKIIDTAGCIVISDSEEEQGEEVETRGATASSPSTGSGTPRVTS

PTHPLSQMNHPPLPDPLGRPDEDSSSSSSSSCSSASDSESESEEMKCSSG

GGASVTSSHHGRGGFGGAASSSLLSCGHQSSGGASTGPRKKKSKRISELD

NEKVRNIMKDKNTPFCTPNVQTRRGRVKIDEVSRMFRNTNRSLEYKNLPF

TIPSMHQVLDEAIKACKTMQVNNKGIQIIYTRNHEVKSEVDAVRCRLGTM

CNLALSTPFLMEHTMPVTHPPEVAQRTADACNEGVKAAWSLKELHTHQLC

PRSSDYRNMIIHAATPVDLLGALNLCLPLMQKFPKQVMVRIFSTNQGGFM

LPIYETAAKAYAVGQFEQPTETPPEDLDTLSLAIEAAIQDLRNKSQ

-continued

IE2-4 nt amino acid sequence (SEQ ID NO: 21):
MGDILAQAVNHAGIDSSSTGPTLTTHSCSVSSAPLNKPTPTSVAVTNTPL

PGASATPELSPRKKPRKTTRPFKVIIKPPVPPAPIMLPLIKQEDIKPEPD

FTIQYRNKIIDTAGCIVISDSEEEQGEEVETRGATASSPSTGSGTPRVTS

PTHPLSQMNHPPLPDPLGRPDEDSSSSSSSSCSSASDSESESEEMKCSSG

GGASVTSSHHGRGGFGGAASSSLLSCGHQSSGGASTGPRKKKSKRISELD

NEKVRNIMKDKNTPFCTPNVQTRRGRVKIDEVSRMFRNTNRSLEYKNLPF

TIPSMHQVLDEAIKACKTMQVNNKGIQIIYTRNHEVKSEVDAVRCRLGTM

CNLALSTPFLMEHTMPVTHPPEVAQRTADACNEGVKAAWSLKELHTHQLC

PRSSDYRNMIIHAATPVDLLGALNLCLPLMQKFPKQVMVRIFSTNQGGFM

LPIYETAAKAYAVGQFEQPTETPPEDLDTLSLAIEAAIQDLRNKSQ

IE2 H363A amino acid sequence (mutation(s) are shown in bold and underlined) (SEQ ID NO: 22):
MGDILAQAVNHAGIDSSSTGPTLTTHSCSVSSAPLNKPTPTSVAVTNTPL

PGASATPELSPRKKPRKTTRPFKVIIKPPVPPAPIMLPLIKQEDIKPEPD

FTIQYRNKIIDTAGCIVISDSEEEQGEEVETRGATASSPSTGSGTPRVTS

PTHPLSQMNHPPLPDPLGRPDEDSSSSSSSSCSSASDSESESEEMKCSSG

GGASVTSSHHGRGGFGGAASSSLLSCGHQSSGGASTGPRKKKSKRISELD

NEKVRNIMKDKNTPFCTPNVQTRRGRVKIDEVSRMFRNTNRSLEYKNLPF

TIPSMHQVLDEAIKACKTMQVNNKGIQIIYTRNHEVKSEVDAVRCRLGTM

CNLALSTPFLMEATMPVTHPPEVAQRTADACNEGVKAAWSLKELHTHQLC

PRSSDYRNMIIHAATPVDLLGALNLCLPLMQKFPKQVMVRIFSTNQGGFM

LPIYETAAKAYAVGQFEQPTETPPEDLDTLSLAIEAAIQDLRNKSQ

IE2 H369A amino acid sequence (mutation(s) are shown in bold and underlined) (SEQ ID NO: 23):
MGDILAQAVNHAGIDSSSTGPTLTTHSCSVSSAPLNKPTPTSVAVTNTPL

PGASATPELSPRKKPRKTTRPFKVIIKPPVPPAPIMLPLIKQEDIKPEPD

FTIQYRNKIIDTAGCIVISDSEEEQGEEVETRGATASSPSTGSGTPRVTS

PTHPLSQMNHPPLPDPLGRPDEDSSSSSSSSCSSASDSESESEEMKCSSG

GGASVTSSHHGRGGFGGAASSSLLSCGHQSSGGASTGPRKKKSKRISELD

NEKVRNIMKDKNTPFCTPNVQTRRGRVKIDEVSRMFRNTNRSLEYKNLPF

TIPSMHQVLDEAIKACKTMQVNNKGIQIIYTRNHEVKSEVDAVRCRLGTM

CNLALSTPFLMEHTMPVTAPPEVAQRTADACNEGVKAAWSLKELHTHQLC

PRSSDYRNMIIHAATPVDLLGALNLCLPLMQKFPKQVMVRIFSTNQGGFM

LPIYETAAKAYAVGQFEQPTETPPEDLDTLSLAIEAAIQDLRNKSQ

IE2 H363A/H369A amino acid sequence (mutation(s) are shown in bold and underlined) (SEQ ID NO: 24):
MGDILAQAVNHAGIDSSSTGPTLTTHSCSVSSAPLNKPTPTSVAVTNTPL

PGASATPELSPRKKPRKTTRPFKVIIKPPVPPAPIMLPLIKQEDIKPEPD

FTIQYRNKIIDTAGCIVISDSEEEQGEEVETRGATASSPSTGSGTPRVTS

PTHPLSQMNHPPLPDPLGRPDEDSSSSSSSSCSSASDSESESEEMKCSSG

GGASVTSSHHGRGGFGGAASSSLLSCGHQSSGGASTGPRKKKSKRISELD

NEKVRNIMKDKNTPFCTPNVQTRRGRVKIDEVSRMFRNTNRSLEYKNLPF

TIPSMHQVLDEAIKACKTMQVNNKGIQIIYTRNHEVKSEVDAVRCRLGTM

-continued

CNLALSTPFLMEATMPVTAPPEVAQRTADACNEGVKAAWSLKELHTHQLC

PRSSDYRNMIIHAATPVDLLGALNLCLPLMQKFPKQVMVRIFSTNQGGFM

LPIYETAAKAYAVGQFEQPTETPPEDLDTLSLAIEAAIQDLRNKSQ

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned herein are incorporated in their entirety.

Materials and Methods

DATABASE SEARCHING: Tandem mass spectra (MS/MS) were extracted from a gradient 4-20% SDS-PAGE gel (Bio-Rad, USA) via in-gel trypsin digestion and subsequent peptide extraction. Charge state de-convolution and de-isotoping were not performed. All MS/MS samples were analyzed using Sequest (XCorr Only) (Thermo Fisher Scientific, San Jose, CA, USA; version IseNode in Proteome Discoverer 2.1.0.81). Sequest (XCorr Only) was set up to search crap_ncbi.fasta; Heidi_20170828.fasta; human-_refseq.fasta (unknown version, 73204 entries) assuming the digestion enzyme non-specific. Sequest (XCorr Only) was searched with a fragment ion mass tolerance of 0.60 Da and a parent ion tolerance of 10.0 PPM. Carbamidomethyl of cysteine was specified in Sequest (XCorr Only) as a fixed modification. De-amidation of asparagine, oxidation of methionine and acetyl of the N-terminus were specified in Sequest (XCorr Only) as variable modifications.

CRITERIA FOR PROTEIN IDENTIFICATION: Scaffold (version Scaffold_4.8.4, Proteome Software Inc., Portland, OR) was used to validate MS/MS based peptide and protein identifications. Peptide identifications were accepted if they could be established at greater than 36.0% probability by the Scaffold Local FDR algorithm. Protein identifications were accepted if they could be established at greater than 98.0% probability to achieve an FDR less than 1.0% and contained at least 5 identified peptides. Protein probabilities were assigned by the Protein Prophet algorithm [33]. Proteins that contained similar peptides and could not be differentiated based on MS/MS analysis alone were grouped to satisfy the principles of parsimony.

Example 1. Assessment of the First-Generation Triplex

Figure 2A:
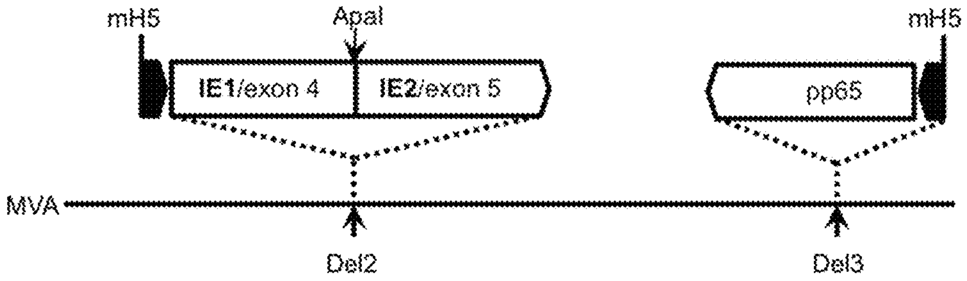
FIGS. 2A-2C show the Triplex gene organization in Modified Vaccinia Ankara (MVA) virus and its stability post-passaging in chicken embryonic fibroblasts (CEFs).
Figure 2B:
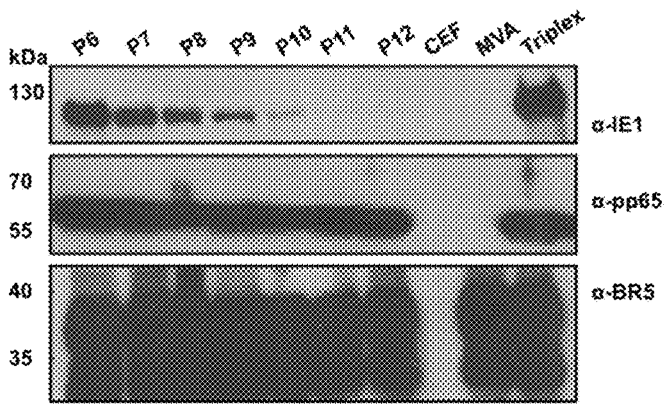
Figure 2C:
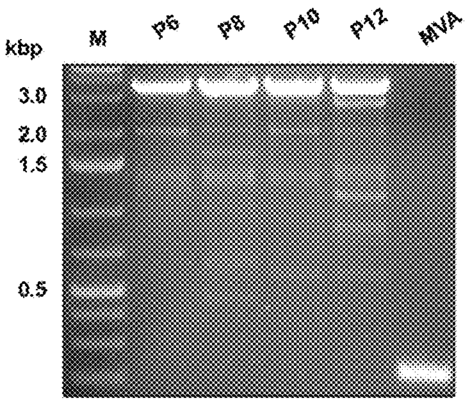

In this study, "stability" was assessed by the integrity of the gene of interest within MVA being monitored via polymerase chain reaction (PCR), DNA sequencing and western blot to ensure the full-length gene is present and full-length protein is present. The original design of Triplex contained a pSyn promoter that, upon serial passaging, caused instability resulting in greatly reduced protein expression. The pSyn promoter was previously replaced with a modified vaccinia virus H5 (mH5) promoter (FIG. 2A), upon which increased IEfusion protein stability was observed while maintaining immunogenicity [1, 2]. To further improve expression stability, the nuclear localization sequence and transcriptional activation domains encoded within exon 2/exon 3 and the overlapping reading frames of IE1 and IE2 from HCMV AD169 were omitted to prevent gene activation events that may be associated with carcinogenesis and reduce the number of possible transcription units. (FIG. 2A) [3]. Therefore, IE1/IE2 fusion with a seamless junction in between, without adding additional nucleotides or amino acids, was inserted into the Del2 site of Modified Vaccinia Ankara (MVA) while unmodified phosphoprotein pp65 [4] was inserted into the Del3 site of MVA [1]. After these modifications, IEfusion stability was observed at the RNA level over 10 viral passages in CEF although not at either the protein (FIG. 2B) or the DNA level (FIG. 2C) [1]. For propagation the IEfusion sample underwent approximately 5 passages prior to evaluation. Thus, in FIG. 2B, the sample marked as P1 was likely passaged five times prior to analysis in CEF. Clinical Triplex used in FIG. 2B, on the other hand, did not undergo as many passages; therefore reduced stability was already observed in P1 for IEfusion (FIGS. 2B and 2C).

Therefore, the first-generation Triplex might not be acceptable to the Food and Drug Administration (FDA) as a Phase 3 manufacturing solution without rigorous validation.

Example 2. Generation of IEfusion variants

Although the genomic architecture of the first-generation Triplex and the new Triplex constructs disclosed herein are similar, IEfusion inserted at other sites in MVA (Scheme I shown in FIG. 1) was evaluated in addition to exploring gene modifications to IEfusion to reduce spontaneous mutation hot spots and/or increase expression via codon optimization for pox virus (i.e., wobble position (4 nt) and vaccinia virus expression (VacO) optimization). First generation Triplex contains IEfusion in Del2 and pp65 in Del3 in MVA using the HCMV AD169 DNA sequence, generated via a transfer plasmid that would facilitate homologous recombination of IEfusion into wild-type MVA [3]. See FIG. 2. Because this process can be time consuming, the Bacterial Artificial Chromosome (BAC) technology was utilized. By applying BAC technology [11, 12] and en passant mutagenesis [13, 14] to generate new MVA constructs expressing pp65 and various iterations of IEfusion, each of the proposed viral constructs (Table 2) was rapidly generated and tested.

TABLE 2

MVA Constructs Expressing IEfusion Generated via BAC Technology

| | Insertion Sites | | | | | |
|---|---|---|---|---|---|---|
| Gene | Del2 | G1L/I8R | IGR3 | 044/045L | Del3 | New Del3 |
| IEfus | X | X | X | ND | ND | ND |
| IEfus 4 nt | X | X | X | X | ND | ND |
| IEfus VacO | X | X | X | ND | ND | ND |
| IE1 | ND | ✓ | X | X | ND | ND |
| IE1 4 nt | ND | ✓ | ✓ | X | ND | ND |
| IE1 VacO | ND | ✓ | ✓ | X | ND | ND |
| IE2 | ND | X | X | X | X | X |
| IE2 4 nt | ND | X | X | X | X | X |
| IE2 VacO | ND | X | X | X | X | X |
| pp65 | ND | ND | ND | ND | ✓ | ND |

"X" denotes unstable; "✓" denotes stable site; and "ND" indicates not determined.

As shown in Table 2, some versions of IEfusion (IEfus) were inserted into the following sites in MVA: Del2, G1L, IGR3, or 044L/045L. After inserting IEfusion into Del3, G1L/18R, IGR3, and 044L/045L, some sites did aid in stabilizing gene expression to some extent (data not shown), but likely insufficient to meet FDA standards for late stage clinical evaluation. FIG. 3 shows the nucleic acid sequence alignment of IEfusion constructs. FIG. 4 shows that IEfusion 4nt stabilized IEfusion expression beyond five viral passages (P5) when constructed within the IGR3 site in MVA.

Example 3. Assessment of IEfusion variants

Mutation hot spots were removed by disrupting the runs of consecutive C or G nucleotide bases [15], followed by vaccinia virus codon (designated as VacO) optimizing the DNA sequence of IEfusion. Constructs shown in Table 2 marked with an "X" were analyzed for stability via PCR and by western blot to monitor the integrity of the gene within its insertion site and expression after passage. This type of analysis provides insight regarding instability at either the DNA or protein levels.

Based on the knowledge that removal of spontaneous mutation hot spots minimizes instability, all IEfusion constructs shown in Table 2 were evaluated.

Figure 4A:
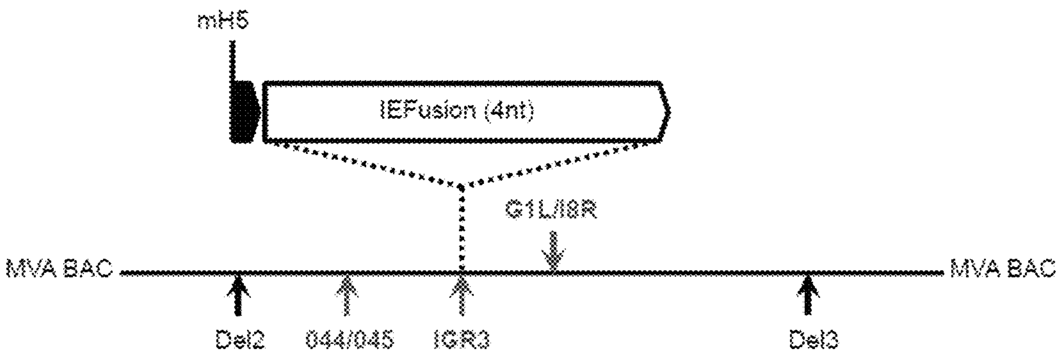
FIGS. 4A-4C show the stability analysis of IEfusion 4nt in IGR3 insertion site on MVA-BAC.
Figure 4B:
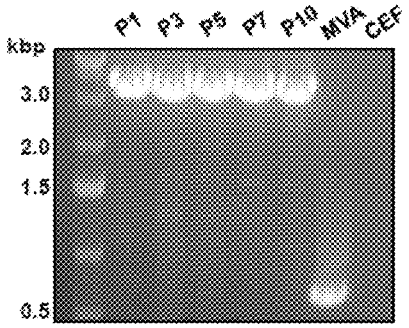

IEfusion 4nt inserted in IGR3 (FIG. 4) shows increased stability over various IEfusion constructs that were modified and inserted into Del2, G1L, and 044L/045L insertion sites (Table 2 and FIG. 4A). The genes of interest were amplified via PCR for gene stability analyses, including the flanking regions in the MVA (expected IEfusion size shown in Table 3).

TABLE 3

PCR product sizes for genes engineered within specific sites

| Gene | G1L/I8R (bp) | IGR3 (bp) | 044/045L (bp) | Del3 (bp) | Protein Size (kDa) |
|---|---|---|---|---|---|
| IEfusion | 4274 | 3640 | n/a | n/a | ~130 |
| IE1 | 2783 | 2155 | 1998 | n/a | ~55 |
| IE2 | 3051 | 2423 | 2265 | n/a | ~68 |
| pp65 | n/a | n/a | n/a | 2923 | ~65 |
| Empty | 1538 | 818 | 667 | 1072 | n/a |

Figure 4C:
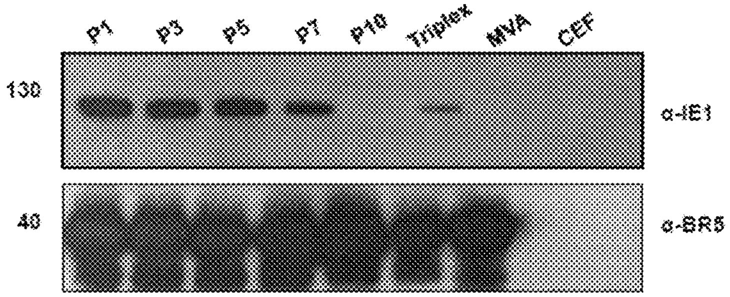
Figure 5:
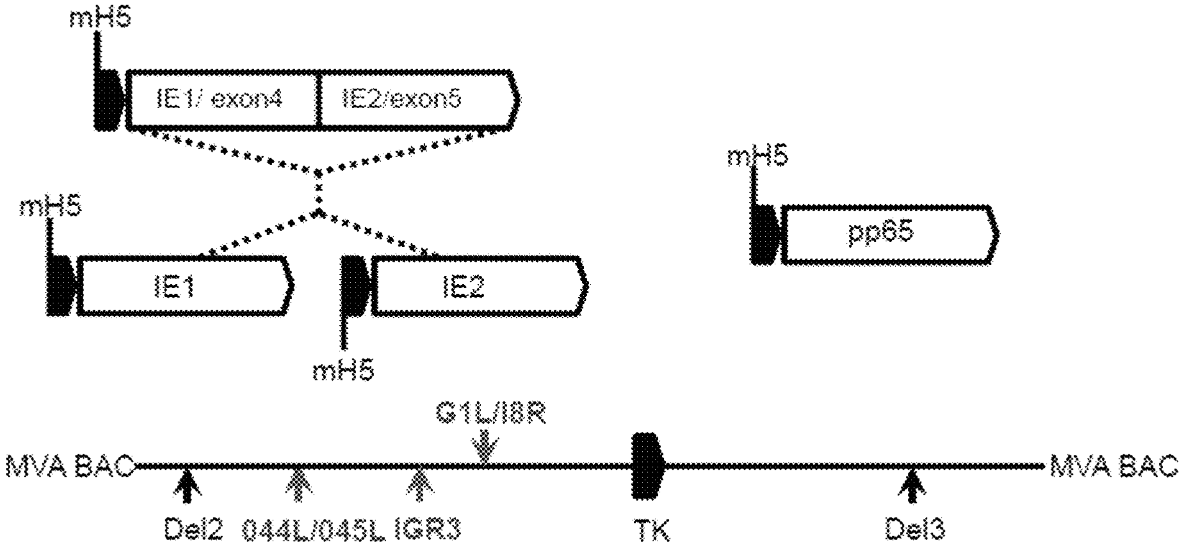
FIG. 5 is a schematic of potential sites on MVA-BAC and de-construction of IEfusion into IE1 and IE2. The potential sites in MVA BAC available for insertion of either IE1 or IE2 genes are 044L/045L, IGR3, and G1L/18R. Upon separation of IE1 and IE2, each gene is to be controlled by the mH5 promoter.

When the integrity of the full-length gene was compromised during passaging, non-specific PCR products would emerge and aberrant DNA sequencing results were observed around passage 3 (P3) or products similar to the size of the negative control (FIG. 4B); however, with instability at the protein level, a decrease in expression of the full-length product was observed at P7 (FIG. 4C). Although it seemed that some improvement in stability was observed over serial viral passaging in CEF (data not shown), protein expression of full-length IEfusion was not maintained over prolonged passaging. Based on this information, it was concluded that IE1 and IE2 would not be stably expressed as a protein fusion of ~130 kDa unless modifications were made at either the DNA or amino acid level. Consequently, IEfusion without further modification as a fused sequence may not be optimal for maintaining stable expression of IEfusion in MVA that withstands ten or more passages.

Example 4: Development of an Innovative Strategy for Stable Expression of IE1, IE2, and Pp65 in MVA The goal was to find the most stable combination of insertion sites and gene modifications to generate an MVA that stably expresses all three antigens at a minimum of 10 passages for large-scale propagation of the vaccine virus. A new vaccine construction strategy was initiated considering three main points to find the most stable combination of insertion sites that allows stable expression of IE1, IE2, and pp65: 1) splitting IEfusion into its IE1/IE2 components; 2) inserting variant gene sequences of all three genes into separate insertion sites in MVA; and 3) explore new insertion sites in MVA. Since there was limited success in enhancing stability with IE1 and IE2 as a fusion protein post nucleotide modifications, IE1 and IE2 were separated and each gene was inserted in separate insertion sites, and then stability of each gene in each of the new sites was analyzed. The original IEfusion construct was used as a template to split IE1 and IE2, with each component under the control of separate mH5 promoters [1]. Table 2 shows all the constructs generated in an attempt to give rise to an MVA that stably expresses IE1 and IE2 over ≥10 passages. Furthermore, other modifications, such as removal of consecutive C and G nucleotides as well as codon-optimization of the genes as was done for IEfusion, were incorporated. Different sequence modifications of IE1 and IE2 genes were analyzed for stability in CEFs, also using BAC technology to generate the various MVA constructs. Because instability in Del2 has been observed [15], Del2 site was not further pursued as a candidate site.

Figure 9A:
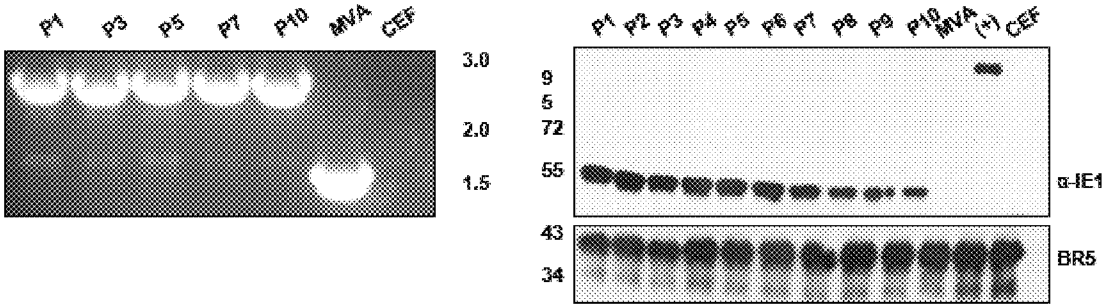
FIGS. 9A-9C show the stability analysis of IE1 NCO, 4nt, and VacO in G1L/18R insertion site on MVA-BAC. PCR (left) and Western blot analyses (right) of IE1 NCO (9A), 4nt (9B), and VacO (9C). Left: 1.0% agarose gel of PCR product analyzing stability of IE1 in G1L/18R, passaged up to P10 in CEF. Right: Western blot analysis of IE1 passaged up to P10 in CEF cells. IE1 and IEfusion was probed using a purified anti-IE1 mouse monoclonal antibody (mAB) p63-27. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.
Figure 9B:
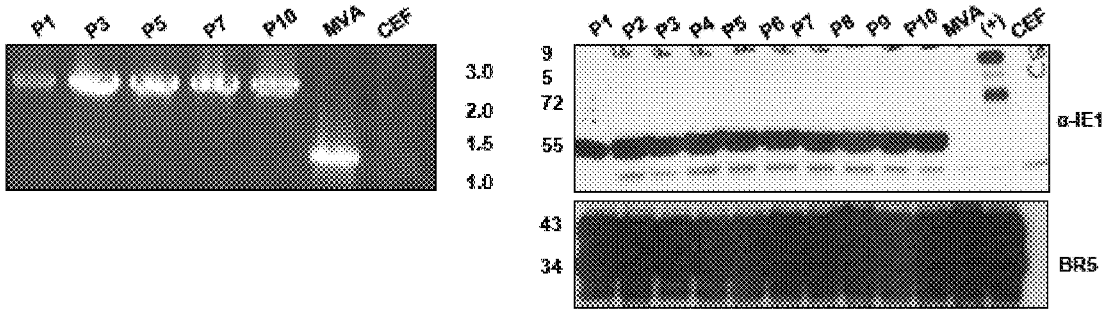
Figure 9C:
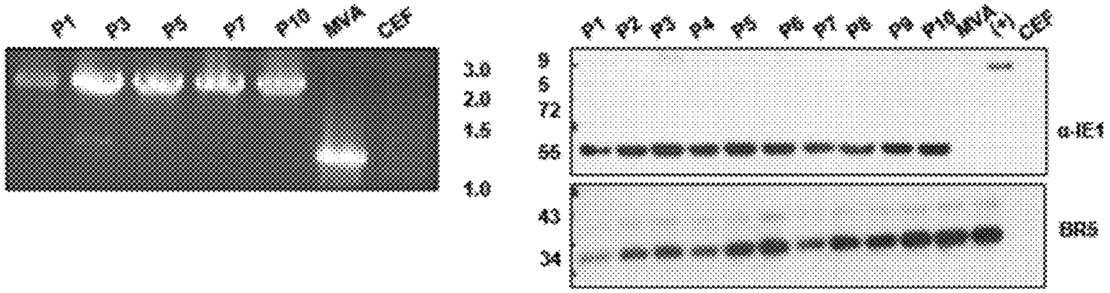
Figure 10A:
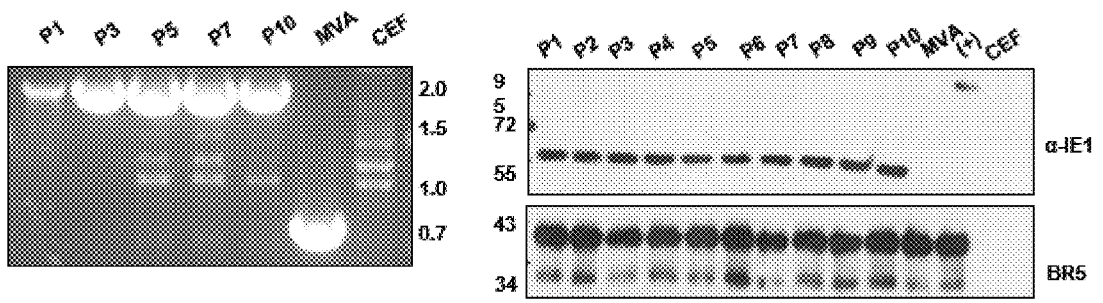
FIGS. 10A-10B show the stability analysis of IE1 4nt and VacO in IGR3 insertion site on MVA-BAC. PCR (left) and Western blot analyses (right) of IE1 4nt (10A), and VacO (10B). Left: 1.0% agarose gel of PCR product analyzing stability of IE1 IGR3, passaged up to P10 in CEF. Right: Western blot analysis of IE1 passaged up to P10 in CEF cells. IE1 and IEfusion were probed using a purified anti-IE1 mouse monoclonal antibody (mAB) p63-27. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.
Figure 10B:
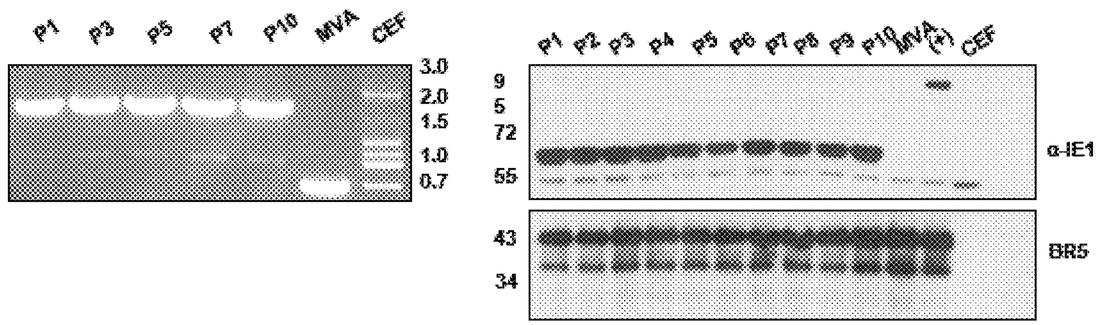
Figure 11A:
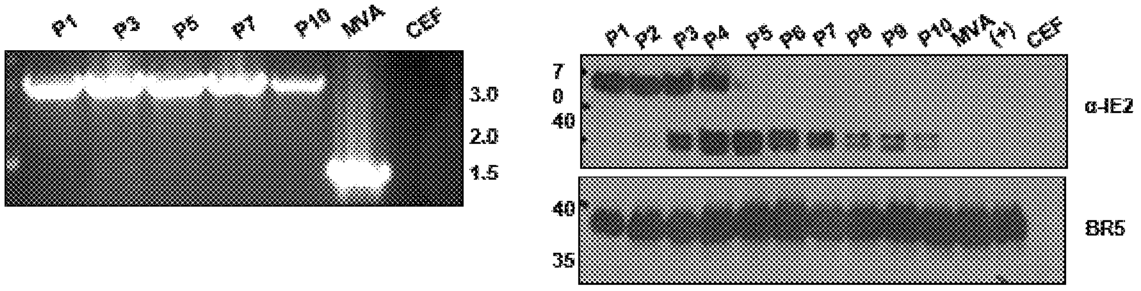
FIGS. 11A-11B show stability analysis of IE2 NCO and 4nt in G1L/18R insertion site on MVA-BAC. PCR (left) and Western blot analyses (right) of IE2 NCO (11A) and 4nt (11B). Left: 1.0% agarose gel of PCR product analyzing stability of IE2 G1L/18R, passaged up to P10 in CEF. Right: Western blot analysis of IE2 passaged up ten times (P1-P10) in CEF cells. IE2 was probed using an anti-IE2 mAB 2.9.5. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.
Figure 11B:
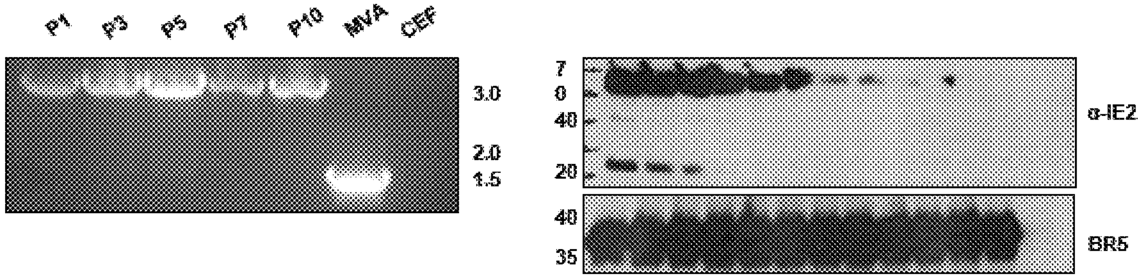
Figure 12:
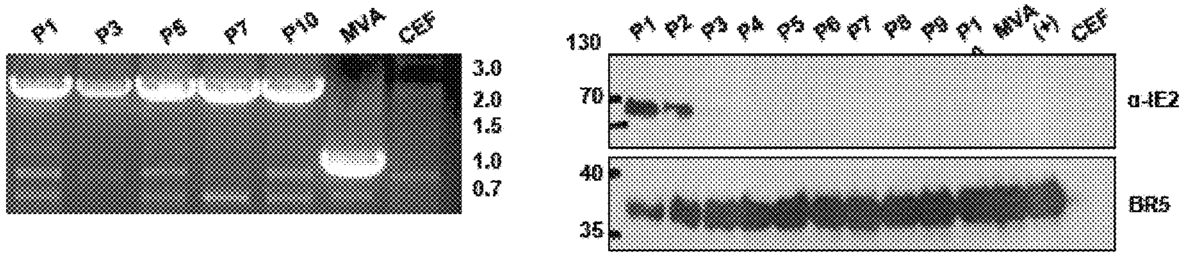
FIG. 12 shows stability analysis of IE2 VacO in IGR3 insertion site on MVA-BAC. PCR (left) and Western blot analyses (right) of IE2 VacO. Left: 1.0% agarose gel of PCR product analyzing stability of IE2 IGR3, passaged up to P10 in CEF. Right: Western blot analysis of IE2 passaged up to P10 in CEF cells. IE2 was probed using an anti-IE2 mAB 2.9.5. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.
Figure 13A:
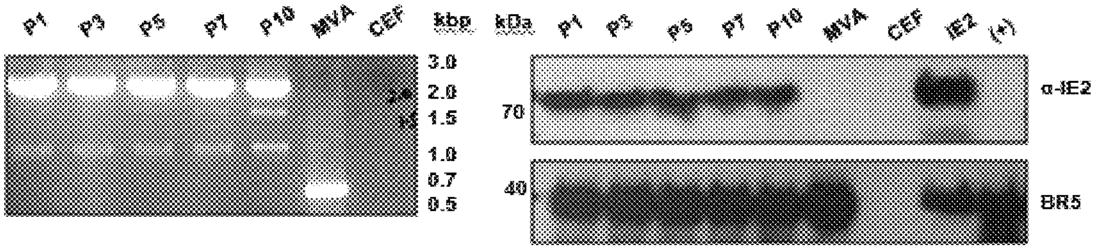
FIGS. 13A-13B show stability analysis of IE2H363A NCO and 4nt in 044/045L insertion site on MVA-BAC. PCR (left) and Western blot analyses (right) of IE2 NCO (13A) and 4nt (13B). Left: 1.0% agarose gel of PCR product analyzing stability of IE2 mutants in 044/045L, passaged up to P10 in CEF. Right: Western blot analysis of IE2 mutants passaged up to P10 in CEF cells. IE2 was probed using an anti-IE2 mAB 2.9.5. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.
Figure 13B:
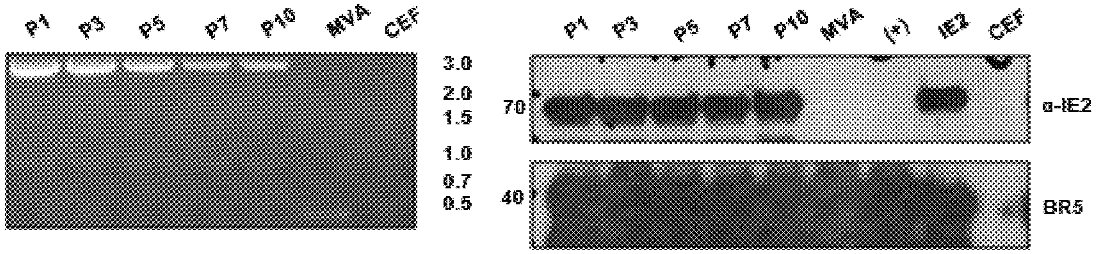
Figure 14A:
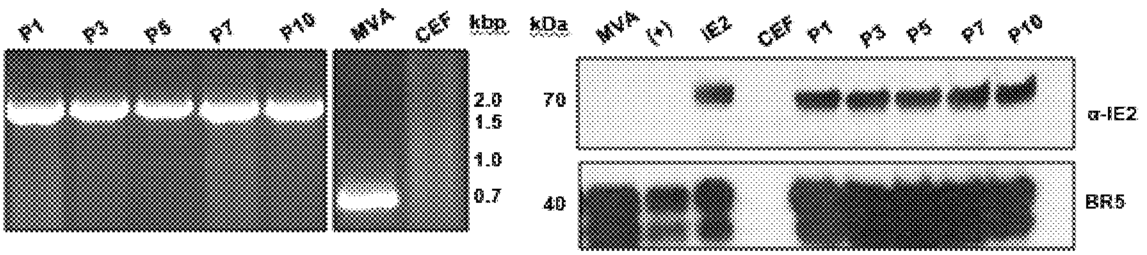
FIGS. 14A-14C show stability analysis of IE2H369A NCO, 4nt, and VacO in 044/045L insertion site on MVA-BAC. PCR (left) and Western blot analyses (right) of IE2 NCO (14A), 4nt (14B), and VacO (14C). Left: 1.0% agarose gel of PCR product analyzing stability of IE2 mutants in 044/045L, passaged up to P10 in CEF. Right: Western blot analysis of IE2 mutants passaged up to P10 in CEF cells. IE2 was probed using an anti-IE2 mAB 2.9.5. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.
Figure 14B:
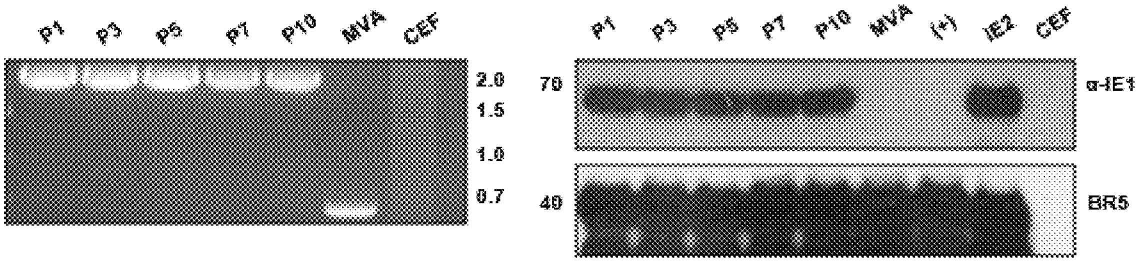
Figure 14C:
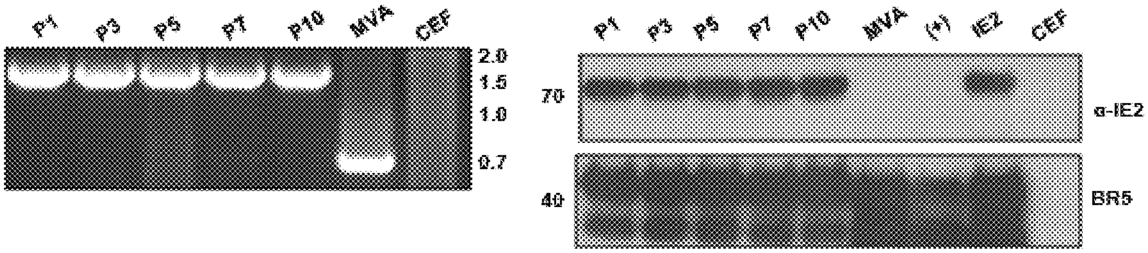
Figure 15A:
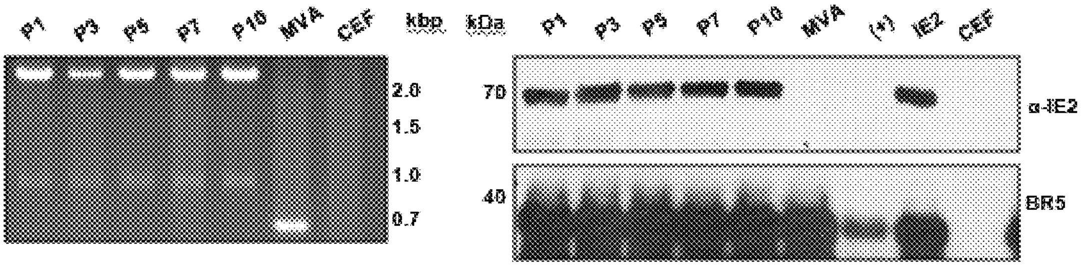
FIGS. 15A-15C show stability analysis of IE2H363/369A NCO, 4nt, and VacO in 044/045L insertion site on MVA-BAC. PCR (left) and Western blot analyses (right) of IE2 NCO (15A), 4nt (15B), and VacO (15C). Left: 1.0% agarose gel of PCR product analyzing stability of IE2 mutants in 044/045L, passaged up to P10 in CEF. Right: Western blot analysis of IE2 mutants passaged up to P10 in CEF cells. IE2 was probed using an anti-IE2 mAB 2.9.5. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.
Figure 15B:
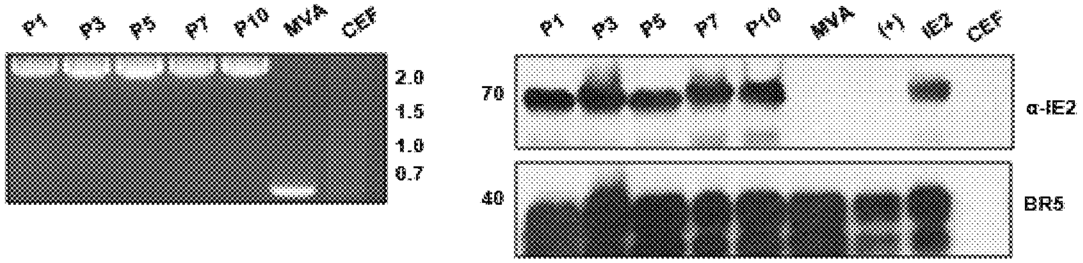
Figure 15C:
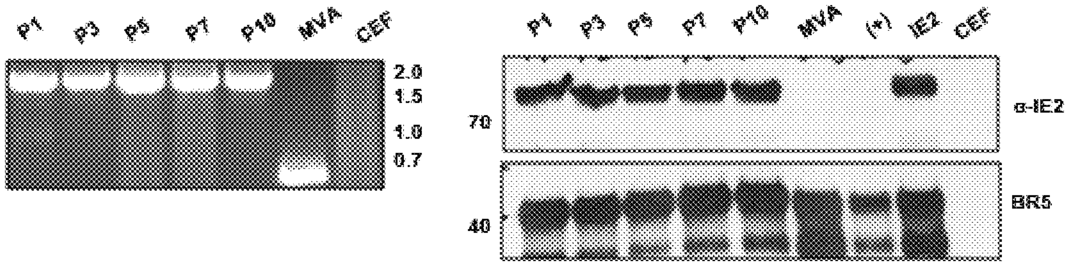

Based on the experimental setup to evaluate stability of the genes in CEFs, five potential candidates for the IE1 gene to be expressed in either G1L or IGR3 were obtained (Table 2). Only IE1 (non-codon optimized (NCO), four nucleotide optimization (4nt), and vaccinia optimized (VacO)) showed stability in G1L (FIG. 9) while only IE1 (4nt) and IE1 (VacO) demonstrated stability in IGR3 (FIG. 10). IE2 constructs were more difficult to generate upon virus reconstitution in BHK cells using fowl pox helper virus [11, 16]. Attempting to reconstitute IE2-containing MVA was more difficult than what was experienced with IE1. After many transfection attempts, followed by stability analyses, stable IE2-expressing MVA constructs that produced full-length IE2 protein over several virus passages in CEFs were not obtained (FIGS. 11 and 12). FIG. 6 shows the nucleic acid sequence alignment of IE2 constructs.

Example 5: Exploration of IE2 DNA and Amino Acid Sequences

Figure 7A:
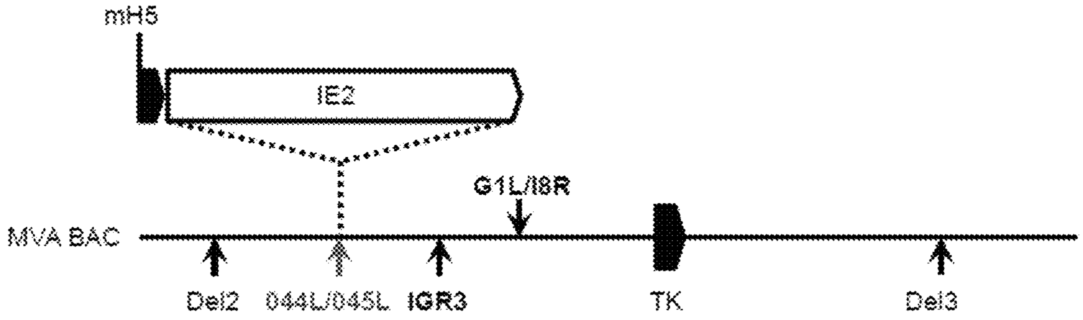
FIGS. 7A-7C show the stability analysis of IE2 in 044L/045L insertion site on MVA.
Figure 7B:
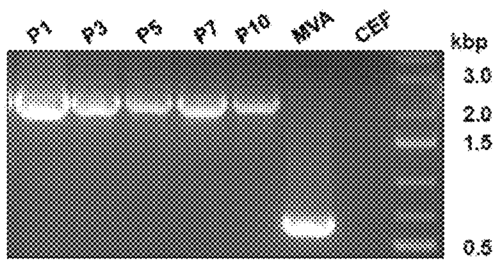
Figure 7C:
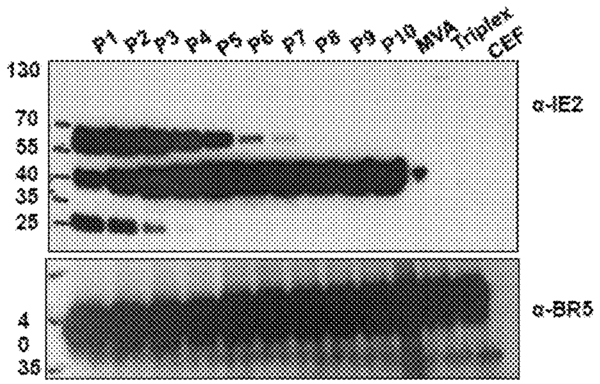

Although none of the IE2-expressing MVA constructs produced full-length IE2 protein, one construct, MVA:IE2 (044L/045L) (Table 2), expressed IE2-related products throughout all ten virus passages (FIG. 7). Alternative protein products of IE2, resulting in ~20 kDa and ~40 kDa fragments, have been previously described for IE2 [17-19]. To determine the identity of these alternative protein products, an in-gel trypsin digestion, followed by LC-MS/MS, was performed. Mass spectrometry data analysis revealed that the ~20 kDa product was mostly the C-terminal portion (48% coverage) of IE2 whereas the ~40 kDa product was mostly the N-terminus (34% coverage) (Table 4). Full-length IE2 was included in analyses as control (protein probability calculations performed as described in materials and methods).

TABLE 4

Mass spectrometry identification of peptides corresponding to IE2 from HCMV AD169

| kDa | Exclusive Unique Spectra | Exclusive Unique Peptides | % Coverage | Max $X_{corr}$ | Probability |
|---|---|---|---|---|---|
| 63 | 160 | 94 | 83 | 3.37 | 100% |
| 40 | 31 | 22 | 34 | 3.94 | 100% |
| 20 | 37 | 27 | 48 | 3.19 | 100% |

As observed in FIG. 7B, there was a concomitant disappearance of both ~20 kDa and the full-length ~60 kDa product, while the ~40 kDa product remained "stable" over ten passages. These results suggest that perhaps there is an element within the ~20 kDa product that may not be tolerated by either CEF cells or MVA. Upon DNA sequencing of PCR products in an attempt to identify mutations within regions of the DNA sequence, the IE2 gene sequence was observed to be stochastically mutated during passaging, thereby resulting in premature stop codons within IE2, yielding a truncated, yet stable, IE2 product that is recognized by an IE2-specific antibody [17].

Example 6: Generation of IE2 Mutations of C-Terminal Histidines

Figure 8A:
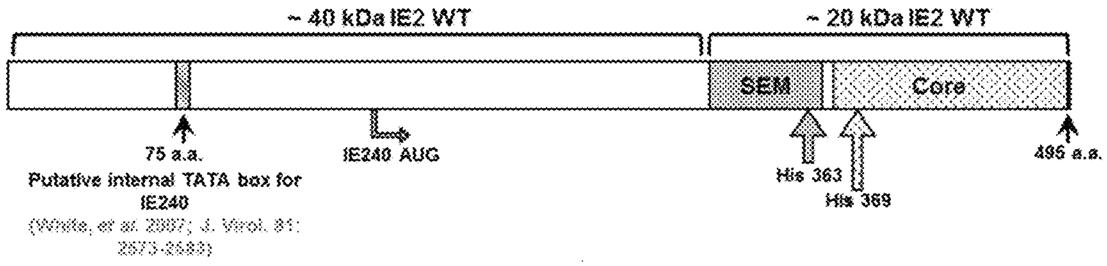
FIGS. 8A-8C show the stability analysis of IE2 H363A mutant in 044L/045L insertion site on MVA.
Figure 8B:
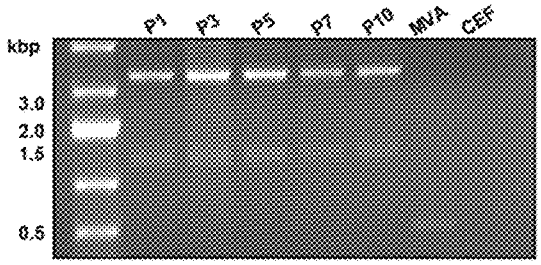

IE1 has properties at the nucleotide level that render it unstable in some locations; inserting IE1 into a different site in MVA mitigated instability. IE2 instability could not be resolved solely by this method. Putative IE2 functional domains have been reported [20]. The C-terminus of IE2 has been described as part of a "core" domain, important for DNA binding, transactivation, and autorepression (FIG. 8A). The region adjacent to the core domain contains a Zn-finger binding domain that can be mutated without affecting IE2 protein interaction with DNA. The area adjacent to the core domain was named the "specific and essential modulator" domain (SEM) (FIG. 8A). Although mutations within the SEM region did not impair all functions previously associated with IE2, it has been observed that different sequence requirements within this region affect different IE2 functions. Two His residues within the C-terminus of IE2 were identified within the presumed Zn-finger binding domain (FIG. 8A), His446 and His452 [21, 22]. Mutating these IE2 residues does not abolish DNA binding capabilities nor hinder IE2 expression within HCMV or in a heterologous system such as adenovirus [23]. As a result of mutating the last 37 amino acid residues, it was determined to be required for IE2 autorepressive and transactivating functions [24-27]. Two histidine (H) residues were mutated to alanine (A) using site-directed mutagenesis, although no other C-terminal residues from either the SEM nor core domains were altered. This determination was due to the notion that if the last ~37 amino acid residues in the C-terminus are important for IE2 activities, these residues may possibly encode immunogenic epitopes. Mutating residues within the SEM are well tolerated, without affecting IE2 activity [20]; therefore, whether modifications within this region could help with the genetic and protein stability of the IE2 gene and its protein product in MVA upon viral passaging in CEFs was further explored.

There were challenges to find a location and identify a sequence for IE2 that would render it "stable" for expression in MVA. Similar to the original construction of Triplex containing IEfusion, N-terminal signal peptide, nuclear localization sequences, as well as activation domains (exons 1, 2, and 3; amino acids 1-85) were omitted when generating MVA expressing IE2 [18, 26]; hence, these deletions changed the amino acid residue numbers from His446 and His452 to His363 to His369, respectively. The following single and double mutants of IE2 were generated for insertion into the 044/045L site on MVA: H363A, H369A, and H363A/H369A (Table 5). In Table 5 below, X □=unstable; ✓□=stable. Roman numeral identifies the iteration and mutation of IE2.

TABLE 5

Summary of IE2 mutants within MVA.

| Version | Mutants H363A | H369A | H363/369A |
|---|---|---|---|
| IE2 NCO | ✓□ (i) | □✓(ii) | □✓(iii) |
| IE2 4nt | □✓(iv) | □✓(v) | □✓(vi) |
| IE2 VacO | ×□ | □✓(vii) | □✓(viii) |

Figure 8C:
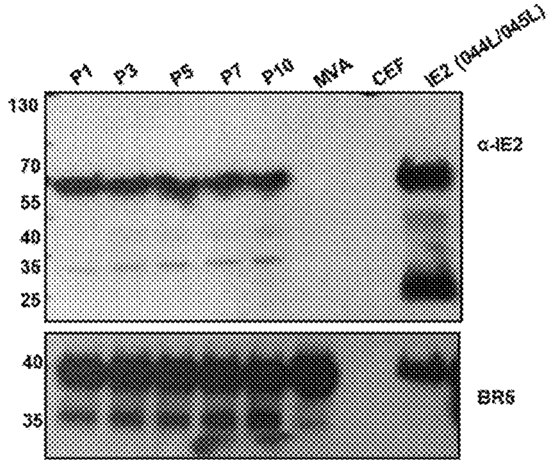

After transfection and viral reconstitution, all constructs were passaged in CEFs. It was observed that upon serial passaging, IE2 expression was stable based on Western blot analysis (FIG. 8C). Furthermore, PCR analysis revealed amplification of the expected gene product resulting in a "stable" construct upon 10 passages (FIGS. 8B, 13-15). While only IE2 NCO and IE2 4nt iterations could be generated for the H363A mutant (FIG. 13), IE2 NCO, 4nt, and VacO versions of H369A (FIG. 14) and H363A/H369A (FIG. 15) were constructed. Eight versions of IE2 mutants were passaged and analyzed via PCR and Western Blot analysis. These results suggest that mutating His residues within the C-terminus containing the putative Zn-binding domain helps stabilize IE2 expression and gene sequence upon viral passage.

Figure 16A:
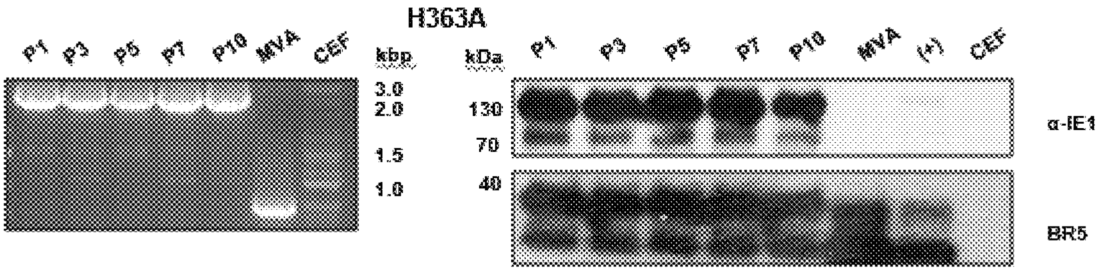
FIGS. 16A-16C show stability analysis of IEfusion 4nt mutants in IGR3 insertion site on MVA-BAC. PCR (left) and Western blot analyses (right) of IEfusion 4nt H363A (16A), H369A (16B), and H363A/H369A (16C). Left: 1.0% agarose gel of PCR product analyzing stability of IEfusion mutants in IGR3, passaged up to P10 in CEF. Right: Western blot analysis of IEfusion mutants passaged up to P10 in CEF cells. IEfusion was probed using a purified anti-IE1 mouse monoclonal antibody (mAB) p63-27. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.
Figure 16B:
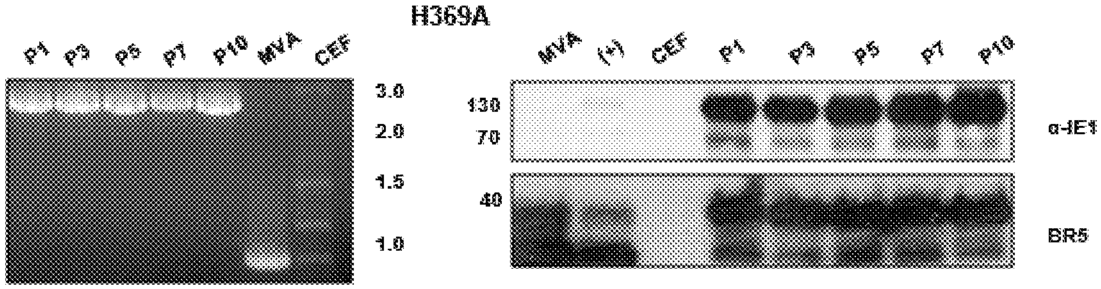
Figure 16C:
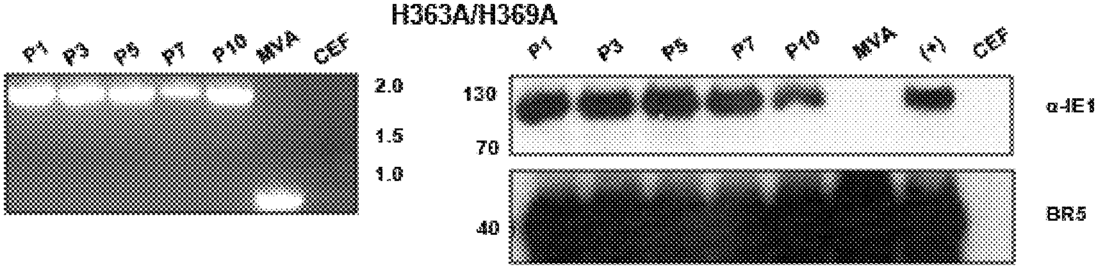

Identifying IE2 as a major contributor of instability, IEfusion was reassessed. The corresponding His was mutated to Ala residues on the C-terminus of IEfusion. Based on previous data (FIG. 4), residues on the 4nt version of IEfusion that was engineered for insertion into the IGR3 site were mutated-either H363A and/or H369A mutants of IEfusion 4nt. In contrast to Triplex, prolonged stability to P10 was observed for all three mutant versions of IEfusion 4nt at the protein level; however minor non-specific PCR products were observed for the double mutant (FIG. 16C, left). These constructs became candidates for further analysis in combination with pp65.

Example 7: Combining all Three HCMV Antigens into a Single MVA

Two constructs were identified to stably express both IE1 and pp65: (A) MVA BAC:IE1 4nt (IGR3):: pp65 (Del3) and (B) MVA BAC:: IE1 VacO (IGR3):: pp65 (Del3). Once the effect of mutating H363A and/or H369A on IE2 stability was evaluated, various mutant IE2 versions were inserted into MVA site 044L/045L of either of the aforementioned constructs. Based on the previous studies evaluating the stability of IE2, it became apparent that, although IE1 has properties at the nucleotide level that render it unstable in some locations, the instability was mitigated by inserting IE1 into a different site in MVA. In contrast, IE2 was difficult to find a location and sequence that would render it "stable" for expression in MVA. Upon mutation of C-terminal His, the gene and protein stability within the 044L/045L site was improved. Identifying IE2 as a major contributor of instability, IEfusion was reassessed. Mutants of IEfusion were generated, including mutagenizing the His residues that lie on the C-terminus of the IE2 portion. However, due to the instability of genes inserted in Del2, inserting genes within that site was not pursued. Either H363A and/or H369A mutants of IEfusion, IEfusion 4nt, and IEfusion VacO were generated. These variants of IEfusion were either inserted in IGR3 or 044L/045L, while also containing pp65 in Del3. Upon completion of the Triplex variants, vaccination of transgenic HLA-expressing mice can be used to compare immunogenicity generated by IEfusion mutants versus re-derived Triplex with separated IE1 and IE2 genes, all with His mutations as described in FIG. 8.

Figure 17:
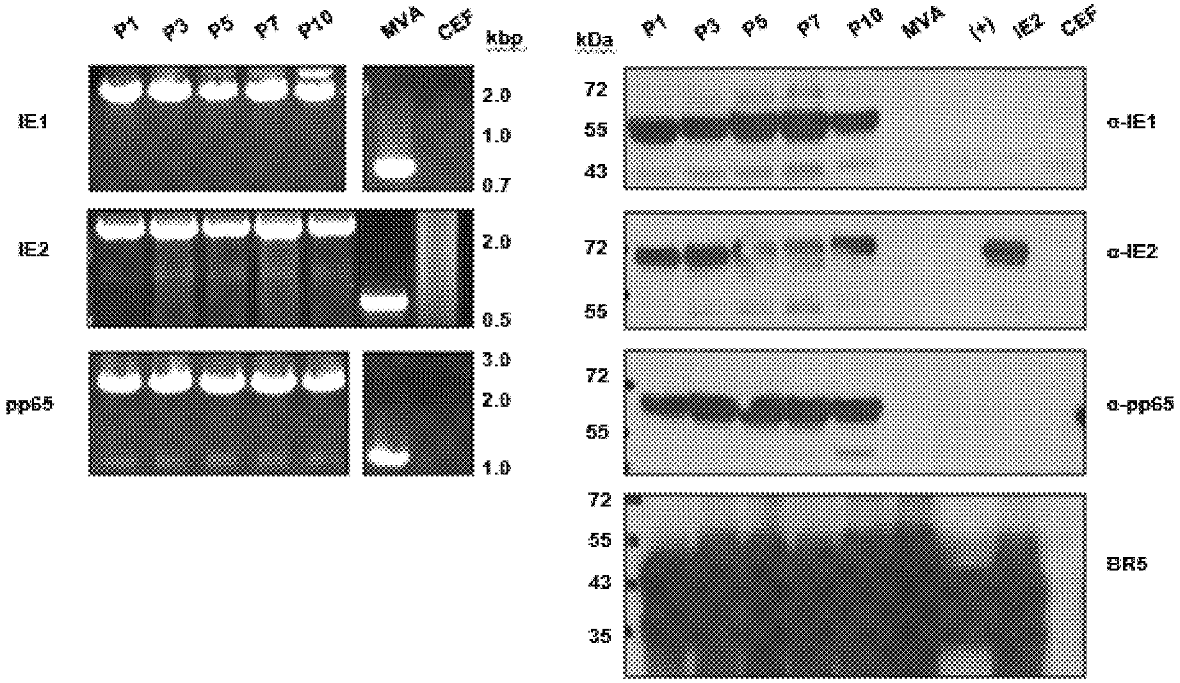
FIG. 17 shows stability analysis of construct A(i). PCR (left) and Western blot analyses (right) of IE1, IE2, and pp65. Left: 1.0% agarose gel of PCR product analyzing stability of IE1 in IGR3, IE2 in 044/045L, and pp65 in Del3, passaged up to P10 in CEF. Right: Western blot analysis of IEfusion and pp65 passaged up to P10 in CEF cells. IE1 was probed using a purified anti-IE1 mouse monoclonal antibody (mAB) p63-27; IE2 was probed using an anti-IE2 mAB 2.9.5; and pp65 was probed using purified mouse mAB 28-103. As an infection/loading control (bottom), BR5 antibody was used to probe against an envelope MVA glycoprotein. "CEF" is uninfected, negative control; lane labeled "MVA" is wild-type MVA not expressing any antigen; lane labeled (+) is virus used to generate clinical lots of Triplex.
Figure 18:
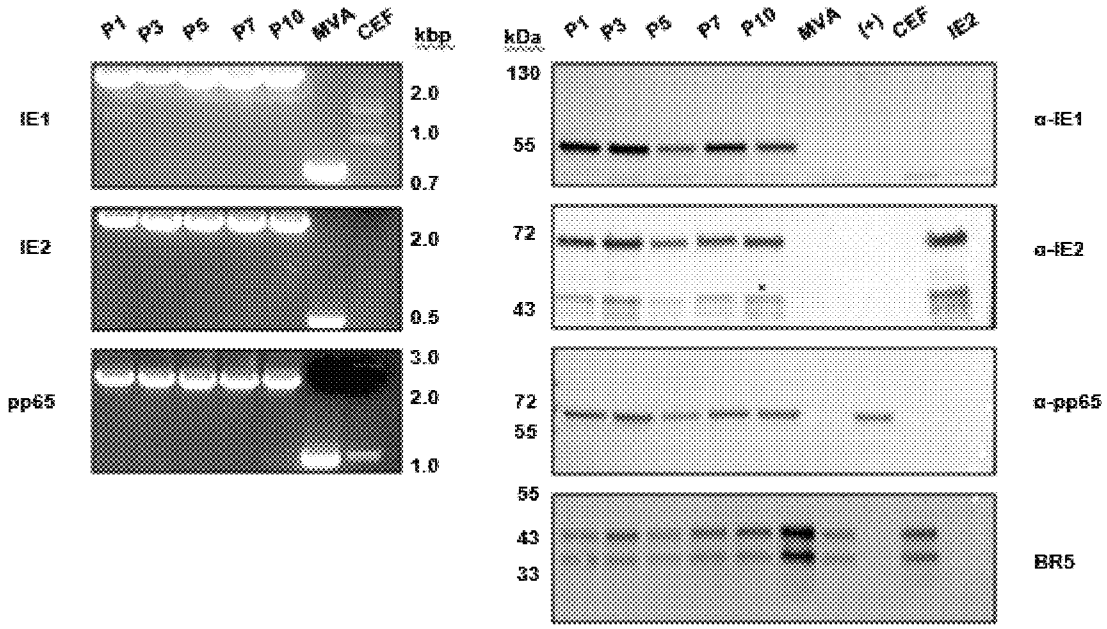
FIG. 18 shows stability analysis of construct A(v). PCR (left) and Western blot analyses (right) of IE1, IE2, and pp65. Left: 1.0% agarose gel of PCR product analyzing stability of IE1 in IGR3, IE2 in 044/045L, and pp65 in Del3, passaged up to P10 in CEF. Right: Western blot analysis of IEfusion and pp65 passaged up to P10 in CEF cells. IE1 was probed using a purified anti-IE1 mouse monoclonal antibody (mAB) p63-2; IE2 was probed using an anti-IE2 mAB 2.9.5.

Furthermore, mutation of C-terminal His prolonged gene and protein stability within the 044L/045L site for IE2 and IGR3 site for IEfusion. Three constructs (IE2 NCO H363A (i); IE2 4nt H369A (v); IE2 4nt H363A/H369A (vi)) in the context of (A) appeared stable up to P10 with all three antigens (IE1, IE2, pp65) being expressed from a single MVA (FIGS. 17-19). Five constructs in the context of (B) appeared to stably express all three antigens from a single MVA (FIGS. 20-24). However, construct B(ii) (FIG. 21) appeared to show decreased pp65 expression by P10. A decrease of IE1 expression in construct B(v) was also observed by P10 (FIG. 23). Overall, it appeared that six constructs (A(i), A(v), A(vi), B(i), B(iii), and B(vii)) showed stable expression of all three antigens over ten viral serial passages, as assessed by PCR and Western Blot analyses. These results show that single and double mutations within the putative Zn-finger binding domain of IE2 helped stabilize expression of all three antigens.

Mutants of IEfusion were also characterized for stable expression over ten serial virus passages (FIGS. 25 and 26). IEfusion 4nt H363A (IGR3):: pp65 (Del3) showed increased stability (FIG. 25) beyond P7 compared to IEfusion IGR3 (FIG. 9). A slight decrease of IEfusion PCR product was observed for P10 (FIG. 25, left) while a slight decrease in pp65 protein was observed via Western blot (FIG. 25, right) by P10. In contrast IEfusion 4nt H369A (IGR3):: pp65 (Del3) demonstrated a decrease in IEfusion and pp65 proteins (FIG. 26, right) by P7<n > P10. No significant decrease observed for IEfusion PCR product; however, there was a marked decrease of pp65 PCR product by P10. These results show that IEfusion 4nt H363A (IGR3):: pp65 (Del3) stably expresses these CMV antigens and the H363A mutation aids in the maintenance of intact protein expression and PCR product integrity.

Example 8: Immunogenicity of the Second-Generation Triplex

Upon complete construction of the new Triplex variants, immunogenicity studies took place to compare immunogenicity generated by IEfusion variant mutants and re-derived, second-generation Triplex with separated IE1 and IE2 variants, compared to first-generation Triplex. Transgenic C56BL/6 mice expressing HLA-B HLA-B*0702 (B7) or HLA-A*0201 (HHD-II) class I molecules were immunized with six second-generation Triplex constructs (A(i), A(v), B(i), B(iii), B(vii), IEfusion 4nt H363A (IGR3):: pp65 (Del3)) in addition to Triplex. Mice were vaccinated two times in 3-week intervals with the various constructs by the intraperitoneal (i.p.) route with either $2.5\times10^7$ PFU (for B7 mice) or $5\times10^7$ PFU (for HHD-II), followed by splenocyte isolation. Human MHC-restricted T-cell responses elicited by second-generation Triplex were compared to original Triplex and an unvaccinated, naïve group as assessed by ELISpot (Table 6). For Table 6, transgenic C57BL/6 mice expressing HLA-B*0702 (B7, top) or HLA-A*0201 (HHD-II, bottom) class I molecules were immunized with various constructs expressing either IEfusion/pp65 (IEFus) or IE1/IE2/pp65. Antigen-specific T-cell responses were determined by IFN-γ Enzyme-linked immune absorbent spot (ELISpot) assay using pp65-, IE1-, and IE2-specific libraries, HLA-B*0702- or HLA-A*0201-restricted immunodominant epitopes of pp65 and IE1. DMSO was used as a negative control. Mean and standard error of the mean (SEM) values were calculated from (N) number of either HLA-B7 (top) or HHD-II (bottom) mice. SFC: cytokine-specific spot-forming cells.

TABLE 6

Human MHC-restricted T-cell responses elicited by second-generation Triplex

IFNγ SFCs/10^6 Splenocytes

| | HLA-B7 | | | | | | | | |
|---|---|---|---|---|---|---|---|---|---|
| | $pp65_{265-275}$ | | | pp65 Library | | | $IE1_{316-324}$ | | |
| | Mean | SEM | N | Mean | SEM | N | Mean | SEM | N |
| A(i) | 2223.75 | 595.6837 | 4 | 2611.25 | 736.1 | 4 | n/a | n/a | n/a |
| B(i) | 1730 | 235.4782 | 4 | 1690 | 316.2541 | 4 | n/a | n/a | n/a |
| IEfus | 1323.5 | 294.2412 | 5 | 1788 | 642.6461 | 5 | n/a | n/a | n/a |
| B(iii) | 1512.5 | 275.8094 | 4 | 1067.5 | 221.7121 | 4 | n/a | n/a | n/a |
| A(v) | 1114 | 395.1025 | 5 | 1165.5 | 279.8911 | 5 | n/a | n/a | n/a |
| B(vii) | 770.5 | 329.918 | 5 | 1060.5 | 528.679 | 5 | n/a | n/a | n/a |

TABLE 6-continued

Human MHC-restricted T-cell responses elicited by second-generation Triplex

| | | | | | | | | | |
|---|---|---|---|---|---|---|---|---|---|
| Triplex | 2098.333 | 428.2331 | 12 | 2781.667 | 639.9631 | 12 | n/a | n/a | n/a |
| Naïve | 218.125 | 93.84926 | 4 | 320 | 76.91987 | 4 | n/a | n/a | n/a |

IFNγ SFCs/10^6 Splenocytes

| | HHD-II | | | | | | | | |
|---|---|---|---|---|---|---|---|---|---|
| | IE1 Library | | | IE2 Library | | | DMSO | | |
| | Mean | SEM | N | Mean | SEM | N | Mean | SEM | N |
| A(i) | 2132.5 | 1230.693 | 4 | 821.875 | 257.2903 | 4 | 46.875 | 9.09298 | 4 |
| B(i) | 795 | 333.4791 | 4 | 939.375 | 130.3096 | 4 | 59.375 | 14.15594 | 4 |
| IEfus | 877.9167 | 85.47518 | 6 | 833.3333 | 131.0624 | 6 | 157.9167 | 29.61149 | 6 |
| B(iii) | 850.625 | 192.8794 | 4 | 1206.875 | 109.9544 | 4 | 76.875 | 3.590352 | 4 |
| A(v) | 1254 | 213.9591 | 5 | 955 | 115.9418 | 5 | 69 | 8.351646 | 5 |
| B(vii) | 1263.25 | 177.4413 | 5 | 1860.5 | 60.21524 | 5 | 81 | 7.441438 | 5 |
| Triplex | 1570.75 | 371.4581 | 10 | 1131.25 | 115.3607 | 10 | 74.5 | 13.21195 | 10 |
| Naïve | 78.25 | 39.02643 | 4 | 38.125 | 10.22533 | 4 | 27 | 7.30582 | 4 |

FIG. 27A shows that second-generation Triplex constructs elicited T-cell responses comparable to Triplex. However, construct B(i) seemed to underperform compared to other second-generation Triplex constructs in B7 mice (FIG. 27A, left). Construct A(i) was the most similar to Triplex in both B7 and HHD-II mice with respect to elicited T-cell responses (FIG. 27A).

T-cell stimulation from splenocytes isolated from immunized mice was also performed to evaluate antigen-specific T-cell responses, as analyzed by FACS analysis (Table 7). For Table 7, transgenic C57BL/6 mice expressing HLA-B*0702 (B7, top) or HLA-A*0201 (HHD-II, bottom) class I molecules were immunized with various constructs expressing either IEfusion/pp65 (IEFus) or IE1/IE2/pp65. Antigen-specific T-cell responses were evaluated by intracellular cytokine staining (ICS) following stimulation with pp65-, IE1-, and IE2-specific libraries or HLA-B*0702- or HLA-A*0201-restricted immunodominant epitopes of pp65 and IE1. DMSO was used as a negative control. Percentages of IFN-γ-secreting CD8+-T cells following stimulation of splenocytes from B7 or HHD-II-immunized mice with different stimuli are shown. Mean and standard error of the mean (SEM) values were calculated from (N) number of either HLA-B7 (top) or HHD-II (bottom) mice.

TABLE 7

HLA-B*0702- or HLA-A*0201-restricted $CD8_+$ T-cell stimulation by second-generation Triplex % IFNγ+ CD8+ T-cells

| | HLA-B7 | | | | | | | | |
|---|---|---|---|---|---|---|---|---|---|
| | pp65 $_{265-275}$ | | | pp65 Library | | | IE1 $_{316-324}$ | | |
| | Mean | SEM | N | Mean | SEM | N | Mean | SEM | N |
| A(i) | 4.54 | 1.172945 | 4 | 7.17 | 0.678085 | 4 | n/a | n/a | n/a |
| B(i) | 2.345 | 0.27094 | 4 | 3.27 | 0.792675 | 4 | n/a | n/a | n/a |
| IEfus | 4.608 | 1.559819 | 5 | 5.26 | 1.313579 | 5 | n/a | n/a | n/a |
| B(iii) | 4.555 | 0.399176 | 4 | 6.11 | 2.117176 | 4 | n/a | n/a | n/a |
| A(v) | 3.474 | 0.879901 | 5 | 2.408 | 1.333332 | 5 | n/a | n/a | n/a |
| B(vii) | 2.44 | 1.139715 | 5 | 3.076 | 2.173167 | 5 | n/a | n/a | n/a |
| Triplex | 4.409167 | 0.749607 | 12 | 6.396667 | 1.240025 | 12 | n/a | n/a | n/a |
| Naïve | 0.0575 | 0.024958 | 4 | 0.0425 | 0.004787 | 4 | n/a | n/a | n/a |

% IFNγ+ CD8+ T-cells

| | HLA-B7 | | | | | | | | |
|---|---|---|---|---|---|---|---|---|---|
| | IE1 Library | | | IE2 Library | | | DMSO | | |
| | Mean | SEM | N | Mean | SEM | N | Mean | SEM | N |
| A(i) | 0.1525 | 0.020565 | 4 | 0.4425 | 0.118489 | 4 | 0.1325 | 0.010308 | 4 |
| B(i) | 0.23 | 0.04916 | 4 | 0.6375 | 0.087785 | 4 | 0.21 | 0.01354 | 4 |
| IEfus | 0.1 | 0.007746 | 5 | 0.156 | 0.024819 | 5 | 0.044 | 0.005099 | 5 |
| B(iii) | 0.101 | 0.030716 | 4 | 0.2725 | 0.029262 | 4 | 0.10775 | 0.024807 | 4 |
| A(v) | 0.16 | 0.018708 | 5 | 0.262 | 0.01241 | 5 | 0.166 | 0.031718 | 5 |

TABLE 7-continued

HLA-B*0702- or HLA-A*0201-restricted $CD8_+$ T-cell stimulation by second-generation Triplex

| | | | | | | | | | |
|---|---|---|---|---|---|---|---|---|---|
| B(vii) | 0.122 | 0.02245 | 5 | 0.164 | 0.023152 | 5 | 0.098 | 0.020591 | 5 |
| Triplex | 0.076833 | 0.014534 | 12 | 0.220667 | 0.037906 | 12 | 0.077583 | 0.017541 | 12 |
| Naïve | 0.0525 | 0.0075 | 4 | 0.0775 | 0.004787 | 4 | 0.0625 | 0.01315 | 4 |

% IFNγ+ CD8+ T-cells

| | HHD-II | | | | | | | | |
|---|---|---|---|---|---|---|---|---|---|
| | pp65 $_{265-275}$ | | | pp65 Library | | | IE1 $_{316-324}$ | | |
| | Mean | SEM | N | Mean | SEM | N | Mean | SEM | N |
| A(i) | 4.205 | 1.50755 | 4 | 7.215 | 3.182162 | 4 | 2.135 | 1.420214 | 4 |
| B(i) | 0.8 | 0.257326 | 4 | 2.89 | 0.296283 | 4 | 0.8875 | 0.161832 | 4 |
| IEfus | 0.963333 | 0.211403 | 6 | 3.75 | 0.795294 | 6 | 0.87 | 0.229478 | 6 |
| B(iii) | 1.345 | 0.332979 | 4 | 4.245 | 1.22999 | 4 | 0.85 | 0.228838 | 4 |
| A(v) | 1.992 | 1.056259 | 5 | 5.876 | 2.617607 | 5 | 8.16 | 2.502093 | 5 |
| B(vii) | 2.834 | 1.620934 | 5 | 6.579999 | 2.948816 | 5 | 9.162001 | 4.286136 | 5 |
| Triplex | 2.789 | 0.737751 | 11 | 6.963 | 1.650295 | 11 | 1.526 | 0.604693 | 11 |
| Naïve | 0.21 | 0.030822 | 4 | 0.1375 | 0.03326 | 4 | 0.115 | 0.045185 | 4 |

% IFNγ+ $CD8_+$ T-cells

| | HHD-II | | | | | | | | |
|---|---|---|---|---|---|---|---|---|---|
| | IE1 Library | | | IE2 Library | | | DMSO | | |
| | Mean | SEM | N | Mean | SEM | N | Mean | SEM | N |
| A(i) | 7.6225 | 1.670601 | 4 | 0.185 | 0.030687 | 4 | 0.115 | 0.011902 | 4 |
| B(i) | 2.835 | 0.561583 | 4 | 0.3925 | 0.086446 | 4 | 0.2025 | 0.04289 | 4 |
| IEfus | 2.053333 | 0.383855 | 6 | 0.188333 | 0.079053 | 6 | 0.096667 | 0.004216 | 6 |
| B(iii) | 2.37 | 0.420872 | 4 | 0.36 | 0.052281 | 4 | 0.0825 | 0.011087 | 4 |
| A(v) | 7.448 | 2.382548 | 5 | 0.19 | 0.040125 | 5 | 0.114 | 0.010296 | 5 |
| B(vii) | 4.908 | 1.599661 | 5 | 0.73 | 0.182428 | 5 | 0.16 | 0.027203 | 5 |
| Triplex | 2.813 | 0.612812 | 11 | 0.249 | 0.038387 | 11 | 0.091 | 0.01546 | 11 |
| Naïve | 0.1625 | 0.01315 | 4 | 0.1225 | 0.021747 | 4 | 0.185 | 0.006455 | 4 |

FIG. 27B reiterates observations via ELISpot analysis (FIG. 27A). However, in B7 mice, B(vii) seemed to have higher T-cell stimulation than other constructs, including Triplex (FIG. 27B, left). Overall, all constructs in B7 (FIG. 27B, left) and HHD-II (FIG. 27B, right) performed as well as original Triplex.

Example 9: Mechanism of IE2 Stability Via Zn-Finger his Mutations

Increased stability of IE2 expressed in MVA has been observed upon mutation of one or two His residues that reside within the C-terminus of IE2 protein. To examine the effect of IE2 mutants on overall IE2 stability, an MVA was constructed to harbor two copies of IE2: IE2 NCO (wild-type) in G1L and the other in the 044/045L site harboring an IE2 mutant. MVA constructs harboring two copies of IE2 were passaged to P5 in baby hamster kidney (BHK) cells (FIG. 28). PCR analyses of both copies of IE2 show no non-specific PCR products-only products of the correct size (FIG. 28A). Western Blot analysis, on the other hand, show consistent expression of IE2 in constructs containing two IE2 copies whereas MVA:IE2 NCO (G1L) shows a decrease in full-length IE2 expression and the emergence of a ~40 kDa band (FIG. 28B), demonstrating a truncated product previously observed (FIG. 7). While the Western Blot showing expression of IE2 from MVAs with two IE2 copies had some degradation products, there was no concomitant increase in degradation products expected to accumulate from the passage and degradation of IE2 observed in MVA: IE2 NCO (G1L). These results could suggest a "rescue" of the IE2 instability previously observed as a result of the presence of the mutant IE2 gene insert.

REFERENCES

The references listed below, and all references cited in the specification are hereby incorporated by reference in their entirety.

1. Wang, Z., et al., Modified H5 promoter improves stability of insert genes while maintaining immunogenicity during extended passage of genetically engineered MVA vaccines. Vaccine, 2010. 28(6): p. 1547-57.
2. Wang, Z., et al., Vaccine properties of a novel marker gene-free recombinant modified vaccinia Ankara expressing immunodominant CMV antigens pp65 and IE1. Vaccine, 2007. 25(6): p. 1132-41.
3. Wang, Z., et al., A fusion protein of HCMV IE1 exon4 and IE2 exon5 stimulates potent cellular immunity in an MVA vaccine vector. Virology, 2008. 377(2): p. 379-90.
4. Britt, W. J. and D. Auger, Identification of a 65 000 dalton virion envelope protein of human cytomegalovirus. Virus Res, 1985. 4(1): p. 31-6.
5. Meisinger-Henschel, C., et al., Introduction of the six major genomic deletions of modified vaccinia virus Ankara (MVA) into the parental vaccinia virus is not sufficient to reproduce an MVA-like phenotype in cell culture and in mice. J Virol, 2010. 84(19): p. 9907-19.
6. Dimier, J., et al., Deletion of major nonessential genomic regions in the vaccinia virus Lister strain enhances attenuation without altering vaccine efficacy in mice. J Virol, 2011. 85(10): p. 5016-26.
7. Hedengren-Olcott, M., et al., The vaccinia virus G1L putative metalloproteinase is essential for viral replication in vivo. J Virol, 2004. 78(18): p. 9947-53.

8. Bayliss, C. D. and G. L. Smith, Vaccinia virion protein 18R has both DNA and RNA helicase activities: implications for vaccinia virus transcription. J Virol, 1996. 70(2): p. 794-800.
9. Manuel, E. R., et al., Intergenic region 3 of modified vaccinia Ankara is a functional site for insert gene expression and allows for potent antigen-specific immune responses. Virology, 2010. 403(2): p. 155-62.
10. Intergenic regions as insertion sites in the genome of Modified Vaccinia Virus Ankara (MVA). P. Howley, et al., U.S. Pat. No. 7,550,157 B2 (23 June, 2009).
11. Cottingham, M. G., et al., Recombination-mediated genetic engineering of a bacterial artificial chromosome clone of modified vaccinia virus Ankara (MVA). PLOS One, 2008. 3(2): p. e1638.
12. Cottingham, M. G. and S.C. Gilbert, Rapid generation of markerless recombinant MVA vaccines by en passant recombineering of a self-excising bacterial artificial chromosome. J Virol Methods, 2010. 168(1-2): p. 233-6.
13. Tischer, B. K., et al., A self-excisable infectious bacterial artificial chromosome clone of varicella-zoster virus allows analysis of the essential tegument protein encoded by ORF9. J Virol, 2007. 81(23): p. 13200-8.
14. Tischer, B. K., G. A. Smith, and N. Osterrieder, En passant mutagenesis: a two step markerless red recombination system. Methods Mol Biol, 2010. 634: p. 421-30.
15. Wyatt, L. S., et al., Elucidating and minimizing the loss by recombinant vaccinia virus of human immunodeficiency virus gene expression resulting from spontaneous mutations and positive selection. J Virol, 2009. 83(14): p. 7176-84.
16. Wussow, F., et al., A vaccine based on the rhesus cytomegalovirus UL128 complex induces broadly neutralizing antibodies in rhesus macaques. J Virol, 2013. 87(3): p. 1322-32.
17. Plachter, B., et al., Analysis of proteins encoded by IE regions 1 and 2 of human cytomegalovirus using monoclonal antibodies generated against recombinant antigens. Virology, 1993. 193(2): p. 642-52.
18. White, E. A., et al., The IE2 60-kilodalton and 40-kilodalton proteins are dispensable for human cytomegalovirus replication but are required for efficient delayed early and late gene expression and production of infectious virus. J Virol, 2007. 81(6): p. 2573-83.
19. Sanders, R. L. and D. H. Spector, Human cytomegalovirus IE2 86 and IE2 40 proteins differentially regulate UL84 protein expression posttranscriptionally in the absence of other viral gene products. J Virol, 2010. 84(10): p. 5158-70.
20. Asmar, J., et al., The putative zinc finger of the human cytomegalovirus IE2 86-kilodalton protein is dispensable for DNA binding and autorepression, thereby demarcating a concise core domain in the C terminus of the protein. J Virol, 2004. 78(21): p. 11853-64.
21. Macias, M. P. and M. F. Stinski, An in vitro system for human cytomegalovirus immediate early 2 protein (IE2)-mediated site-dependent repression of transcription and direct binding of IE2 to the major immediate early promoter. Proc Natl Acad Sci USA, 1993. 90(2): p. 707-11.
22. Petrik, D.T., K. P. Schmitt, and M. F. Stinski, The autoregulatory and transactivating functions of the human cytomegalovirus IE86 protein use independent mechanisms for promoter binding. J Virol, 2007. 81(11): p. 5807-18.
23. Tang, A., et al., Functionally inactivated dominant viral antigens of human cytomegalovirus delivered in replication incompetent adenovirus type 6 vectors as vaccine candidates. Hum Vaccin Immunother, 2017. 13(12): p. 2763-2771.
24. Chiou, C. J., et al., Identification and mapping of dimerization and DNA-binding domains in the C terminus of the IE2 regulatory protein of human cytomegalovirus. J Virol, 1993. 67(10): p. 6201-14.
25. Hermiston, T. W., C. L. Malone, and M. F. Stinski, Human cytomegalovirus immediate-early two protein region involved in negative regulation of the major immediate-early promoter. J Virol, 1990. 64(7): p. 3532-6.
26. Pizzorno, M. C., et al., The functionally active IE2 immediate-early regulatory protein of human cytomegalovirus is an 80-kilodalton polypeptide that contains two distinct activator domains and a duplicated nuclear localization signal. J Virol, 1991. 65(7): p. 3839-52.
27. Stenberg, R. M., et al., Promoter-specific trans activation and repression by human cytomegalovirus immediate-early proteins involves common and unique protein domains. J Virol, 1990. 64(4): p. 1556-65.
28. P. Howley, et al., Intergenic regions as novel sites for insertion of HIV DNA sequences in the genome of Modified Vaccina Virus Ankara. U.S. Pat. No. 7,501,127 B2 (10 March, 2009).
29. Timm, et al., Genetic stability of recombinant MVA-BNA. 2006 May 22; 24(21):4618-21. Epub 2005 Aug 24.
30. B. Moss, et al., Recombinant Modified Vaccinia Ankara (MVA) vaccinia virus containing restructured insertion sites. U.S. Patent Application Publication No. US 2012/0263750 A1.
31. La Rosa, Longmate et al., MVA vaccine encoding CMV antigens safely induces durable expansion of CMV-specific T cells in healthy adults. Blood 2017 129(1): 114-125.
32. Sylwester, Mitchell et al., Broadly targeted human cytomegalovirus-specific CD4+ and CD8+ T cells dominate the memory compartments of exposed subjects. Journal of Experimental Medicine 2005 202(5): 673-685.
33. Nesvizhskii, A. I., Keller, A., Kolker, E. and Aebersold, R. A statistical model for identifying proteins by tandem mass spectrometry. Anal Chem. 2003: 75(17), pp. 4646-58.

We claim:

1. An expression system for co-expressing cytomegalovirus (CMV) antigens comprising a genetically modified recombinant Vaccinia Ankara (rMVA) vector inserted with three nucleic acid sequences encoding three CMV antigens or antigenic portions thereof, wherein the three CMV antigens or antigenic fragments thereof include (a) an IE1 exon 4 (IE1/e4) antigen or antigenic portion thereof inserted in rMVA insertion site IGR3, (b) an IE2 exon 5 (IE2/e5) antigen or antigenic portion thereof inserted in rMVA insertion site 044L/045L, and (c) pp65 antigen or antigenic portion thereof inserted in rMVA insertion site Del3.

2. The expression system of claim 1, wherein each of the three nucleic acid sequences are operably linked to and under the control of a single promoter.

3. The expression system of claim 2, wherein the promoter is an mH5 promoter.

4. The expression system of claim 1, wherein the nucleic acid sequence of the IE1/e4 or IE2/e5 antigen or antigenic portion thereof is codon optimized.

5. The expression system of claim 1, wherein one or more of the three the amino acid sequences of the CMV antigens comprise one or more mutations to improve the genetic stability of the rMVA upon viral passaging.

6. The expression system of claim 1, wherein the rMVA expressing the CMV antigens is genetically stable for at least 10 passages.

7. An immunogenic composition comprising an rMVA vector inserted with three nucleic acid sequences encoding three CMV antigens or antigenic portions thereof, wherein the three CMV antigens or antigenic fragments thereof include (a) an IE1 exon 4 (IE1/e4) antigen or antigenic portion thereof inserted in rMVA insertion site IGR3, (b) an IE2 exon 5 (IE2/e5) antigen or antigenic portion thereof inserted in rMVA insertion site 044L/045L, and (c) pp65 antigen or antigenic portion thereof inserted in rMVA insertion site Del3.

8. The vaccine composition of claim 7, wherein each of the three nucleic acid sequences are operably linked to and under the control of a single promoter.

9. The vaccine composition of claim 8, wherein the promoter is mH5 promoter.

10. The vaccine composition of claim 7, wherein the nucleic acid sequence of the IE1/e4 or IE2/e5 antigen or antigenic portion thereof is codon optimized.

11. The vaccine composition of claim 7, wherein one or more of the amino acid sequences of the CMV antigens comprise one or more mutations to improve the genetic stability of the rMVA upon viral passaging.

12. The vaccine composition of claim 7, wherein the rMVA expressing the CMV antigens is genetically stable for at least 10 passages.

13. A method of eliciting or modifying an immune response in a subject by administering the vaccine of claim 7 to a subject in need thereof.

14. The method of claim 13, wherein the subject is a mammal.

15. The method of claim 13, wherein the subject is human.

16. The method of claim 4, wherein the nucleic acid sequence of the IE1/e4 or IE2/e5 antigen or antigenic portion thereof is a four nucleotide optimized (4nt) nucleic acid sequence of the IE2/e5 antigen or antigenic portion thereof.

17. The method of claim 5, wherein the one or more mutations is a mutation in the IE2/e5 antigen or antigenic portion thereof comprising (i) H363A, (ii) H369A, or (iii) both H363A and H369A.

18. The method of claim 10, wherein the nucleic acid sequence of the IE1/e4 or IE2/e5 antigen or antigenic portion thereof is a four nucleotide optimized (4nt) nucleic acid sequence of the IE2/e5 antigen or antigenic portion thereof.

19. The method of claim 11, wherein the one or more mutations is a mutation in the IE2/e5 antigen or antigenic portion thereof comprising (i) H363A, (ii) H369A, or (iii) both H363A and H369A.

* * * * *